United States Patent
Ngo et al.

(10) Patent No.: US 11,672,828 B2
(45) Date of Patent: Jun. 13, 2023

(54) CELLULAR RECEPTORS AND USES THEREOF

(71) Applicant: TRUSTEES OF BOSTON UNIVERSITY, Boston, MA (US)

(72) Inventors: John T. Ngo, Cambridge, MA (US); Jeffrey Blye McMahan, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 17/171,329

(22) Filed: Feb. 9, 2021

(65) Prior Publication Data

US 2021/0244764 A1    Aug. 12, 2021

Related U.S. Application Data

(60) Provisional application No. 62/972,303, filed on Feb. 10, 2020, provisional application No. 63/000,676, filed on Mar. 27, 2020.

(51) Int. Cl.
| | | |
|---|---|---|
| *A61K 35/17* | (2015.01) | |
| *C07K 14/725* | (2006.01) | |
| *C07K 14/705* | (2006.01) | |
| *C07K 16/28* | (2006.01) | |
| *C07K 16/44* | (2006.01) | |

(52) U.S. Cl.
CPC ............ *A61K 35/17* (2013.01); *C07K 14/705* (2013.01); *C07K 14/7051* (2013.01); *C07K 14/70521* (2013.01); *C07K 16/28* (2013.01); *C07K 16/2809* (2013.01); *C07K 16/2818* (2013.01); *C07K 16/44* (2013.01); *C07K 2319/03* (2013.01); *C07K 2319/30* (2013.01); *C07K 2319/60* (2013.01); *C07K 2319/71* (2013.01); *C07K 2319/74* (2013.01); *C07K 2319/80* (2013.01)

(58) Field of Classification Search
CPC .............................. C12N 2501/42; A61P 35/00
See application file for complete search history.

(56) References Cited

U.S. PATENT DOCUMENTS

| | | |
|---|---|---|
| 6,187,757 B1 | 2/2001 | Clackson et al. |
| 10,517,945 B2 | 12/2019 | Benz et al. |
| 2018/0118808 A1 | 5/2018 | Young et al. |

FOREIGN PATENT DOCUMENTS

| | | | |
|---|---|---|---|
| WO | WO-2012012571 A1 * | 1/2012 | ........... C12Q 1/6816 |
| WO | 2018213848 A1 | 11/2018 | |
| WO | 2019079569 A1 | 4/2019 | |
| WO | 2020028744 A1 | 2/2020 | |

OTHER PUBLICATIONS

Taqvi et al. 2006; Biomaterial-based botch signaling for the differentiation of hematopoietic stem cells into T cells. Journal of Biomedical Materials Research Part A DOI 10.100022/jma.a, pp. 689-697.*
Narui et al. 2013; Membrane tethered delta activates notch and reveals a role for spatio-mechanical regulation of the signaling pathway. Biophysical Journal. 105: 2655-2665, plus Supporting Methods pp. 1-17.*
Stanley et al. (2009; Regulation of notch signaling during T- and B-cell development by O-fucose glycans. Immunol. Rev. 230(1):201-215, abstract only.*
Kriegsmann et al. 2018; Cell-based immunotherapy approaches for multiple myeloma. British Journal of Cancer. 120:38-44.*
Tague et al. 2018; Chemogenetic control of gene expression and cell signaling with antiviral drugs. Nature Methods. 15:519-522.*
McMahan et al. 2018; Post-translational control of synthetic Notch receptors and ligands. Biophysical Journal. 114((3): Supple. 1 p. 179a.*
Wikipedia. 2022; Biotinylation. On the web at Wikipedia.org/siki/biotinylation. pp. 1-5.*
Beckett et al. "A minimal peptide substrate in biotin holoenzyme synthetase-catalyzed biotinylation." Protein Science 8(4): 921-929 (1999).
Branon et al. "Efficient proximity labeling in living cells and organisms with TurboID." Nature Biotechnology 36(9): 880-887 (2018).
Chen et al. "Site-specific labeling of cell surface proteins with biophysical probes using biotin ligase." Nature Methods 2(2): 99-104 (2005).
Cho et al. "Universal chimeric antigen receptors for multiplexed and logical control of T cell responses." Cell 173(6): 1426-1438 (2018).
Dengl et al. "Engineered hapten-binding antibody derivatives for modulation of pharmacokinetic properties of small molecules and targeted payload delivery." Immunological Reviews 270(1): 165-177 (2016).
Dengl et al. "Hapten-directed spontaneous disulfide shuffling: a universal technology for site-directed covalent coupling of payloads to antibodies." The FASEB Journal 29(5): 1763-1779 (2015).
Howarth et al. "Targeting quantum dots to surface proteins in living cells with biotin ligase." Proceedings of the National Academy of Sciences 102(21): 7583-7588 (2005).
Liu et al. "Retargeted human avidin-CAR T cells for adoptive immunotherapy of EGFRvIII expressing gliomas and their evaluation via optical imaging." Oncotarget 6(27): 23735-23747 (2015).
Weber et al. "A synthetic time-delay circuit in mammalian cells and mice." Proceedings of the National Academy of Sciences 104(8): 2643-2648 (2007).
Weber et al. "Vitamin H-regulated transgene expression in mammalian cells." Nucleic Acids Research 35(17): e116 pp. 1-13 (2007).

* cited by examiner

*Primary Examiner* — Karen Cochrane Carlson
(74) *Attorney, Agent, or Firm* — Nixon Peabody LLP; Ronald I. Eisenstein; Nicole D. Kling

(57) ABSTRACT

Described herein are polypeptides, systems, and methods that relate to using domains that bind specifically to a biotinylamide to control receptor and cellular activity.

23 Claims, 36 Drawing Sheets

Specification includes a Sequence Listing.

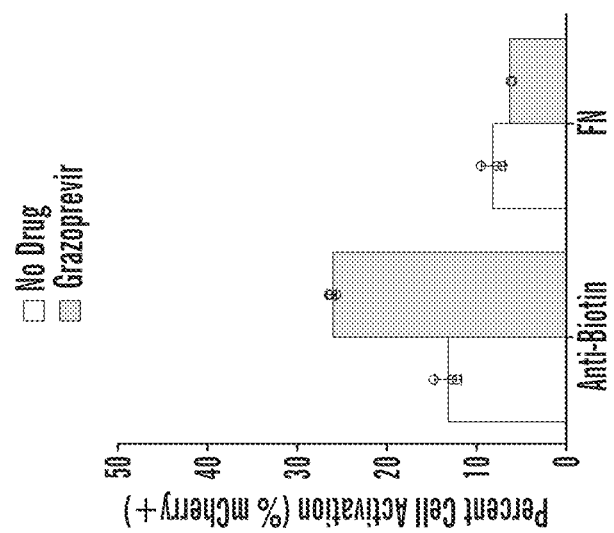
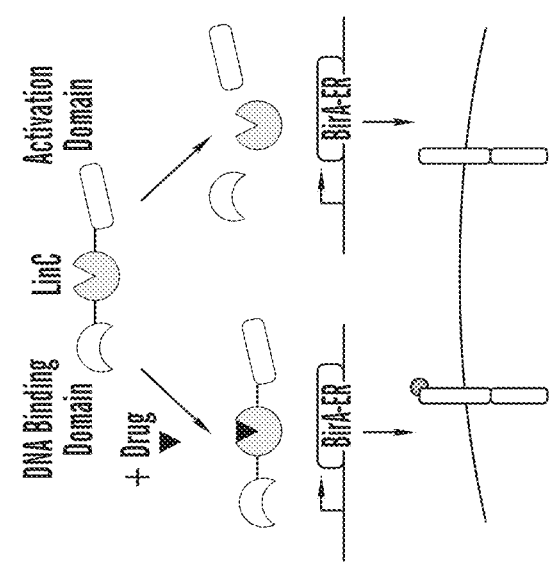
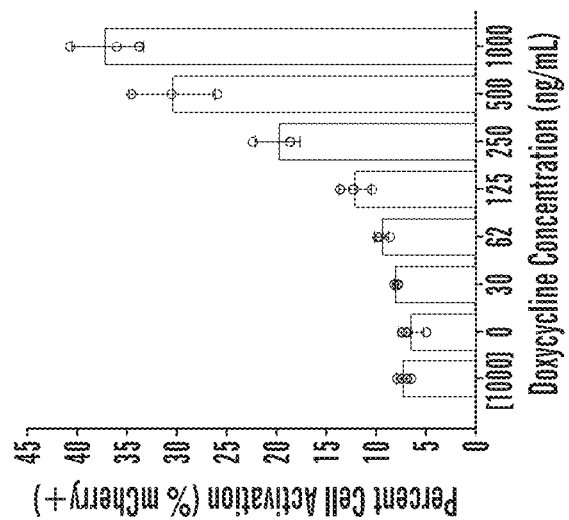
FIG. 2D
FIG. 2E
FIG. 2F

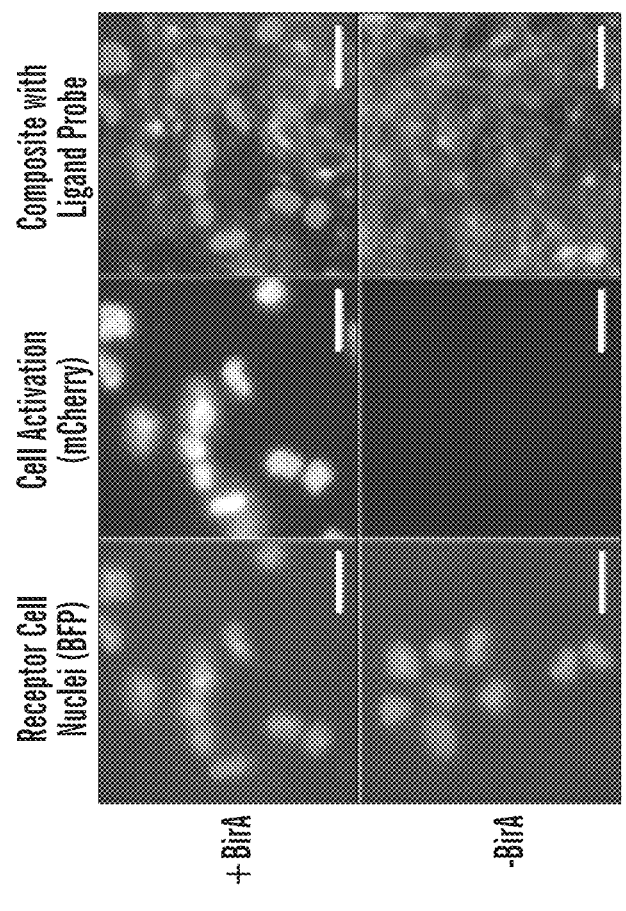
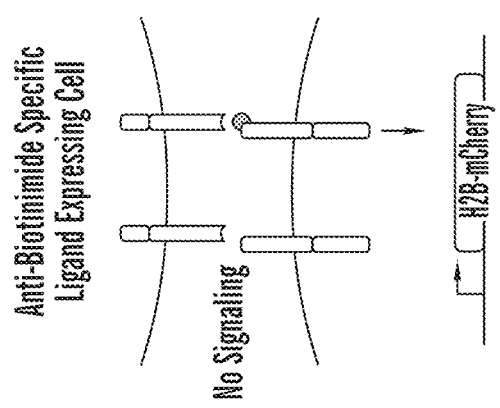
FIG. 3B
FIG. 3A

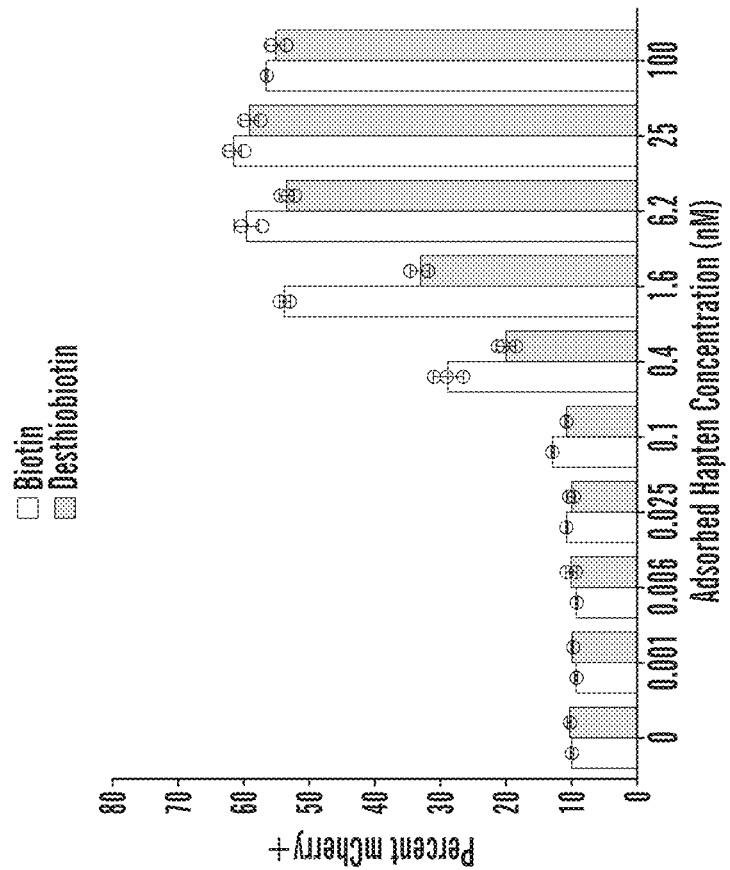
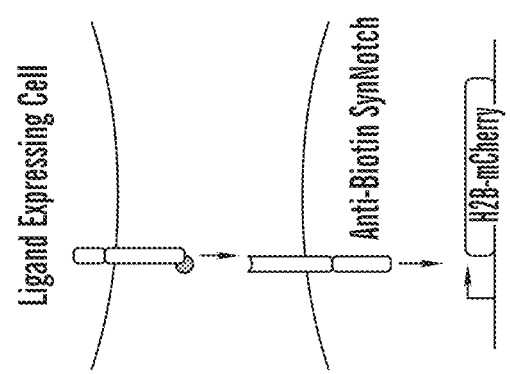
FIG. 4B
FIG. 4A

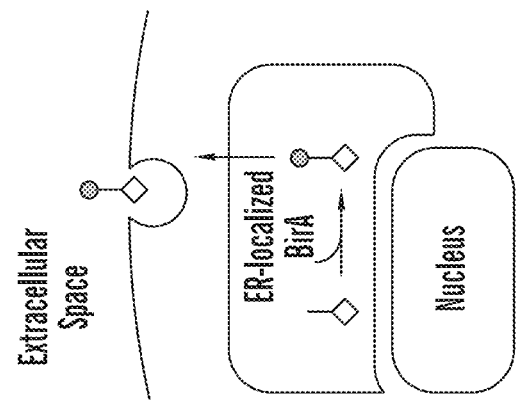
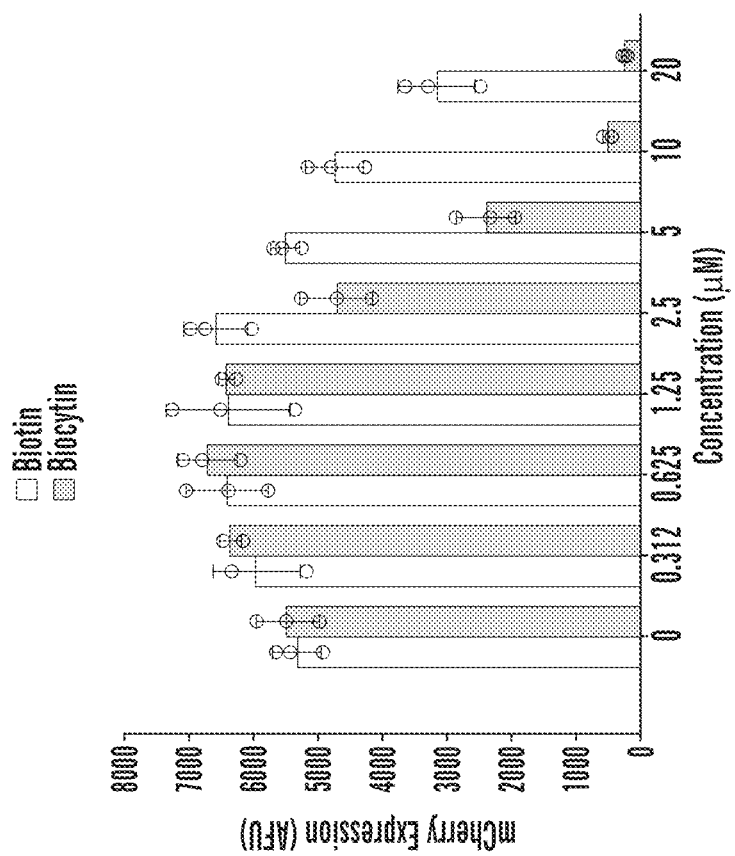
FIG. 4C
FIG. 4D

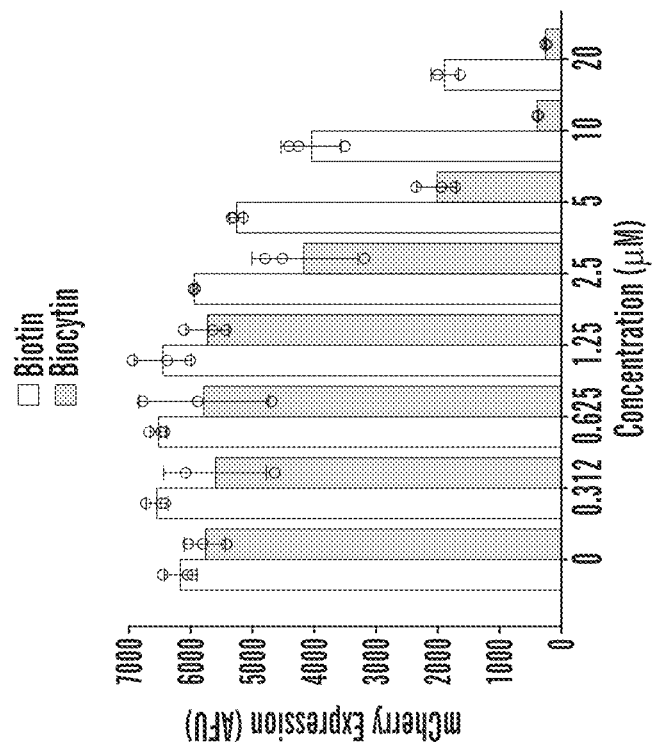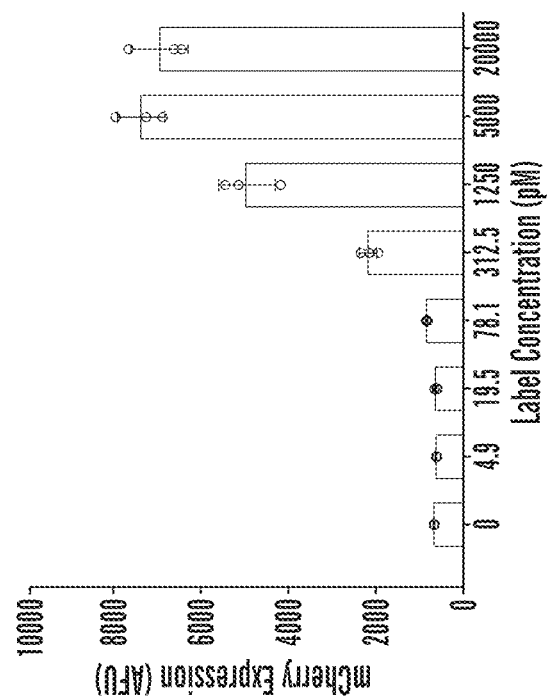
FIG. 7A
FIG. 7B

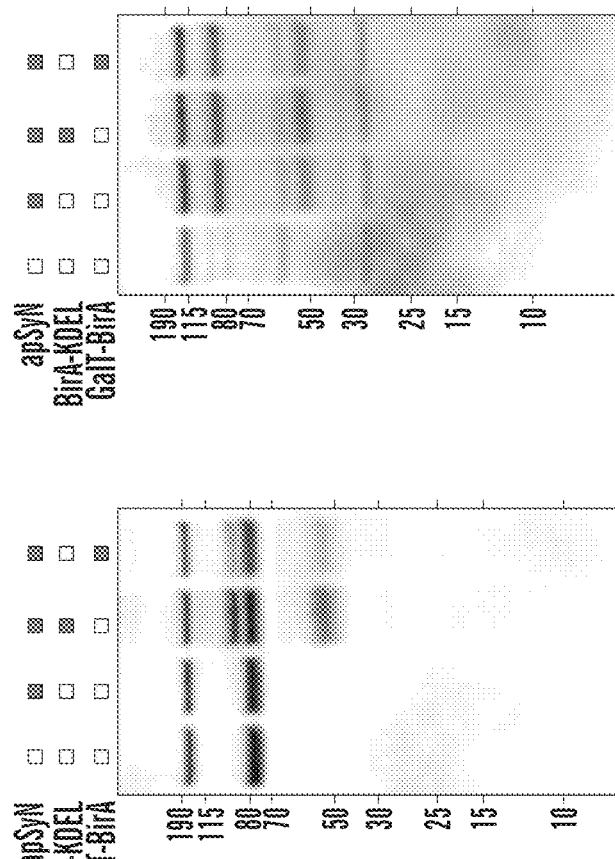
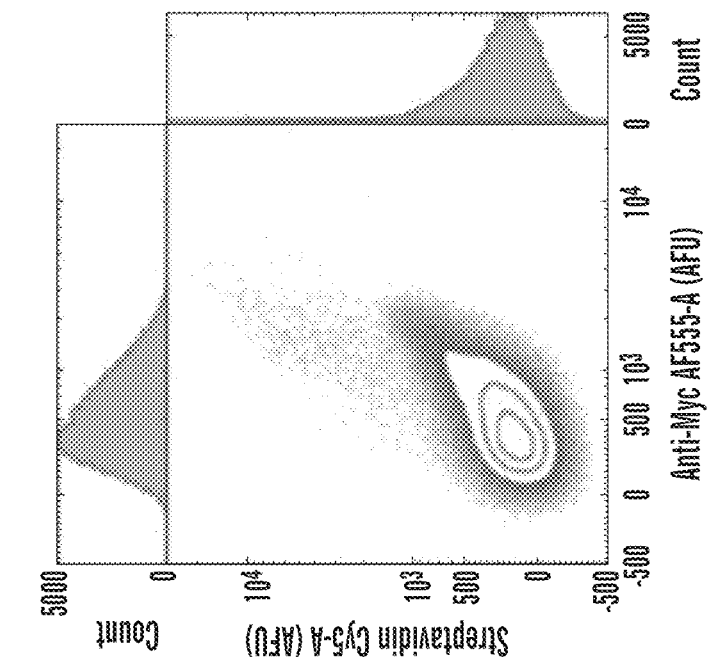
FIG. 9A  FIG. 9B  FIG. 9C

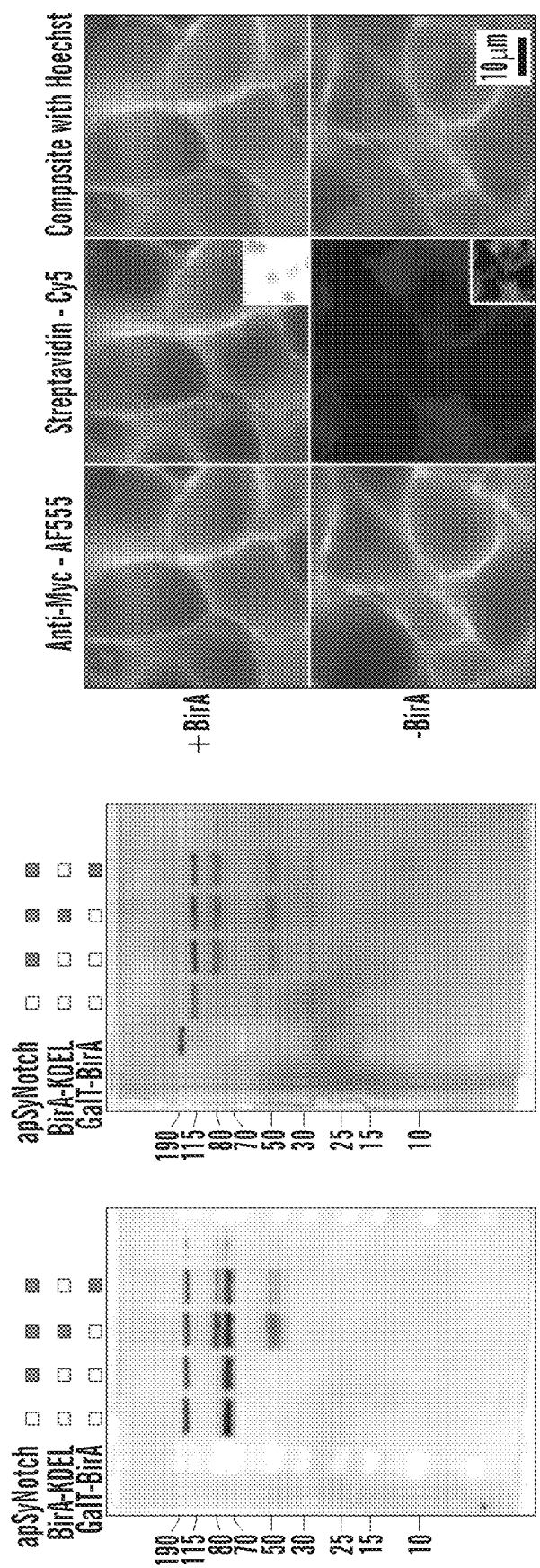

SEQUENCE LISTING

```
<160> NUMBER OF SEQ ID NOS: 133

<210> SEQ ID NO 1
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ser Ser Gly Phe Asn Asn Lys Asp Thr
            20                  25                  30

Phe Phe Gln Trp Val Lys Gln Arg Pro Glu Glu Gly Leu Glu Trp Ile
        35                  40                  45

Gly Arg Ile Asp Pro Ala Asn Gly Phe Thr Lys Tyr Asp Pro Lys Phe
    50                  55                  60

Gln Gly Lys Ala Thr Ile Thr Val Asp Thr Ser Ser Asn Thr Ala Tyr
65                  70                  75                  80

Leu Gln Leu Asn Ser Leu Thr Ser Glu Asp Thr Ala Leu Tyr Tyr Cys
                85                  90                  95

Thr Arg Trp Asp Thr Tyr Gly Ala Ala Trp Phe Ala Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190
```

```
Ser Thr Trp Pro Ser Glu Thr Val Thr Cys Asn Val Ala His Pro Ala
        195                 200                 205

Ser Ser Thr Lys Val Asp Lys Lys Ile Val Pro Arg
    210                 215                 220

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ser Trp Phe Gln Gln Lys Gln Gly Lys Ser Pro Gln Leu Leu Val
        35                  40                  45

Tyr Ser Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Ser Ser Ile Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Ser Ser Arg Ser Ser Ser Ser Gly Gly Gly Ser Gly Gly
1               5                   10                  15

Gly Gly

<210> SEQ ID NO 4
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gly Asn Ile His Asn Tyr Leu Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ala Lys Thr Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln His Phe Trp Ser Ser Ile Tyr Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Thr Phe Phe Gln
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ile Asp Pro Ala Asn Gly Phe Thr Lys Tyr Asp Pro Lys Phe Gln
1               5                   10                  15

Gly

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

```
Trp Asp Thr Tyr Gly Ala Ala Trp Phe Ala Tyr
1               5                   10
```

<210> SEQ ID NO 10

<400> SEQUENCE: 10

000

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Arg Ala Ser Glu Ser Val Asp Asn Tyr Gly Ile Ser Tyr Met His
1               5                   10                  15
```

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Trp Tyr Gln Gln Arg Pro Gly Gln Pro Pro Lys Leu Leu Ile Tyr
1               5                   10                  15
```

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Gln His Ser Arg Glu Val Pro Trp Thr
1               5
```

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Asn Tyr Trp Met Asn
1               5
```

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Gln Ile Tyr Pro Gly Asn Gly Asp Ala Lys Tyr Ser Gly Lys Ser Arg
1               5                   10                  15
```

Asp

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Tyr Gly Tyr Asp Glu Ala Trp Phe Ala Tyr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ala Ser Gly Asn Ile His Asn Tyr Leu Ser
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Ala Lys Thr Leu Ala Asp
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln His Phe Trp Ser Ser Ile Tyr Thr
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Thr Phe Phe Gln
1               5

<210> SEQ ID NO 21
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 21

Arg Ile Asp Pro Ala Asn Gly Phe Thr Lys Tyr Ala Gln Lys Phe Gln
1               5                   10                  15

Gly

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Asp Thr Tyr Gly Ala Ala Trp Phe Ala Tyr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ala Ser Gly Asn Ile His Asn Tyr Leu Ser
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Ala Lys Thr Leu Ala Asp
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln His Phe Trp Ser Ser Ile Tyr Thr
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Thr Phe Phe Gln
1               5

```
<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ile Asp Pro Cys Asn Gly Phe Thr Lys Tyr Asp Pro Lys Gln Gly
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Asp Thr Tyr Gly Ala Ala Trp Phe Ala Tyr
1               5                   10

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000
```

```
<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

<210> SEQ ID NO 46
<400> SEQUENCE: 46
000

<210> SEQ ID NO 47
```

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

```
<210> SEQ ID NO 59
<400> SEQUENCE: 59

000

<210> SEQ ID NO 60
<400> SEQUENCE: 60

000

<210> SEQ ID NO 61
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: SITE
<222> LOCATION: (2)..(5)
<223> OTHER INFORMATION: This region may encompass 2-4 residues
<220> FEATURE:
<221> NAME/KEY: MOD_RES
<222> LOCATION: (7)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: SITE
<222> LOCATION: (20)..(24)
<223> OTHER INFORMATION: This region may encompass 3-5 residues

<400> SEQUENCE: 61

Cys Xaa Xaa Xaa Xaa Cys Xaa Xaa Xaa Xaa Xaa Xaa Xaa Xaa Xaa
1               5                   10                  15

Xaa Xaa His Xaa Xaa Xaa Xaa Xaa His
            20                  25

<210> SEQ ID NO 62
<400> SEQUENCE: 62

000

<210> SEQ ID NO 63
<400> SEQUENCE: 63

000

<210> SEQ ID NO 64
<400> SEQUENCE: 64

000

<210> SEQ ID NO 65
<400> SEQUENCE: 65
```

000

<210> SEQ ID NO 66
<400> SEQUENCE: 66
000

<210> SEQ ID NO 67
<400> SEQUENCE: 67
000

<210> SEQ ID NO 68
<400> SEQUENCE: 68
000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

```
<400> SEQUENCE: 88
000

<210> SEQ ID NO 89
<400> SEQUENCE: 89
000

<210> SEQ ID NO 90
<400> SEQUENCE: 90
000

<210> SEQ ID NO 91
<400> SEQUENCE: 91
000

<210> SEQ ID NO 92
<400> SEQUENCE: 92
000

<210> SEQ ID NO 93
<400> SEQUENCE: 93
000

<210> SEQ ID NO 94
<400> SEQUENCE: 94
000

<210> SEQ ID NO 95
<400> SEQUENCE: 95
000

<210> SEQ ID NO 96
<400> SEQUENCE: 96
000

<210> SEQ ID NO 97
<400> SEQUENCE: 97
000

<210> SEQ ID NO 98
<400> SEQUENCE: 98
000

<210> SEQ ID NO 99
<400> SEQUENCE: 99
```

000

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Leu Asn Asp Ile Phe Glu Ala Gln Lys Ile Glu Trp His
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: T, H, G, D, P, S, M, or L
<220> FEATURE:
<221> NAME/KEY: MOD_RES
<222> LOCATION: (2)..(2)
<223> OTHER INFORMATION: S, L, D, V, W, M, E, or T
<220> FEATURE:
<221> NAME/KEY: MOD_RES
<222> LOCATION: (3)..(3)
<223> OTHER INFORMATION: S, P, L, K, D, T, W, N, H, A, or R
<220> FEATURE:
<221> NAME/KEY: MOD_RES
<222> LOCATION: (4)..(4)
<223> OTHER INFORMATION: A, M, K, T, N, G, D, E, or P
<220> FEATURE:
<221> NAME/KEY: MOD_RES
<222> LOCATION: (5)..(5)
<223> OTHER INFORMATION: I, P, L, or T
<220> FEATURE:
<221> NAME/KEY: MOD_RES
<222> LOCATION: (6)..(6)
<223> OTHER INFORMATION: F or L
<220> FEATURE:
<221> NAME/KEY: MOD_RES
<222> LOCATION: (7)..(7)
<223> OTHER INFORMATION: D, R, E, L, N, A, or T
<220> FEATURE:
<221> NAME/KEY: MOD_RES
<222> LOCATION: (8)..(8)
<223> OTHER INFORMATION: A, S, or G
<220> FEATURE:
<221> NAME/KEY: MOD_RES
<222> LOCATION: (9)..(9)
<223> OTHER INFORMATION: M, Q, or T
<220> FEATURE:
<221> NAME/KEY: MOD_RES
<222> LOCATION: (11)..(11)
<223> OTHER INFORMATION: M or T
<220> FEATURE:
<221> NAME/KEY: MOD_RES
<222> LOCATION: (12)..(12)
<223> OTHER INFORMATION: V, E, L, M, T, Y, Q or D
<220> FEATURE:
<221> NAME/KEY: MOD_RES
<222> LOCATION: (13)..(13)
<223> OTHER INFORMATION: W, V, F, L, Y, or Q
<220> FEATURE:
<221> NAME/KEY: MOD_RES
<222> LOCATION: (14)..(14)
<223> OTHER INFORMATION: I, Y, H, V, S, L, or W

<400> SEQUENCE: 101

```
Xaa Xaa Xaa Xaa Xaa Xaa Xaa Xaa Xaa Lys Xaa Xaa Xaa Xaa
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L, I, T, M, or F
<220> FEATURE:
<221> NAME/KEY: MOD_RES
<222> LOCATION: (2)..(2)
<223> OTHER INFORMATION: F, L, or M
<220> FEATURE:
<221> NAME/KEY: MOD_RES
<222> LOCATION: (3)..(3)
<223> OTHER INFORMATION: E or D
<220> FEATURE:
<221> NAME/KEY: MOD_RES
<222> LOCATION: (4)..(4)
<223> OTHER INFORMATION: A, G, or S
<220> FEATURE:
<221> NAME/KEY: MOD_RES
<222> LOCATION: (5)..(5)
<223> OTHER INFORMATION: M, Q, or L
<220> FEATURE:
<221> NAME/KEY: MOD_RES
<222> LOCATION: (7)..(7)
<223> OTHER INFORMATION: M or V

<400> SEQUENCE: 102

Xaa Xaa Xaa Xaa Xaa Lys Xaa
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, N, V, T, or M
<220> FEATURE:
<221> NAME/KEY: MOD_RES
<222> LOCATION: (2)..(2)
<223> OTHER INFORMATION: F or L
<220> FEATURE:
<221> NAME/KEY: MOD_RES
<222> LOCATION: (3)..(3)
<223> OTHER INFORMATION: E, D, or A
<220> FEATURE:
<221> NAME/KEY: MOD_RES
<222> LOCATION: (4)..(4)
<223> OTHER INFORMATION: A, S, or G
<220> FEATURE:
<221> NAME/KEY: MOD_RES
<222> LOCATION: (5)..(5)
<223> OTHER INFORMATION: M, Q, or A
<220> FEATURE:
<221> NAME/KEY: MOD_RES
<222> LOCATION: (7)..(7)
<223> OTHER INFORMATION: M or I

<400> SEQUENCE: 103

Xaa Xaa Xaa Xaa Xaa Lys Xaa
1               5
```

```
<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: H, N, or S
<220> FEATURE:
<221> NAME/KEY: MOD_RES
<222> LOCATION: (3)..(3)
<223> OTHER INFORMATION: A, S, or T
<220> FEATURE:
<221> NAME/KEY: MOD_RES
<222> LOCATION: (6)..(6)
<223> OTHER INFORMATION: I or V
<220> FEATURE:
<221> NAME/KEY: MOD_RES
<222> LOCATION: (7)..(7)
<223> OTHER INFORMATION: E, L, or Y
<220> FEATURE:
<221> NAME/KEY: MOD_RES
<222> LOCATION: (8)..(8)
<223> OTHER INFORMATION: W, L, or M

<400> SEQUENCE: 104

Leu Xaa Xaa Gln Lys Xaa Xaa Xaa
1               5

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid except L, V, I, W, F, or Y
<220> FEATURE:
<221> NAME/KEY: MOD_RES
<222> LOCATION: (5)..(5)
<223> OTHER INFORMATION: F or L
<220> FEATURE:
<221> NAME/KEY: MOD_RES
<222> LOCATION: (6)..(6)
<223> OTHER INFORMATION: E or D
<220> FEATURE:
<221> NAME/KEY: MOD_RES
<222> LOCATION: (7)..(7)
<223> OTHER INFORMATION: A, G, S, or T
<220> FEATURE:
<221> NAME/KEY: MOD_RES
<222> LOCATION: (8)..(8)
<223> OTHER INFORMATION: Q or M
<220> FEATURE:
<221> NAME/KEY: MOD_RES
<222> LOCATION: (10)..(10)
<223> OTHER INFORMATION: I, M, or V
<220> FEATURE:
<221> NAME/KEY: MOD_RES
<222> LOCATION: (11)..(11)
<223> OTHER INFORMATION: E, L, V, Y, or I
<220> FEATURE:
<221> NAME/KEY: MOD_RES
<222> LOCATION: (12)..(12)
<223> OTHER INFORMATION: W, Y, V, F, L, or I
```

```
<220> FEATURE:
<221> NAME/KEY: MOD_RES
<222> LOCATION: (13)..(13)
<223> OTHER INFORMATION: Any amino acid except D and E

<400> SEQUENCE: 105

Leu Xaa Xaa Ile Xaa Xaa Xaa Xaa Lys Xaa Xaa Xaa Xaa
1               5                   10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid except L, V, I, W, F, or Y
<220> FEATURE:
<221> NAME/KEY: MOD_RES
<222> LOCATION: (5)..(5)
<223> OTHER INFORMATION: F or L
<220> FEATURE:
<221> NAME/KEY: MOD_RES
<222> LOCATION: (6)..(6)
<223> OTHER INFORMATION: E or D
<220> FEATURE:
<221> NAME/KEY: MOD_RES
<222> LOCATION: (7)..(7)
<223> OTHER INFORMATION: A, G, S, or T
<220> FEATURE:
<221> NAME/KEY: MOD_RES
<222> LOCATION: (8)..(8)
<223> OTHER INFORMATION: Q or M
<220> FEATURE:
<221> NAME/KEY: MOD_RES
<222> LOCATION: (10)..(10)
<223> OTHER INFORMATION: I, M, or V
<220> FEATURE:
<221> NAME/KEY: MOD_RES
<222> LOCATION: (11)..(11)
<223> OTHER INFORMATION: E, L, V, Y, or I
<220> FEATURE:
<221> NAME/KEY: MOD_RES
<222> LOCATION: (12)..(12)
<223> OTHER INFORMATION: W, Y, V, F, L, or I
<220> FEATURE:
<221> NAME/KEY: MOD_RES
<222> LOCATION: (13)..(13)
<223> OTHER INFORMATION: R or H

<400> SEQUENCE: 106

Leu Xaa Xaa Ile Xaa Xaa Xaa Xaa Lys Xaa Xaa Xaa Xaa
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu Gly Gly Ile Phe Glu Ala Met Lys Met Glu Leu Arg Asp
1               5                   10
```

```
<210> SEQ ID NO 108
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Phe Leu His Asp Phe Leu Asn Ala Gln Lys Val Glu Leu Tyr Pro
1               5                   10                  15

Val Thr Ser Ser Gly
            20

<210> SEQ ID NO 109
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Met Ala Gly Gly Leu Asn Asp Ile Phe Glu Ala Gln Lys Ile Glu Trp
1               5                   10                  15

His Glu Asp Thr Gly Gly Ser
            20

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Leu Asn Asp Ile Phe Glu Ala Gln Lys Ile Glu Trp His
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Thr Asn Trp Val Ala Gln Ala Phe Lys Met Thr Phe Asp Pro
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: T, S, E, Q, D, N, or A
<220> FEATURE:
<221> NAME/KEY: MOD_RES
<222> LOCATION: (2)..(2)
<223> OTHER INFORMATION: T, P, W, T, H, Y, I, Q, or P
<220> FEATURE:
<221> NAME/KEY: MOD_RES
```

```
<222> LOCATION: (3)..(3)
<223> OTHER INFORMATION: N, S, E, A, T, F, G, or Y
<220> FEATURE:
<221> NAME/KEY: MOD_RES
<222> LOCATION: (4)..(4)
<223> OTHER INFORMATION: W, H, D, H, S, or P
<220> FEATURE:
<221> NAME/KEY: MOD_RES
<222> LOCATION: (5)..(5)
<223> OTHER INFORMATION: V, L, D, or G
<220> FEATURE:
<221> NAME/KEY: MOD_RES
<222> LOCATION: (6)..(6)
<223> OTHER INFORMATION: A, R, F, L, or P
<220> FEATURE:
<221> NAME/KEY: MOD_RES
<222> LOCATION: (7)..(7)
<223> OTHER INFORMATION: Q, E, P, T, Y, R, N, or S
<220> FEATURE:
<221> NAME/KEY: MOD_RES
<222> LOCATION: (8)..(8)
<223> OTHER INFORMATION: A, L, or P
<220> FEATURE:
<221> NAME/KEY: MOD_RES
<222> LOCATION: (9)..(9)
<223> OTHER INFORMATION: F or M
<220> FEATURE:
<221> NAME/KEY: MOD_RES
<222> LOCATION: (14)..(14)
<223> OTHER INFORMATION: D, S, T, or H
<220> FEATURE:
<221> NAME/KEY: MOD_RES
<222> LOCATION: (15)..(15)
<223> OTHER INFORMATION: P, R, K, S, T, or G

<400> SEQUENCE: 112

Xaa Xaa Xaa Xaa Xaa Xaa Xaa Xaa Xaa Lys Met Thr Phe Xaa Xaa
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: T, S, E, Q, D, N, or A
<220> FEATURE:
<221> NAME/KEY: MOD_RES
<222> LOCATION: (2)..(2)
<223> OTHER INFORMATION: T, P, W, T, H, Y, I, Q, or P
<220> FEATURE:
<221> NAME/KEY: MOD_RES
<222> LOCATION: (3)..(3)
<223> OTHER INFORMATION: N, S, E, A, T, F, G, or Y
<220> FEATURE:
<221> NAME/KEY: MOD_RES
<222> LOCATION: (4)..(4)
<223> OTHER INFORMATION: W, H, D, H, S, or P
<220> FEATURE:
<221> NAME/KEY: MOD_RES
<222> LOCATION: (5)..(5)
<223> OTHER INFORMATION: V, L, D, or G
<220> FEATURE:
<221> NAME/KEY: MOD_RES
<222> LOCATION: (6)..(6)
<223> OTHER INFORMATION: A, R, F, L, or P
<220> FEATURE:
<221> NAME/KEY: MOD_RES
<222> LOCATION: (7)..(7)
<223> OTHER INFORMATION: Q, E, P, T, Y, R, N, or S
<220> FEATURE:
<221> NAME/KEY: MOD_RES
<222> LOCATION: (9)..(9)
```

```
<223> OTHER INFORMATION: F or M
<220> FEATURE:
<221> NAME/KEY: MOD_RES
<222> LOCATION: (14)..(14)
<223> OTHER INFORMATION: D, S, T, or H
<220> FEATURE:
<221> NAME/KEY: MOD_RES
<222> LOCATION: (15)..(15)
<223> OTHER INFORMATION: P, R, K, S, T, or G

<400> SEQUENCE: 113

Xaa Xaa Xaa Xaa Xaa Xaa Xaa Ala Xaa Lys Met Thr Phe Xaa Xaa
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: T, S, E, Q, D, N, or A
<220> FEATURE:
<221> NAME/KEY: MOD_RES
<222> LOCATION: (2)..(2)
<223> OTHER INFORMATION: T, P, W, T, H, Y, I, Q, or P
<220> FEATURE:
<221> NAME/KEY: MOD_RES
<222> LOCATION: (3)..(3)
<223> OTHER INFORMATION: N, S, E, A, T, F, G, or Y
<220> FEATURE:
<221> NAME/KEY: MOD_RES
<222> LOCATION: (4)..(4)
<223> OTHER INFORMATION: W, H, D, H, S, or P
<220> FEATURE:
<221> NAME/KEY: MOD_RES
<222> LOCATION: (5)..(5)
<223> OTHER INFORMATION: V, L, D, or G
<220> FEATURE:
<221> NAME/KEY: MOD_RES
<222> LOCATION: (6)..(6)
<223> OTHER INFORMATION: A, R, F, L, or P
<220> FEATURE:
<221> NAME/KEY: MOD_RES
<222> LOCATION: (7)..(7)
<223> OTHER INFORMATION: Q, E, P, T, Y, R, N, or S
<220> FEATURE:
<221> NAME/KEY: MOD_RES
<222> LOCATION: (14)..(14)
<223> OTHER INFORMATION: D, S, T, or H
<220> FEATURE:
<221> NAME/KEY: MOD_RES
<222> LOCATION: (15)..(15)
<223> OTHER INFORMATION: P, R, K, S, T, or G

<400> SEQUENCE: 114

Xaa Xaa Xaa Xaa Xaa Xaa Xaa Ala Met Lys Met Thr Phe Xaa Xaa
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: T, S, E, Q, D, N, or A
<220> FEATURE:
<221> NAME/KEY: MOD_RES
```

```
<222> LOCATION: (2)..(2)
<223> OTHER INFORMATION: T, P, W, T, H, Y, I, Q, or P
<220> FEATURE:
<221> NAME/KEY: MOD_RES
<222> LOCATION: (3)..(3)
<223> OTHER INFORMATION: N, S, E, A, T, F, G, or Y
<220> FEATURE:
<221> NAME/KEY: MOD_RES
<222> LOCATION: (4)..(4)
<223> OTHER INFORMATION: W, H, D, H, S, or P
<220> FEATURE:
<221> NAME/KEY: MOD_RES
<222> LOCATION: (5)..(5)
<223> OTHER INFORMATION: V, L, D, or G
<220> FEATURE:
<221> NAME/KEY: MOD_RES
<222> LOCATION: (6)..(6)
<223> OTHER INFORMATION: A, R, F, L, or P
<220> FEATURE:
<221> NAME/KEY: MOD_RES
<222> LOCATION: (7)..(7)
<223> OTHER INFORMATION: Q, E, P, T, Y, R, N, or S
<220> FEATURE:
<221> NAME/KEY: MOD_RES
<222> LOCATION: (8)..(8)
<223> OTHER INFORMATION: A, L, or P
<220> FEATURE:
<221> NAME/KEY: MOD_RES
<222> LOCATION: (9)..(9)
<223> OTHER INFORMATION: F or M
<220> FEATURE:
<221> NAME/KEY: MOD_RES
<222> LOCATION: (12)..(12)
<223> OTHER INFORMATION: T or E
<220> FEATURE:
<221> NAME/KEY: MOD_RES
<222> LOCATION: (14)..(14)
<223> OTHER INFORMATION: D, S, T, or H
<220> FEATURE:
<221> NAME/KEY: MOD_RES
<222> LOCATION: (15)..(15)
<223> OTHER INFORMATION: P, R, K, S, T, or G

<400> SEQUENCE: 115

Xaa Xaa Xaa Xaa Xaa Xaa Xaa Xaa Xaa Lys Met Xaa Phe Xaa Xaa
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Leu Asn Asp Ile Phe Glu Ala Ala Ala Ala Glu Trp His Glu
1               5                   10                  15

<210> SEQ ID NO 117
<211> LENGTH: 4
<212> TYPE: PRT
<213> ORGANISM: Unknown
<220> FEATURE:
<223> OTHER INFORMATION: Description of Unknown:
      "KDEL" motif peptide

<400> SEQUENCE: 117

Lys Asp Glu Leu
1

<210> SEQ ID NO 118
<211> LENGTH: 8247
```

<212> TYPE: DNA
<213> ORGANISM: Homo sapiens

<400> SEQUENCE: 118

| | | | | | |
|---|---|---|---|---|---|
| agggattcgc | gggcgaccac | ccggcgcagg | agcggccgcg | tttcggcctc | agaatccatt | 60 |
| gaagacttga | acaagtgggc | cctatttctt | gtgtctcctt | ttatacttga | agcagaacac | 120 |
| atagcatttg | tgacggagag | catttgggta | caaagtgaga | atttacagag | atcatcctct | 180 |
| tcagaaacag | ttcggttttt | gcccactagg | gatgatgtgg | tttctcatga | ggttacttgc | 240 |
| tctaaaggac | tttatatttt | ggaaccataa | gagcaccctt | gtggcccagg | cactttatgg | 300 |
| atgatccctt | ttagtgctcc | cagtaacctt | ccaagattgt | caagtggtca | gactgttgtt | 360 |
| tgccattagc | ttgcagacct | ggggatcctt | atcggctaat | tgctgaagca | agtgtggaca | 420 |
| acttcagcaa | gctggggggtg | gcgttcatgg | aagatagact | ccacatggat | aatggactgg | 480 |
| taccccaaaa | gattgtgtcg | gtgcacttgc | aggactccac | tctgaaggaa | gttaaggatc | 540 |
| aggtctcaaa | caagcaagcc | cagatcctag | agccgaagcc | tgaaccttct | cttgagatta | 600 |
| agcctgagca | ggacggtatg | gagcatgttg | gcagagatga | cccaaaggct | cttggtgaag | 660 |
| aacccaaaca | aaggagaggc | agtgcctctg | ggagtgagcc | tgctggggac | agtgacaggg | 720 |
| gaggggccc | cgttgagcat | tatcacctcc | atctgtctag | ttgccacgag | tgtctggaac | 780 |
| ttgagaacag | caccattgag | tcagtcaagt | ttgcgtctgc | cgagaacatt | ccagaccttc | 840 |
| cctacgatta | tagcagcagt | ttggagagtg | ttgctgatga | gacctccccc | gaaagagaag | 900 |
| ggaggagagt | caacctcacg | ggaaaggcac | ccaacatcct | cctctatgtg | ggctccgact | 960 |
| cccaggaagc | cctcggccgg | ttccacgagg | tccggtctgt | gctggccgac | tgtgtggaca | 1020 |
| ttgacagtta | tattctctac | cacctgctgg | aggacagtgc | tctcagagac | ccgtggacgg | 1080 |
| acaactgtct | gctgttggtc | attgctacca | gggagtccat | tcccgaagac | ctgtaccaga | 1140 |
| agttcatggc | ctatctttct | cagggaggga | aggtgttggg | cctgtcttca | tccttcacct | 1200 |
| ttggtggctt | tcaggtgaca | agcaagggtg | cactgcacaa | gacagtccag | aacttggttt | 1260 |
| tctccaaggc | tgaccagagc | gaggtgaagc | tcagcgtctt | gagcagtggc | tgcaggtacc | 1320 |
| aggaaggccc | cgtccggctc | agccccggca | ggctccaggg | ccacctggag | aatgaggaca | 1380 |
| aggacaggat | gattgtgcat | gtgccttttg | gaactcgcgg | gggagaagct | gttctttgcc | 1440 |
| aggtgcactt | agaactacct | cccagctcca | acatagtgca | aactccagaa | gatttttaact | 1500 |
| tgctcaagtc | aagcaatttt | agaagatacg | aagtccttag | agagattctg | acaacccttg | 1560 |
| gcctcagctg | tgacatgaaa | caagttcctg | ccttaactcc | tctttacttg | ctgtcagctg | 1620 |
| cggaggaaat | cagggatcct | cttatgcagt | ggcttgggaa | acatgtggac | tccgagggag | 1680 |
| aaataaaatc | cggccagctc | tctcttagat | ttgtttcatc | ctacgtgtct | gaagtagaaa | 1740 |
| taacccatc | ttgtatacct | gtggtgacca | acatggaggc | cttctcatca | gaacatttca | 1800 |
| acttagagat | ctatcgccaa | aatctgcaga | ccaagcagtt | ggggaaagta | attttgtttg | 1860 |
| ccgaagtgac | ccccacaacg | atgcgtctcc | tggatgggct | gatgtttcag | acaccgcagg | 1920 |
| aaatggcctt | aatagtgatc | gcggcccggc | agaccgaggg | caaaggacgg | ggagggaatg | 1980 |
| tgtggctgag | ccctgtggga | tgtgctctttt | ctactctgct | catctccatt | ccactgagat | 2040 |
| cccagctggg | acagaggatc | ccgtttgtcc | agcatctgat | gtccgtggct | gtcgtggaag | 2100 |
| cagtgaggtc | cattcccgag | tatcaggata | tcaacttacg | agtgaagtgg | cccaacgata | 2160 |
| tttattacag | tgacctcatg | aagatcggcg | gagttctggt | taactcaaca | ctcatgggag | 2220 |

```
aaacatttta tatacttatt ggctgtggat ttaatgtgac taacagtaac cctaccatct    2280
gcatcaacga cctcatcaca gaatacaata acaacacaa ggcagaactg aagcccttaa    2340
gagccgatta tctcatcgcc agagtcgtga ctgtgctgga gaaactgatc aaagagtttc    2400
aggacaaagg gcccaacagc gtccttcccc tttattaccg atactgggtc cacagtggtc    2460
agcaagtcca tctgggcagc gcagagggac caaaggtgtc catcgttggc ctggacgatt    2520
ctggcttcct ccaggttcac caggagggcg gcgaggttgt gactgtgcac ccggacggca    2580
actccttcga catgctgaga aacctcatcc tccccaaacg gcggtaatgc cgggcgtccc    2640
cgagacgcgg ctgcctgtcc gtgcccatgc atctggaaat ctaatttaga gttgtaggtg    2700
aattttcttt tcctccaatt catttgttaa gtctttgttc tttttctgtg tttctgtttg    2760
tttttaggtt tgttttgttg tcgttttctt tggtgtttga agaggctctg ggatagatgg    2820
ttaagaagta gaaaatttag tttagggaaa gccctcccac aggtgggaaa ttgctctccc    2880
ctctgtggct tggacttacg tttattgtca aggggagttt ttacatggaa atgacaatgg    2940
gaaaattcag atattttctt agtagtgcag acctttaccc ctagtctatg aaaaaacaaa    3000
ccaaaatatg ctcttgcgcc caggccagtg gtgagttaga ggtatgctat cactgttgt    3060 aagcatctgg ggaggtactg aactgtaaga acatgcttgg acacttagtc attgttctgt    3120
gtttttatta atgaagaaaa gggaagacag acttccaaga gttactgtcc acccggtggt    3180
gtggccccat agcgaagtct aaatgcctgt agagatagag ctagctggtg tggttgcagt    3240
gaccttgtag aggaaatcag ttcattactt tgacatcatt cagtgagctc tcctttccta    3300
aggaagttta aatgtcctta gttagggact gactttctta agtaagttta aatttactac    3360
atattgtgaa gagacaggat caagttcaga atccttaaat gtctgattag gcatcacttg    3420
gatgaggagg tgggcgattt ggctctgaca gctggagatg aaggcacact cataccacat    3480
acaagggagg atttggagct tttaagccag tttcagattt actctgaaat gtggagcatt    3540
cctgcaagac tgtgcagctc acggaatata aagacatgg catttactc agaagtcata    3600 agttttgcc ccctcatt accctcgtatt accaagaaag aaaatgttat cgatactaaa    3660
caccatcagt tcagagggag gatgtgtgtg tgtgcccgca tatgtgtgtg cgtgcgtgtg    3720
tgcgcacata gctttaaaag aagacattca aaatttgatg tgctacaagc ctcatgaaag    3780
aacaaaagaa atgaagcctt ttgatatgca ttcgctattc ccagatgtac gccatgcctt    3840
ttccatgtcc ctcctatctc tgttgaactt atgaatcata ctcattactt ttcagctttt    3900
taaaaggcca attttgtcc agttttctct cttccagtcc cagctgaaat tagtggaaag    3960
aaagtttgat ggagctttca gctttgaaca aaatcccttc attgtaaact agcaccatct    4020
ttatccaggt cttacccagt caggctaatt ccagaaactt gtggttttta gtatagtctg    4080 tctacctta gccaggcaca ggacagccct atgaaaaaat acccaatata tattttttgg    4140
aaatgaaaca ttaaagaac ttaaaaagta atttttggaa atgaggcttc aattagaatt    4200 attttctca aaaacaaac aaacaaaaaa cacaaaaaaa accactcttc tccaaatgcc    4260
caagccttct ttcaaaatta gttagaaact taagtaaaat acaagtccac accatcccca    4320
aattacaaaa tggacttacc cttgagaggg catctgcaga atatcatcag ggacaaagat    4380
ctcgaggcta acgatgtagg tttcatttct cagactttgt aatataaggc aagccctctc    4440
tcagagctgc catcatcact ttttgaattt ctttgggggt tatttaatga aaacatgct    4500 atgttttgtt ttaagctgaa gtcctattct ggacactctg ctttgggaaa aaatgttatc    4560
atttaatttc ctttctgcaa attaaaacta atgaagtgtg gccttgtcaa aggctatgga    4620
```

```
gatgttccgg gcatactgct gtgctctgtg cttttccagca ggcgctcctc cctcacgcag    4680
gagactcagt tgtcctgaga gagatgaagc agccttgaag cagatgctgc gttttccata    4740
aacctgattt tgcctcacat gaaccaaaga ctctcaaaac tccgcttcta tagaattagc    4800
tgaataaagg cattttactg atagctgttc gtgttagcga aacctgtcta cctgctatag    4860
cacactctcc gatttgggcc atttatgcac cccgcaacct gggatctcaa ggagctttaa    4920
agtcttaatg ggaacttggc attttcctga tgatctttaa aatgtggtca ctaaactcag    4980
gattggcgtg tgcttttaga acactggagt agcccttgtt ttagaggctg tgcattgagt    5040
atcgaccgta ttttgtaaaa ggcaagatat cctcccttcc aggctggtaa cgggtttcaa    5100
ggggactctt gaggaagtgc cccctaaaat agaacacagc aataactggg cttcctgtcc    5160
ccacccccac cccagcagtg ctctctggca ctgggaactc tgctagggag tggtggaagt    5220
aggaaggatt tgtgtgcaaa ggaaaatcgt ggttgagttt cactgcagca ggctgacgtt    5280
gcctgatgtg agagcaagtg gccgactggg gtgcgggtgc acaggtcggg ggagcacagg    5340
ccacagagcg cagcctctgg gggtccccca aggcacagca tatacagcat ggtcgcccct    5400
tgccctggag tctgggaaca aagagaggag ccagcctccc cgcactgctt cagatggaaa    5460
agggaggcag ggtgggcttc cgttctccag atctgtttgc tcttaacagg cagaacatgg    5520
gagaatcctt attcctggtt aatcactatg catatttgaa ataaagaaa gcgtaagcct    5580 ctgcaatttt aacttctcaa aggatgtctc tgaaaagaat cactttaaac caatgcctat    5640
aaaaagcaag tctaccaaaa taaactaaga ctttctatgt ggtttgggct ccctcttatt    5700
tttacaagtt tcatttttaa aagtaggcaa ctactttggg ttacagtatt tttattcata    5760
tttaaacatt tttacaaaat aaataaagtg ttttacatag taaggaatat gtacgtattt    5820
ccaagtatta agaagccaag tgttttttttt tttgacgtat tattgacaaa tgtattcagc    5880
gccatacaca agagaaatat tattactcca aagaacgaaa gttaacaaaa ctccaaagca    5940
aaaacccttt taatggaggt gagaaataaa tttaatgtaa caacagctag attgttttta    6000 ggattttct tttcttttgt ggaaacttct tgacttgact tttcatctga acagttttc    6060 cccccaagat tttaatctta tatgtcatac ttaagtttag gaacagcttg ataaattagc    6120
attctagata acacaagggc catgattcac taaaattcca agctactgta attttatggc    6180
atttatttgc aaatgttctt tgtatctcat tttatctgta gcagtcccca ctagtctacc    6240
ttaaccatct tatagctctg gtaaattaaa acttacgtag actttataca agatccattg    6300
gccgtattaa acctcccca ctcttagggc ttagggcgga agggacgaag gcagggctga    6360
taggactttt aaaaggataa aaggagtggg ggcaagggag gcggaaaata caggctcttg    6420
cagataccct ccgcgctgcc ctccacaccc agcccactgc tctacaaagg tatgaatgga    6480
atggcttttc tagaaaaggg cttccaagaa cataaggaa ttccttttccc tgggaggccc    6540 cgtggagggc tgagccagcc ttgaattggg cttatttctc aaatccatt gatctggcat    6600 ttttgtcaac atggtacatg ttagggccta cgatgatttt ttttctttt ttgtaaaaga    6660 gaggcatatg tattaaaatg cttcctcttc ccctgccgga gcctcacaga agtcaagaaa    6720
cgctatcccc agcttaaatg tgcagactct tcaagatgga ggtcacaata ttaggttgcc    6780
acagtaacag ctctgctgac ttcacactca gccctggccg tcctgaagcc agctcgtgta    6840
agaatcttcc ttcatgttct aggttatgaa aacgaagttt gtttagacaa ggacgttttc    6900
actagtacac attttcaagt acatacacac tctgttacgc ctgtccacgt tgtcacttgt    6960
```

| | | |
|---|---|---|
| aaatctatga tagggtcttt tttctcaaca gtaaccttg ttattgaact gctccgatag | 7020 | |
| ccttgattta ttttactaa atacagcccc aaaagttaat aacaaggtag acacaaaagc | 7080 | |
| attttgcagt actttattga aaaatgtcgg tggtatctcc tagtaatcaa acctacacct | 7140 | |
| ttcaagaatc acggtttaat tacaagactc atgaacataa aaaataata ccctcggctt | 7200 | |
| atttcctgtg cacacactca caaggagctg tgaatgaggt atagctgagt gcgtggagag | 7260 | |
| gcgggcacat cccttcctac catccagccc cttcgctgca tgacccacgg tcctaaattt | 7320 | |
| gcaaattgtg actcttacca tgaggcccac tgacagacac cctgtaggga ttgtgtcagg | 7380 | |
| tcctcactaa gtgacacagg gttggcaaaa aaaaaaaaa aaaagtcagt tcacattttg | 7440 | |
| agagcagttg gtgtaggtgc acttgatttt agaacgatga gtttaaaaca tttgtgaaaa | 7500 | |
| cctctttcca ttcagaaagg tggaaaaagt ttcctaaaat aaaccatttt gataaagcag | 7560 | |
| caaaatgctg cagtgttgat agtgtgaaga aaattgaagg acggcggttc aatgcattgt | 7620 | |
| gcagttcaga gccatgacag gattttttcca tgttgagatc tttaagcaaa acccataaaa | 7680 | |
| agtaaaaatt aatggaagct cattttttaa acactgctgg tgctttatga aaggatttct | 7740 | |
| gtttacctgt tgcacacgta acatgttctt acgaagtttt ctcgctgtgt agaaaatgct | 7800 | |
| taaaatgtct acatcatttt cattacaccc ccttaagcat gtttttcctt cacaaggtgc | 7860 | |
| agtccattga cagtgttccg tattgcacgt gcaatttaac tttattagca ctatttgtag | 7920 | |
| caaacacgag cctagtgaat tacagatctg tgtgggccag agggattttg ccacgtaata | 7980 | |
| atgaagcttg acagggtcat tctcataaac tgtctggcta catatatatt tttgcattta | 8040 | |
| atgcctattc aatatattct gaaggtgcta ctccttggtgt tatcaagagt tcatagggggt | 8100 | |
| taggggaag taagagcttg ttaatgtatt tgggaagcac acctatgttc acagacacaa | 8160 | |
| aatgaattg catggtcacc cccttagtct tggtttgttg gcttttgta ttgaagaaag | 8220 | |
| ggttaaataa aaacaaaaat aatgaga | 8247 | |

<210> SEQ ID NO 119
<211> LENGTH: 9228
<212> TYPE: DNA
<213> ORGANISM: Homo sapiens

<400> SEQUENCE: 119

| | | |
|---|---|---|
| aaggcgggct cgccctgccg gcggcgcggc catgctcatc acgctgtgct acctgtacct | 60 | |
| gtgggcgcgc tgggtcgcc ggccggctga gctcgtgcgc gccacggtgc ggcggctgcg | 120 | |
| tgcctcgcgc tgttccttca ccttctgcgg cgcggccgcg cagcccccgg cgcccgcgt | 180 | |
| gtgcctgagc cgtggcggcc gcgtcttctg cgtcagcgac agccagtcca ttgaagactt | 240 | |
| gaacaagtgg gccctatttc ttgtgtctcc ttttatactt gaagcagaac acatagcatt | 300 | |
| tgtgacggag agcatttggg tacaaagtga gaatttacag agatcatcct cttcagaaac | 360 | |
| aacggagtgt cgttctgtcg tccaggctgg agtgcagtgg tgtggtctcg gctcaccaca | 420 | |
| acctctgcct actgggttcc agtgattctc ctgcctcagc atcccgagta gctgggacta | 480 | |
| caggtgcacg ctaccatgcc cggctaattt ttgtattttt agtagaggcg ggggtttcac | 540 | |
| catgccatcc aggctggttt cgaactcctg acctcgtgat ccacctgtct cggcctccca | 600 | |
| aagtgctggg attacaggtg tgagccaccg cgcctggccc tgtattttca aattctttac | 660 | |
| ctctgcgttt ccagccttgc tccatccaat ttgttactag agcttttttaa caatttcacg | 720 | |
| ttgaattaag atgatttgga agaggagaaa caagagtcag aaaaattagc agcatccgtg | 780 | |
| atctgactct gggtaccagt gggttgttga gatttctgtt ccccactcac tgcagagctg | 840 | |

-continued

```
ctgcctgcca atgcccccctg ttgggcaggg ccacctgtgc tagtttaacc tggggtcttt    900
cactcccgga ctgcttcttg gatgtgagtt ttaagttgag cagagaagat atgccttgcc    960
tgctgccata cattgtaaca tcaagtcaag agctttagtt acttaacaga tttctgctgg   1020
ctgctattat aggaggaaac tcctttgttt agggacagcc agggcttcct tagctttgat   1080
ctttgggagt gagccttttg cttgacttcc cttctctttt ccatgccttt gtttccatct   1140
cgaagtgcaa atttaaagtg tcctgtttgc ctttatccac tggaaggcaa acaccctgga   1200
cgacgtatca gtgacagcgc ggttctgctt tgatcggagc acccagcgct gcttgaaggc   1260
gtttgcatgg tccatggctc atggaccacg ctcctagaaa acggaaatgc acttagattg   1320
tcaagtggtc agactgttgt ttgccattag cttgcagacc tggggatcct tatcggctaa   1380
ttgctgaagc aagtgtggac aacttcagca agctgggggt ggcgttcatg gaagatagac   1440
tccacatgga taatggactg gtaccccaaa agattgtgtc ggtgcacttg caggactcca   1500
ctctgaagga agttaaggat caggtctcaa acaagcaagc ccagatccta gagccgaagc   1560
ctgaaccttc tcttgagatt aagcctgagc aggacggtat ggagcatgtt ggcagagatg   1620
acccaaaggc tcttggtgaa gaacccaaac aaaggagagg cagtgcctct gggagtgagc   1680
ctgctgggga cagtgacagg ggaggggggcc ccgttgagca ttatcacctc catctgtcta   1740
gttgccacga gtgtctggaa cttgagaaca gcaccattga gtcagtcaag tttgcgtctg   1800
ccgagaacat tccagacctt ccctacgatt atagcagcag tttggagagt gttgctgatg   1860
agacctcccc cgaaagagaa gggaggagag tcaacctcac gggaaaggca cccaacatcc   1920
tcctctatgt gggctccgac tcccaggaag ccctcggccg gttccacgag gtccggtctg   1980
tgctggccga ctgtgtggac attgacagtt atattctcta ccacctgctg gaggacagtg   2040
ctctcagaga cccgtggacg gacaactgtc tgctgttggt cattgctacc agggagtcca   2100
ttcccgaaga cctgtaccag aagttcatgg cctatctttc tcaggagggg aaggtgttgg   2160
gcctgtcttc atccttcacc tttggtggct ttcaggtgac aagcaagggt gcactgcaca   2220
agacagtcca gaacttggtt ttctccaagg ctgaccagag cgaggtgaag ctcagcgtct   2280
tgagcagtgg ctgcaggtac caggaaggcc ccgtccggct cagccccggc aggctccagg   2340
gccacctgga gaatgaggac aaggacagga tgattgtgca tgtgcctttt ggaactcgcg   2400
ggggagaagc tgttctttgc caggtgcact agaactacc tcccagctcc aacatagtgc   2460
aaactccaga agatttttaac ttgctcaagt caagcaattt tagaagatac gaagtcctta   2520
gagagattct gacaaccctt ggcctcagct gtgcatgaca acaagttcct gccttaactc   2580
ctctttactt gctgtcagct gcggaggaaa tcagggatcc tcttatgcag tggcttggga   2640
aacatgtgga ctccgaggga gaaataaaat ccggccagct ctctcttaga tttgtttcat   2700
cctacgtgtc tgaagtagaa ataacccat cttgtatacc tgtggtgacc aacatggagg   2760
ccttctcatc agaacatttc aacttagaga tctatcgcca aaatctgcag accaagcagt   2820
tggggaaagt aattttgttt gccgaagtga cccccacaac gatgcgtctc ctggatgggc   2880
tgatgtttca gacaccgcag gaaatgggct aatagtgat cgcggcccgg cagaccgagg   2940
gcaaaggacg gggagggaat gtgtggctga gccctgtggg atgtgctctt tctactctgc   3000
tcatctccat tccactgaga tcccagctgg acagaggat cccgtttgtc cagcatctga   3060
tgtccgtggt gtcgtggaa gcagtgaggt ccattcccga gtatcaggat atcaacttac   3120
gagtgaagtg gcccaacgat atttattaca gtgacctcat gaagatcggc ggagttctgg   3180
```

```
ttaactcaac actcatggga gaaacatttt atatacttat tggctgtgga tttaatgtga      3240
ctaacagtaa ccctaccatc tgcatcaacg acctcatcac agaatacaat aaacaacaca      3300
aggcagaact gaagccctta agagccgatt atctcatcgc cagagtcgtg actgtgctgg      3360
agaaactgat caaagagttt caggacaaag ggcccaacag cgtccttccc ctttattacc      3420
gatactgggt ccacagtggt cagcaagtcc atctgggcag cgcagaggga ccaaaggtgt      3480
ccatcgttgg cctggacgat tctggcttcc tccaggttca ccaggagggc ggcgaggttg      3540
tgactgtgca cccggacggc aactccttcg acatgctgag aaacctcatc ctccccaaac      3600
ggcggtaatg ccgggcgtcc ccgagacgcg gctgcctgtc cgtgcccatg catctggaaa      3660
tctaatttag agttgtaggt gaattttctt ttcctccaat tcatttgtta agtctttgtt      3720
ctttttctgt gtttctgttt gttttttaggt ttgttttgtt gtcgttttct ttggtgtttg     3780
aagaggctct gggatagatg gttaagaagt agaaaattta gtttagggaa agccctccca      3840
caggtgggaa attgctctcc cctctgtggc ttggacttac gtttattgtc aaggggagtt      3900
tttacatgga aatgacaatg ggaaaattca gatattttct tagtagtgca gacctttacc      3960
cctagtctat gaaaaaacaa accaaaatat gctcttgcgc ccaggccagt ggtgagttag      4020
aggtatgcta tcactgtttg taagcatctg ggaggtact gaactgtaag aacatgcttg       4080
gacacttagt cattgttctg tgtttttatt aatgaagaaa agggaagaca gacttccaag      4140
agttactgtc cacccggtgg tgtggccca tagcgaagtc taaatgcctg tagagataga      4200
gctagctggt gtggttgcag tgaccttgta gaggaaatca gttcattact ttgacatcat      4260
tcagtgagct ctccttttcct aaggaagttt aaatgtcctt agttagggac tgactttctt    4320
aagtaagttt aaatttacta catattgtga agagacagga tcaagttcag aatccttaaa     4380
tgtctgatta ggcatcactt ggatgaggag gtgggcgatt tggctctgac agctggagat     4440
gaaggcacac tcataccaca tacaagggag gatttggagc ttttaagcca gtttcagatt     4500
tactctgaaa tgtggagcat tcctgcaaga ctgtgcagct cacggaatat agaagacatg     4560
gcattttact cagaagtcat aagttttgc ccccctcatt tacctcgtat taccaagaaa      4620
gaaaatgtta tcgatactaa acaccatcag ttcagaggga ggatgtgtgt gtgtgcccgc     4680
atatgtgtgt gcgtgcgtgt gtgcgcacat agctttaaaa gaagacattc aaaatttgat     4740
gtgctacaag cctcatgaaa gaacaaaaga atgaagcct tttgatatgc attcgctatt      4800
cccagatgta cgccatgcct tttccatgtc cctcctatct ctgttgaact tatgaatcat     4860
actcattact tttcagcttt ttaaaaggcc aattttgtc cagttttctc tcttccagtc      4920
ccagctgaaa ttagtggaaa gaaagtttga tggagctttc agctttgaac aaaatccctt     4980
cattgtaaac tagcaccatc tttatccagg tcttacccag tcaggctaat tccagaaact    5040
tgtggttttt agtatagtct gtctacctt agccaggcac aggacagccc tatgaaaaaa      5100
tacccaatat atattttttg gaaatgaaac attaaaagaa cttaaaaagt aattttttgga   5160
aatgaggctt caattagaat tatttttctc aaaaaacaaa caaacaaaaa acacaaaaaa      5220
aaccactctt ctccaaatgc ccaagccttc tttcaaaatt agttagaaac ttaagtaaaa     5280
tacaagtcca caccatcccc aaattacaaa atggacttac ccttgagagg gcatctgcag    5340
aatatcatca gggacaaaga tctcgaggct aacgatgtag gtttcatttc tcagactttg    5400
taatataagg caagccctct ctcagagctg ccatcatcac ttttttgaatt tctttggggg  5460
ttatttaatg aaaaacatgc tatgttttgt tttaagctga agtcctattc tggacactct    5520
gctttgggaa aaaatgttat catttaattt cctttctgca aattaaaact aatgaagtgt    5580
```

```
ggccttgtca aaggctatgg agatgttccg ggcatactgc tgtgctctgt gctttccagc   5640
aggcgctcct ccctcacgca ggagactcag ttgtcctgag agagatgaag cagccttgaa   5700
gcagatgctg cgttttccat aaacctgatt ttgcctcaca tgaaccaaag actctcaaaa   5760
ctccgcttct atagaattag ctgaataaag gcattttact gatagctgtt cgtgttagcg   5820
aaacctgtct acctgctata gcacactctc cgatttgggc catttatgca ccccgcaacc   5880
tgggatctca aggagcttta aagtcttaat gggaacttgg cattttcctg atgatcttta   5940
aaatgtggtc actaaactca ggattggcgt gtgcttttag aacactggag tagcccttgt   6000
tttagaggct gtgcattgag tatcgaccgt attttgtaaa aggcaagata tcctcccttc   6060
caggctggta acgggtttca aggggactct tgaggaagtg cccctaaaa tagaacacag    6120 caataactgg gcttcctgtc cccaccccca ccccagcagt gctctctggc actgggaact   6180
ctgctaggga gtggtggaag taggaaggat ttgtgtgcaa aggaaaatcg tggttgagtt   6240
tcactgcagc aggctgacgt tgcctgatgt gagagcaagt ggccgactgg ggtgcgggtg   6300
cacaggtcgg gggagcacag gccacagagc gcagcctctg ggggtccccc aaggcacagc   6360
atatacagca tggtcgcccc ttgccctgga gtctgggaac aaagagagga gccagcctcc   6420
ccgcactgct tcagatggaa aagggaggca gggtgggctt ccgttctcca gatctgtttg   6480
ctcttaacag gcagaacatg ggagaatcct tattcctggt taatcactat gcatatttga   6540
aataaaagaa agcgtaagcc tctgcaattt taacttctca aaggatgtct ctgaaaagaa   6600
tcactttaaa ccaatgccta taaaaagcaa gtctaccaaa ataaactaag actttctatg   6660
tggtttgggc tccctcttat ttttacaagt ttcattttta aaagtaggca actactttgg   6720
gttacagtat ttttattcat atttaaacat ttttacaaaa taaataaagt gttttacata   6780
gtaaggaata tgtacgtatt tccaagtatt aagaagccaa gtgtttttt ttttgacgta    6840 ttattgacaa atgtattcag cgccatacac aagagaaata ttattactcc aaagaacgaa   6900
agttaacaaa actccaaagc aaaaacccctt ttaatggagg tgagaaataa atttaatgta  6960
acaacagcta gattgttttt aggattttc ttttcttttg tggaaacttc ttgacttgac    7020
ttttcatctg aacagttttt ccccccaaga ttttaatctt atatgtcata cttaagttta   7080
ggaacagctt gaataattag cattctagat aacacaaggg ccatgattca ctaaaattcc   7140
aagctactgt aattttatgg catttatttg caaatgttct ttgtatctca ttttatctgt   7200
agcagtcccc actagtctac cttaaccatc ttatagctct ggtaaattaa aacttacgta   7260
gactttatac aagatccatt ggccgtatta aacctccccc actcttaggg cttagggcgg   7320
aagggacgaa ggcagggctg ataggacttt taaaaggata aaaggagtgg gggcaaggga   7380
ggcggaaaat acaggctctt gcagataccc tccgcgctgc cctccacacc cagcccactg   7440
ctctacaaag gtatgaatgg aatggctttt ctagaaaagg gcttccaaga acataaagga   7500 attccttttcc ctgggaggcc ccgtggaggg ctgagccagc cttgaattgg gcttatttct   7560
caaatccatt tgatctggca ttttttgtcaa catggtacat gttagggcct acgatgattt   7620
tttttctttt tttgtaaaag agaggcatat gtattaaaat gcttcctctt cccctgccgg   7680
agcctcacag aagtcaagaa acgctatccc cagcttaaat gtgcagactc ttcaagatgg   7740
aggtcacaat attaggttgc cacagtaaca gctctgctga cttcacactc agccctggcc   7800
gtcctgaagc cagctcgtgt aagaatcttc cttcatgttc taggttatga aaacgaagtt   7860
tgtttagaca aggacgtttt cactagtaca cattttcaag tacatacaca ctctgttacg   7920
```

| | |
|---|---|
| cctgtccacg ttgtcacttg taaatctatg atagggtctt ttttctcaac agtaaccttt | 7980 |
| gttattgaac tgctccgata gccttgattt attttacta aatacagccc caaaagttaa | 8040 |
| taacaaggta gacacaaaag cattttgcag tactttattg aaaaatgtcg gtggtatctc | 8100 |
| ctagtaatca aacctacacc tttcaagaat cacggtttaa ttacaagact catgaacata | 8160 |
| aaaaataat accctcggct tatttcctgt gcacacactc acaaggagct gtgaatgagg | 8220 |
| tatagctgag tgcgtggaga ggcgggcaca tcccttccta ccatccagcc ccttcgctgc | 8280 |
| atgacccacg gtcctaaatt tgcaaattgt gactcttacc atgaggccca ctgacagaca | 8340 |
| ccctgtaggg attgtgtcag gtcctcacta agtgacacag ggttggcaaa aaaaaaaaa | 8400 |
| aaaaagtcag ttcacatttt gagagcagtt ggtgtaggtg cacttgatttt tagaacgatg | 8460 |
| agtttaaaac atttgtgaaa acctctttcc attcagaaag gtggaaaaag tttcctaaaa | 8520 |
| taaaccattt tgataaagca gcaaaatgct gcagtgttga tagtgtgaag aaaattgaag | 8580 |
| gacggcggtt caatgcattg tgcagttcag agccatgaca ggattttttcc atgttgagat | 8640 |
| ctttaagcaa aacccataaa aagtaaaaat taatggaagc tcattttta aacactgctg | 8700 |
| gtgctttatg aaaggatttc tgtttacctg ttgcacacgt aacatgttct tacgaagttt | 8760 |
| tctcgctgtg tagaaaatgc ttaaaatgtc tacatcattt tcattacacc cccttaagca | 8820 |
| tgttttcct tcacaaggtg cagtccattg acagtgttcc gtattgcacg tgcaatttaa | 8880 |
| ctttattagc actatttgta gcaaacacga gcctagtgaa ttacagatct gtgtgggcca | 8940 |
| gagggatttt gccacgtaat aatgaagctt gacagggtca ttctcataaa ctgtctggct | 9000 |
| acatatatat ttttgcattt aatgcctatt caatatattc tgaaggtgct actcttggtg | 9060 |
| ttatcaagag ttcataggg ttaggggaa gtaagagctt gttaatgtat tgggaagca | 9120 |
| cacctatgtt cacagacaca aaatggaatt gcatggtcac cccctagtc ttggtttgtt | 9180 |
| ggcttttgt attgaagaaa gggttaaata aaaacaaaaa taatgaga | 9228 |

<210> SEQ ID NO 120
<211> LENGTH: 8405
<212> TYPE: DNA
<213> ORGANISM: Homo sapiens

<400> SEQUENCE: 120

| | |
|---|---|
| aaggacaggt agggatcccc cgcggatgcc gtgctggcga ggcagggcct gagcagccag | 60 |
| tggagaaggg cagcgggaag tgcgctgtgc aggagccaga cgtctcagcc cgtgtggcca | 120 |
| gaggtggcag gggcgcggcc tgagcggggc tggggcgcgg gcaggatttg gggctgcgcc | 180 |
| gagggcgtc ccgacctggc cctttgccac gtccattgaa gacttgaaca agtgggccct | 240 |
| atttcttgtg tctccttta tacttgaagc agaacacata gcatttgtga cggagagcat | 300 |
| ttgggtacaa agtgagaatt tacagagatc atcctcttca gaaacagttc ggttttttgcc | 360 |
| cactagggat gatgtggttt ctcatgaggt tacttgctct aaaggacttt atattttgga | 420 |
| accataagag cacccttgtg gcccaggcac tttatggatg atcccttta gtgctcccag | 480 |
| taaccttcca agattgtcaa gtggtcagac tgttgtttgc cattagcttg cagacctggg | 540 |
| gatcctatc ggctaattgc tgaagcaagt gtggacaact tcagcaagct ggggtggcg | 600 |
| ttcatggaag atagactcca catggataat ggactggtac cccaaaagat tgtgtcggtg | 660 |
| cacttgcagg actccactct gaaggaagtt aaggatcagg tctcaaacaa gcaagcccag | 720 |
| atcctagagc cgaagcctga accttctctt gagattaagc ctgagcagga cggtatggag | 780 |
| catgttggca gagatgaccc aaaggctctt ggtgaagaac ccaaacaaag gagaggcagt | 840 |

```
gcctctggga gtgagcctgc tggggacagt gacaggggag ggggcccccgt tgagcattat    900
cacctccatc tgtctagttg ccacgagtgt ctggaacttg agaacagcac cattgagtca    960
gtcaagtttg cgtctgccga gaacattcca gaccttccct acgattatag cagcagtttg   1020
gagagtgttg ctgatgagac ctcccccgaa agagaaggga ggagagtcaa cctcacggga   1080
aaggcaccca acatcctcct ctatgtgggc tccgactccc aggaagccct cggccggttc   1140
cacgaggtcc ggtctgtgct ggccgactgt gtggacattg acagttatat tctctaccac   1200
ctgctggagg acagtgctct cagagacccg tggacggaca actgtctgct gttggtcatt   1260
gctaccaggg agtccattcc cgaagacctg taccagaagt tcatggccta tctttctcag   1320
ggagggaagg tgttgggcct gtcttcatcc ttcacctttg gtggctttca ggtgacaagc   1380
aagggtgcac tgcacaagac agtccagaac ttggttttct ccaaggctga ccagagcgag   1440
gtgaagctca gcgtcttgag cagtggctgc aggtaccagg aaggcccccgt ccggctcagc   1500
cccggcaggc tccagggcca cctggagaat gaggacaagg acaggatgat tgtgcatgtg   1560
ccttttggaa ctcgcggggg agaagctgtt ctttgccagg tgcacttaga actacctccc   1620
agctccaaca tagtgcaaac tccagaagat tttaacttgc tcaagtcaag caattttaga   1680
agatacgaag tccttagaga gattctgaca acccttggcc tcagctgtga catgaaacaa   1740
gttcctgcct taactcctct ttacttgctg tcagctgcgg aggaaatcag ggatcctctt   1800
atgcagtggc ttgggaaaca tgtggactcc gagggagaaa taaaatccgg ccagctctct   1860
cttagatttg tttcatccta cgtgtctgaa gtagaaataa ccccatcttg tatacctgtg   1920
gtgaccaaca tggaggcctt ctcatcagaa catttcaact tagagatcta tcgccaaaat   1980
ctgcagacca agcagttggg gaaagtaatt ttgtttgccg aagtgacccc cacaacgatg   2040
cgtctcctgg atgggctgat gtttcagaca ccgcaggaaa tgggcttaat agtgatcgcg   2100
gcccggcaga ccgagggcaa aggacgggga gggaatgtgt ggctgagccc tgtgggatgt   2160
gctctttcta ctctgctcat ctccattcca ctgagatccc agctgggaca gaggatcccg   2220
tttgtccagc atctgatgtc cgtgctgtc gtggaagcag tgaggtccat tcccgagtat   2280
caggatatca acttacgagt gaagtggccc aacgatattt attacagtga cctcatgaag   2340
atcggcggag ttctggttaa ctcaacactc atgggagaaa cattttatat acttattggc   2400
tgtggatta atgtgactaa cagtaaccct accatctgca tcaacgacct catcacagaa   2460
tacaataaac aacacaaggc agaactgaag cccttaagag ccgattatct catcgccaga   2520
gtcgtgactg tgctggagaa actgatcaaa gagtttcagg acaaagggcc caacagcgtc   2580
cttcccctt attaccgata ctgggtccac agtggtcagc aagtccatct gggcagcgca   2640
gagggaccaa aggtgtccat cgttggcctg gacgattctg gcttcctcca ggttcaccag   2700
gagggcggcg aggttgtgac tgtgcacccg gacggcaact ccttcgacat gctgagaaac   2760
ctcatcctcc ccaaacggcg gtaatgccgg gcgtccccga gacgcggctg cctgtccgtg   2820
cccatgcatc tggaaatcta atttagagtt gtaggtgaat tttcttttcc tccaattcat   2880
ttgttaagtc tttgttcttt ttctgtgttt ctgtttgttt ttaggtttgt tttgttgtcg   2940
ttttctttgg tgtttgaaga ggctctggga tagatggtta agaagtagaa aatttagttt   3000
agggaaagcc ctcccacagg tgggaaattg ctctcccctc tgtggcttgg acttacgttt   3060
attgtcaagg ggagttttta catggaaatg acaatgggaa aattcagata ttttcttagt   3120
agtgcagacc tttacccccta gtctatgaaa aaacaaacca aaatatgctc ttgcgcccag   3180
```

```
gccagtggtg agttagaggt atgctatcac tgtttgtaag catctgggga ggtactgaac    3240
tgtaagaaca tgcttggaca cttagtcatt gttctgtgtt tttattaatg aagaaaaggg    3300
aagacagact tccaagagtt actgtccacc cggtggtgtg gccccatagc gaagtctaaa    3360
tgcctgtaga gatagagcta gctggtgtgg ttgcagtgac cttgtagagg aaatcagttc    3420
attactttga catcattcag tgagctctcc tttcctaagg aagtttaaat gtccttagtt    3480
agggactgac tttcttaagt aagtttaaat ttactacata ttgtgaagag acaggatcaa    3540
gttcagaatc cttaaatgtc tgattaggca tcacttggat gaggaggtgg gcgatttggc    3600
tctgacagct ggagatgaag gcacactcat accacataca agggaggatt tggagctttt    3660
aagccagttt cagatttact ctgaaatgtg gagcattcct gcaagactgt gcagctcacg    3720
gaatatagaa gacatggcat tttactcaga agtcataagt ttttgccccc ctcatttacc    3780
tcgtattacc aagaaagaaa atgttatcga tactaaacac catcagttca gagggaggat    3840
gtgtgtgtgt gcccgcatat gtgtgtgcgt gcgtgtgtgc gcacatagct ttaaaagaag    3900
acattcaaaa tttgatgtgc tacaagcctc atgaaagaac aaaagaaatg aagccttttg    3960
atatgcattc gctattccca gatgtacgcc atgccttttc catgtccctc ctatctctgt    4020
tgaacttatg aatcatactc attactttc agcttttta aaggccaatt tttgtccagt       4080
tttctctctt ccagtcccag ctgaaattag tggaaagaaa gtttgatgga gctttcagct    4140
ttgaacaaaa tcccttcatt gtaaactagc accatcttta tccaggtctt acccagtcag    4200
gctaattcca gaaacttgtg gttttagta tagtctgtct acctttagcc aggcacagga      4260
cagccctatg aaaaaatacc caatatatat ttttggaaa tgaaacatta aaagaactta      4320
aaaagtaatt tttggaaatg aggcttcaat tagaattatt tttctcaaaa aacaaacaaa    4380
caaaaaacac aaaaaaaacc actcttctcc aaatgcccaa gccttctttc aaaattagtt    4440
agaaacttaa gtaaaataca agtccacacc atccccaaat tacaaaatgg acttacccctt   4500 gagagggcat ctgcagaata tcatcaggga caaagatctc gaggctaacg atgtaggttt    4560
catttctcag actttgtaat ataaggcaag ccctctctca gagctgccat catcactttt    4620
tgaatttctt tggggttat ttaatgaaaa acatgctatg ttttgtttta agctgaagtc      4680
ctattctgga cactctgctt tgggaaaaaa tgttatcatt taatttcctt tctgcaaatt    4740
aaaactaatg aagtgtggcc ttgtcaaagg ctatggagat gttccgggca tactgctgtg    4800
ctctgtgctt tccagcaggc gctcctccct cacgcaggag actcagttgt cctgagagag    4860
atgaagcagc cttgaagcag atgctgcgtt ttccataaac ctgattttgc ctcacatgaa    4920
ccaaagactc tcaaaactcc gcttctatag aattagctga ataaaggcat tttactgata    4980
gctgttcgtg ttagcgaaac ctgtctacct gctatagcac actctccgat ttgggccatt    5040
tatgcacccc gcaacctggg atctcaagga gctttaaagt cttaatggga acttggcatt    5100
ttcctgatga tctttaaaat gtggtcacta aactcaggat tggcgtgtgc ttttagaaca    5160
ctggagtagc ccttgtttta gaggctgtgc attgagtatc gaccgtattt tgtaaaaggc    5220
aagatatcct cccttccagg ctggtaacgg gtttcaaggg gactcttgag gaagtgcccc    5280
ctaaaataga acacagcaat aactgggctt cctgtcccca cccccacccc agcagtgctc    5340
tctggcactg ggaactctgc tagggagtgg tggaagtagg aaggatttgt gtgcaaagga    5400
aaatcgtggt tgagtttcac tgcagcaggc tgacgttgcc tgatgtgaga gcaagtggcc    5460
gactggggtg cgggtgcaca ggtcggggga gcacaggcca cagagcgcag cctctggggg    5520
tcccccaagg cacagcatat acagcatggt cgcccctttgc cctggagtct gggaacaaag    5580
```

-continued

```
agaggagcca gcctccccgc actgcttcag atggaaaagg gaggcagggt gggcttccgt   5640
tctccagatc tgtttgctct taacaggcag aacatgggag aatccttatt cctggttaat   5700
cactatgcat atttgaaata aaagaaagcg taagcctctg caattttaac ttctcaaagg   5760
atgtctctga aaagaatcac tttaaaccaa tgcctataaa aagcaagtct accaaaataa   5820
actaagactt tctatgtggt ttgggctccc tcttattttt acaagtttca tttttaaaag   5880
taggcaacta ctttgggtta cagtatttt attcatattt aaacatttt acaaaataaa    5940 taaagtgttt tacatagtaa ggaatatgta cgtatttcca agtattaaga agccaagtgt   6000
tttttttttt gacgtattat tgacaaatgt attcagcgcc atacacaaga gaaatattat   6060
tactccaaag aacgaaagtt aacaaaactc caaagcaaaa acccttttaa tggaggtgag   6120
aaataaattt aatgtaacaa cagctagatt gttttagga ttttctttt cttttgtgga     6180 aacttcttga cttgacttt catctgaaca gttttccc ccaagatttt aatcttatat      6240
gtcatactta agtttaggaa cagcttgaat aattagcatt ctagataaca caagggccat   6300
gattcactaa aattccaagc tactgtaatt ttatggcatt tatttgcaaa tgttctttgt   6360
atctcatttt atctgtagca gtccccacta gtctacctta accatcttat agctctggta   6420
aattaaaact tacgtagact ttatacaaga tccattggcc gtattaaacc tcccccactc   6480
ttagggctta gggcggaagg gacgaaggca gggctgatag gacttttaaa aggataaaag   6540 gagtggggc aagggaggcg gaaaatacag gctcttgcag ataccctccg cgctgccctc    6600
cacacccagc ccactgctct acaaaggtat gaatggaatg gcttttctag aaaagggctt   6660
ccaagaacat aaaggaattc ctttccctgg gaggcccgt ggagggctga gccagccttg    6720
aattgggctt atttctcaaa tccatttgat ctggcatttt tgtcaacatg gtacatgtta   6780
gggcctacga tgattttttt ttctttttg taaaagagag gcatatgtat taaaatgctt    6840
cctcttcccc tgccggagcc tcacagaagt caagaaacgc tatccccagc ttaaatgtgc   6900
agactcttca agatggaggt cacaatatta ggttgccaca gtaacagctc tgctgacttc   6960
acactcagcc ctggccgtcc tgaagccagc tcgtgtaaga atcttccttc atgttctagg   7020
ttatgaaaac gaagtttgtt tagacaagga cgttttcact agtacacatt ttcaagtaca   7080
tacacactct gttacgcctg tccacgttgt cacttgtaaa tctatgatag ggtctttttt   7140
ctcaacagta acctttgtta ttgaactgct ccgatagcct tgatttattt ttactaaata   7200
cagccccaaa agttaataac aaggtagaca caaaagcatt ttgcagtact ttattgaaaa   7260
atgtcggtgg tatctcctag taatcaaacc tacaccttc aagaatcacg gtttaattac    7320
aagactcatg aacataaaaa aataatacc tcggcttatt tcctgtgcac acactcacaa    7380
ggagctgtga atgaggtata gctgagtgcg tggagaggcg ggcacatccc ttcctaccat   7440 ccagccccctt cgctgcatga cccacggtcc taaatttgca aattgtgact cttaccatga   7500
ggcccactga cagacaccct gtagggattg tgtcaggtcc tcactaagtg acacagggtt   7560
ggcaaaaaaa aaaaaaaaaa agtcagttca cattttgaga gcagttggtg taggtgcact   7620
tgattttaga acgatgagtt taaacatttt gtgaaaacct ctttccattc agaaaggtgg   7680
aaaaagtttc ctaaaataaa ccatttttgat aaagcagcaa aatgctgcag tgttgatagt   7740
gtgaagaaaa ttgaaggacg gcggttcaat gcattgtgca gttcagagcc atgacaggat   7800
ttttccatgt tgagatcttt aagcaaaacc cataaaaagt aaaaattaat ggaagctcat   7860
tttttaaaca ctgctggtgc tttatgaaag gatttctgtt tacctgttgc acacgtaaca   7920
```

-continued

| | |
|---|---|
| tgttcttacg aagttttctc gctgtgtaga aaatgcttaa aatgtctaca tcattttcat | 7980 |
| tacaccccct taagcatgtt tttccttcac aaggtgcagt ccattgacag tgttccgtat | 8040 |
| tgcacgtgca atttaacttt attagcacta tttgtagcaa acacgagcct agtgaattac | 8100 |
| agatctgtgt gggccagagg gattttgcca cgtaataatg aagcttgaca gggtcattct | 8160 |
| cataaactgt ctggctacat atatatttt gcatttaatg cctattcaat atattctgaa | 8220 |
| ggtgctactc ttggtgttat caagagttca taggggttag ggggaagtaa gagcttgtta | 8280 |
| atgtatttgg gaagcacacc tatgttcaca gacacaaaat ggaattgcat ggtcaccccc | 8340 |
| ttagtcttgg tttgttggct ttttgtattg aagaaagggt taaataaaaa caaaaataat | 8400 |
| gagac | 8405 |

<210> SEQ ID NO 121
<211> LENGTH: 8273
<212> TYPE: DNA
<213> ORGANISM: Homo sapiens

<400> SEQUENCE: 121

| | |
|---|---|
| aaggcgggct cgccctgccg gcggcgcggc catgctcatc acgctgtgct acctgtacct | 60 |
| gtgggcgcgc tggggtcgcc ggccggctga gctcgtgcgc gccacggtgc ggcggctgcg | 120 |
| tgcctcgcgc tgttccttca ccttctgcgg cgcggccgcg cagccccgg gcgcccgcgt | 180 |
| gtgcctgagc cgtggcggcc gcgtcttctg cgtcagcgac agccagtcca ttgaagactt | 240 |
| gaacaagtgg gccctatttc ttgtgtctcc ttttatactt gaagcagaac acatagcatt | 300 |
| tgtgacggag agcatttggg tacaaagtga gaatttacag agatcatcct cttcagaaac | 360 |
| aattgtcaag tggtcagact gttgtttgcc attagcttgc agacctgggg atccttatcg | 420 |
| gctaattgct gaagcaagtg tggacaactt cagcaagctg ggggtggcgt tcatggaaga | 480 |
| tagactccac atggataatg gactggtacc ccaaaagatt gtgtcggtgc acttgcagga | 540 |
| ctccactctg aaggaagtta aggatcaggt ctcaaacaag caagcccaga tcctagagcc | 600 |
| gaagcctgaa ccttctcttg agattaagcc tgagcaggac ggtatggagc atgttggcag | 660 |
| agatgaccca aaggctcttg gtgaagaacc caaacaaagg agaggcagtg cctctgggag | 720 |
| tgagcctgct ggggacagtg acaggggagg gggccccgtt gagcattatc acctccatct | 780 |
| gtctagttgc cacgagtgtc tggaacttga gaacagcacc attgagtcag tcaagtttgc | 840 |
| gtctgccgag aacattccag accttcccta cgattatagc agcagtttgg agagtgttgc | 900 |
| tgatgagacc tcccccgaaa gagaagggag gagagtcaac ctcacgggaa aggcaccccaa | 960 |
| catcctcctc tatgtgggct ccgactccca ggaagccctc ggccggttcc acgaggtccg | 1020 |
| gtctgtgctg gccgactgtg tggacattga cagttatatt ctctaccacc tgctggagga | 1080 |
| cagtgctctc agagacccgt ggacggacaa ctgtctgctg ttggtcattg ctaccaggga | 1140 |
| gtccattccc gaagacctgt accagaagtt catggcctat ctttctcagg agggaaggt | 1200 |
| gttgggcctg tcttcatcct tcacctttgg tggctttcag gtgacaagca agggtgcact | 1260 |
| gcacaagaca gtccagaact tggttttctc caaggctgac cagagcgagg tgaagctcag | 1320 |
| cgtcttgagc agtggctgca ggtaccagga aggcccgtc cggctcagcc ccggcaggct | 1380 |
| ccagggccac ctggagaatg aggacaagga caggatgatt gtgcatgtgc cttttggaac | 1440 |
| tcgcggggga gaagctgttc tttgccaggt gcacttagaa ctacctccca gctccaacat | 1500 |
| agtgcaaact ccagaagatt ttaacttgct caagtcaagc aatttagaa gatacgaagt | 1560 |
| ccttagagag attctgacaa cccttggcct cagctgtgac atgaaacaag ttcctgcctt | 1620 |

```
aactcctctt tacttgctgt cagctgcgga ggaaatcagg gatcctctta tgcagtggct   1680
tgggaaacat gtggactccg agggagaaat aaaatccggc cagctctctc ttagatttgt   1740
ttcatcctac gtgtctgaag tagaaataac cccatcttgt atacctgtgg tgaccaacat   1800
ggaggccttc tcatcagaac atttcaactt agagatctat cgccaaaatc tgcagaccaa   1860
gcagttgggg aaagtaattt tgtttgccga agtgacccc acaacgatgc gtctcctgga    1920
tgggctgatg tttcagacac cgcaggaaat gggcttaata gtgatcgcgg cccggcagac   1980
cgagggcaaa ggacggggag ggaatgtgtg gctgagccct gtgggatgtg ctctttctac   2040
tctgctcatc tccattccac tgagatccca gctgggacag aggatcccgt tgtccagca    2100
tctgatgtcc gtggctgtcg tggaagcagt gaggtccatt cccgagtatc aggatatcaa   2160
cttacgagtg aagtggccca acgatattta ttacagtgac ctcatgaaga tcggcggagt   2220
tctggttaac tcaacactca tgggagaaac atttatata cttattggct gtggatttaa    2280
tgtgactaac agtaacccta ccatctgcat caacgacctc atcacagaat acaataaaca   2340
acacaaggca gaactgaagc ccttaagagc cgattatctc atcgccagag tcgtgactgt   2400
gctggagaaa ctgatcaaag agtttcagga caaagggccc aacagcgtcc ttccccttta   2460
ttaccgatac tgggtccaca gtggtcagca agtccatctg ggcagcgcag agggaccaaa   2520
ggtgtccatc gttggcctgg acgattctgg cttcctccag gttcaccagg agggcggcga   2580
ggttgtgact gtgcacccgg acggcaactc cttcgacatg ctgagaaacc tcatcctccc   2640
caaacggcgg taatgccggg cgtccccgag acgcggctgc ctgtccgtgc ccatgcatct   2700
ggaaatctaa tttagagttg taggtgaatt ttcttttcct ccaattcatt tgttaagtct   2760
ttgttctttt tctgtgtttc tgtttgtttt taggtttgtt ttgttgtcgt tttcttggt    2820
gtttgaagag gctctgggat agatggttaa gaagtagaaa atttagttta gggaaagccc   2880
tcccacaggt gggaaattgc tctcccctct gtggcttgga cttacgttta ttgtcaaggg   2940
gagttttac atggaaatga caatgggaaa attcagatat tttcttagta gtgcagacct    3000
ttaccctag tctatgaaaa aacaaaccaa aatatgctct tgcgcccagg ccagtggtga    3060
gttagaggta tgctatcact gtttgtaagc atctggggag gtactgaact gtaagaacat   3120
gcttggacac ttagtcattg ttctgtgttt ttattaatga agaaaaggga agacagactt   3180
ccaagagtta ctgtccaccc ggtggtgtgg ccccatagcg aagtctaaat gcctgtagag   3240
atagagctag ctggtgtggt tgcagtgacc ttgtagagga aatcagttca ttactttgac   3300
atcattcagt gagctctcct ttcctaagga agtttaaatg tccttagtta gggactgact   3360
ttcttaagta agtttaaatt tactacatat tgtgaagaga caggatcaag ttcagaatcc   3420
ttaaatgtct gattaggcat cacttggatg aggaggtggg cgatttggct ctgacagctg   3480
gagatgaagg cacactcata ccacatacaa gggaggattt ggagcttta agccagtttc    3540
agatttactc tgaaatgtgg agcattcctg caagactgtg cagctcacgg aatatagaag   3600
acatggcatt ttactcagaa gtcataagtt tttgcccccc tcatttacct cgtattacca   3660
agaaagaaaa tgttatcgat actaaacacc atcagttcag agggaggatg tgtgtgtgtg   3720
cccgcatatg tgtgtgcgtg cgtgtgtgcg cacatagctt taaaagaaga cattcaaaat   3780
ttgatgtgct acaagcctca tgaaagaaca aagaaatga agccttttga tatgcattcg    3840
ctattcccag atgtacgcca tgccttttcc atgtccctcc tatctctgtt gaacttatga   3900
atcatactca ttacttttca gcttttaaa aggccaattt ttgtccagtt ttctctcttc    3960
```

```
cagtcccagc tgaaattagt ggaaagaaag tttgatggag ctttcagctt tgaacaaaat   4020
cccttcattg taaactagca ccatctttat ccaggtctta cccagtcagg ctaattccag   4080
aaacttgtgg ttttttagtat agtctgtcta cctttagcca ggcacaggac agccctatga   4140
aaaaataccc aatatatatt ttttggaaat gaaacattaa aagaacttaa aaagtaattt   4200
ttggaaatga ggcttcaatt agaattattt ttctcaaaaa acaaacaaac aaaaaacaca   4260
aaaaaaacca ctcttctcca aatgcccaag ccttctttca aaattagtta gaaacttaag   4320
taaaatacaa gtccacacca tccccaaatt acaaaatgga cttacccttg agagggcatc   4380
tgcagaatat catcagggac aaagatctcg aggctaacga tgtaggtttc atttctcaga   4440
ctttgtaata taaggcaagc cctctctcag agctgccatc atcactttttt gaatttcttt   4500 gggggttatt taatgaaaaa catgctatgt tttgttttaa gctgaagtcc tattctggac   4560
actctgcttt gggaaaaaat gttatcattt aatttccttt ctgcaaatta aaactaatga   4620
agtgtggcct tgtcaaaggc tatggagatg ttccgggcat actgctgtgc tctgtgcttt   4680
ccagcaggcg ctcctccctc acgcaggaga ctcagttgtc ctgagagaga tgaagcagcc   4740
ttgaagcaga tgctgcgttt tccataaacc tgattttgcc tcacatgaac caaagactct   4800
caaaactccg cttctataga attagctgaa taaaggcatt ttactgatag ctgttcgtgt   4860
tagcgaaacc tgtctacctg ctatagcaca ctctccgatt tgggccattt atgcaccccg   4920
caacctggga tctcaaggag cttttaaagtc ttaatgggaa cttggcattt tcctgatgat   4980
ctttaaaatg tggtcactaa actcaggatt ggcgtgtgct tttagaacac tggagtagcc   5040
cttgttttag aggctgtgca ttgagtatcg accgtatttt gtaaaaggca agatatcctc   5100
ccttccaggc tggtaacggg tttcaagggg actcttgagg aagtgccccc taaaatagaa   5160
cacagcaata actgggcttc ctgtccccac ccccaccccca gcagtgctct ctggcactgg   5220
gaactctgct agggagtggt ggaagtagga aggatttgtg tgcaaaggaa aatcgtggtt   5280
gagtttcact gcagcaggct gacgttgcct gatgtgagag caagtggccg actgggtgc   5340 gggtgcacag gtcgggggag cacaggccac agagcgcagc ctctgggggt ccccaaggc   5400 acagcatata cagcatggtc gccccttgcc ctggagtctg ggaacaaaga gaggagccag   5460
cctccccgca ctgcttcaga tggaaagggg aggcagggtg ggcttccgtt ctccagatct   5520
gtttgctctt aacaggcaga acatgggaga atccttattc ctggttaatc actatgcata   5580
tttgaaataa agaaagcgt aagcctctgc aattttaact tctcaaagga tgtctctgaa   5640
aagaatcact ttaaaccaat gcctataaaa agcaagtcta ccaaaataaa ctaagacttt   5700
ctatgtggtt tgggctccct cttatttta caagtttcat ttttaaaagt aggcaactac   5760
tttgggttac agtattttta ttcatattta aacatttta caaataaat aaagtgtttt   5820 acatagtaag gaatatgtac gtatttccaa gtattaagaa gccaagtgtt ttttttttg   5880 acgtattatt gacaaatgta ttcagcgcca tacacaagag aaatattatt actccaaaga   5940
acgaaagtta acaaaactcc aaagcaaaaa ccctttttaat ggaggtgaga aataaattta   6000
atgtaacaac agctagattg ttttttaggat ttttctttc ttttgtggaa acttcttgac   6060
ttgacttttc atctgaacag ttttttccccc caagatttta atcttatatg tcatacttaa   6120
gtttaggaac agcttgaata attagcattc tagataacac aagggccatg attcactaaa   6180
attccaagct actgtaattt tatggcattt atttgcaaat gttctttgta tctcatttta   6240
tctgtagcag tccccactag tctaccttaa ccatcttata gctctggtaa attaaaactt   6300
acgtagactt tatacaagat ccattggccg tattaaacct ccccactct tagggcttag    6360
```

-continued

```
ggcggaaggg acgaaggcag ggctgatagg acttttaaaa ggataaaagg agtgggggca      6420
agggaggcgg aaaatacagg ctcttgcaga taccctccgc gctgccctcc acacccagcc      6480
cactgctcta caaaggtatg aatggaatgg cttttctaga aaagggcttc caagaacata      6540
aaggaattcc tttccctggg aggccccgtg gagggctgag ccagccttga attgggctta      6600
tttctcaaat ccatttgatc tggcattttt gtcaacatgg tacatgttag ggcctacgat      6660
gatttttttt tctttttttgt aaagagagg catatgtatt aaaatgcttc ctcttcccct      6720
gccggagcct cacagaagtc aagaaacgct atccccagct taaatgtgca gactcttcaa      6780
gatggaggtc acaatattag gttgccacag taacagctct gctgacttca cactcagccc      6840
tggccgtcct gaagccagct cgtgtaagaa tcttccttca tgttctaggt tatgaaaacg      6900
aagtttgttt agacaaggac gttttcacta gtacacattt tcaagtacat acacactctg      6960
ttacgcctgt ccacgttgtc acttgtaaat ctatgatagg gtctttttc tcaacagtaa       7020 cctttgttat tgaactgctc cgatagcctt gatttatttt tactaaatac agccccaaaa      7080
gttaataaca aggtagacac aaaagcattt tgcagtactt tattgaaaaa tgtcggtggt      7140
atctcctagt aatcaaacct acacctttca agaatcacgg tttaattaca agactcatga      7200
acataaaaaa ataataccct cggcttattt cctgtgcaca cactcacaag gagctgtgaa      7260
tgaggtatag ctgagtgcgt ggagaggcgg gcacatccct tcctaccatc cagcccttc       7320 gctgcatgac ccacggtcct aaatttgcaa attgtgactc ttaccatgag gcccactgac      7380
agacaccctg tagggattgt gtcaggtcct cactaagtga cacagggttg gcaaaaaaaa      7440 aaaaaaaaa gtcagttcac attttgagag cagttggtgt aggtgcactt gattttagaa       7500
cgatgagttt aaaacatttg tgaaaacctc tttccattca gaaaggtgga aaaagtttcc      7560
taaaataaac cattttgata aagcagcaaa atgctgcagt gttgatagtg tgaagaaaat      7620
tgaaggacgg cggttcaatg cattgtgcag ttcagagcca tgacaggatt tttccatgtt      7680 gagatctttta agcaaaaccc ataaaaagta aaaattaatg gaagctcatt ttttaaacac    7740
tgctggtgct ttatgaaagg attcctgtttt acctgttgca cacgtaacat gttcttacga    7800
agttttctcg ctgtgtagaa aatgcttaaa atgtctacat catttcatt acacccctt       7860 aagcatgttt ttccttcaca aggtgcagtc cattgacagt gttccgtatt gcacgtgcaa     7920
tttaacttta ttagcactat ttgtagcaaa cacgagccta gtgaattaca gatctgtgtg    7980
ggccagaggg attttgccac gtaataatga agcttgacag ggtcattctc ataaactgtc     8040
tggctacata tatattttg catttaatgc ctattcaata tattctgaag gtgctactct       8100
tggtgttatc aagagttcat aggggttagg gggaagtaag agcttgttaa tgtatttggg    8160
aagcacacct atgttcacag acacaaaatg gaattgcatg gtcacccct tagtcttggt      8220 ttgttggctt tttgtattga agaaagggtt aaataaaaac aaaaataatg aga             8273
```

<210> SEQ ID NO 122
<211> LENGTH: 8101
<212> TYPE: DNA
<213> ORGANISM: Homo sapiens

<400> SEQUENCE: 122

```
agggattcgc gggcgaccac ccggcgcagg agcggccgcg tttcggcctc agaatccatt        60
gaagacttga acaagtgggc cctatttctt gtgtctcctt ttatacttga agcagaacac      120
atagcatttg tgacggagag catttgggta caaagtgaga atttacagag atcatcctct      180
```

```
tcagaaacaa ttgtcaagtg gtcagactgt tgtttgccat tagcttgcag acctggggat    240
ccttatcggc taattgctga agcaagtgtg gacaacttca gcaagctggg ggtggcgttc    300
atggaagata gactccacat ggataatgga ctggtacccc aaaagattgt gtcggtgcac    360
ttgcaggact ccactctgaa ggaagttaag gatcaggtct caaacaagca agcccagatc    420
ctagagccga agcctgaacc ttctcttgag attaagcctg agcaggacgg tatggagcat    480
gttggcagag atgacccaaa ggctcttggt gaagaaccca acaaaggag aggcagtgcc     540 tctgggagtg agcctgctgg ggacagtgac aggggagggg gccccgttga gcattatcac    600
ctccatctgt ctagttgcca cgagtgtctg gaacttgaga acagcaccat tgagtcagtc    660
aagtttgcgt ctgccgagaa cattccagac cttccctacg attatagcag cagtttggag    720
agtgttgctg atgagacctc ccccgaaaga gaagggagga gagtcaacct cacgggaaag    780
gcacccaaca tcctcctcta tgtgggctcc gactcccagg aagccctcgg ccggttccac    840
gaggtccggt ctgtgctggc cgactgtgtg gacattgaca gttatattct ctaccacctg    900
ctggaggaca gtgctctcag agacccgtgg acggacaact gtctgctgtt ggtcattgct    960
accagggagt ccattcccga agacctgtac cagaagttca tggcctatct ttctcaggga   1020
gggaaggtgt gggcctgtc ttcatccttc acctttggtg gctttcaggt gacaagcaag    1080
ggtgcactgc acaagacagt ccagaacttg gttttctcca aggctgacca gagcgaggtg   1140
aagctcagcg tcttgagcag tggctgcagg taccaggaag gccccgtccg gctcagcccc   1200
ggcaggctcc agggccacct ggagaatgag gacaaggaca ggatgattgt gcatgtgcct   1260
tttggaactc gcgggggaga agctgttctt tgccaggtgc acttagaact acctcccagc   1320
tccaacatag tgcaaactcc agaagatttt aacttgctca gtcaagcaa ttttagaaga    1380 tacgaagtcc ttagagagat tctgacaacc cttggcctca gctgtgacat gaaacaagtt   1440
cctgccttaa ctcctctta cttgctgtca gctgcggagg aaatcaggga tcctcttatg    1500
cagtggcttg gaaacatgt ggactccgag ggagaaataa aatccggcca gctctctctt    1560
agatttgttt catcctacgt gtctgaagta gaaataaccc catcttgtat acctgtggtg   1620
accaacatgg aggccttctc atcagaacat ttcaacttag agatctatcg ccaaaatctg   1680
cagaccaagc agttggggaa agtaattttg tttgccgaag tgacccccac aacgatgcgt   1740
ctcctggatg ggctgatgtt tcagacaccg caggaaatgg gcttaatagt gatcgcggcc   1800
cggcagaccg agggcaaagg acggggaggg aatgtgtggc tgagccctgt gggatgtgct   1860
ctttctactc tgctcatctc cattccactg agatcccagc tgggacagag gatcccgttt   1920
gtccagcatc tgatgtccgt ggctgtcgtg aagcagtga ggtccattcc cgagtatcag    1980
gatatcaact acgagtgaa gtggcccaac gatatttatt acagtgacct catgaagatc    2040
ggcggagttc tggttaactc aacactcatg ggagaaacat tttatatact tattggctgt   2100
ggatttaatg tgactaacag taaccctacc atctgcatca acgacctcat cacagaatac   2160
aataaacaac acaaggcaga actgaagccc ttaagagccg attatctcat cgccagagtc   2220
gtgactgtgc tggagaaact gatcaaagag tttcaggaca aagggcccaa cagcgtcctt   2280
cccctttatt accgatactg ggtccacagt ggtcagcaag tccatctggg cagcgcgagg   2340
ggaccaaagg tgtccatcgt tggcctggac gattctggct tcctccaggt tcaccaggag   2400
ggcggcgagg ttgtgactgt gcacccggac ggcaactcct tcgacatgct gagaaacctc   2460
atcctcccca acggcggta atgccgggcg tccccgagac gcggctgcct gtccgtgccc    2520
atgcatctgg aaatctaatt tagagttgta ggtgaatttt cttttcctcc aattcatttg   2580
```

```
ttaagtctttt gttcttttc tgtgtttctg tttgttttta ggtttgtttt gttgtcgttt    2640
tctttggtgt ttgaagaggc tctgggatag atggttaaga agtagaaaat ttagtttagg    2700
gaaagccctc ccacaggtgg gaaattgctc tccctctgt ggcttggact tacgtttatt    2760
gtcaagggga gttttacat ggaaatgaca atgggaaat tcagatattt tcttagtagt     2820
gcagaccttt accctagtc tatgaaaaaa caaaccaaaa tatgctcttg cgcccaggcc    2880
agtggtgagt tagaggtatg ctatcactgt ttgtaagcat ctggggaggt actgaactgt   2940
aagaacatgc ttggacactt agtcattgtt ctgtgttttt attaatgaag aaaagggaag   3000
acagacttcc aagagttact gtccacccgg tggtgtggcc ccatagcgaa gtctaaatgc   3060
ctgtagagat agagctagct ggtgtggttg cagtgacctt gtagaggaaa tcagttcatt   3120
actttgacat cattcagtga gctctccttt cctaaggaag tttaaatgtc cttagttagg    3180
gactgacttt cttaagtaag tttaaattta ctacatattg tgaagagaca ggatcaagtt   3240
cagaatcctt aaatgtctga ttaggcatca cttggatgag gaggtgggcg atttggctct   3300
gacagctgga gatgaaggca cactcatacc acatacaagg gaggatttgg agcttttaag   3360
ccagtttcag atttactctg aaatgtggag cattcctgca agactgtgca gctcacggaa   3420
tatagaagac atggcatttt actcagaagt cataagtttt tgccccctc atttacctcg     3480 tattaccaag aaagaaaatg ttatcgatac taaacaccat cagttcagag ggaggatgtg   3540
tgtgtgtgcc cgcatatgtg tgtgcgtgcg tgtgtgcgca catagcttta aagaagaca    3600 ttcaaaattt gatgtgctac aagcctcatg aagaacaaa agaaatgaag ccttttgata     3660
tgcattcgct attcccagat gtacgccatg ccttttccat gtccctccta tctctgttga   3720
acttatgaat catactcatt actttcagc ttttaaaag gccaattttt gtccagtttt      3780
ctctcttcca gtcccagctg aaattagtgg aagaaagtt tgatggagct ttcagctttg     3840
aacaaaatcc cttcattgta aactagcacc atctttatcc aggtcttacc cagtcaggct    3900
aattccagaa acttgtggtt tttagtatag tctgtctacc tttagccagg cacaggacag    3960
ccctatgaaa aaatacccaa tatatatttt ttggaaatga acattaaaa gaacttaaaa    4020 agtaatttt ggaaatgagg cttcaattag aattattttt ctcaaaaaac aaacaaacaa    4080
aaaacacaaa aaaaaccact cttctccaaa tgcccaagcc ttctttcaaa attagttaga    4140
aacttaagta aaatacaagt ccacaccatc cccaaattac aaaatggact tacccttgag    4200
agggcatctg cagaatatca tcagggacaa agatctcgag gctaacgatg taggtttcat    4260
ttctcagact ttgtaatata aggcaagccc tctctcagag ctgccatcat cacttttga    4320 atttctttgg gggttattta atgaaaaaca tgctatgttt tgttttaagc tgaagtccta    4380
ttctggacac tctgctttgg gaaaaaatgt tatcatttaa tttcctttct gcaaattaaa   4440
actaatgaag tgtggccttg tcaaaggcta tggagatgtt ccgggcatac tgctgtgctc    4500 tgtgcttttcc agcaggcgct cctccctcac gcaggagact cagttgtcct gagagagatg   4560
aagcagcctt gaagcagatg ctgcgttttc cataaacctg attttgcctc acatgaacca    4620
aagactctca aaactccgct tctatagaat tagctgaata aaggcatttt actgatagct    4680
gttcgtgtta gcgaaacctg tctacctgct atagcacact ctccgatttg gccatttat    4740 gcaccccgca acctgggatc tcaaggagct ttaaagtctt aatgggaact tggcatttc    4800 ctgatgatct ttaaaatgtg gtcactaaac tcaggattgg cgtgtgcttt tagaacactg    4860
gagtagccct tgttttagag gctgtgcatt gagtatcgac cgtatttgt aaaaggcaag     4920
```

```
atatcctccc ttccaggctg gtaacgggtt tcaaggggac tcttgaggaa gtgcccccta    4980
aaatagaaca cagcaataac tgggcttcct gtccccaccc ccaccccagc agtgctctct    5040
ggcactggga actctgctag ggagtggtgg aagtaggaag gatttgtgtg caaaggaaaa    5100
tcgtggttga gtttcactgc agcaggctga cgttgcctga tgtgagagca agtggccgac    5160
tggggtgcgg gtgcacaggt cggggagca caggccacag agcgcagcct ctggggtcc      5220 cccaaggcac agcatataca gcatggtcgc cccttgccct ggagtctggg aacaaagaga    5280
ggagccagcc tccccgcact gcttcagatg gaaaagggag gcagggtggg cttccgttct    5340
ccagatctgt ttgctcttaa caggcagaac atgggagaat ccttattcct ggttaatcac    5400
tatgcatatt tgaaataaaa gaaagcgtaa gcctctgcaa ttttaacttc tcaaaggatg    5460
tctctgaaaa gaatcacttt aaaccaatgc ctataaaaag caagtctacc aaaataaact    5520
aagactttct atgtggtttg ggctccctct tatttttaca agtttcattt ttaaaagtag    5580
gcaactactt tgggttacag tattttttatt catatttaaa catttttaca aaataaataa    5640
agtgttttac atagtaagga atatgtacgt atttccaagt attaagaagc caagtgtttt    5700
tttttttgac gtattattga caaatgtatt cagcgccata cacaagagaa atattattac    5760
tccaaagaac gaaagttaac aaaactccaa agcaaaaacc cttttaatgg aggtgagaaa    5820
taaatttaat gtaacaacag ctagattgtt tttaggattt ttcttttctt ttgtggaaac    5880
ttcttgactt gactttttcat ctgaacagtt tttcccccca agattttaat cttatatgtc    5940
atacttaagt ttaggaacag cttgaataat tagcattcta gataacacaa gggccatgat    6000
tcactaaaat tccaagctac tgtaatttta tggcatttat ttgcaaatgt tctttgtatc    6060
tcattttatc tgtagcagtc cccactagtc taccttaacc atcttatagc tctggtaaat    6120
taaaacttac gtagacttta tacaagatcc attggccgta ttaaacctcc cccactctta    6180
gggcttaggg cggaagggac gaaggcaggg ctgataggac ttttaaaagg ataaaaggag    6240
tgggggcaag ggaggcggaa aatacaggct cttgcagata ccctccgcgc tgccctccac    6300
acccagccca ctgctctaca aaggtatgaa tggaatggct tttctagaaa agggcttcca    6360
agaacataaa ggaattcctt tccctgggag gccccgtgga gggctgagcc agccttgaat    6420
tgggcttatt tctcaaatcc atttgatctg gcattttgt caacatggta catgttaggg    6480
cctacgatga ttttttttttc tttttgtaa aagagaggca tatgtattaa aatgcttcct    6540
cttcccctgc cggagcctca cagaagtcaa gaaacgctat ccccagctta aatgtgcaga    6600
ctcttcaaga tggaggtcac aatattaggt tgccacagta acagctctgc tgacttcaca    6660
ctcagccctg gccgtcctga agccagctcg tgtaagaatc ttccttcatg ttctaggtta    6720
tgaaaacgaa gtttgtttag acaaggacgt tttcactagt acacattttc aagtacatac    6780
acactctgtt acgcctgtcc acgttgtcac ttgtaaatct atgatagggt cttttttctc    6840
aacagtaacc tttgttattg aactgctccg atagccttga tttattttta ctaaatacag    6900
ccccaaaagt taataacaag gtagacacaa aagcattttg cagtacttta ttgaaaaatg    6960
tcggtggtat ctcctagtaa tcaaacctac accttttcaag aatcacggtt taattacaag    7020
actcatgaac ataaaaaaat aatacccctcg gcttatttcc tgtgcacaca ctcacaagga    7080
gctgtgaatg aggtatagct gagtgcgtgg agaggcgggc acatcccttc ctaccatcca    7140
gccccttcgc tgcatgaccc acggtcctaa atttgcaaat tgtgactctt accatgaggc    7200 ccactgcacag acaccctgta gggattgtgt caggtcctca ctaagtgaca cagggttggc    7260
aaaaaaaaaa aaaaaaaagt cagttcacat tttgagagca gttggtgtag gtgcacttga    7320
```

```
ttttagaacg atgagtttaa aacatttgtg aaaacctctt tccattcaga aaggtggaaa    7380
aagtttccta aaataaacca ttttgataaa gcagcaaaat gctgcagtgt tgatagtgtg    7440
aagaaaattg aaggacggcg gttcaatgca ttgtgcagtt cagagccatg acaggatttt    7500
tccatgttga gatctttaag caaaacccat aaaaagtaaa aattaatgga agctcatttt    7560
ttaaacactg ctggtgcttt atgaaaggat ttctgtttac ctgttgcaca cgtaacatgt    7620
tcttacgaag ttttctcgct gtgtagaaaa tgcttaaaat gtctacatca ttttcattac    7680
acccccttaa gcatgttttt ccttcacaag gtgcagtcca ttgacagtgt tccgtattgc    7740
acgtgcaatt taactttatt agcactattt gtagcaaaca cgagcctagt gaattacaga    7800
tctgtgtggg ccagagggat tttgccacgt aataatgaag cttgacaggg tcattctcat    7860
aaactgtctg gctacatata tatttttgca tttaatgcct attcaatata ttctgaaggt    7920
gctactcttg gtgttatcaa gagttcatag gggttagggg gaagtaagag cttgttaatg    7980
tatttgggaa gcacacctat gttcacagac acaaaatgga aattgcatgg t caccccctta   8040
gtcttggttt gttggctttt tgtattgaag aaagggttaa ataaaaacaa aataatgag    8100
a                                                                     8101

<210> SEQ ID NO 123
<211> LENGTH: 8304
<212> TYPE: DNA
<213> ORGANISM: Homo sapiens

<400> SEQUENCE: 123
agacgtctca gcccgtgtgg ccagaggtgg caggggcgcg gcctgagcgg ggctggggcg      60
cgggcaggat ttggggctgc gccgaggggc gtcccgacct ggccctttgc cacggtaggt     120
tccggctccc atgcctccgc tgccatctgc gctgtccttg gcgactacgc cttcaccccc     180
ctgggtgcgt ttcagcggtc ccggagcctg gcgggagcgg ggccaggagc gctccgcggc     240
cggtatcagg cctgcagtcc attgaagact tgaacaagtg ggcccatttt cttgtgtctc     300
cttttatact tgaagcagaa cacatagcat ttgtgacgga gagcatttgg gtacaaagtg     360
agaatttaca gagatcatcc tcttcagaaa caattgtcaa gtggtcagac tgttgtttgc     420
cattagcttg cagacctggg gatccttatc ggctaattgc tgaagcaagt gtggacaact     480
tcagcaagct gggggtggcg ttcatggaag atagactcca catggataat ggactggtac     540
cccaaaagat tgtgtcggtg cacttgcagg actccactct gaaggaagtt aaggatcagg     600
tctcaaacaa gcaagcccag atcctagagc cgaagcctga accttctctt gagattaagc     660
ctgagcagga cggtatggag catgttggca gagatgaccc aaaggctctt ggtgaagaac     720
ccaaacaaag gagaggcagt gcctctggga gtgagcctgc tggggacagt gacagggggag    780
ggggccccgt tgagcattat cacctccatc tgtctagttg ccacgagtgt ctggaacttg     840
agaacagcac cattgagtca gtcaagtttg cgtctgccga gaacattcca gaccttccct     900
acgattatag cagcagtttg gagagtgttg ctgatgagac ctcccccgaa agagaaggga     960
ggagagtcaa cctcacggga aaggcaccca acatcctcct ctatgtgggc tccgactccc    1020
aggaagccct cggccggttc cacgaggtcc ggtctgtgct ggccgactgt gtggacattg    1080
acagttatat tctctaccac ctgctggagg acagtgctct cagagacccg tggacggaca    1140
actgtctgct gttggtcatt gctaccaggg agtccattcc cgaagacctg taccagaagt    1200
tcatggccta tctttctcag ggagggaagg tgttgggcct gtcttcatcc ttcacctttg    1260
```

```
gtggctttca ggtgacaagc aagggtgcac tgcacaagac agtccagaac ttggttttct    1320
ccaaggctga ccagagcgag gtgaagctca gcgtcttgag cagtggctgc aggtaccagg    1380
aaggccccgt ccggctcagc cccggcaggc tccagggcca cctggagaat gaggacaagg    1440
acaggatgat tgtgcatgtg ccttttggaa ctcgcggggg agaagctgtt ctttgccagg    1500
tgcacttaga actacctccc agctccaaca tagtgcaaac tccagaagat tttaacttgc    1560
tcaagtcaag caattttaga agatacgaag tccttagaga gattctgaca acccttggcc    1620
tcagctgtga catgaaacaa gttcctgcct taactcctct ttacttgctg tcagctgcgg    1680
aggaaatcag ggatcctctt atgcagtggc ttgggaaaca tgtggactcc gagggagaaa    1740
taaaatccgg ccagctctct cttagatttg tttcatccta cgtgtctgaa gtagaaataa    1800
ccccatcttg tatacctgtg gtgaccaaca tggaggcctt ctcatcagaa catttcaact    1860
tagagatcta tcgccaaaat ctgcagacca agcagttggg gaaagtaatt ttgtttgccg    1920
aagtgacccc cacaacgatg cgtctcctgg atgggctgat gtttcagaca ccgcaggaaa    1980
tgggcttaat agtgatcgcg gcccggcaga ccgagggcaa aggacgggga gggaatgtgt    2040
ggctgagccc tgtgggatgt gctctttcta ctctgctcat ctccattcca ctgagatccc    2100
agctgggaca gaggatcccg tttgtccagc atctgatgtc cgtggctgtc gtggaagcag    2160
tgaggtccat tcccgagtat caggatatca acttacgagt gaagtggccc aacgatattt    2220
attacagtga cctcatgaag atcggcgagt tctggttaa ctcaacactc atgggagaaa    2280
cattttatat acttattggc tgtggattta atgtgactaa cagtaaccct accatctgca    2340
tcaacgacct catcacagaa tacaataaac aacacaaggc agaactgaag cccttaagag    2400
ccgattatct catcgccaga gtcgtgactg tgctggagaa actgatcaaa gagtttcagg    2460
acaaagggcc caacagcgtc cttcccctt attaccgata ctgggtccac agtggtcagc    2520
aagtccatct gggcagcgca gagggaccaa aggtgtccat cgttggcctg gacgattctg    2580
gcttcctcca ggttcaccag gagggcggcg aggttgtgac tgtgcacccg gacggcaact    2640
ccttcgacat gctgagaaac ctcatcctcc ccaaacggcg gtaatgccgg gcgtcccga    2700
gacgcggctg cctgtccgtg cccatgcatc tggaaatcta atttagagtt gtaggtgaat    2760
tttcttttcc tccaattcat ttgttaagtc tttgttcttt ttctgtgttt ctgtttgttt    2820
ttaggtttgt tttgttgtcg ttttctttgg tgtttgaaga ggctctggga tagatggtta    2880
agaagtagaa aatttagttt agggaaagcc ctcccacagg tgggaaattg ctctcccctc    2940
tgtggcttgg acttacgttt attgtcaagg ggagttttta catggaaatg acaatgggaa    3000
aattcagata tttcttagt agtgcagacc tttaccccta gtctatgaaa aaacaaacca    3060
aaatatgctc ttgcgcccag gccagtggtg agttagaggt atgctatcac tgtttgtaag    3120
catctgggga ggtactgaac tgtaagaaca tgcttggaca cttagtcatt gttctgtgtt    3180
tttattaatg aagaaaggg aagacagact tccaagagtt actgtccacc cggtggtgtg    3240
gccccatagc gaagtctaaa tgcctgtaga gatagagcta gctggtgtgg ttgcagtgac    3300
cttgtagagg aaatcagttc attactttga catcattcag tgagctctcc tttcctaagg    3360
aagtttaaat gtcctagtt agggactgac tttcttaagt aagtttaaat ttactacata    3420
ttgtgaagag acaggatcaa gttcagaatc cttaaatgtc tgattaggca tcacttggat    3480
gaggaggtgg gcgatttggc tctgacagct ggagatgaag gcacactcat accacataca    3540
agggaggatt tggagctttt aagccagttt cagatttact ctgaaatgtg gagcattcct    3600
gcaagactgt gcagctcacg gaatatagaa gacatggcat tttactcaga agtcataagt    3660
```

```
ttttgccccc ctcatttacc tcgtattacc aagaaagaaa atgttatcga tactaaacac   3720
catcagttca gagggaggat gtgtgtgtgt gcccgcatat gtgtgtgcgt gcgtgtgtgc   3780
gcacatagct ttaaaagaag acattcaaaa tttgatgtgc tacaagcctc atgaaagaac   3840
aaaagaaatg aagccttttg atatgcattc gctattccca gatgtacgcc atgccttttc   3900
catgtccctc ctatctctgt tgaacttatg aatcatactc attacttttc agctttttaa   3960
aaggccaatt tttgtccagt tttctctctt ccagtcccag ctgaaattag tggaaagaaa   4020
gtttgatgga gctttcagct ttgaacaaaa tcccttcatt gtaaactagc accatcttta   4080
tccaggtctt acccagtcag gctaattcca gaaacttgtg gtttttagta tagtctgtct   4140
acctttagcc aggcacagga cagccctatg aaaaaatacc caatatatat tttttggaaa   4200
tgaaacatta aaagaactta aaaagtaatt tttggaaatg aggcttcaat tagaattatt   4260
tttctcaaaa aacaaacaaa caaaaaacac aaaaaaaacc actcttctcc aaatgcccaa   4320
gccttctttc aaaattagtt agaaacttaa gtaaaataca agtccacacc atccccaaat   4380
tacaaaatgg acttaccctt gagagggcat ctgcagaata tcatcaggga caaagatctc   4440
gaggctaacg atgtaggttt catttctcag actttgtaat ataaggcaag ccctctctca   4500
gagctgccat catcactttt tgaatttctt tgggggttat ttaatgaaaa acatgctatg   4560
ttttgtttta agctgaagtc ctattctgga cactctgctt tgggaaaaaa tgttatcatt   4620
taatttcctt tctgcaaatt aaaactaatg aagtgtggcc ttgtcaaagg ctatggagat   4680
gttccgggca tactgctgtg ctctgtgctt tccagcaggc gctcctccct cacgcaggag   4740
actcagttgt cctgagagag atgaagcagc cttgaagcag atgctgcgtt ttccataaac   4800
ctgattttgc ctcacatgaa ccaaagactc tcaaaactcc gcttctatag aattagctga   4860
ataaaggcat tttactgata gctgttcgtg ttagcgaaac ctgtctacct gctatagcac   4920
actctccgat ttgggccatt tatgcacccc gcaacctggg atctcaagga gctttaaagt   4980
cttaatggga acttggcatt ttcctgatga tctttaaaat gtggtcacta aactcaggat   5040
tggcgtgtgc ttttagaaca ctggagtagc ccttgtttta gaggctgtgc attgagtatc   5100
gaccgtattt tgtaaaaggc aagatatcct cccttccagg ctggtaacgg gtttcaaggg   5160
gactcttgag gaagtgcccc ctaaaataga acacagcaat aactgggctt cctgtcccca   5220
cccccacccc agcagtgctc tctggcactg ggaactctgc tagggagtgg tggaagtagg   5280
aaggatttgt gtgcaaagga aaatcgtggt tgagtttcac tgcagcaggc tgacgttgcc   5340
tgatgtgaga gcaagtggcc gactggggtg cgggtgcaca ggtcggggga gcacaggcca   5400
cagagcgcag cctctggggg tcccccaagg cacagcatat acagcatggt cgccccttgc   5460
cctggagtct gggaacaaag agaggagcca gcctccccgc actgcttcag atggaaaagg   5520
gaggcagggt gggcttccgt tctccagatc tgtttgctct taacaggcag aacatgggag   5580
aatccttatt cctggttaat cactatgcat atttgaaata aaagaaagcg taagcctctg   5640
caattttaac ttctcaaagg atgtctctga aaagaatcac tttaaaccaa tgcctataaa   5700
aagcaagtct accaaaataa actaagactt tctatgtggt ttgggctccc tcttattttt   5760
acaagtttca tttttaaaag taggcaacta ctttgggtta cagtattttt attcatattt   5820
aaacattttt acaaaataaa taaagtgttt tacatagtaa ggaatatgta cgtatttcca   5880
agtattaaga agccaagtgt ttttttttt gacgtattat tgacaaatgt attcagcgcc   5940
atacacaaga gaaatattat tactccaaag aacgaaagtt aacaaaactc caaagcaaaa   6000
```

```
acccttttaa tggaggtgag aaataaattt aatgtaacaa cagctagatt gttttttagga    6060
tttttctttt cttttgtgga aacttcttga cttgactttt catctgaaca gttttttcccc    6120
ccaagatttt aatcttatat gtcatactta agtttaggaa cagcttgaat aattagcatt    6180
ctagataaca caagggccat gattcactaa aattccaagc tactgtaatt ttatggcatt    6240
tatttgcaaa tgttctttgt atctcatttt atctgtagca gtccccacta gtctaccta     6300
accatcttat agctctggta aattaaaact tacgtagact ttatacaaga tccattggcc    6360
gtattaaacc tcccccactc ttagggctta gggcggaagg gacgaaggca gggctgatag    6420
gacttttaaa aggataaaag gagtgggggc aaggaggcg gaaaatacag gctcttgcag     6480
ataccctccg cgctgccctc cacacccagc ccactgctct acaaaggtat gaatggaatg    6540
gcttttctag aaaagggctt ccaagaacat aaaggaattc ctttccctgg gaggccccgt    6600
ggagggctga gccagccttg aattgggctt atttctcaaa tccatttgat ctggcatttt    6660
tgtcaacatg gtacatgtta gggcctacga tgattttttt ttctttttg taaaagagag     6720
gcatatgtat aaaatgctt cctcttcccc tgccggagcc tcacagaagt caagaaacgc     6780
tatccccagc ttaaatgtgc agactcttca agatggaggt cacaatatta ggttgccaca    6840
gtaacagctc tgctgacttc acactcagcc ctggccgtcc tgaagccagc tcgtgtaaga    6900
atcttccttc atgttctagg ttatgaaaac gaagtttgtt tagacaagga cgttttcact    6960
agtacacatt ttcaagtaca tacacactct gttacgcctg tccacgttgt cacttgtaaa    7020
tctatgatag ggtcttttttt ctcaacagta acctttgtta ttgaactgct ccgatagcct   7080
tgatttattt ttactaaata cagccccaaa agttaataac aaggtagaca caaaagcatt    7140
ttgcagtact ttattgaaaa atgtcggtgg tatctcctag taatcaaacc tacacctttc    7200
aagaatcacg gtttaattac aagactcatg aacataaaaa aataatacc tcggcttatt     7260
tcctgtgcac acactcacaa ggagctgtga atgaggtata gctgagtgcg tggagaggcg    7320
ggcacatccc ttcctaccat ccagcccctt cgctgcatga cccacggtcc taaatttgca    7380
aattgtgact cttaccatga ggcccactga cagacaccct gtagggattg tgtcaggtcc    7440
tcactaagtg acacagggtt ggcaaaaaaa aaaaaaaaa agtcagttca cattttgaga    7500
gcagttggtg taggtgcact tgattttaga acgatgagtt taaacatttt gtgaaaacct    7560
cttccattc agaaaggtgg aaaaagtttc ctaaaataaa ccattttgat aaagcagcaa     7620
aatgctgcag tgttgatagt gtgaagaaaa ttgaaggacg gcggttcaat gcattgtgca    7680
gttcagagcc atgacaggat ttttccatgt tgagatcttt aagcaaaacc cataaaaagt    7740
aaaaattaat ggaagctcat ttttttaaaca ctgctggtgc tttatgaaag gatttctgtt   7800
tacctgttgc acacgtaaca tgttcttacg aagttttctc gctgtgtaga aaatgcttaa    7860
aatgtctaca tcattttcat tacacccccct taagcatgtt tttccttcac aaggtgcagt   7920
ccattgacag tgttccgtat tgcacgtgca atttaacttt attagcacta tttgtagcaa    7980
acacgagcct agtgaattac agatctgtgt gggccagagg gattttgcca cgtaataatg    8040
aagcttgaca gggtcattct cataaactgt ctggctacat atatattttt gcatttaatg    8100
cctattcaat atattctgaa ggtgctactc ttggtgttat caagagttca taggggttag    8160
ggggaagtaa gagcttgtta atgtatttgg gaagcacacc tatgttcaca gacacaaaat    8220
ggaattgcat ggtcaccccc ttagtcttgg tttgttggct ttttgtattg aagaagggt     8280
taaataaaaa caaaaataat gaga                                           8304
```

<210> SEQ ID NO 124
<211> LENGTH: 8259
<212> TYPE: DNA
<213> ORGANISM: Homo sapiens

<400> SEQUENCE: 124

| | | | | | |
|---|---|---|---|---|---|
| aaggacaggt | agggatcccc | cgcggatgcc | gtgctggcga | ggcagggcct | gagcagccag | 60 |
| tggagaaggg | cagcgggaag | tgcgctgtgc | aggagccaga | cgtctcagcc | cgtgtggcca | 120 |
| gaggtggcag | gggcgcggcc | tgagcggggc | tggggcgcgg | gcaggatttg | gggctgcgcc | 180 |
| gaggggcgtc | ccgacctggc | cctttgccac | gtccattgaa | gacttgaaca | agtgggccct | 240 |
| atttcttgtg | tctcctttta | tacttgaagc | agaacacata | gcatttgtga | cggagagcat | 300 |
| ttgggtacaa | agtgagaatt | tacagagatc | atcctcttca | gaaacaattg | tcaagtggtc | 360 |
| agactgttgt | ttgccattag | cttgcagacc | tggggatcct | tatcggctaa | ttgctgaagc | 420 |
| aagtgtggac | aacttcagca | agctgggggt | ggcgttcatg | gaagatagac | tccacatgga | 480 |
| taatggactg | gtaccccaaa | agattgtgtc | ggtgcacttg | caggactcca | ctctgaagga | 540 |
| agttaaggat | caggtctcaa | acaagcaagc | ccagatccta | gagccgaagc | ctgaaccttc | 600 |
| tcttgagatt | aagcctgagc | aggacggtat | ggagcatgtt | ggcagagatg | acccaaaggc | 660 |
| tcttggtgaa | gaacccaaac | aaaggagagg | cagtgcctct | gggagtgagc | ctgctgggga | 720 |
| cagtgacagg | ggagggggcc | ccgttgagca | ttatcacctc | catctgtcta | gttgccacga | 780 |
| gtgtctggaa | cttgagaaca | gcaccattga | gtcagtcaag | tttgcgtctg | ccgagaacat | 840 |
| tccagacctt | ccctacgatt | atagcagcag | tttggagagt | gttgctgatg | agacctcccc | 900 |
| cgaaagagaa | gggaggagag | tcaacctcac | gggaaaggca | cccaacatcc | tcctctatgt | 960 |
| gggctccgac | tcccaggaag | ccctcggccg | gttccacgag | gtccggtctg | tgctggccga | 1020 |
| ctgtgtggac | attgacagtt | atattctcta | ccacctgctg | gaggacagtg | ctctcagaga | 1080 |
| cccgtggacg | gacaactgtc | tgctgttggt | cattgctacc | agggagtcca | ttcccgaaga | 1140 |
| cctgtaccag | aagttcatgg | cctatctttc | tcagggaggg | aaggtgttgg | gcctgtcttc | 1200 |
| atccttcacc | tttggtggct | ttcaggtgac | aagcaagggt | gcactgcaca | agacagtcca | 1260 |
| gaacttggtt | ttctccaagg | ctgaccagag | cgaggtgaag | ctcagcgtct | tgagcagtgg | 1320 |
| ctgcaggtac | caggaaggcc | ccgtccggct | cagccccggc | aggctccagg | gccacctgga | 1380 |
| gaatgaggac | aaggacagga | tgattgtgca | tgtgcctttt | ggaactcgcg | ggggagaagc | 1440 |
| tgttctttgc | caggtgcact | tagaactacc | tcccagctcc | aacatagtgc | aaactccaga | 1500 |
| agattttaac | ttgctcaagt | caagcaattt | tagaagatac | gaagtcctta | gagagattct | 1560 |
| gacaaccctt | ggcctcagct | gtgacatgaa | acaagttcct | gccttaactc | ctctttactt | 1620 |
| gctgtcagct | gcggaggaaa | tcagggatcc | tcttatgcag | tggcttggga | acatgtggga | 1680 |
| ctccgaggga | gaaataaaat | ccggccagct | ctctcttaga | tttgtttcat | cctacgtgtc | 1740 |
| tgaagtagaa | ataaccccat | cttgtatacc | tgtggtgacc | aacatggagg | ccttctcatc | 1800 |
| agaacatttc | aacttagaga | tctatcgcca | aaatctgcag | accaagcagt | ggggaaagt | 1860 |
| aattttgttt | gccgaagtga | cccccacaac | gatgcgtctc | ctggatgggc | tgatgtttca | 1920 |
| gacaccgcag | gaaatgggct | taatagtgat | cgcggcccgg | cagaccgagg | gcaaaggacg | 1980 |
| gggagggaat | gtgtggctga | gccctgtggg | atgtgctctt | tctactctgc | tcatctccat | 2040 |
| tccactgaga | tcccagctgg | gacagaggat | ccgtttgtc | cagcatctga | gtccgtggc | 2100 |
| tgtcgtggaa | gcagtgaggt | ccattcccga | gtatcaggat | atcaacttac | gagtgaagtg | 2160 |

```
gcccaacgat atttattaca gtgacctcat gaagatcggc ggagttctgg ttaactcaac    2220
actcatggga gaaacatttt atatacttat tggctgtgga tttaatgtga ctaacagtaa    2280
ccctaccatc tgcatcaacg acctcatcac agaatacaat aaacaacaca aggcagaact    2340
gaagccctta agagccgatt atctcatcgc cagagtcgtg actgtgctgg agaaactgat    2400
caaagagttt caggacaaag ggcccaacag cgtccttccc ctttattacc gatactgggt    2460
ccacagtggt cagcaagtcc atctgggcag cgcagaggga ccaaaggtgt ccatcgttgg    2520
cctggacgat tctggcttcc tccaggttca ccaggagggc ggcgaggttg tgactgtgca    2580 cccgacggc aactccttcg acatgctgag aaacctcatc ctccccaaac ggcggtaatg    2640
ccgggcgtcc ccgagacgcg gctgcctgtc cgtgcccatg catctggaaa tctaatttag    2700
agttgtaggt gaatttgctt ttcctccaat tcatttgtta agtctttgtt cttttttctgt    2760 gtttctgttt gtttttaggt ttgttttgtt gtcgttttct ttggtgtttg aagaggctct    2820
gggatagatg gttaagaagt agaaaattta gtttagggaa agccctccca caggtgggaa    2880
attgctctcc cctctgtggc ttggacttac gtttattgtc aaggggagtt tttacatgga    2940
aatgacaatg ggaaaattca gatattttct tagtagtgca gacctttacc cctagtctat    3000
gaaaaaacaa accaaaatat gctcttgcgc ccaggccagt ggtgagttag aggtatgcta    3060
tcactgtttg taagcatctg ggaggtact gaactgtaag aacatgcttg gacacttagt    3120
cattgttctg tgttttatt aatgaagaaa agggaagaca gacttccaag agttactgtc    3180
cacccggtgg tgtggcccca tagcgaagtc taaatgcctg tagagataga gctagctggt    3240
gtggttgcag tgaccttgta gaggaaatca gttcattact ttgacatcat tcagtgagct    3300
ctcctttcct aaggaagttt aaatgtcctt agttagggac tgactttctt aagtaagttt    3360
aaatttacta catattgtga agagacagga tcaagttcag aatccttaaa tgtctgatta    3420
ggcatcactt ggatgaggag gtgggcgatt tggctctgac agctggagat gaaggcacac    3480
tcataccaca tacaagggag gatttggagc ttttaagcca gtttcagatt tactctgaaa    3540
tgtggagcat tcctgcaaga ctgtgcagct cacggaatat agaagacatg gcatttact    3600 cagaagtcat aagttttgc cccctcatt tacctcgtat taccaagaaa gaaaatgtta    3660
tcgatactaa acaccatcag ttcagaggga ggatgtgtgt gtgtgcccgc atatgtgtgt    3720
gcgtgcgtgt gtgcgcacat agctttaaaa gaagacattc aaaatttgat gtgctacaag    3780
cctcatgaaa gaacaaaaga aatgaagcct tttgatatgc attcgctatt cccagatgta    3840
cgccatgcct tttccatgtc cctcctatct ctgttgaact tatgaatcat actcattact    3900
tttcagcttt ttaaaaggcc aattttttgtc cagttttctc tcttccagtc ccagctgaaa    3960
ttagtggaaa gaaagtttga tggagctttc agctttgaac aaaatccctt cattgtaaac    4020
tagcaccatc tttatccagg tcttacccag tcaggctaat tccagaaact tgtggttttt    4080
agtatagtct gtctaccttt agccaggcac aggacagccc tatgaaaaaa tacccaatat    4140 atatttttg gaaatgaaac attaaaagaa cttaaaaagt aattttttgga aatgaggctt    4200 caattagaat tattttttctc aaaaaacaaa caaacaaaaa acacaaaaaa aaccactctt    4260
ctccaaatgc ccaagccttc tttcaaaatt agttagaaac ttaagtaaaa tacaagtcca    4320
caccatcccc aaattacaaa atggacttac ccttgagagg gcatctgcag aatatcatca    4380
gggacaaaga tctcgaggct aacgatgtag gtttcatttc tcagactttg taatataagg    4440
caagccctct ctcagagctg ccatcatcac tttttgaatt tctttggggg ttatttaatg    4500
aaaaacatgc tatgttttgt tttaagctga agtcctattc tggacactct gctttgggaa    4560
```

```
aaaatgttat catttaattt cctttctgca aattaaaact aatgaagtgt ggccttgtca    4620
aaggctatgg agatgttccg ggcatactgc tgtgctctgt gctttccagc aggcgctcct    4680
ccctcacgca ggagactcag ttgtcctgag agagatgaag cagccttgaa gcagatgctg    4740
cgttttccat aaacctgatt ttgcctcaca tgaaccaaag actctcaaaa ctccgcttct    4800
atagaattag ctgaataaag gcattttact gatagctgtt cgtgttagcg aaacctgtct    4860
acctgctata gcacactctc cgatttgggc cattttatgca ccccgcaacc tgggatctca    4920
aggagcttta aagtcttaat gggaacttgg cattttcctg atgatcttta aaatgtggtc    4980
actaaactca ggattggcgt gtgcttttag aacactggag tagcccttgt tttagaggct    5040
gtgcattgag tatcgaccgt attttgtaaa aggcaagata tcctcccttc caggctggta    5100
acgggtttca aggggactct tgaggaagtg ccccctaaaa tagaacacag caataactgg    5160
gcttcctgtc cccaccccca ccccagcagt gctctctggc actgggaact ctgctaggga    5220
gtggtggaag taggaaggat ttgtgtgcaa aggaaaatcg tggttgagtt tcactgcagc    5280
aggctgacgt tgcctgatgt gagagcaagt ggccgactgg ggtgcgggtg cacaggtcgg    5340
gggagcacag gccacagagc gcagcctctg ggggtccccc aaggcacagc atatacagca    5400
tggtcgcccc ttgccctgga gtctgggaac aaagagagga gccagcctcc ccgcactgct    5460
tcagatggaa aagggaggca gggtgggctt ccgttctcca gatctgtttg ctcttaacag    5520
gcagaacatg ggagaatcct tattcctggt taatcactat gcatatttga aataaaagaa    5580
agcgtaagcc tctgcaattt taacttctca aaggatgtct ctgaaaagaa tcactttaaa    5640
ccaatgccta taaaaagcaa gtctaccaaa ataaactaag actttctatg tggtttgggc    5700
tccctcttat ttttacaagt ttcattttta aaagtaggca actactttgg gttacagtat    5760
ttttattcat atttaaacat ttttacaaaa taaataaagt gttttacata gtaaggaata    5820
tgtacgtatt tccaagtatt aagaagccaa gtgttttttt ttttgacgta ttattgacaa    5880
atgtattcag cgccatacac aagagaaata ttattactcc aaagaacgaa agttaacaaa    5940
actccaaagc aaaaacccctt ttaatggagg tgagaaataa atttaatgta acaacagcta    6000
gattgttttt aggattttttc ttttcttttg tggaaacttc ttgacttgac ttttcatctg    6060
aacagttttt ccccccaaga ttttaatctt atatgtcata cttaagttta ggaacagctt    6120
gaataattag cattctagat aacacaaggg ccatgattca ctaaaattcc aagctactgt    6180
aattttatgg catttatttg caaatgttct ttgtatctca ttttatctgt agcagtcccc    6240
actagtctac cttaaccatc ttatagctct ggtaaattaa aacttacgta gactttatac    6300
aagatccatt ggccgtatta aacctcccc actcttaggg cttagggcgg aagggacgaa    6360
ggcagggctg ataggacttt taaaaggata aaaggagtgg gggcaaggga ggcggaaaat    6420
acaggctctt gcagataccc tccgcgctgc cctccacacc cagcccactg ctctacaaag    6480
gtatgaatgg aatggctttt ctagaaaagg cttccaaga acataaagga attcctttcc    6540
ctgggaggcc ccgtggaggg ctgagccagc cttgaattgg gcttatttct caaatccatt    6600
tgatctggca ttttttgtcaa catggtacat gttagggcct acgatgattt ttttttcttt    6660
tttgtaaaag agaggcatat gtattaaaat gcttcctctt cccctgccgg agcctcacag    6720
aagtcaagaa acgctatccc cagcttaaat gtgcagactc ttcaagatgg aggtcacaat    6780
attaggttgc cacagtaaca gctctgctga cttcacactc agccctggcc gtcctgaagc    6840
cagctcgtgt aagaatcttc cttcatgttc taggttatga aaacgaagtt tgtttagaca    6900
```

```
aggacgtttt cactagtaca cattttcaag tacatacaca ctctgttacg cctgtccacg    6960
ttgtcacttg taaatctatg atagggtctt ttttctcaac agtaacettt gttattgaac    7020 tgctccgata gccttgattt attttttacta aatacagccc caaaagttaa taacaaggta    7080
gacacaaaag cattttgcag tactttattg aaaaatgtcg gtggtatctc ctagtaatca    7140
aacctacacc tttcaagaat cacggtttaa ttacaagact catgaacata aaaaaataat    7200
accctcggct tatttcctgt gcacacactc acaaggagtc gtgaatgagg tatagctgag    7260
tgcgtggaga ggcgggcaca tcccttccta ccatccagcc ccttcgctgc atgacccacg    7320
gtcctaaatt tgcaaattgt gactcttacc atgaggccca ctgacagaca ccctgtaggg    7380
attgtgtcag gtcctcacta agtgacacag ggttggcaaa aaaaaaaaaa aaaaagtcag    7440
ttcacatttt gagagcagtt ggtgtaggtg cacttgatttt tagaacgatg agtttaaaac    7500
atttgtgaaa acctctttcc attcagaaag gtggaaaaag tttcctaaaa taaaccattt    7560
tgataaagca gcaaaatgct gcagtgttga tagtgtgaag aaaattgaag acggcggtt     7620 caatgcattg tgcagttcag agccatgaca ggattttttcc atgttgagat ctttaagcaa    7680
aacccataaa aagtaaaaat taatggaagc tcatttttta aacactgctg gtgctttatg    7740
aaaggatttc tgtttacctg ttgcacacgt aacatgttct tacgaagttt tctcgctgtg    7800
tagaaaatgc ttaaaatgtc tacatcattt tcattacacc cccttaagca tgttttttcct   7860 tcacaaggtg cagtccattg acagtgttcc gtattgcacg tgcaatttaa ctttattagc    7920
actatttgta gcaaacacga gcctagtgaa ttacagatct gtgtgggcca gagggatttt    7980
gccacgtaat aatgaagctt gacagggtca ttctcataaa ctgtctggct acatatatat    8040
ttttgcattt aatgcctatt caatatattc tgaaggtgct actcttggtg ttatcaagag    8100
ttcatagggg ttaggggaa gtaagagctt gttaatgtat tgggaagca cctatgtt       8160 cacagacaca aaatggaatt gcatggtcac ccccttagtc ttggtttgtt ggcttttgt     8220 attgaagaaa gggttaaata aaacaaaaa taatgagac                            8259

<210> SEQ ID NO 125
<211> LENGTH: 8117
<212> TYPE: DNA
<213> ORGANISM: Homo sapiens

<400> SEQUENCE: 125
gcaggtgctt aaacagtcac agctaaacaa gaaacacacg gttcctgcgg cctgcagagg      60
agcatcagag tccattgaag acttgaacaa gtgggcccta tttcttgtgt ctcctttat     120 acttgaagca gaacacatag catttgtgac ggagagcatt tgggtacaaa gtgagaattt    180
acagagatca tcctcttcag aaacaattgt caagtggtca gactgttgtt tgccattagc    240
ttgcagacct ggggatcctt atcggctaat tgctgaagca agtgtggaca acttcagcaa    300
gctgggggtg gcgttcatgg aagatagact ccacatggat aatggactgg taccccaaaa    360
gattgtgtcg gtgcacttgc aggactccac tctgaaggaa gttaaggatc aggtctcaaa    420
caagcaagcc cagatcctag agccgaagcc tgaaccttct cttgagatta gcctgagca    480 ggacggtatg gagcatgttg gcagagatga cccaaaggct cttggtgaag aacccaaaca    540
aaggagaggc agtgcctctg ggagtgagcc tgctggggac agtgacaggg gagggggccc    600
cgttgagcat tatcacctcc atctgtctag ttgccacgag tgtctggaac ttgagaacag    660
caccattgag tcagtcaagt ttgcgtctgc cgagaacatt ccagaccttc cctacgatta    720
tagcagcagt ttggagagtg ttgctgatga gacctccccc gaaagagaag ggaggagagt    780
```

```
caacctcacg ggaaaggcac ccaacatcct cctctatgtg ggctccgact cccaggaagc    840
cctcggccgg ttccacgagg tccggtctgt gctggccgac tgtgtggaca ttgacagtta    900
tattctctac cacctgctgg aggacagtgc tctcagagac ccgtggacgg acaactgtct    960
gctgttggtc attgctacca gggagtccat tcccgaagac ctgtaccaga agttcatggc   1020
ctatctttct cagggaggga aggtgttggg cctgtcttca tccttcacct ttggtggctt   1080
tcaggtgaca agcaagggtg cactgcacaa gacagtccag aacttggttt tctccaaggc   1140
tgaccagagc gaggtgaagc tcagcgtctt gagcagtggc tgcaggtacc aggaaggccc   1200
cgtccggctc agccccggca ggctccaggg ccacctggag aatgaggaca aggacaggat   1260
gattgtgcat gtgccttttg aactcgcggg ggagaagct gttctttgcc aggtgcactt   1320
agaactacct cccagctcca acatagtgca aactccagaa gattttaact tgctcaagtc   1380
aagcaatttt agaagatacg aagtccttag agagattctg acaacccttg gcctcagctg   1440
tgacatgaaa caagttcctg ccttaactcc tctttacttg ctgtcagctg cggaggaaat   1500
cagggatcct cttatgcagt ggcttgggaa acatgtggac tccgagggag aaataaaatc   1560
cggccagctc tctcttagat ttgtttcatc ctacgtgtct gaagtagaaa taaccccatc   1620
ttgtatacct gtggtgacca acatggaggc cttctcatca gaacatttca acttagagat   1680
ctatcgccaa aatctgcaga ccaagcagtt ggggaaagta attttgtttg ccgaagtgac   1740
ccccacaacg atgcgtctcc tggatgggct gatgtttcag acaccgcagg aaatgggctt   1800
aatagtgatc gcggcccggc agaccgaggg caaaggacgg ggagggaatg tgtggctgag   1860
ccctgtggga tgtgctcttt ctactctgct catctccatt ccactgagat cccagctggg   1920
acagaggatc ccgtttgtcc agcatctgat gtccgtggct gtcgtggaag cagtgaggtc   1980
cattcccgag tatcaggata tcaacttacg agtgaagtgg cccaacgata tttattacag   2040
tgacctcatg aagatcggcg gagttctggt taactcaaca ctcatgggag aaacatttta   2100
tatacttatt ggctgtggat ttaatgtgac taacagtaac cctaccatct gcatcaacga   2160
cctcatcaca gaatacaata aacaacacaa ggcagaactg aagcccttaa gagccgatta   2220
tctcatcgcc agagtcgtga ctgtgctgga gaaactgatc aaagagtttc aggacaaagg   2280
gcccaacagc gtccttcccc tttattaccg atactgggtc cacagtggtc agcaagtcca   2340
tctgggcagc gcagagggac caaaggtgtc catcgttggc ctggacgatt ctggcttcct   2400
ccaggttcac caggagggcg gcgaggttgt gactgtgcac ccggacggca actccttcga   2460
catgctgaga aacctcatcc tccccaaacg gcggtaatgc cggcgtccc cgagacgcgg   2520 ctgcctgtcc gtgcccatgc atctggaaat ctaatttaga gttgtaggtg aattttcttt   2580
tcctccaatt catttgttaa gtctttgttc tttttctgtg tttctgtttg ttttaggtt   2640 tgttttgttg tcgttttctt tggtgtttga agaggctctg ggatagatgg ttaagaagta   2700
gaaaatttag tttagggaaa gccctcccac aggtgggaaa ttgctctccc ctctgtggct   2760
tggacttacg tttattgtca aggggagttt ttacatggaa atgacaatgg gaaaattcag   2820 atatttctt agtagtgcag accttaccc ctagtctatg aaaaaacaaa ccaaatatg   2880 ctcttgcgcc caggccagtg gtgagttaga ggtatgctat cactgtttgt aagcatctgg   2940
ggaggtactg aactgtaaga acatgcttgg acacttagtc attgttctgt gttttatta   3000 atgaagaaaa gggaagacag acttccaaga gttactgtcc acccggtggt gtggccccat   3060
agcgaagtct aaatgcctgt agagatagag ctagctggtg tggttgcagt gaccttgtag   3120
```

```
aggaaatcag ttcattactt tgacatcatt cagtgagctc tcctttccta aggaagttta    3180
aatgtcctta gttagggact gactttctta agtaagtta  aatttactac atattgtgaa    3240
gagacaggat caagttcaga atccttaaat gtctgattag gcatcacttg gatgaggagg    3300
tgggcgattg ggctctgaca gctggagatg aaggcacact cataccacat acaagggagg    3360
atttggagct tttaagccag tttcagattt actctgaaat gtggagcatt cctgcaagac    3420
tgtgcagctc acggaatata gaagacatgg cattttactc agaagtcata agttttgcc     3480 cccctcattt acctcgtatt accaagaaag aaaatgttat cgatactaaa caccatcagt    3540
tcagagggag gatgtgtgtg tgtgcccgca tatgtgtgtg cgtgcgtgtg tgcgcacata    3600
gctttaaaag aagacattca aaatttgatg tgctacaagc ctcatgaaag aacaaaagaa    3660
atgaagcctt ttgatatgca ttcgctattc ccagatgtac gccatgcctt ttccatgtcc    3720
ctcctatctc tgttgaactt atgaatcata ctcattactt ttcagctttt taaaaggcca    3780 attttttgtcc agttttctct cttccagtcc cagctgaaat tagtggaaag aaagtttgat   3840
ggagctttca gctttgaaca aaatcccttc attgtaaact agcaccatct ttatccaggt    3900
cttacccagt caggctaatt ccagaaactt gtggttttta gtatagtctg tctacccttta   3960 gccaggcaca ggacagccct atgaaaaaat acccaatata tattttttgg aaatgaaaca    4020
ttaaaagaac ttaaaaagta attttttggaa atgaggcttc aattagaatt attttttctca   4080 aaaaacaaac aaacaaaaaa cacaaaaaaa accactcttc tccaaatgcc caagccttct    4140
ttcaaaatta gttagaaact taagtaaaat acaagtccac accatcccca aattacaaaa    4200
tggacttacc cttgagaggg catctgcaga atatcatcag ggacaaagat ctcgaggcta    4260
acgatgtagg tttcatttct cagactttgt aatataaggc aagccctctc tcagagctgc    4320
catcatcact ttttgaattt cttgggggt  tatttaatga aaaacatgct atgttttgtt    4380
ttaagctgaa gtcctattct ggacactctg ctttgggaaa aatgttatc atttaatttc    4440 ctttctgcaa attaaaacta atgaagtgtg gccttgtcaa aggctatgga gatgttccgg    4500
gcatactgct gtgctctgtg cttttccagca ggcgctcctc cctcacgcag gagactcagt    4560
tgtcctgaga gagatgaagc agccttgaag cagatgctgc gttttccata aacctgattt    4620
tgcctcacat gaaccaaaga ctctcaaaac tccgcttcta tagaattagc tgaataaagg    4680
cattttactg atagctgttc gtgttagcga aacctgtcta cctgctatag cacactctcc    4740
gatttgggcc atttatgcac cccgcaacct gggatctcaa ggagctttaa agtcttaatg    4800
ggaacttggc attttcctga tgatctttaa aatgtggtca ctaaactcag gattggcgtg    4860
tgcttttaga acactggagt agcccttgtt ttagaggctg tgcattgagt atcgaccgta    4920
ttttgtaaaa ggcaagatat cctcccttcc aggctggtaa cgggtttcaa ggggactctt    4980
gaggaagtgc cccctaaaat agaacacagc aataactggg cttcctgtcc ccacccccac    5040
cccagcagtg ctctctggca ctgggaactc tgctagggag tggtggaagt aggaaggatt    5100
tgtgtgcaaa ggaaaatcgt ggttgagttt cactgcagca ggctgacgtt gcctgatgtg    5160
agagcaagtg gccgactggg gtgcgggtgc acaggtcggg ggagcacagg ccacagagcg    5220
cagcctctgg gggtccccca aggcacagca tatacagcat ggtcgcccct tgccctggag    5280
tctgggaaca aagagaggag ccagcctccc cgcactgctt cagatggaaa agggaggcag    5340
ggtgggcttc cgttctccag atctgtttgc tcttaacagg cagaacatgg gagaatcctt    5400
attcctggtt aatcactatg catatttgaa ataaagaaa  gcgtaagcct ctgcaatttc    5460
aacttctcaa aggatgtctc tgaaaagaat cactttaaac caatgcctat aaaaagcaag    5520
```

```
tctaccaaaa taaactaaga ctttctatgt ggtttgggct ccctcttatt tttacaagtt    5580
tcatttttaa aagtaggcaa ctactttggg ttacagtatt tttattcata tttaaacatt    5640
tttacaaaat aaataaagtg ttttacatag taaggaatat gtacgtattt ccaagtatta    5700
agaagccaag tgtttttttt tttgacgtat tattgacaaa tgtattcagc gccatacaca    5760
agagaaatat tattactcca aagaacgaaa gttaacaaaa ctccaaagca aaaacccttt    5820
taatggaggt gagaaataaa tttaatgtaa caacagctag attgttttta ggattttttct   5880 tttcttttgt ggaaacttct tgacttgact tttcatctga acagttttttc cccccaagat   5940 tttaatctta tatgtcatac ttaagtttag gaacagcttg aataattagc attctagata    6000
acacaagggc catgattcac taaaattcca agctactgta attttatggc atttatttgc    6060
aaatgttctt tgtatctcat tttatctgta gcagtcccca ctagtctacc ttaaccatct    6120
tatagctctg gtaaattaaa acttacgtag actttataca agatccattg gccgtattaa    6180
acctccccca ctcttagggc ttagggcgga agggacgaag gcagggctga taggactttt    6240
aaaaggataa aaggagtggg ggcaagggag gcggaaaata caggctcttg cagatacccct  6300 ccgcgctgcc ctccacaccc agcccactgc tctacaaagg tatgaatgga atggcttttc    6360
tagaaaaggg cttccaagaa cataaaggaa ttcctttccc tgggaggccc cgtggagggc   6420
tgagccagcc ttgaatttggg cttatttctc aaatccattt gatctggcat ttttgtcaac   6480
atggtacatg ttagggccta cgatgatttt ttttttcttt ttgtaaaaga gaggcatatg    6540
tattaaaatg cttcctcttc ccctgccgga gcctcacaga agtcaagaaa cgctatcccc    6600
agcttaaatg tgcagactct tcaagatgga ggtcacaata ttaggttgcc acagtaacag    6660
ctctgctgac ttcacactca gccctggccg tcctgaagcc agctcgtgta agaatcttcc    6720
ttcatgttct aggttatgaa aacgaagttt gtttagacaa ggacgttttc actagtacac    6780
attttcaagt acatacacac tctgttacgc ctgtccacgt tgtcacttgt aaatctatga   6840
tagggtcttt tttctcaaca gtaaccttttg ttattgaact gctccgatag ccttgattta   6900
tttttactaa atacagcccc aaaagttaat aacaaggtag acacaaaagc attttgcagt    6960
actttattga aaaatgtcgg tggtatctcc tagtaatcaa acctacacct ttcaagaatc    7020
acggtttaat tacaagactc atgaacataa aaaaataata ccctcggctt atttcctgtg    7080
cacacactca caaggagctg tgaatgaggt atagctgagt gcgtggagag gcgggcacat    7140
cccttcctac catccagccc cttcgctgca tgacccacgg tcctaaattt gcaaattgtg    7200
actcttacca tgaggcccac tgacagacac cctgtaggga ttgtgtcagg tcctcactaa    7260
gtgacacagg gttggcaaaa aaaaaaaaaa aaaagtcagt tcacattttg agagcagttg    7320
gtgtaggtgc acttgattttt agaacgatga gtttaaaaca tttgtgaaaa cctcttttcca   7380 ttcagaaagg tggaaaaagt ttcctaaaat aaaccatttt gataaagcag caaaatgctg    7440
cagtgttgat agtgtgaaga aaattgaagg acggcggttc aatgcattgt gcagttcaga    7500
gccatgacag gattttttcca tgttgagatc tttaagcaaa acccataaaa agtaaaaatt    7560
aatggaagct catttttttaa acactgctgg tgctttatga aaggatttct gtttacctgt    7620
tgcacacgta acatgttctt acgaagtttt ctcgctgtgt agaaaatgct taaaatgtct    7680
acatcatttt cattacaccc ccttaagcat gttttttcctt cacaaggtgc agtccattga    7740
cagtgttccg tattgcacgt gcaatttaac tttattagca ctatttgtag caaacacgag    7800
cctagtgaat tacagatctg tgtgggccag agggattttttg ccacgtaata atgaagcttg   7860
```

-continued

```
acagggtcat tctcataaac tgtctggcta catatatatt tttgcattta atgcctattc    7920
aatatattct gaaggtgcta ctcttggtgt tatcaagagt tcatagggt tagggggaag    7980 taagagcttg ttaatgtatt tgggaagcac acctatgttc acagacacaa aatggaattg    8040
catggtcacc cccttagtct tggtttgttg gcttttttgta ttgaagaaag ggttaaataa    8100
aaacaaaaat aatgaga                                                     8117
```

<210> SEQ ID NO 126
<211> LENGTH: 726
<212> TYPE: PRT
<213> ORGANISM: Homo sapiens

<400> SEQUENCE: 126

| Met | Glu | Asp | Arg | Leu | His | Met | Asp | Asn | Gly | Leu | Val | Pro | Gln | Lys | Ile |
|---|---|---|---|---|---|---|---|---|---|---|---|---|---|---|---|
| 1 | | | | 5 | | | | | 10 | | | | | 15 | |

| Val | Ser | Val | His | Leu | Gln | Asp | Ser | Thr | Leu | Lys | Glu | Val | Lys | Asp | Gln |
|---|---|---|---|---|---|---|---|---|---|---|---|---|---|---|---|
| | | | 20 | | | | | 25 | | | | | 30 | | |

| Val | Ser | Asn | Lys | Gln | Ala | Gln | Ile | Leu | Glu | Pro | Lys | Pro | Glu | Pro | Ser |
|---|---|---|---|---|---|---|---|---|---|---|---|---|---|---|---|
| | | 35 | | | | | 40 | | | | | 45 | | | |

| Leu | Glu | Ile | Lys | Pro | Glu | Gln | Asp | Gly | Met | Glu | His | Val | Gly | Arg | Asp |
|---|---|---|---|---|---|---|---|---|---|---|---|---|---|---|---|
| | 50 | | | | | 55 | | | | | 60 | | | | |

| Asp | Pro | Lys | Ala | Leu | Gly | Glu | Pro | Lys | Gln | Arg | Arg | Gly | Ser | Ala |
|---|---|---|---|---|---|---|---|---|---|---|---|---|---|---|
| 65 | | | | | 70 | | | | | 75 | | | | | 80 |

| Ser | Gly | Ser | Glu | Pro | Ala | Gly | Asp | Ser | Asp | Arg | Gly | Gly | Pro | Val |
|---|---|---|---|---|---|---|---|---|---|---|---|---|---|---|
| | | | | 85 | | | | | 90 | | | | | 95 |

| Glu | His | Tyr | His | Leu | His | Leu | Ser | Ser | Cys | His | Glu | Cys | Leu | Glu | Leu |
|---|---|---|---|---|---|---|---|---|---|---|---|---|---|---|---|
| | | | 100 | | | | | 105 | | | | | 110 | | |

| Glu | Asn | Ser | Thr | Ile | Glu | Ser | Val | Lys | Phe | Ala | Ser | Ala | Glu | Asn | Ile |
|---|---|---|---|---|---|---|---|---|---|---|---|---|---|---|---|
| | | | 115 | | | | | 120 | | | | | 125 | | |

| Pro | Asp | Leu | Pro | Tyr | Asp | Tyr | Ser | Ser | Ser | Leu | Glu | Ser | Val | Ala | Asp |
|---|---|---|---|---|---|---|---|---|---|---|---|---|---|---|---|
| 130 | | | | | 135 | | | | | 140 | | | | | |

| Glu | Thr | Ser | Pro | Glu | Arg | Glu | Gly | Arg | Arg | Val | Asn | Leu | Thr | Gly | Lys |
|---|---|---|---|---|---|---|---|---|---|---|---|---|---|---|---|
| 145 | | | | | 150 | | | | | 155 | | | | | 160 |

| Ala | Pro | Asn | Ile | Leu | Leu | Tyr | Val | Gly | Ser | Asp | Ser | Gln | Glu | Ala | Leu |
|---|---|---|---|---|---|---|---|---|---|---|---|---|---|---|---|
| | | | 165 | | | | | 170 | | | | | 175 | | |

| Gly | Arg | Phe | His | Glu | Val | Arg | Ser | Val | Leu | Ala | Asp | Cys | Val | Asp | Ile |
|---|---|---|---|---|---|---|---|---|---|---|---|---|---|---|---|
| | | | 180 | | | | | 185 | | | | | 190 | | |

| Asp | Ser | Tyr | Ile | Leu | Tyr | His | Leu | Leu | Glu | Asp | Ser | Ala | Leu | Arg | Asp |
|---|---|---|---|---|---|---|---|---|---|---|---|---|---|---|---|
| | | 195 | | | | | 200 | | | | | 205 | | | |

| Pro | Trp | Thr | Asp | Asn | Cys | Leu | Leu | Leu | Val | Ile | Ala | Thr | Arg | Glu | Ser |
|---|---|---|---|---|---|---|---|---|---|---|---|---|---|---|---|
| | 210 | | | | | 215 | | | | | 220 | | | | |

| Ile | Pro | Glu | Asp | Leu | Tyr | Gln | Lys | Phe | Met | Ala | Tyr | Leu | Ser | Gln | Gly |
|---|---|---|---|---|---|---|---|---|---|---|---|---|---|---|---|
| 225 | | | | | 230 | | | | | 235 | | | | | 240 |

| Gly | Lys | Val | Leu | Gly | Leu | Ser | Ser | Ser | Phe | Thr | Phe | Gly | Gly | Phe | Gln |
|---|---|---|---|---|---|---|---|---|---|---|---|---|---|---|---|
| | | | 245 | | | | | 250 | | | | | 255 | | |

| Val | Thr | Ser | Lys | Gly | Ala | Leu | His | Lys | Thr | Val | Gln | Asn | Leu | Val | Phe |
|---|---|---|---|---|---|---|---|---|---|---|---|---|---|---|---|
| | | | 260 | | | | | 265 | | | | | 270 | | |

| Ser | Lys | Ala | Asp | Gln | Ser | Glu | Val | Lys | Leu | Ser | Val | Leu | Ser | Ser | Gly |
|---|---|---|---|---|---|---|---|---|---|---|---|---|---|---|---|
| | | 275 | | | | | 280 | | | | | 285 | | | |

| Cys | Arg | Tyr | Gln | Glu | Gly | Pro | Val | Arg | Leu | Ser | Pro | Gly | Arg | Leu | Gln |
|---|---|---|---|---|---|---|---|---|---|---|---|---|---|---|---|
| | | 290 | | | | | 295 | | | | | 300 | | | |

| Gly | His | Leu | Glu | Asn | Glu | Asp | Lys | Asp | Arg | Met | Ile | Val | His | Val | Pro |
|---|---|---|---|---|---|---|---|---|---|---|---|---|---|---|---|
| 305 | | | | | 310 | | | | | 315 | | | | | 320 |

| Phe | Gly | Thr | Arg | Gly | Gly | Glu | Ala | Val | Leu | Cys | Gln | Val | His | Leu | Glu |
|---|---|---|---|---|---|---|---|---|---|---|---|---|---|---|---|

-continued

```
                325                 330                 335
Leu Pro Pro Ser Ser Asn Ile Val Gln Thr Pro Glu Asp Phe Asn Leu
            340                 345                 350

Leu Lys Ser Ser Asn Phe Arg Arg Tyr Glu Val Leu Arg Glu Ile Leu
            355                 360                 365

Thr Thr Leu Gly Leu Ser Cys Asp Met Lys Gln Val Pro Ala Leu Thr
370                 375                 380

Pro Leu Tyr Leu Leu Ser Ala Ala Glu Ile Arg Asp Pro Leu Met
385                 390                 395                 400

Gln Trp Leu Gly Lys His Val Asp Ser Glu Gly Ile Lys Ser Gly
                405                 410                 415

Gln Leu Ser Leu Arg Phe Val Ser Ser Tyr Val Ser Glu Val Glu Ile
            420                 425                 430

Thr Pro Ser Cys Ile Pro Val Val Thr Asn Met Glu Ala Phe Ser Ser
            435                 440                 445

Glu His Phe Asn Leu Glu Ile Tyr Arg Gln Asn Leu Gln Thr Lys Gln
            450                 455                 460

Leu Gly Lys Val Ile Leu Phe Ala Glu Val Thr Pro Thr Thr Met Arg
465                 470                 475                 480

Leu Leu Asp Gly Leu Met Phe Gln Thr Pro Gln Glu Met Gly Leu Ile
                485                 490                 495

Val Ile Ala Ala Arg Gln Thr Glu Gly Lys Gly Arg Gly Gly Asn Val
            500                 505                 510

Trp Leu Ser Pro Val Gly Cys Ala Leu Ser Thr Leu Leu Ile Ser Ile
            515                 520                 525

Pro Leu Arg Ser Gln Leu Gly Gln Arg Ile Pro Phe Val Gln His Leu
530                 535                 540

Met Ser Val Ala Val Val Glu Ala Val Arg Ser Ile Pro Glu Tyr Gln
545                 550                 555                 560

Asp Ile Asn Leu Arg Val Lys Trp Pro Asn Asp Ile Tyr Tyr Ser Asp
                565                 570                 575

Leu Met Lys Ile Gly Gly Val Leu Val Asn Ser Thr Leu Met Gly Glu
            580                 585                 590

Thr Phe Tyr Ile Leu Ile Gly Cys Gly Phe Asn Val Thr Asn Ser Asn
            595                 600                 605

Pro Thr Ile Cys Ile Asn Asp Leu Ile Thr Glu Tyr Asn Lys Gln His
            610                 615                 620

Lys Ala Glu Leu Lys Pro Leu Arg Ala Asp Tyr Leu Ile Ala Arg Val
625                 630                 635                 640

Val Thr Val Leu Glu Lys Leu Ile Lys Glu Phe Gln Asp Lys Gly Pro
                645                 650                 655

Asn Ser Val Leu Pro Leu Tyr Tyr Arg Tyr Trp Val His Ser Gly Gln
            660                 665                 670

Gln Val His Leu Gly Ser Ala Glu Gly Pro Lys Val Ser Ile Val Gly
            675                 680                 685

Leu Asp Asp Ser Gly Phe Leu Gln Val His Gln Glu Gly Gly Glu Val
690                 695                 700

Val Thr Val His Pro Asp Gly Asn Ser Phe Asp Met Leu Arg Asn Leu
705                 710                 715                 720

Ile Leu Pro Lys Arg Arg
                725

<210> SEQ ID NO 127
```

```
<211> LENGTH: 726
<212> TYPE: PRT
<213> ORGANISM: Homo sapiens

<400> SEQUENCE: 127

Met Glu Asp Arg Leu His Met Asp Asn Gly Leu Val Pro Gln Lys Ile
1               5                   10                  15

Val Ser Val His Leu Gln Asp Ser Thr Leu Lys Glu Val Lys Asp Gln
            20                  25                  30

Val Ser Asn Lys Gln Ala Gln Ile Leu Glu Pro Lys Pro Glu Pro Ser
        35                  40                  45

Leu Glu Ile Lys Pro Glu Gln Asp Gly Met Glu His Val Gly Arg Asp
    50                  55                  60

Asp Pro Lys Ala Leu Gly Glu Pro Lys Gln Arg Arg Gly Ser Ala
65                  70                  75                  80

Ser Gly Ser Glu Pro Ala Gly Asp Ser Asp Arg Gly Gly Pro Val
                85                  90                  95

Glu His Tyr His Leu His Leu Ser Ser Cys His Glu Cys Leu Glu Leu
            100                 105                 110

Glu Asn Ser Thr Ile Glu Ser Val Lys Phe Ala Ser Ala Glu Asn Ile
        115                 120                 125

Pro Asp Leu Pro Tyr Asp Tyr Ser Ser Ser Leu Glu Ser Val Ala Asp
    130                 135                 140

Glu Thr Ser Pro Glu Arg Glu Gly Arg Arg Val Asn Leu Thr Gly Lys
145                 150                 155                 160

Ala Pro Asn Ile Leu Leu Tyr Val Gly Ser Asp Ser Gln Glu Ala Leu
                165                 170                 175

Gly Arg Phe His Glu Val Arg Ser Val Leu Ala Asp Cys Val Asp Ile
            180                 185                 190

Asp Ser Tyr Ile Leu Tyr His Leu Leu Glu Asp Ser Ala Leu Arg Asp
        195                 200                 205

Pro Trp Thr Asp Asn Cys Leu Leu Val Ile Ala Thr Arg Glu Ser
    210                 215                 220

Ile Pro Glu Asp Leu Tyr Gln Lys Phe Met Ala Tyr Leu Ser Gln Gly
225                 230                 235                 240

Gly Lys Val Leu Gly Leu Ser Ser Ser Phe Thr Phe Gly Phe Gln
                245                 250                 255

Val Thr Ser Lys Gly Ala Leu His Lys Thr Val Gln Asn Leu Val Phe
            260                 265                 270

Ser Lys Ala Asp Gln Ser Glu Val Lys Leu Ser Val Leu Ser Ser Gly
        275                 280                 285

Cys Arg Tyr Gln Glu Gly Pro Val Arg Leu Ser Pro Gly Arg Leu Gln
    290                 295                 300

Gly His Leu Glu Asn Glu Asp Lys Asp Arg Met Ile Val His Val Pro
305                 310                 315                 320

Phe Gly Thr Arg Gly Gly Glu Ala Val Leu Cys Gln Val His Leu Glu
                325                 330                 335

Leu Pro Pro Ser Ser Asn Ile Val Gln Thr Pro Glu Asp Phe Asn Leu
            340                 345                 350

Leu Lys Ser Ser Asn Phe Arg Arg Tyr Glu Val Leu Arg Glu Ile Leu
        355                 360                 365

Thr Thr Leu Gly Leu Ser Cys Asp Met Lys Gln Val Pro Ala Leu Thr
    370                 375                 380

Pro Leu Tyr Leu Leu Ser Ala Ala Glu Glu Ile Arg Asp Pro Leu Met
```

```
                385                 390                 395                 400
        Gln Trp Leu Gly Lys His Val Asp Ser Glu Gly Ile Lys Ser Gly
                        405                 410                 415

Gln Leu Ser Leu Arg Phe Val Ser Ser Tyr Val Ser Glu Val Glu Ile
                    420                 425                 430

Thr Pro Ser Cys Ile Pro Val Thr Asn Met Glu Ala Phe Ser Ser
                    435                 440                 445

Glu His Phe Asn Leu Glu Ile Tyr Arg Gln Asn Leu Gln Thr Lys Gln
        450                 455                 460

Leu Gly Lys Val Ile Leu Phe Ala Glu Val Thr Pro Thr Met Arg
        465                 470                 475                 480

Leu Leu Asp Gly Leu Met Phe Gln Thr Pro Gln Glu Met Gly Leu Ile
                            485                 490                 495

Val Ile Ala Ala Arg Gln Thr Glu Gly Lys Gly Arg Gly Gly Asn Val
                        500                 505                 510

Trp Leu Ser Pro Val Gly Cys Ala Leu Ser Thr Leu Leu Ile Ser Ile
                    515                 520                 525

Pro Leu Arg Ser Gln Leu Gly Gln Arg Ile Pro Phe Val Gln His Leu
        530                 535                 540

Met Ser Val Ala Val Val Glu Ala Val Arg Ser Ile Pro Glu Tyr Gln
        545                 550                 555                 560

Asp Ile Asn Leu Arg Val Lys Trp Pro Asn Asp Ile Tyr Tyr Ser Asp
                        565                 570                 575

Leu Met Lys Ile Gly Gly Val Leu Val Asn Ser Thr Leu Met Gly Glu
                    580                 585                 590

Thr Phe Tyr Ile Leu Ile Gly Cys Gly Phe Asn Val Thr Asn Ser Asn
                595                 600                 605

Pro Thr Ile Cys Ile Asn Asp Leu Ile Thr Glu Tyr Asn Lys Gln His
                    610                 615                 620

Lys Ala Glu Leu Lys Pro Leu Arg Ala Asp Tyr Leu Ile Ala Arg Val
        625                 630                 635                 640

Val Thr Val Leu Glu Lys Leu Ile Lys Glu Phe Gln Asp Lys Gly Pro
                            645                 650                 655

Asn Ser Val Leu Pro Leu Tyr Tyr Arg Tyr Trp Val His Ser Gly Gln
                        660                 665                 670

Gln Val His Leu Gly Ser Ala Glu Gly Pro Lys Val Ser Ile Val Gly
                    675                 680                 685

Leu Asp Asp Ser Gly Phe Leu Gln Val His Gln Glu Gly Gly Glu Val
        690                 695                 700

Val Thr Val His Pro Asp Gly Asn Ser Phe Asp Met Leu Arg Asn Leu
        705                 710                 715                 720

Ile Leu Pro Lys Arg Arg
                        725

<210> SEQ ID NO 128
<211> LENGTH: 726
<212> TYPE: PRT
<213> ORGANISM: Homo sapiens

<400> SEQUENCE: 128

Met Glu Asp Arg Leu His Met Asp Asn Gly Leu Val Pro Gln Lys Ile
1               5                   10                  15

Val Ser Val His Leu Gln Asp Ser Thr Leu Lys Glu Val Lys Asp Gln
            20                  25                  30
```

Val Ser Asn Lys Gln Ala Gln Ile Leu Glu Pro Lys Glu Pro Ser
         35                  40                  45

Leu Glu Ile Lys Pro Glu Gln Asp Gly Met Glu His Val Gly Arg Asp
 50                  55                  60

Asp Pro Lys Ala Leu Gly Glu Pro Lys Gln Arg Arg Gly Ser Ala
 65                  70                  75                  80

Ser Gly Ser Glu Pro Ala Gly Asp Ser Asp Arg Gly Gly Pro Val
                 85                  90                  95

Glu His Tyr His Leu His Leu Ser Ser Cys His Glu Cys Leu Glu Leu
             100                 105                 110

Glu Asn Ser Thr Ile Glu Ser Val Lys Phe Ala Ser Ala Glu Asn Ile
             115                 120                 125

Pro Asp Leu Pro Tyr Asp Tyr Ser Ser Ser Leu Glu Ser Val Ala Asp
     130                 135                 140

Glu Thr Ser Pro Glu Arg Glu Gly Arg Arg Val Asn Leu Thr Gly Lys
 145                 150                 155                 160

Ala Pro Asn Ile Leu Leu Tyr Val Gly Ser Asp Ser Gln Glu Ala Leu
                 165                 170                 175

Gly Arg Phe His Glu Val Arg Ser Val Leu Ala Asp Cys Val Asp Ile
             180                 185                 190

Asp Ser Tyr Ile Leu Tyr His Leu Leu Glu Asp Ser Ala Leu Arg Asp
     195                 200                 205

Pro Trp Thr Asp Asn Cys Leu Leu Val Ile Ala Thr Arg Glu Ser
     210                 215                 220

Ile Pro Glu Asp Leu Tyr Gln Lys Phe Met Ala Tyr Leu Ser Gln Gly
 225                 230                 235                 240

Gly Lys Val Leu Gly Leu Ser Ser Ser Phe Thr Phe Gly Gly Phe Gln
                 245                 250                 255

Val Thr Ser Lys Gly Ala Leu His Lys Thr Val Gln Asn Leu Val Phe
             260                 265                 270

Ser Lys Ala Asp Gln Ser Glu Val Lys Leu Ser Val Leu Ser Ser Gly
     275                 280                 285

Cys Arg Tyr Gln Glu Gly Pro Val Arg Leu Ser Pro Gly Arg Leu Gln
     290                 295                 300

Gly His Leu Glu Asn Glu Asp Lys Asp Arg Met Ile Val His Val Pro
 305                 310                 315                 320

Phe Gly Thr Arg Gly Gly Glu Ala Val Leu Cys Gln Val His Leu Glu
                 325                 330                 335

Leu Pro Pro Ser Ser Asn Ile Val Gln Thr Pro Glu Asp Phe Asn Leu
             340                 345                 350

Leu Lys Ser Ser Asn Phe Arg Arg Tyr Glu Val Leu Arg Glu Ile Leu
     355                 360                 365

Thr Thr Leu Gly Leu Ser Cys Asp Met Lys Gln Val Pro Ala Leu Thr
 370                 375                 380

Pro Leu Tyr Leu Leu Ser Ala Ala Glu Glu Ile Arg Asp Pro Leu Met
 385                 390                 395                 400

Gln Trp Leu Gly Lys His Val Asp Ser Glu Gly Glu Ile Lys Ser Gly
                 405                 410                 415

Gln Leu Ser Leu Arg Phe Val Ser Ser Tyr Val Ser Glu Val Glu Ile
             420                 425                 430

Thr Pro Ser Cys Ile Pro Val Val Thr Asn Met Glu Ala Phe Ser Ser
     435                 440                 445

Glu His Phe Asn Leu Glu Ile Tyr Arg Gln Asn Leu Gln Thr Lys Gln

```
                450            455              460
Leu Gly Lys Val Ile Leu Phe Ala Glu Val Thr Pro Thr Thr Met Arg
465                 470                 475                 480

Leu Leu Asp Gly Leu Met Phe Gln Thr Pro Gln Met Gly Leu Ile
                485                 490                 495

Val Ile Ala Ala Arg Gln Thr Glu Gly Lys Gly Arg Gly Gly Asn Val
                500                 505                 510

Trp Leu Ser Pro Val Gly Cys Ala Leu Ser Thr Leu Leu Ile Ser Ile
                515                 520                 525

Pro Leu Arg Ser Gln Leu Gly Gln Arg Ile Pro Phe Val Gln His Leu
                530                 535                 540

Met Ser Val Ala Val Val Glu Ala Val Arg Ser Ile Pro Glu Tyr Gln
545                 550                 555                 560

Asp Ile Asn Leu Arg Val Lys Trp Pro Asn Asp Ile Tyr Tyr Ser Asp
                565                 570                 575

Leu Met Lys Ile Gly Gly Val Leu Val Asn Ser Thr Leu Met Gly Glu
                580                 585                 590

Thr Phe Tyr Ile Leu Ile Gly Cys Gly Phe Asn Val Thr Asn Ser Asn
                595                 600                 605

Pro Thr Ile Cys Ile Asn Asp Leu Ile Thr Glu Tyr Asn Lys Gln His
                610                 615                 620

Lys Ala Glu Leu Lys Pro Leu Arg Ala Asp Tyr Leu Ile Ala Arg Val
625                 630                 635                 640

Val Thr Val Leu Glu Lys Leu Ile Lys Glu Phe Gln Asp Lys Gly Pro
                645                 650                 655

Asn Ser Val Leu Pro Leu Tyr Tyr Arg Tyr Trp Val His Ser Gly Gln
                660                 665                 670

Gln Val His Leu Gly Ser Ala Glu Gly Pro Lys Val Ser Ile Val Gly
                675                 680                 685

Leu Asp Asp Ser Gly Phe Leu Gln Val His Gln Glu Gly Gly Glu Val
                690                 695                 700

Val Thr Val His Pro Asp Gly Asn Ser Phe Asp Met Leu Arg Asn Leu
705                 710                 715                 720

Ile Leu Pro Lys Arg Arg
                725

<210> SEQ ID NO 129
<211> LENGTH: 873
<212> TYPE: PRT
<213> ORGANISM: Homo sapiens

<400> SEQUENCE: 129

Met Leu Ile Thr Leu Cys Tyr Leu Tyr Leu Trp Ala Arg Trp Gly Arg
1               5                   10                  15

Arg Pro Ala Glu Leu Val Arg Ala Thr Val Arg Arg Leu Arg Ala Ser
                20                  25                  30

Arg Cys Ser Phe Thr Phe Cys Gly Ala Ala Gln Pro Pro Gly Ala
                35                  40                  45

Arg Val Cys Leu Ser Arg Gly Gly Arg Val Phe Cys Val Ser Asp Ser
50                  55                  60

Gln Ser Ile Glu Asp Leu Asn Lys Trp Ala Leu Phe Leu Val Ser Pro
65                  70                  75                  80

Phe Ile Leu Glu Ala Glu His Ile Ala Phe Val Thr Glu Ser Ile Trp
                85                  90                  95
```

```
Val Gln Ser Glu Asn Leu Gln Arg Ser Ser Ser Glu Thr Ile Val
            100                 105                 110

Lys Trp Ser Asp Cys Cys Leu Pro Leu Ala Cys Arg Pro Gly Asp Pro
        115                 120                 125

Tyr Arg Leu Ile Ala Glu Ala Ser Val Asp Asn Phe Ser Lys Leu Gly
        130                 135                 140

Val Ala Phe Met Glu Asp Arg Leu His Met Asp Asn Gly Leu Val Pro
145                 150                 155                 160

Gln Lys Ile Val Ser Val His Leu Gln Asp Ser Thr Leu Lys Glu Val
                165                 170                 175

Lys Asp Gln Val Ser Asn Lys Gln Ala Gln Ile Leu Glu Pro Lys Pro
            180                 185                 190

Glu Pro Ser Leu Glu Ile Lys Pro Glu Gln Asp Gly Met Glu His Val
            195                 200                 205

Gly Arg Asp Asp Pro Lys Ala Leu Gly Glu Glu Pro Lys Gln Arg Arg
        210                 215                 220

Gly Ser Ala Ser Gly Ser Glu Pro Ala Gly Asp Ser Asp Arg Gly Gly
225                 230                 235                 240

Gly Pro Val Glu His Tyr His Leu His Leu Ser Ser Cys His Glu Cys
                245                 250                 255

Leu Glu Leu Glu Asn Ser Thr Ile Glu Ser Val Lys Phe Ala Ser Ala
            260                 265                 270

Glu Asn Ile Pro Asp Leu Pro Tyr Asp Tyr Ser Ser Leu Glu Ser
            275                 280                 285

Val Ala Asp Glu Thr Ser Pro Glu Arg Glu Gly Arg Arg Val Asn Leu
            290                 295                 300

Thr Gly Lys Ala Pro Asn Ile Leu Leu Tyr Val Gly Ser Asp Ser Gln
305                 310                 315                 320

Glu Ala Leu Gly Arg Phe His Glu Val Arg Ser Val Leu Ala Asp Cys
                325                 330                 335

Val Asp Ile Asp Ser Tyr Ile Leu Tyr His Leu Leu Glu Asp Ser Ala
            340                 345                 350

Leu Arg Asp Pro Trp Thr Asp Asn Cys Leu Leu Leu Val Ile Ala Thr
            355                 360                 365

Arg Glu Ser Ile Pro Glu Asp Leu Tyr Gln Lys Phe Met Ala Tyr Leu
            370                 375                 380

Ser Gln Gly Gly Lys Val Leu Gly Leu Ser Ser Ser Phe Thr Phe Gly
385                 390                 395                 400

Gly Phe Gln Val Thr Ser Lys Gly Ala Leu His Lys Thr Val Gln Asn
                405                 410                 415

Leu Val Phe Ser Lys Ala Asp Gln Ser Glu Val Lys Leu Ser Val Leu
            420                 425                 430

Ser Ser Gly Cys Arg Tyr Gln Glu Gly Pro Val Arg Leu Ser Pro Gly
        435                 440                 445

Arg Leu Gln Gly His Leu Glu Asn Glu Asp Lys Asp Arg Met Ile Val
        450                 455                 460

His Val Pro Phe Gly Thr Arg Gly Gly Glu Ala Val Leu Cys Gln Val
465                 470                 475                 480

His Leu Glu Leu Pro Pro Ser Ser Asn Ile Val Gln Thr Pro Glu Asp
                485                 490                 495

Phe Asn Leu Leu Lys Ser Ser Asn Phe Arg Arg Tyr Glu Val Leu Arg
            500                 505                 510

Glu Ile Leu Thr Thr Leu Gly Leu Ser Cys Asp Met Lys Gln Val Pro
```

```
            515                 520                 525
Ala Leu Thr Pro Leu Tyr Leu Leu Ser Ala Ala Glu Glu Ile Arg Asp
    530                 535                 540

Pro Leu Met Gln Trp Leu Gly Lys His Val Asp Ser Glu Gly Glu Ile
545                 550                 555                 560

Lys Ser Gly Gln Leu Ser Leu Arg Phe Val Ser Ser Tyr Val Ser Glu
                565                 570                 575

Val Glu Ile Thr Pro Ser Cys Ile Pro Val Val Thr Asn Met Glu Ala
            580                 585                 590

Phe Ser Ser Glu His Phe Asn Leu Glu Ile Tyr Arg Gln Asn Leu Gln
        595                 600                 605

Thr Lys Gln Leu Gly Lys Val Ile Leu Phe Ala Glu Val Thr Pro Thr
    610                 615                 620

Thr Met Arg Leu Leu Asp Gly Leu Met Phe Gln Thr Pro Gln Glu Met
625                 630                 635                 640

Gly Leu Ile Val Ile Ala Ala Arg Gln Thr Glu Gly Lys Gly Arg Gly
                645                 650                 655

Gly Asn Val Trp Leu Ser Pro Val Gly Cys Ala Leu Ser Thr Leu Leu
            660                 665                 670

Ile Ser Ile Pro Leu Arg Ser Gln Leu Gly Gln Arg Ile Pro Phe Val
        675                 680                 685

Gln His Leu Met Ser Val Ala Val Val Glu Ala Val Arg Ser Ile Pro
    690                 695                 700

Glu Tyr Gln Asp Ile Asn Leu Arg Val Lys Trp Pro Asn Asp Ile Tyr
705                 710                 715                 720

Tyr Ser Asp Leu Met Lys Ile Gly Gly Val Leu Val Asn Ser Thr Leu
                725                 730                 735

Met Gly Glu Thr Phe Tyr Ile Leu Ile Gly Cys Gly Phe Asn Val Thr
            740                 745                 750

Asn Ser Asn Pro Thr Ile Cys Ile Asn Asp Leu Ile Thr Glu Tyr Asn
        755                 760                 765

Lys Gln His Lys Ala Glu Leu Lys Pro Leu Arg Ala Asp Tyr Leu Ile
    770                 775                 780

Ala Arg Val Val Thr Val Leu Glu Lys Leu Ile Lys Glu Phe Gln Asp
785                 790                 795                 800

Lys Gly Pro Asn Ser Val Leu Pro Leu Tyr Tyr Arg Tyr Trp Val His
                805                 810                 815

Ser Gly Gln Gln Val His Leu Gly Ser Ala Glu Gly Pro Lys Val Ser
            820                 825                 830

Ile Val Gly Leu Asp Asp Ser Gly Phe Leu Gln Val His Gln Glu Gly
        835                 840                 845

Gly Glu Val Val Thr Val His Pro Asp Gly Asn Ser Phe Asp Met Leu
    850                 855                 860

Arg Asn Leu Ile Leu Pro Lys Arg Arg
865                 870

<210> SEQ ID NO 130
<211> LENGTH: 726
<212> TYPE: PRT
<213> ORGANISM: Homo sapiens

<400> SEQUENCE: 130

Met Glu Asp Arg Leu His Met Asp Asn Gly Leu Val Pro Gln Lys Ile
1               5                   10                  15
```

-continued

```
Val Ser Val His Leu Gln Asp Ser Thr Leu Lys Glu Val Lys Asp Gln
            20                  25                  30

Val Ser Asn Lys Gln Ala Gln Ile Leu Glu Pro Lys Pro Glu Pro Ser
        35                  40                  45

Leu Glu Ile Lys Pro Glu Gln Asp Gly Met Glu His Val Gly Arg Asp
    50                  55                  60

Asp Pro Lys Ala Leu Gly Glu Pro Lys Gln Arg Arg Gly Ser Ala
65                  70                  75                  80

Ser Gly Ser Glu Pro Ala Gly Asp Ser Asp Arg Gly Gly Pro Val
            85                  90                  95

Glu His Tyr His Leu His Leu Ser Ser Cys His Glu Cys Leu Glu Leu
            100                 105                 110

Glu Asn Ser Thr Ile Glu Ser Val Lys Phe Ala Ser Ala Glu Asn Ile
        115                 120                 125

Pro Asp Leu Pro Tyr Asp Tyr Ser Ser Ser Leu Glu Ser Val Ala Asp
    130                 135                 140

Glu Thr Ser Pro Glu Arg Glu Gly Arg Arg Val Asn Leu Thr Gly Lys
145                 150                 155                 160

Ala Pro Asn Ile Leu Leu Tyr Val Gly Ser Asp Ser Gln Glu Ala Leu
            165                 170                 175

Gly Arg Phe His Glu Val Arg Ser Val Leu Ala Asp Cys Val Asp Ile
        180                 185                 190

Asp Ser Tyr Ile Leu Tyr His Leu Leu Glu Asp Ser Ala Leu Arg Asp
    195                 200                 205

Pro Trp Thr Asp Asn Cys Leu Leu Leu Val Ile Ala Thr Arg Glu Ser
210                 215                 220

Ile Pro Glu Asp Leu Tyr Gln Lys Phe Met Ala Tyr Leu Ser Gln Gly
225                 230                 235                 240

Gly Lys Val Leu Gly Leu Ser Ser Ser Phe Thr Phe Gly Gly Phe Gln
            245                 250                 255

Val Thr Ser Lys Gly Ala Leu His Lys Thr Val Gln Asn Leu Val Phe
        260                 265                 270

Ser Lys Ala Asp Gln Ser Glu Val Lys Leu Ser Val Leu Ser Ser Gly
    275                 280                 285

Cys Arg Tyr Gln Glu Gly Pro Val Arg Leu Ser Pro Gly Arg Leu Gln
    290                 295                 300

Gly His Leu Glu Asn Glu Asp Lys Asp Arg Met Ile Val His Val Pro
305                 310                 315                 320

Phe Gly Thr Arg Gly Gly Glu Ala Val Leu Cys Gln Val His Leu Glu
            325                 330                 335

Leu Pro Pro Ser Ser Asn Ile Val Gln Thr Pro Glu Asp Phe Asn Leu
        340                 345                 350

Leu Lys Ser Ser Asn Phe Arg Arg Tyr Glu Val Leu Arg Glu Ile Leu
    355                 360                 365

Thr Thr Leu Gly Leu Ser Cys Asp Met Lys Gln Val Pro Ala Leu Thr
370                 375                 380

Pro Leu Tyr Leu Leu Ser Ala Ala Glu Glu Ile Arg Asp Pro Leu Met
385                 390                 395                 400

Gln Trp Leu Gly Lys His Val Asp Ser Glu Gly Glu Ile Lys Ser Gly
            405                 410                 415

Gln Leu Ser Leu Arg Phe Val Ser Ser Tyr Val Ser Glu Val Glu Ile
        420                 425                 430

Thr Pro Ser Cys Ile Pro Val Val Thr Asn Met Glu Ala Phe Ser Ser
```

435                 440                 445
Glu His Phe Asn Leu Glu Ile Tyr Arg Gln Asn Leu Gln Thr Lys Gln
    450                 455                 460

Leu Gly Lys Val Ile Leu Phe Ala Glu Val Thr Pro Thr Thr Met Arg
465                 470                 475                 480

Leu Leu Asp Gly Leu Met Phe Gln Thr Pro Gln Glu Met Gly Leu Ile
                485                 490                 495

Val Ile Ala Ala Arg Gln Thr Glu Gly Lys Gly Arg Gly Gly Asn Val
            500                 505                 510

Trp Leu Ser Pro Val Gly Cys Ala Leu Ser Thr Leu Leu Ile Ser Ile
        515                 520                 525

Pro Leu Arg Ser Gln Leu Gly Gln Arg Ile Pro Phe Val Gln His Leu
    530                 535                 540

Met Ser Val Ala Val Val Glu Ala Val Arg Ser Ile Pro Glu Tyr Gln
545                 550                 555                 560

Asp Ile Asn Leu Arg Val Lys Trp Pro Asn Asp Ile Tyr Tyr Ser Asp
                565                 570                 575

Leu Met Lys Ile Gly Gly Val Leu Val Asn Ser Thr Leu Met Gly Glu
            580                 585                 590

Thr Phe Tyr Ile Leu Ile Gly Cys Gly Phe Asn Val Thr Asn Ser Asn
        595                 600                 605

Pro Thr Ile Cys Ile Asn Asp Leu Ile Thr Glu Tyr Asn Lys Gln His
    610                 615                 620

Lys Ala Glu Leu Lys Pro Leu Arg Ala Asp Tyr Leu Ile Ala Arg Val
625                 630                 635                 640

Val Thr Val Leu Glu Lys Leu Ile Lys Glu Phe Gln Asp Lys Gly Pro
                645                 650                 655

Asn Ser Val Leu Pro Leu Tyr Tyr Arg Tyr Trp Val His Ser Gly Gln
            660                 665                 670

Gln Val His Leu Gly Ser Ala Glu Gly Pro Lys Val Ser Ile Val Gly
        675                 680                 685

Leu Asp Asp Ser Gly Phe Leu Gln Val His Gln Glu Gly Gly Glu Val
    690                 695                 700

Val Thr Val His Pro Asp Gly Asn Ser Phe Asp Met Leu Arg Asn Leu
705                 710                 715                 720

Ile Leu Pro Lys Arg Arg
                725

<210> SEQ ID NO 131
<211> LENGTH: 726
<212> TYPE: PRT
<213> ORGANISM: Homo sapiens

<400> SEQUENCE: 131

Met Glu Asp Arg Leu His Met Asp Asn Gly Leu Val Pro Gln Lys Ile
1               5                   10                  15

Val Ser Val His Leu Gln Asp Ser Thr Leu Lys Glu Val Lys Asp Gln
                20                  25                  30

Val Ser Asn Lys Gln Ala Gln Ile Leu Glu Pro Lys Pro Glu Pro Ser
            35                  40                  45

Leu Glu Ile Lys Pro Glu Gln Asp Gly Met Glu His Val Gly Arg Asp
    50                  55                  60

Asp Pro Lys Ala Leu Gly Glu Glu Pro Lys Gln Arg Arg Gly Ser Ala
65                  70                  75                  80

```
Ser Gly Ser Glu Pro Ala Gly Asp Ser Asp Arg Gly Gly Pro Val
                85                  90                  95

Glu His Tyr His Leu His Leu Ser Ser Cys His Glu Cys Leu Glu Leu
            100                 105                 110

Glu Asn Ser Thr Ile Glu Ser Val Lys Phe Ala Ser Ala Glu Asn Ile
            115                 120                 125

Pro Asp Leu Pro Tyr Asp Tyr Ser Ser Leu Glu Ser Val Ala Asp
            130             135                 140

Glu Thr Ser Pro Glu Arg Glu Gly Arg Arg Val Asn Leu Thr Gly Lys
145             150                 155                 160

Ala Pro Asn Ile Leu Leu Tyr Val Gly Ser Asp Ser Gln Glu Ala Leu
                165                 170                 175

Gly Arg Phe His Glu Val Arg Ser Val Leu Ala Asp Cys Val Asp Ile
                180                 185                 190

Asp Ser Tyr Ile Leu Tyr His Leu Leu Glu Asp Ser Ala Leu Arg Asp
            195                 200                 205

Pro Trp Thr Asp Asn Cys Leu Leu Val Ile Ala Thr Arg Glu Ser
            210                 215                 220

Ile Pro Glu Asp Leu Tyr Gln Lys Phe Met Ala Tyr Leu Ser Gln Gly
225             230                 235                 240

Gly Lys Val Leu Gly Leu Ser Ser Phe Thr Phe Gly Gly Phe Gln
                245                 250                 255

Val Thr Ser Lys Gly Ala Leu His Lys Thr Val Gln Asn Leu Val Phe
            260                 265                 270

Ser Lys Ala Asp Gln Ser Glu Val Lys Leu Ser Val Leu Ser Ser Gly
            275                 280                 285

Cys Arg Tyr Gln Glu Gly Pro Val Arg Leu Ser Pro Gly Arg Leu Gln
290             295                 300

Gly His Leu Glu Asn Glu Asp Lys Asp Arg Met Ile Val His Val Pro
305             310                 315                 320

Phe Gly Thr Arg Gly Gly Glu Ala Val Leu Cys Gln Val His Leu Glu
            325                 330                 335

Leu Pro Pro Ser Ser Asn Ile Val Gln Thr Pro Glu Asp Phe Asn Leu
            340                 345                 350

Leu Lys Ser Ser Asn Phe Arg Arg Tyr Glu Val Leu Arg Glu Ile Leu
            355                 360                 365

Thr Thr Leu Gly Leu Ser Cys Asp Met Lys Gln Val Pro Ala Leu Thr
            370                 375                 380

Pro Leu Tyr Leu Leu Ser Ala Ala Glu Glu Ile Arg Asp Pro Leu Met
385             390                 395                 400

Gln Trp Leu Gly Lys His Val Asp Ser Glu Gly Glu Ile Lys Ser Gly
                405                 410                 415

Gln Leu Ser Leu Arg Phe Val Ser Ser Tyr Val Ser Glu Val Glu Ile
            420                 425                 430

Thr Pro Ser Cys Ile Pro Val Val Thr Asn Met Glu Ala Phe Ser Ser
            435                 440                 445

Glu His Phe Asn Leu Glu Ile Tyr Arg Gln Asn Leu Gln Thr Lys Gln
            450                 455                 460

Leu Gly Lys Val Ile Leu Phe Ala Glu Val Thr Pro Thr Thr Met Arg
465             470                 475                 480

Leu Leu Asp Gly Leu Met Phe Gln Thr Pro Gln Glu Met Gly Leu Ile
                485                 490                 495

Val Ile Ala Ala Arg Gln Thr Glu Gly Lys Gly Arg Gly Gly Asn Val
```

```
                500                 505                 510
Trp Leu Ser Pro Val Cys Ala Leu Ser Thr Leu Leu Ile Ser Ile
        515                 520                 525
Pro Leu Arg Ser Gln Leu Gly Gln Arg Ile Pro Phe Val Gln His Leu
        530                 535                 540
Met Ser Val Ala Val Val Glu Ala Val Arg Ser Ile Pro Glu Tyr Gln
545                 550                 555                 560
Asp Ile Asn Leu Arg Val Lys Trp Pro Asn Asp Ile Tyr Tyr Ser Asp
                565                 570                 575
Leu Met Lys Ile Gly Gly Val Leu Val Asn Ser Thr Leu Met Gly Glu
                580                 585                 590
Thr Phe Tyr Ile Leu Ile Gly Cys Gly Phe Asn Val Thr Asn Ser Asn
                595                 600                 605
Pro Thr Ile Cys Ile Asn Asp Leu Ile Thr Glu Tyr Asn Lys Gln His
        610                 615                 620
Lys Ala Glu Leu Lys Pro Leu Arg Ala Asp Tyr Leu Ile Ala Arg Val
625                 630                 635                 640
Val Thr Val Leu Glu Lys Leu Ile Lys Glu Phe Gln Asp Lys Gly Pro
                645                 650                 655
Asn Ser Val Leu Pro Leu Tyr Tyr Arg Tyr Trp Val His Ser Gly Gln
                660                 665                 670
Gln Val His Leu Gly Ser Ala Glu Gly Pro Lys Val Ser Ile Val Gly
        675                 680                 685
Leu Asp Asp Ser Gly Phe Leu Gln Val His Gln Glu Gly Gly Glu Val
        690                 695                 700
Val Thr Val His Pro Asp Gly Asn Ser Phe Asp Met Leu Arg Asn Leu
705                 710                 715                 720
Ile Leu Pro Lys Arg Arg
                725

<210> SEQ ID NO 132
<211> LENGTH: 726
<212> TYPE: PRT
<213> ORGANISM: Homo sapiens

<400> SEQUENCE: 132

Met Glu Asp Arg Leu His Met Asp Asn Gly Leu Val Pro Gln Lys Ile
1               5                   10                  15
Val Ser Val His Leu Gln Asp Ser Thr Leu Lys Glu Val Lys Asp Gln
                20                  25                  30
Val Ser Asn Lys Gln Ala Gln Ile Leu Glu Pro Lys Pro Glu Pro Ser
            35                  40                  45
Leu Glu Ile Lys Pro Gln Asp Gly Met Glu His Val Gly Arg Asp
        50                  55                  60
Asp Pro Lys Ala Leu Gly Glu Glu Pro Lys Gln Arg Arg Gly Ser Ala
65                  70                  75                  80
Ser Gly Ser Glu Pro Ala Gly Asp Ser Asp Arg Gly Gly Pro Val
                85                  90                  95
Glu His Tyr His Leu His Leu Ser Ser Cys His Glu Cys Leu Glu Leu
            100                 105                 110
Glu Asn Ser Thr Ile Glu Ser Val Lys Phe Ala Ser Ala Glu Asn Ile
        115                 120                 125
Pro Asp Leu Pro Tyr Asp Tyr Ser Ser Ser Leu Glu Ser Val Ala Asp
    130                 135                 140
```

-continued

```
Glu Thr Ser Pro Glu Arg Glu Gly Arg Arg Val Asn Leu Thr Gly Lys
145                 150                 155                 160

Ala Pro Asn Ile Leu Leu Tyr Val Gly Ser Asp Ser Gln Glu Ala Leu
            165                 170                 175

Gly Arg Phe His Glu Val Arg Ser Val Leu Ala Asp Cys Val Asp Ile
            180                 185                 190

Asp Ser Tyr Ile Leu Tyr His Leu Glu Asp Ser Ala Leu Arg Asp
        195                 200                 205

Pro Trp Thr Asp Asn Cys Leu Leu Val Ile Ala Thr Arg Glu Ser
    210                 215                 220

Ile Pro Glu Asp Leu Tyr Gln Lys Phe Met Ala Tyr Leu Ser Gln Gly
225                 230                 235                 240

Gly Lys Val Leu Gly Leu Ser Ser Phe Thr Phe Gly Gly Phe Gln
            245                 250                 255

Val Thr Ser Lys Gly Ala Leu His Lys Thr Val Gln Asn Leu Val Phe
            260                 265                 270

Ser Lys Ala Asp Gln Ser Glu Val Lys Leu Ser Val Leu Ser Ser Gly
            275                 280                 285

Cys Arg Tyr Gln Glu Gly Pro Val Arg Leu Ser Pro Gly Arg Leu Gln
            290                 295                 300

Gly His Leu Glu Asn Glu Asp Lys Asp Arg Met Ile Val His Val Pro
305                 310                 315                 320

Phe Gly Thr Arg Gly Gly Glu Ala Val Leu Cys Gln Val His Leu Glu
            325                 330                 335

Leu Pro Pro Ser Ser Asn Ile Val Gln Thr Pro Glu Asp Phe Asn Leu
            340                 345                 350

Leu Lys Ser Ser Asn Phe Arg Arg Tyr Glu Val Leu Arg Glu Ile Leu
            355                 360                 365

Thr Thr Leu Gly Leu Ser Cys Asp Met Lys Gln Val Pro Ala Leu Thr
            370                 375                 380

Pro Leu Tyr Leu Leu Ser Ala Ala Glu Glu Ile Arg Asp Pro Leu Met
385                 390                 395                 400

Gln Trp Leu Gly Lys His Val Asp Ser Glu Gly Glu Ile Lys Ser Gly
            405                 410                 415

Gln Leu Ser Leu Arg Phe Val Ser Ser Tyr Val Ser Glu Val Glu Ile
            420                 425                 430

Thr Pro Ser Cys Ile Pro Val Val Thr Asn Met Glu Ala Phe Ser Ser
            435                 440                 445

Glu His Phe Asn Leu Glu Ile Tyr Arg Gln Asn Leu Gln Thr Lys Gln
            450                 455                 460

Leu Gly Lys Val Ile Leu Phe Ala Glu Val Thr Pro Thr Thr Met Arg
465                 470                 475                 480

Leu Leu Asp Gly Leu Met Phe Gln Thr Pro Gln Glu Met Gly Leu Ile
            485                 490                 495

Val Ile Ala Ala Arg Gln Thr Glu Gly Lys Gly Arg Gly Gly Asn Val
            500                 505                 510

Trp Leu Ser Pro Val Gly Cys Ala Leu Ser Thr Leu Leu Ile Ser Ile
            515                 520                 525

Pro Leu Arg Ser Gln Leu Gly Gln Arg Ile Pro Phe Val Gln His Leu
            530                 535                 540

Met Ser Val Ala Val Val Glu Ala Val Arg Ser Ile Pro Glu Tyr Gln
545                 550                 555                 560

Asp Ile Asn Leu Arg Val Lys Trp Pro Asn Asp Ile Tyr Tyr Ser Asp
```

565                 570                 575
Leu Met Lys Ile Gly Gly Val Leu Val Asn Ser Thr Leu Met Gly Glu
            580                 585                 590

Thr Phe Tyr Ile Leu Ile Gly Cys Gly Phe Asn Val Thr Asn Ser Asn
            595                 600                 605

Pro Thr Ile Cys Ile Asn Asp Leu Ile Thr Glu Tyr Asn Lys Gln His
            610                 615                 620

Lys Ala Glu Leu Lys Pro Leu Arg Ala Asp Tyr Leu Ile Ala Arg Val
625                 630                 635                 640

Val Thr Val Leu Glu Lys Leu Ile Lys Glu Phe Gln Asp Lys Gly Pro
                645                 650                 655

Asn Ser Val Leu Pro Leu Tyr Tyr Arg Tyr Trp Val His Ser Gly Gln
                660                 665                 670

Gln Val His Leu Gly Ser Ala Glu Gly Pro Lys Val Ser Ile Val Gly
            675                 680                 685

Leu Asp Asp Ser Gly Phe Leu Gln Val His Gln Glu Gly Gly Glu Val
            690                 695                 700

Val Thr Val His Pro Asp Gly Asn Ser Phe Asp Met Leu Arg Asn Leu
705                 710                 715                 720

Ile Leu Pro Lys Arg Arg
                725

<210> SEQ ID NO 133
<211> LENGTH: 726
<212> TYPE: PRT
<213> ORGANISM: Homo sapiens

<400> SEQUENCE: 133

Met Glu Asp Arg Leu His Met Asp Asn Gly Leu Val Pro Gln Lys Ile
1               5                   10                  15

Val Ser Val His Leu Gln Asp Ser Thr Leu Lys Glu Val Lys Asp Gln
                20                  25                  30

Val Ser Asn Lys Gln Ala Gln Ile Leu Glu Pro Lys Pro Glu Pro Ser
            35                  40                  45

Leu Glu Ile Lys Pro Glu Gln Asp Gly Met Glu His Val Gly Arg Asp
        50                  55                  60

Asp Pro Lys Ala Leu Gly Glu Glu Pro Lys Gln Arg Arg Gly Ser Ala
65                  70                  75                  80

Ser Gly Ser Glu Pro Ala Gly Asp Ser Asp Arg Gly Gly Pro Val
                85                  90                  95

Glu His Tyr His Leu His Leu Ser Ser Cys His Glu Cys Leu Glu Leu
            100                 105                 110

Glu Asn Ser Thr Ile Glu Ser Val Lys Phe Ala Ser Ala Glu Asn Ile
        115                 120                 125

Pro Asp Leu Pro Tyr Asp Tyr Ser Ser Ser Leu Glu Ser Val Ala Asp
    130                 135                 140

Glu Thr Ser Pro Glu Arg Glu Gly Arg Arg Val Asn Leu Thr Gly Lys
145                 150                 155                 160

Ala Pro Asn Ile Leu Leu Tyr Val Gly Ser Asp Ser Gln Glu Ala Leu
                165                 170                 175

Gly Arg Phe His Glu Val Arg Ser Val Leu Ala Asp Cys Val Asp Ile
            180                 185                 190

Asp Ser Tyr Ile Leu Tyr His Leu Leu Glu Asp Ser Ala Leu Arg Asp
        195                 200                 205

```
Pro Trp Thr Asp Asn Cys Leu Leu Val Ile Ala Thr Arg Glu Ser
210             215                 220

Ile Pro Glu Asp Leu Tyr Gln Lys Phe Met Ala Tyr Leu Ser Gln Gly
225             230                 235                 240

Gly Lys Val Leu Gly Leu Ser Ser Phe Thr Phe Gly Gly Phe Gln
                245                 250                 255

Val Thr Ser Lys Gly Ala Leu His Lys Thr Val Gln Asn Leu Val Phe
        260                 265                 270

Ser Lys Ala Asp Gln Ser Glu Val Lys Leu Ser Val Leu Ser Ser Gly
            275                 280                 285

Cys Arg Tyr Gln Glu Gly Pro Val Arg Leu Ser Pro Gly Arg Leu Gln
290                 295                 300

Gly His Leu Glu Asn Glu Asp Lys Asp Arg Met Ile Val His Val Pro
305                 310                 315                 320

Phe Gly Thr Arg Gly Gly Glu Ala Val Leu Cys Gln Val His Leu Glu
                325                 330                 335

Leu Pro Pro Ser Ser Asn Ile Val Gln Thr Pro Glu Asp Phe Asn Leu
                340                 345                 350

Leu Lys Ser Ser Asn Phe Arg Arg Tyr Glu Val Leu Arg Glu Ile Leu
                355                 360                 365

Thr Thr Leu Gly Leu Ser Cys Asp Met Lys Gln Val Pro Ala Leu Thr
370                 375                 380

Pro Leu Tyr Leu Leu Ser Ala Ala Glu Glu Ile Arg Asp Pro Leu Met
385                 390                 395                 400

Gln Trp Leu Gly Lys His Val Asp Ser Glu Gly Glu Ile Lys Ser Gly
                405                 410                 415

Gln Leu Ser Leu Arg Phe Val Ser Ser Tyr Val Ser Glu Val Glu Ile
                420                 425                 430

Thr Pro Ser Cys Ile Pro Val Val Thr Asn Met Glu Ala Phe Ser Ser
                435                 440                 445

Glu His Phe Asn Leu Glu Ile Tyr Arg Gln Asn Leu Thr Lys Gln
    450                 455                 460

Leu Gly Lys Val Ile Leu Phe Ala Glu Val Thr Pro Thr Thr Met Arg
465                 470                 475                 480

Leu Leu Asp Gly Leu Met Phe Gln Thr Pro Gln Glu Met Gly Leu Ile
                485                 490                 495

Val Ile Ala Ala Arg Gln Thr Glu Gly Lys Gly Arg Gly Gly Asn Val
                500                 505                 510

Trp Leu Ser Pro Val Gly Cys Ala Leu Ser Thr Leu Leu Ile Ser Ile
                515                 520                 525

Pro Leu Arg Ser Gln Leu Gly Gln Arg Ile Pro Phe Val Gln His Leu
530                 535                 540

Met Ser Val Ala Val Val Glu Ala Val Arg Ser Ile Pro Glu Tyr Gln
545                 550                 555                 560

Asp Ile Asn Leu Arg Val Lys Trp Pro Asn Asp Ile Tyr Tyr Ser Asp
                565                 570                 575

Leu Met Lys Ile Gly Gly Val Leu Val Asn Ser Thr Leu Met Gly Glu
                580                 585                 590

Thr Phe Tyr Ile Leu Ile Gly Cys Gly Phe Asn Val Thr Asn Ser Asn
                595                 600                 605

Pro Thr Ile Cys Ile Asn Asp Leu Ile Thr Glu Tyr Asn Lys Gln His
610                 615                 620

Lys Ala Glu Leu Lys Pro Leu Arg Ala Asp Tyr Leu Ile Ala Arg Val
```

-continued

```
            625                 630                 635                 640
Val Thr Val Leu Glu Lys Leu Ile Lys Glu Phe Gln Asp Lys Gly Pro
                    645                     650                 655

Asn Ser Val Leu Pro Leu Tyr Tyr Arg Tyr Trp Val His Ser Gly Gln
                660                 665                 670

Gln Val His Leu Gly Ser Ala Glu Gly Pro Lys Val Ser Ile Val Gly
            675                 680                 685

Leu Asp Asp Ser Gly Phe Leu Gln Val His Gln Glu Gly Gly Glu Val
        690                 695             700

Val Thr Val His Pro Asp Gly Asn Ser Phe Asp Met Leu Arg Asn Leu
705                 710                 715                 720

Ile Leu Pro Lys Arg Arg
                725
```

CELLULAR RECEPTORS AND USES THEREOF

CROSS-REFERENCE TO RELATED APPLICATIONS

This application claims benefit under 35 U.S.C. § 119(e) of U.S. Provisional Application No. 62/972,303 filed Feb. 10, 2020 and 63/000,676 filed Mar. 27, 2020, the contents of which are incorporated herein by reference in their entirety.

GOVERNMENT SUPPORT

This invention was made with government support under Grant No. GM128859 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 9, 2021, is named 701586-097030US-PT_SL.txt and is 163,056 bytes in size.

TECHNICAL FIELD

The technology described herein relates to compositions and methods for controlling cell signaling. e.g., in CAR-T therapeutic applications.

BACKGROUND

Engineered cell surface receptors have become an essential tool in controlling cell activity in all biological applications. Whether for in vitro tissue engineering uses, or as a CAR-T therapy for cancer, such receptor technologies permit users to direct cells' activity as the user wishes. Recent years have seen various approaches that attempt to fine-tune the control of such receptors, essentially providing on and off switches for cells. However, these systems still have much room for improvement. For example, compounds occurring naturally in the human body frequently affect them, or they are not nearly as responsive as needed.

SUMMARY

Provided herein is an improvement in such receptor control. The inventors have found that by leveraging small molecules, e.g., biotinylamides in combination with reagents specific for those small molecules (e.g., the biotinylamides), they can provide strong and exquisitely tunable control of receptor activation. This technology can be applied to a wide variety of cell types and activities. This is illustrated by the following embodiments which use biotinylamides, but other small molecules are similarly applicable, as described elsewhere herein.

In one aspect of any of the embodiments, described herein is a cell surface receptor polypeptide comprising i) an extracellular domain that binds specifically to a biotinylamide. In some embodiments, the polypeptide further comprises ii) an intracellular signaling domain. In some embodiments, the polypeptide is a chimeric antigen receptor (CAR) comprising the domain that binds specifically to a biotinylamide and an intracellular signaling domain. In one aspect of any of the embodiments, described herein a system comprising a) the cell surface receptor polypeptide described herein and b) one or both of:
  i) a surface-attached molecule comprising:
    A, a binding domain specific for a target; and
    B. a biotinylamide and/or a biotin acceptor peptide; and
  ii) a soluble molecule comprising a biotinylamide and/or a biotin acceptor peptide.

In some embodiments, the soluble molecule is a small molecule or an antibody or antibody reagent. In one aspect of any of the embodiments, described herein is method of controlling signaling or activity of a first cell comprising the foregoing system, the method comprising:
  a. contacting the first cell with a surface-attached molecule comprising:
    i. a binding domain specific for a target; and
    ii. a biotinylamide and/or a biotin acceptor peptide
    to induce the signaling or activity of the first cell; and/or
  b. contacting the first cell with a soluble molecule comprising a biotinylamide and/or a biotin acceptor peptide to inhibit the signaling or activity of the first cell.

In one aspect of any of the embodiments, described herein is a first polypeptide comprising i) an extracellular biotinylamide and/or a biotin acceptor peptide and ii) a first intracellular signaling domain. In some embodiments of any of the aspects, the first polypeptide further comprises iii) an extracellular target-binding domain. In one aspect of any of the embodiments, described herein is a system comprising the foregoing first polypeptide and a second polypeptide comprising: i) an extracellular domain that binds specifically to a biotinylamide and ii) a second intracellular signaling domain. In some embodiments of any of the aspects, the first and/or second polypeptide is a CAR. In one aspect of any of the embodiments, described herein is a method of controlling signaling or activity of a first cell comprising the foregoing system, the method comprising:
  a. contacting the first cell with a soluble small molecule comprising a biotinylamide and/or a biotin acceptor peptide to inhibit the signaling or activity of the first cell.

In some embodiments of any of the aspects, the domain that binds specifically to a biotinylamide is an antibody or antibody reagent. In some embodiments of any of the aspects, the antibody reagent is a scFv. In some embodiments of any of the aspects, the antibody reagent comprises the 6 CDRs of SEQ ID NOs: 4-9. In some embodiments of any of the aspects, the antibody reagent comprises SEQ ID NOs: 1 and 2. In some embodiments of any of the aspects, the antibody reagent comprises amino acids 1-119 of SEQ ID NO: 1 and amino acids 1-117 of SEQ ID NO: 2. In some embodiments of any of the aspects, the antibody reagent comprises amino acids 1-119 of SEQ ID NO: 1 and amino acids 1-117 of SEQ ID NO: 2, joined by a peptide linker. In some embodiments of any of the aspects, the peptide linker comprises SEQ ID NO: 3. In some embodiments of any of the aspects, the domain that binds specifically to a biotinylamide binds specifically to biotinamide, biocyntinamide, and/or biocytin. In some embodiments of any of the aspects, the domain that binds specifically to a biotinylamide does not bind to biotin. In some embodiments of any of the aspects, the domain that binds specifically to a biotinylamide binds specifically as compared to binding of the domain with biotin. In some embodiments of any of the aspects, the domain that binds specifically to a biotinylamide binds specifically to biotin lacking its carboxylic acid group as compared to binding of the domain with biotin.

In some embodiments of any of the aspects, the intracellular signaling domain is a nuclear-acting signaling domain. In some embodiments of any of the aspects, the nuclear-acting signaling domain comprises a DNA-binding domain. In some embodiments of any of the aspects, the signaling domain comprises a Notch receptor signaling domain. In some embodiments of any of the aspects, the Notch receptor signaling domain comprises the Notch core. In some embodiments of any of the aspects, the intracellular signaling domain comprises a transcriptional activator. In some embodiments of any of the aspects, the transcriptional activator is GAL4-VP64.

In some embodiments of any of the aspects, one or more of the intracellular signaling domain comprises an intracellular CD28, 4-1BB, and/or CD3ζ signaling domain. In some embodiments of any of the aspects, one or more of the intracellular signaling domains comprises intracellular CD28, 4-1BB, and CD3ζ signaling domains.

In some embodiments of any of the aspects, the surface-attached molecule is bound or conjugated to the first cell, a second cell, a lipid bilayer surface, or a solid surface. In some embodiments of any of the aspects, the solid surface is a bead. In some embodiments of any of the aspects, the lipid bilayer surface is a liposome. In some embodiments of any of the aspects, the surface-attached molecule is not soluble.

In some embodiments of any of the aspects, the surface-attached molecule further comprises a binding domain specific for a target. In some embodiments of any of the aspects, the target is a cell-surface marker on a second cell and the first cell is an immune cell. In some embodiments of any of the aspects, the second cell is a cancer cell.

In some embodiments of any of the aspects, the soluble molecule comprises or is bis-biotinamide. In some embodiments of any of the aspects, the soluble molecule comprises a peptide. In some embodiments of any of the aspects, the soluble molecule comprises a peptide conjugated to a biotinylamide. In some embodiments of any of the aspects, the peptide comprises bovine sersum albumin (BSA). In some embodiments of any of the aspects, the soluble molecule comprises a polymer conjugated to a biotinylamide. In some embodiments of any of the aspects, the polymer is polyethylene glycol (PEG).

In some embodiments of any of the aspects, the signaling or activity of the first cell is immune-promoting signaling or activity. In some embodiments of any of the aspects, the first cell is an immune cell. In some embodiments of any of the aspects, the second cell is a diseased cell. In some embodiments of any of the aspects, the first cell is a T cell and the binding domain specific for a target binds a marker on the surface of a diseased cell. In some embodiments of any of the aspects, the first cell is a T cell and the binding domain specific for a target binds a marker specific to diseased cells. In some embodiments of any of the aspects, the diseased cells are cancer cells. In some embodiments of any of the aspects, the method is a method of treating a subject in need of immunotherapy.

In some embodiments of any of the aspects, method comprises a first step of administering the first cell to the subject. In some embodiments of any of the aspects, method comprises, prior to the contacting step of a), administering the first cell to the subject. In some embodiments of any of the aspects, the method comprises, prior to the contacting step of a), administering a molecule comprising:
 i. a binding domain specific for a target; and
 ii. a biotinylamide and/or a biotin acceptor peptide such that it attaches to a surface in the subject, or is administered already attached to a surface, thereby providing the surface-attached molecule.

In some embodiments of any of the aspects, the method comprises, prior to the contacting step of b), administering the soluble molecule.

In some embodiments of any of the aspects, the signaling or activity of the first cell is tissue generation or regeneration promoting signaling or activity. In some embodiments of any of the aspects, the method is a method of in vitro or in vivo tissue engineering. In some embodiments of any of the aspects, the surface-attached molecule is attached to a tissue engineering scaffold.

In one aspect of any of the embodiments, described herein is a nucleic acid or set of nucleic acids encoding the receptor, polypeptide, or system as described herein. In one aspect of any of the embodiments, described herein is a cell or set of cells comprising or encoding the receptor, polypeptide, system, or nucleic acid described herein. In some embodiments of any of the aspects, the cell further comprises or encodes biotin ligase. In some embodiments of any of the aspects, the biotin ligase is E co/i biotin ligase.

BRIEF DESCRIPTION OF THE DRAWINGS

FIG. 1A demonstrates that the apSyN is transported through the secretory pathway and is biotinylated by endoplasmic reticulum-retained BirA. FIG. 1B demonstrates that Notch signaling occurs through the binding of the receptor to a membrane localized target protein on an adjacent cell or by binding an antibody tethered to a tissue culture plate. The binding and mechanical force triggers release of the intracellular domain, a transcription factor, that activates target genes. FIG. 1C depicts Western blot of cells expressing apSyN with or without BirA. Biotinylation occurs only when cells co-express the modifying enzyme. The only new biotinylated protein is apSyN indicating BirA is specific in the ER. FIG. 1D demonstrates that apSyN biotinylated by BirA is present at the cell surface. Scale bar represents 15 μm. Anti-Myc. Streptavidin. FIG. 1E demonstrates the linear correlation of surface biotinylation with surface expression of apSyN. Expression of BirA slightly decreases the surface expression of apSyN.

FIGS. 2A-2F. FIG. 2A demonstrates that cells expressing a synthetic Notch receptor release an intracellular transcription factor when binding to an adsorbed ligand. The transcription factor drives expression of a reporter gene, such as mCherry FIG. 2B depicts reporter activation of cells expressing apSyN with or without BirA. The synthetic Notch expressing cells activate to Anti-Biotin coated wells only when co-expressed with BirA. FIG. 2C demonstrates that the surface biotin concentration of cells is dependent on the expression level of BirA. A surface stain with Streptavidin displays a bimodal population. FIG. 2D depicts increased expression level of BirA through doxycyline control causes an increased population that can respond to Anti-Biotin coated wells. [1000] represents a sample plated on a well not coated with antibody. FIG. 2E demonstrates that the expression of BirA can be dependent on other synthetic biology tools, such as a grazoprevir inducible system based on NS3 protease. FIG. 2F demonstrates that apSyN expressing cells that contain a Tre3G promoter driving expression of BirA and transfected with TetR-NS3-VP64 activate to a greater extent when cultured with 5 μm Grazoprevir.

FIGS. 3A-3F. FIG. 3A depicts a cell line that expresses a cell surface ligand specific for biotinamide can activate the apSyN dependent on the biotinylation state. FIG. 3B depicts live cell immunofluorescence images of cocultures between receptor expressing cells (BFP labeled nuclei), and ligand expressing cells (benzylguanine-AF647). Reporter activation in magenta. FIG. 3C demonstrates that anti-Biotin ligand expressing cells induce synthetic Notch signaling in cocultures only when apSyN is co-expressed with BirA. GSI—gamma secretase inhibitor, DAPT. FIG. 3D demonstrates that bis-biotinamide and biocytin act as inhibitors of signaling through competitive binding to the ligand. Bis-biotinamide inhibits more effectively via cooperative binding. FIG. 3E demonstrates that a genetically encoded inhibitor of biotinylation dependent signaling is accomplished via cis-inhibition—expressing Anti-Biotin ligands in the receptor cells. FIG. 3F demonstrates that when the cis-ligand is coexpressed with apSyN, the receptor loses the ability to activate to trans Anti-Biotin ligand expressing cells.

FIG. 4A-4D. FIG. 4A demonstrates that receptors that are specific to biotinamide are able to process input dependent on the biotinylation state of the ligand. FIG. 4B demonstrates that anti-Biotin SynNotch expressing cells are able to activate to both biotin-based and desthiobiotin-based substrates. The cells activate with slightly less adsorbed biotin than desthiobiotin. FIG. 4C demonstrates that biocytin can inhibit gene activation through competitive binding to the receptor. Biotin inhibits at greater concentrations. FIG. 4D demonstrates that biotinylated secreted proteins can act as a bridge to mediate signaling between receptor expressing cells and ligand expressing cells when a biotin-binding protein is used.

FIG. 5A demonstrates that cells expressing apSyN are activated to wells adsorbed with an antibody against myc tag. FIG. 5B demonstrates that adsorbed Neutravidin is able to activate apSyN cells, but has decreased activation at higher concentrations. FIG. 5C demonstrates that bulk apSyN is further biotinylated with greater expression of BirA, accomplished with greater mass of DNA transfected.

FIG. 6A demonstrates that apSyN cells co-expressing BirA that are not in contact with Anti-Biotin ligand expressing cells. The cells do not express mCherry. The scale bar is 20 µm. FIG. 6B demonstrates that biotinylated GFP is able to allow activation between Anti-GFP SynNotch expressing cells and Anti-Biotin ligand expressing cells. GFP containing a mutated form of the acceptor peptide is not able to be biotinylated and does not allow cell activation.

FIGS. 7A-7D. FIG. 7A demonstrates that biotinidase-Resistant biotin conjugated BSA is able to activate Anti-Biotin Synthetic Notch expressing cells. FIG. 7B demonstrates that biocytin is able to inhibit activation of Anti-Biotin Synthetic Notch expressing cells on adsorbed desthiobiotin-BSA. FIG. 7C demonstrates the HEK293 cells do not stain positive for EGFR, while A431 cells do. The scale bar is 20 µm. FIG. 7D demonstrates that cells expressing EgA1 Synthetic Notch are activated by coculture with cells overexpressing EGFR, A431 cells.

FIG. 8A. Forward scatter vs. Side scatter gate for HEK cells. FIG. 8B. Forward scatter (Height) vs. Forward scatter (Width) for singlet detection. FIG. 8C. Gating scheme for fluorescent proteins.

FIGS. 9A-9C. FIG. 9A demonstrates that acceptor peptide synthetic Notch is biotinylated by a golgi-localized BirA. FIG. 9B depicts a Western blot probing for myc shows synthetic Notch expression with and without BirA. FIG. 9C demonstrates non-transfected control of staining with an anti-myc antibody and Streptavidin.

(FIG. 11A) The AP-SynNotch is transported through the secretory pathway and is biotinylated by luminal BirA. (FIG. 11B). Western blot of cells expressing AP-SynNotch with or without BirA. Biotinylation occurs only when cells co-express the modifying enzyme, which is either localized to the endoplasmic reticulum (BirA-KDEL) or the Golgi apparatus (GalT-BirA). The only new biotinylated protein is AP-SynNotch indicating BirA is specific to the receptor in the secretory pathway. (FIG. 11C). Linear correlation of surface biotinylation with surface expression of AP-SynNotch when coexpressed with BirA. When cells are not transfected with BirA, there is little Streptavidin signal. (FIG. 11D). Cells expressing a SynNotch receptor release an intracellular transcription factor when binding to an adsorbed ligand. The transcription factor drives expression of a reporter gene, such as mCherry (FIG. 11E). Reporter activation of cells expressing AP-SynNotch with or without BirA. The AP-SynNotch expressing cells activate to Anti-Biotin coated wells only when co-expressed with BirA. (FIG. 11F). The surface biotin concentration of cells is dependent on the expression level of BirA, controlled through a doxycycline dependent transcription factor. A surface stain with Streptavidin displays a bimodal population. (FIG. 11G). Increased expression level of BirA through doxycycline control causes an increased population that activates to Anti-Biotin coated wells. (FIG. 11H). The expression of BirA can be dependent on other synthetic biology tools, such as a grazoprevir inducible system based on NS3 protease. (FIG. 11I). AP-SynNotch expressing cells that contain a TRE3G promoter driving expression of BirA and transfected with TetR-NS3-VP64 activate to a greater extent when cultured with 5 µM grazoprevir.

(FIG. 12A). A cell line that expresses a cell surface ligand specific for biotinamide can activate the AP-SynNotch dependent on the biotinylation state. (FIG. 12B). Live cell immunofluorescence images of cocultures between receptor expressing cells (BFP labeled nuclei), and ligand expressing cells (benzylguanine-AF647). Reporter activation in magenta. (FIG. 12C).

Increased magnification of FIG. 12B shows cell-cell interaction between receptor and ligand expressing cells. (FIG. 12D). Anti-Biotinamide ligand expressing cells induce synthetic Notch signaling in cocultures only when AP-Syn-Notch is co-expressed with BirA. GSI—gamma secretase inhibitor, DAPT. (FIG. 12E). A genetically encoded inhibitor of biotinylation dependent signaling is accomplished via cis-inhibition—expressing Anti-Biotinamide ligands in the receptor cells. (FIG. 12F). When the cis-ligand is coexpressed with AP-SynNotch, the receptor loses the ability to activate to trans Anti-Biotinamide ligand expressing cells. (FIG. 12G). Competitive binding of the ligand via biotinylated molecules can achieve pathway specific inhibition. (1) biotin. (2) biocytin. (3) bis-biotinamide (FIG. 12H). Bis-biotinamide and biocytin act as inhibitors of signaling through competitive binding to the cell-surface ligand. Bis-biotinamide inhibits more effectively via cooperative binding.

(FIG. 13A). Receptors that are specific to biotinamide process inputs dependent on the biotinylation state of the ligand. (FIG. 13B). Anti-Biotinamide SynNotch expressing cells activate to both biotin-based and desthio-biotin-based substrates. The cells activate with slightly less adsorbed biotin than desthiobiotin. (FIG. 13C). Cells expressing Anti-Biotinamide SynNotch were cocultured with cells transfected with an AP-tagged cell surface ligand with or without BirA, or non-transfected cells. (FIG. 13D). Biotin-tetrazine (4) is a bispecific molecule that will bind to the Anti-Biotinamide antibody fragment and TCO-(5), which is conjugated to BSA. (FIG. 13E). Anti-Biotinamide SynNotch expressing cells cultured on TCO-conjugated BSA will bind to exogenously added biotin-tetrazine. (FIG. 13F). Anti-Biotinamide SynNotch expressing cells were cultured on wells coated with TCO-BSA and one day later, biotin-tetrazine was added at different concentrations to the wells. At two days after plating, cellular fluorescence was analyzed with flow cytometry.

(FIG. 14A) The localization of the Anti-Biotinamide scFAB depends on the biotinylation of a mitochondrial-targeted AP fusion protein. (FIG. 14B). U2OS cells were transfected with a construct containing TOM20-mTurquoise2-AP and Anti-Biotinamide scFAB and contransfected either with Citrine-BirA or Citrine. Cells that expressed BirA had distinct mitochondrial localization of the Anti-Biotinamide scFAB. (FIG. 14C). Pearson's Correlations were obtained for 10 images in both cases. Each image was masked for Citrine expression before processing. (FIG. 14D). HEK293 cells were transfected with T3G:mTurquoise2 and TetR-AP (DNA Binding Domain, DBD), Anti-Biotinamide scFAB-p65-RTA (Activating Domain, AD), or both in the presence or absence of BirA. (FIG. 14E). Binding of the Anti-Biotinamide scFAB with biotinamide can be competitively inhibited by the addition of biotin-cadaverine, a cell permeant biotinamide. (FIG. 14F). HEK293 with a UAS:H2B-mCherry reporter were transfected with a construct containing AP-VP64 and Anti-Biotinamide scFAB-Gal4 in the presence or absence of BirA. Cells co-transfected with BirA were treated with 20 µM of biotin-cadaverine.

FIGS. 15A-15G demonstrate that AP-SynNotch is biotinylated by BirA residing in the secretory pathway and activates downstream gene expression when binding to tethered ligands. (FIG. 15A). Uncropped and unadjusted Western Blot for HEK293 cells expressing AP-SynNotch (Well 2), and co-expressing BirA-KDEL (Well 3) or GalT-BirA (Well 4). Non-transfected is Well 1. The Western Blot was probed with Streptavidin-HRP. (FIG. 15B). Uncropped and unadjusted Western Blot for HEK293 cells expressing AP-SynNotch (Well 2), and co-expressing BirA-KDEL (Well 3) or GalT-BirA (Well 4). Non-transfected is Well 1. The Westernc. AP-SynNotch is biotinylated by BirA-KDEL and presented at the cell surface. (FIG. 15D) Non-transduced HEK293 cells were probed with Streptavidin Cy5 and Anti-Myc AF555 and the fluorescence was quantified via flow cytometry. (FIG. 15E). AP-SynNotch expressing cells were cultured on wells coated with different concentrations of Anti-Myc antibody. f. AP-SynNotch expressing cells co-expressing BirA-KDEL were cultured on wells coated with different concentrations of Neutravidin. (FIG. 15G). HEK293 cells were transfected with a construct containing AP-SynNotch at 10 ng per well and co-transfected with different amounts of a construct containing BirA-KDEL Blot was probed with Anti-Myc-HRP.

(FIG. 16A). AP-SynNotch expressing cells that co-express BirA-KDEL and nuclear BFP do not trigger activation of downstream mCherry expression when they are not interacting with Anti-Biotinamide ligand expressing cells. (FIG. 16B). AP-SynNotch cells, which contain an extracellular Anti-GFP nanobody, were cocultured with Anti-Biotinamide ligand expressing cells. Purified GFP, either containing AP or a mutated AP sequence in which the modified lysine and its adjacent residues were mutated to alanine (GLNDIFEAAAAEWHE (SEQ ID NO: 116)), which was expressed in a BirA expressing *E. coli* strain, was added to wells at different concentrations.

(FIG. 17A). Biotinidase-resistant biotin-NHS ester was conjugated to BSA. The ethyl group adjacent to the amide group of biotinamide prevents the hydrolysis and release of biotin by Biotinidase. (FIG. 17B). Anti-biotinamide SynNotch expressing cells are activated when cultured on wells coated with Biotindase-resistant (br) biotin-conjugated BSA. (FIG. 17C). Wells coated with photocleavable-biotin conjugated BSA were either subjected to 30 minutes of 400 nm light or not. Anti-biotinamide SynNotch cells cultured on wells subjected to light activated to a lesser extent to those that had not. (FIG. 17D). Anti-biotinamide SynNotch expressing cells cultured on biotin-BSA were cultured at time of plating with different concentrations of biotin and biocytin. Biocytin is more effective at competitively inhibiting the antibody fragment.

(FIG. 19A). Cells are first gated in a Forward vs.

Side Scatter plot to eliminate dead cells and debris. (FIG. 19B). Cells are then gated for singlets through a Forward Scatter Height vs. Width gate. (FIG. 19C). Finally, if cells have a transfection marker, they are gated positive for that fluorescent marker. The gate is adjusted to only include about 0.1% of cells which do not express the fluorescent marker.

DETAILED DESCRIPTION

Figure 1A:
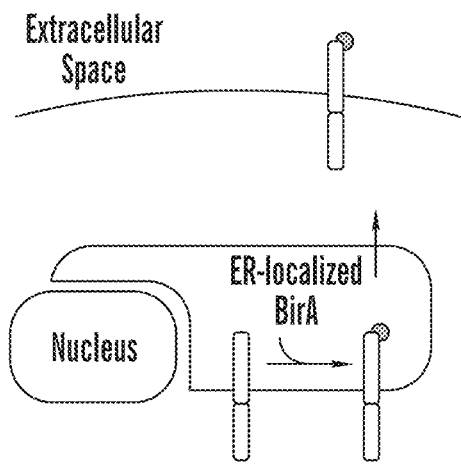
FIGS. 1A-1E.

Provided herein are polypeptides, systems, and methods relating to improved methods of controlling cellular signaling. Specifically, these polypeptides, systems, and methods involve the use of binding domains that preferentially bind to a selected small molecule (e.g., biotinylamides (e.g., as compared to binding to biotin)) in order to provide ON-switch, OFF-switch, and even dosable "dimmer-switch" functionality. Depending on the embodiment, the small molecule can be used to activate or inhibit signaling activity. This represents a surprising advance over prior systems, at least in part, because the present systems are not disrupted by naturally occurring biotin. The current systems also provide a further advantage in that poly-valent biotinylamides are cell impermeant, thereby permitting more accurate tunability and dosing control in those embodiments. Moreover, biotinylamides can be used in soluble, polyvalent, and/or peptide-conjugated forms which each have different half-lifes, permitting tunability in both amplitude as well as persistence. The systems and methods described herein can comprise a first and/or second small molecule controlled signaling polypeptide, wherein the first small molecule-controlled signaling polypeptide comprises a small molecule acceptor peptide and/or a small molecule; and at least a first signaling domain. The second small molecule-controlled signaling polypeptide comprises an domain that binds specifically to the small molecule; and at least a second signaling domain. In some embodiments, a small-molecule controlled signaling polypeptide is engineered, e.g., the portions or domains of each signaling peptide are not found as part of the same polypeptide in nature. In some embodiments of any of the aspects, a small molecule can be ligated or conjugated to the small molecule acceptor peptide of the first small molecule-controlled signaling polypeptide. In some embodiments of any of the aspects, a small molecule can be ligated or conjugated to the first small molecule-controlled signaling polypeptide.

Various different synthetic signaling systems can be provided using one or both of the first and second small molecule-controlled signaling polypeptides. For example, in one aspect of any of the embodiments, provided herein is a synthetic signaling system comprising a first small molecule-controlled signaling polypeptide and a second small molecule-controlled signaling polypeptide. In one aspect of any of the embodiments, provided herein is a synthetic signaling system comprising a first small molecule-controlled signaling polypeptide and a polypeptide comprising a domain that binds specifically to the small molecule. In one aspect of any of the embodiments, provided herein is a synthetic signaling system comprising a second small molecule-controlled signaling polypeptide and a polypeptide comprising a small molecule acceptor peptide and/or a small molecule.

Various suitable small molecules are known in the art and can include, without limitation, biotin, a biotinylamide, fluorescein, digoxigenin, fluorescein isothiocyanate (FITC). In some embodiments of any of the aspects, the small molecule is a molecule not normally found or produced in a cell or organism that the synthetic signaling system will be expressed in or introduced to. In some embodiments of any of the aspects, the small molecule is a molecule that is not toxic to a cell or organism that the synthetic signaling system will be expressed in or introduced to. In some embodiments of any of the aspects, the small molecule is a molecule that does not stimulate signaling in a cell or organism that the synthetic signaling system will be expressed in or introduced to.

In exemplary embodiments, described herein are signaling systems in which one member of the system comprises a domain that binds specifically to a biotinylamide and another member of the system comprises a biotinylamide, or can accept a biotinylamide. Depending on the arrangement of these two members within the system, their binding can either activate or inhibit signaling by the system. As mentioned above, because the system members do not bind, or do not bind strongly, to naturally-occurring biotin, the system is not sensitive to signals that are naturally present in a subject's body. The system is responsive, primarily or substantially, only to externally-controlled stimuli as described below herein.

As used herein, "biotin" refers to a molecule having the structure of Formula I:

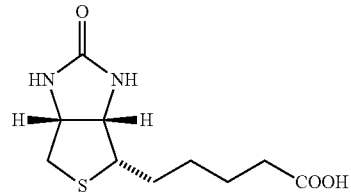

Formula I

As used herein, the term "a biotinylamide" refers to a molecule having the structure of Formula II, wherein $R_1$ and $R_2$ are independently selected from a polypeptide or a linkage to a polypeptide, hydrogen, substituted $C_1$-$C_{15}$alkyl, optionally substituted $C_1$-$C_{15}$alkenyl, or optionally substituted $C_2$-$C_{15}$alkynyl, optionally substituted aryl, or optionally substituted heteroaryl, or the structures of $R_1$ and/or $R_2$ provided below herein. In some embodiments of any of the aspects. $R_1$ and $R_2$ are independently selected from a polypeptide or a linkage to a polypeptide, hydrogen, substituted $C_1$-$C_{15}$alkyl, optionally substituted $C_2$-$C_{15}$alkenyl, or optionally substituted $C_2$-$C_{15}$alkynyl, optionally substituted aryl, or optionally substituted heteroaryl. In some embodiments of any of the aspects, $R_1$ and $R_2$ are independently selected from hydrogen, substituted $C_1$-$C_{15}$alkyl, optionally substituted $C_2$-$C_{15}$alkenyl, or optionally substituted $C_2$-$C_{15}$alkynyl, optionally substituted aryl, or optionally substituted heteroaryl. In some embodiments of any of the aspects, at least one of $R_1$ and $R_2$ is hydrogen. In some embodiments of any of the aspects, at least one of $R_1$ and $R_2$ is substituted with 1, 2, 3, 4, 5 or 6 substituents independently selected from the group consisting of C1-C3alkyl, hydroxy (OH), halogen, oxo (=O), carboxy (CO2), carboxyl, cyano (CN), amide, amine, and aryl.

Formula II

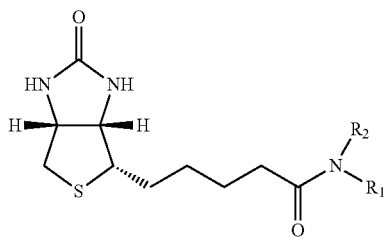

Exemplary biotinylamides include biotinamide, biocyntinamide, and biocytin.

Biotinamide is the acid amide of biotin 5-[(3aS,4S,6aR)-2-oxohexahydro-1H-thieno[3,4-d]imidazol-4-yl]pentanamide (e.g., a molecule having the structure of Formula III).

Formula III

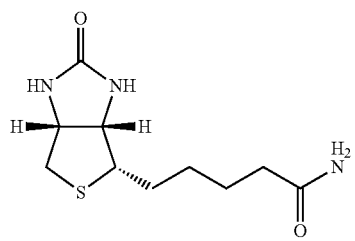

Biocyntinamide is an amino acid amide formed by amidation of the carboxy function of biocytin, having the structure of Formula IV.

Formula IV

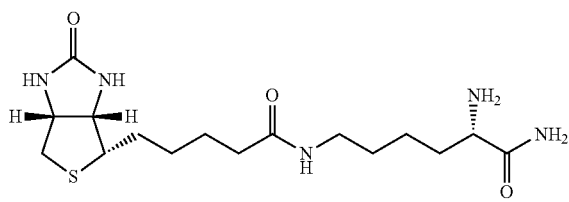

Biocytin is a monocarboxylic acid amide that results from the formal condensation of the carboxylic acid group of biotin with the N(6)-amino group of L-lysine. It is an azabicycloalkane, a thiabicycloalkane, a member of ureas, a monocarboxylic acid amide, a non-proteinogenic L-alpha-amino acid and a L-lysine derivative, having the structure of Formula V.

Formula V

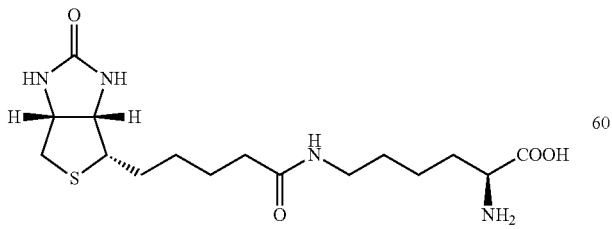

When the biotinylamide has a structure of Formula II and either $R_1$ or $R_2$ are something other than H, that $R_1$ or $R_2$ group may be subject to cleavage, e.g., by a biotinidase present in a cell. Blocking group chemistries for inclusion into $R_1$ or $R_2$ to prevent such cleavage are known in the art. See e.g., Wilbur et al. Biocojugate Chem 2006 17:1514-1522. In some embodiments of any of the aspects, the $R_1$ or $R_2$ of Formula II can independently be:

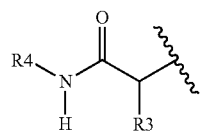

wherein $R_3$ is N—$CH_3$, $CO_2H$, $CH_2OH$, $CH_2OCH_3$, $CH_2CH_3$, or $CH(CH_3)_2$ and $R_4$ is independently selected from a polypeptide or a linkage to a polypeptide, hydrogen, substituted $C_1$-$C_{15}$alkyl, optionally substituted $C_2$-$C_{15}$alkenyl, or optionally substituted $C_1$-$C_{15}$alkynyl, optionally substituted aryl, optionally substituted heteroaryl. In some embodiments of any of the aspects, $R_4$ is substituted with 1, 2, 3, 4, 5 or 6 substituents independently selected from the group consisting of C1-C3alkyl, hydroxy (OH), halogen, oxo (═O), carboxy ($CO_2$), carboxyl, cyano (CN), amide, amine, and aryl.

It is noted herein that biotinylation of certain molecules, e.g., a lysine residue on a protein, results in the presence of a biotinylamide as defined herein. Thus, a biotinylamide as described herein can be provided by the chemical process of biotinylating a lysine residue. Accordingly, in some embodiments of any of the aspects described herein, when a biotinylamide is described herein, such a molecule can be provided as part of a peptide with a biotinyated lysine residue.

Similarly, the structures of flourescein, digoxigenin, and FITC are known in the art, e.g., fluorescein has the structure:

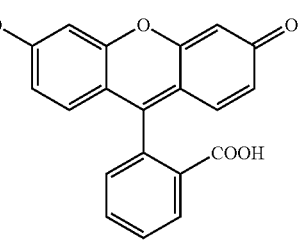

and digoxigenin has the structure:

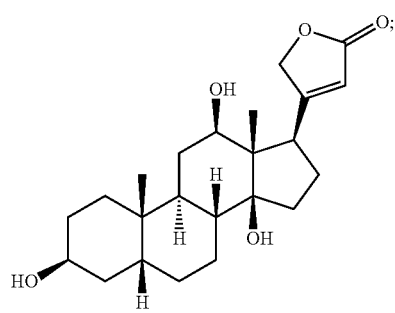

and FITC has the structure of:

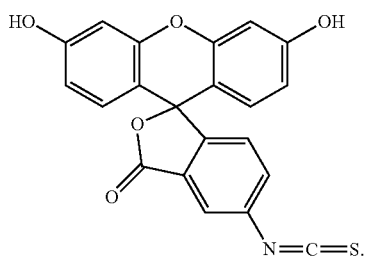 [SMILES: O=C1OC2(c3ccc(O)cc3Oc3cc(O)ccc32)c2ccc(N=C=S)cc21]

In various embodiments of any of the aspects described herein, there is provided a domain that binds specifically to the small molecule. In some embodiments of any of the aspects, the domain that binds specifically to the small molecule binds specifically to that small molecule as compared to other small molecules.

For example, in various embodiments of any of the aspects described herein, there is provided a domain that binds specifically to a biotinylamide. In some embodiments of any of the aspects, the domain that binds specifically to a biotinylamide binds specifically to a biotinylamide as compared to binding with a molecule that does not comprise a biotinylamide or a biotin (e.g., the domain can bind to both a biotinylamide and biotin). In some embodiments of any of the aspects, the domain that binds specifically to a biotinylamide binds specifically to a biotinylamide as compared to binding with biotin. In some embodiments of any of the aspects, the domain that binds specifically to a biotinylamide binds specifically to biotinamide, biocyntinamide, and/or biocytin, e.g., as compared to binding with biotin. In some embodiments of any of the aspects, the domain that binds specifically to a biotinylamide binds specifically to biotin lacking its carboxylic acid group, e.g., as compared to binding with biotin. In some embodiments of any of the aspects, the domain that binds specifically to a biotinylamide does not bind biotin.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments of any of the aspects, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized. In some embodiments of any of the aspects, the conditions relevant for binding specificity are the conditions in vivo, e.g., in a human subject, or in the extracellular in vivo environment.

A domain that binds specifically to a biotinylamide can be an antibody, an antibody reagent (e.g, scFv or nanobody), a scFab, a DARPin (Designed Ankyrin Repeat Protein), a monobody, a synthetic scaffold, or an aptamer. In some embodiments of any of the aspects, the domain that binds specifically to a biotinylamide can be an antibody or antibody reagent. Non-limiting examples of such domains are provided herein. It is contemplated herein that either a scFv or a scFab can be used intracellularly in the various methods and systems described herein. It is also contemplated herein that either a scFv or a scFab can be used extracellularly in the various methods and systems described herein.

In some embodiments of any of the aspects, the domain that binds specifically to a biotinylamide is a scFv. An exemplary scFv can be derived from the monoclonal antibody M33 described in Dengl et al. FASEB J. 2015 29(5): 1763-1779 and Dengl et al. Immunological Reviews 2016 270:165-177, and which corresponds to the sequence and structure of entry 4S1D in the RCSB Protein Data Bank. The heavy and light chain sequences of M33 are provided herein as SEQ ID NOs: 1 and 2, respectively. In some embodiments of any of the aspects, the domain that binds specifically to a biotinylamide comprises the 6 CDRs of SEQ ID NOs: 4-9. In some embodiments of any of the aspects, the domain that binds specifically to a biotinylamide comprises the 3 light chain CDRs of SEQ ID NOs: 4-6. In some embodiments of any of the aspects, the domain that binds specifically to a biotinylamide comprises the 3 heavy chain CDRs of SEQ ID NOs: 7-9. In some embodiments of any of the aspects, the domain that binds specifically to a biotinylamide comprises the 6 CDRs of SEQ ID NOs: 1 and 2. In some embodiments of any of the aspects, the domain that binds specifically to a biotinylamide comprises SEQ ID NOs: 1 and 2. In some embodiments of any of the aspects, the domain that binds specifically to a biotinylamide comprises amino acids 1-119 of SEQ ID NO:1 and amino acids 1-117 of SEQ ID NO: 2. Each of the foregoing references are incorporated herein by reference in their entireties. The polypeptides described herein can be further modified in order to add or modify binding specificity. e.g., a tandem fusion between antibiotintimide scfv and a second scfv (derived from an anti-fluorescein antibody, for example) would have avidity for a chimeric biotinamide-fluorescein chimeric small molecule. Such modifications and additions are specifically contemplated herein. The foregoing references are incorporated by reference herein in their entireties.

A further exemplary scFv is described in Neumann-Schaal et al. Immunology Letters 2013 151:1-2, which is incorporated by reference herein in its entirety. The heavy and light chain CDRs of this antibody are provided as SEQ ID NOs: 11-16. In some embodiments of any of the aspects, the domain that binds specifically to a biotinylamide comprises the one or more of the CDRs of SEQ ID NOs: 11-16. In some embodiments of any of the aspects, the domain that binds specifically to a biotinylamide comprises the 3 light chain CDRs of SEQ ID NOs: 11-13. In some embodiments of any of the aspects, the domain that binds specifically to a biotinylamide comprises the 3 heavy chain CDRs of SEQ ID NOs: 14-16.

A further exemplary scFv is described in Vincent et al. Journal of Immunological Methods 1993 165:177-182, which is incorporated by reference herein in its entirety. Exemplary scFv's are also available commercially, e.g., Cat. No. MA5-11251 (Invitrogen Carlsbad, Calif.) and Cat. No. sc-53179 (Santa Cruz Biotechnology Dallas. Tex.). In some embodiments of any of the aspects, the domain that binds specifically to a biotinylamide comprises the one or more of the CDRs of the scFv of Vincent et al., MA5-11251, or sc-53179.

In selecting or designing a domain that binds specifically to a biotinylamide, it is known in the art that a domain comprising one or more negative charges at the domain's binding pocket entry site can provide the necessary specificity relative to biotin. See, e.g., Dengl et al. Immunological Reviews 2016 270:165-177, which is incorporated by reference herein in its entirety. In some embodiments of any of the aspects, the domain that binds specifically to a biotinylamide comprises at least one negatively charged residue at the binding pocket entry site. In some embodiments of any of the aspects, the domain that binds specifically to a biotinylamid comprises at least two negatively charged residues at the binding pocket entry site. In some embodiments of any of the aspects, the domain that binds specifically to a biotinylamid comprises two negatively charged residues at the binding pocket entry site. In some embodiments of any of the aspects, the negatively charged residue(s) are aspartate. In some embodiments of any of the aspects, the domain is an antibody reagent (e.g., scFv) and the negatively charged residues are found in the heavy chain or heavy chain-derived sequence. In some embodiments of any of the aspects, the at least one negatively charged residue at the binding pocket entry site comprises the first residue of the heavy chain CDR1 and/or the third reside of the heavy chain CDR2, as per Kabat numbering.

In some embodiments of any of the aspects, a domain that binds specifically to a biotinylamide (e.g., an antibody reagent) can bind covalently to the biotinylamide. Covalent attachment of these two molecules can increase the sensitivity of the system and/or lower the doses of either molecule required for the system to function as compared to system in which the domain that binds specifically to a biotinylamide does not form a covalent bond. Such domains are known in the art, and/or can be readily designed by one of skill in the art. By way of non-limiting example, U.S. Pat. No. 10,517,945 describes how to modify antibody reagents generally to provide such covalent bonding with their target binding partners and provides a specific example of how to modify the M33 antibody described herein to provide such activity. In some embodiments of any of the aspects, the domain that binds specifically to a biotinylamide comprises the 6 CDRs of SEQ ID NOs: 17-22. In some embodiments of any of the aspects, the domain that binds specifically to a biotinylamide comprises the 3 light chain CDRs of SEQ ID NOs: 17-19. In some embodiments of any of the aspects, the domain that binds specifically to a biotinylamide comprises the 3 heavy chain CDRs of SEQ ID NOs: 20-22. In some embodiments of any of the aspects, the domain that binds specifically to a biotinylamide comprises the 6 CDRs of SEQ ID NOs: 23-28. In some embodiments of any of the aspects, the domain that binds specifically to a biotinylamide comprises the 3 light chain CDRs of SEQ ID NOs: 23-25. In some embodiments of any of the aspects, the domain that binds specifically to a biotinylamide comprises the 3 heavy chain CDRs of SEQ ID NOs: 26-28. Each of the foregoing references are incorporated herein by reference in their entireties.

In some embodiments of any of the aspects, light chain and heavy chain-derived sequences can be joined into a single polypeptide (e.g., a scFV) by positioning a peptide linker, e.g., a flexible linker between them. The light chain and heavy chain-derived sequences can be provided in N to C terminal order respectively, or in the opposite order. As used herein "peptide linker" refers to an oligo- or polypeptide region from about 2 to 100 amino acids in length, which links together any of the sequences of the polypeptides as described herein. In some embodiment, linkers can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. A non-limiting example of a suitable linker is provided in SEQ ID NO: 3.

|  |  | SEQ ID NO |
|---|---|---|
| Neumann-Schaal et al. Immunology Letters 2013 151:1-2 scFv | | |
| CDR L1 | RASESVDNYGISYMH | 11 |
| CDR L2 | WYQQRPGQPPKLLIY | 12 |
| CDR L3 | QHSREVPWT | 13 |
| CDR H1 | NYWMN | 14 |
| CDR H2 | QIYPGNGDAKYSGKSRD | 15 |
| CDR H3 | SYGYDEAWFAY | 16 |
| M33 (per Kabat numbering scheme) | | |
| CDR L1 | RASGNIHNYLS | 4 |
| CDR L2 | SAKTLAD | 5 |
| CDR L3 | QHFWSSIYT | 6 |
| CDR H1 | DTFFQ | 7 |
| CDR H2 | RIDPANGFTKYDPKFQG | 8 |
| CDR H3 | WDTYGAAWFAY | 9 |
| Covalently-bonding version of M33 (see, e.g., U.S. Pat. No. 10,517,945) | | |
| CDR L1 | RASGNIHNYLS | 17 |
| CDR L2 | SAKTLAD | 18 |
| CDR L3 | QHFWSSIYT | 19 |

-continued

| | | SEQ ID NO |
|---|---|---|
| CDR H1 | DTFFQ | 20 |
| CDR H2 | RIDPANGFTKYAQKFQG | 21 |
| CDR H3 | WDTYGAAWFAY | 20 |
| CDR L1 | RASGNIHNYLS | 23 |
| CDR L2 | SAKTLAD | 24 |
| CDR L3 | QHFWSSIYT | 25 |
| CDR H1 | DTFFQ | 26 |
| CDR H2 | RIDPCNGFTKYDPKQG | 77 |
| CDR H3 | WDTYGAAWFAY | 28 |

Figure 15E:
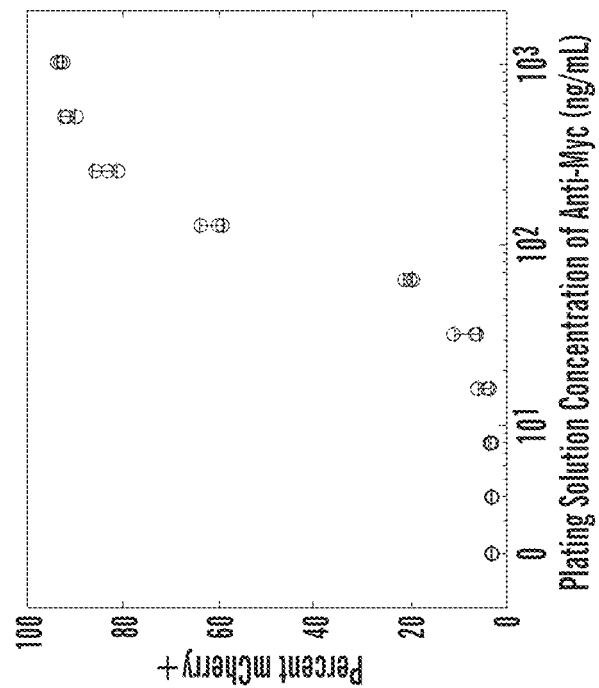
Figure 15D:
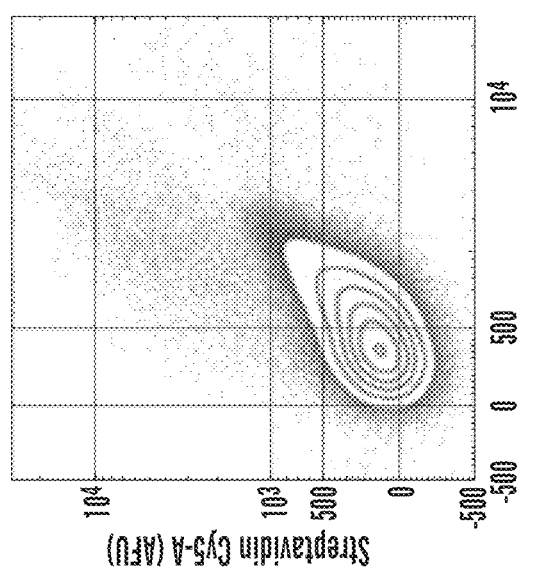

It is contemplated herein that streptavidin, neutravidin, avidin, or the like can also be utilized as a domain that binds specifically to a biotinylamide. Such systems have been described for use in linking biotinylated proteins, see, e.g., Liu et al. Oncotarget 2015 6:23735-47, which is incorporated by reference herein in its entirety. The examples herein demonstrate that, e.g., surface coated neutravidin can activate the biotinylated receptor (FIG. 15F).

Domains that can bind specifically to other small molecules, e.g., fluorescein, digoxigenin, or FITC are also known in the art and can include, by way of non-limiting example the commercially available anti-fluorescein monocolonal antibodies 1F8.-1E4, 6A4, and 8B9.C6.D3; the commercially available anti-digoxygenin monocolonal antibodies 21H8, 611532, 611621, 1.71.256, 9H27L19, DIG45, DIG44; and the digoxygenin-binding reagents DIG10.3 (see, e.g., Tinberg eta al, Nature 2013 501:212-6), and the commercially available anti-FITC monoclonal antibodies 6HC5LC9, NAWESLEE, 8B9.C6. D3, 1F8-1E4, NI 239, F4/1, FL-D6, #9, #8, and LO-FLUO-1. Each of the foregoing references are incorporated herein in their entireties. In some embodiments of any of the aspects, a domain that binds specifically to a small molecule comprises the CDRs of an antibody described or referenced herein.

It is contemplated herein that the small molecule acceptor peptide and/or a small molecule and/or the domain that binds specifically to the small molecule can be extracellular or intracellular. The interactions and signaling control mechanisms described herein include options for either arrangement. Accordingly, in some embodiments of any of the aspects, the domain that binds specifically to the small molecule and/or the small molecule acceptor peptide and/or the small molecule are extracellular. In some embodiments of any of the aspects, the domain that binds specifically to the small molecule and/or the small molecule acceptor peptide and/or the small molecule are intracellular. The whole polypeptides of the systems described herein can be intracellular, extracellular, or transmembrane. The location of the small molecule acceptor peptide and/or the small molecule and/or the domain that binds specifically to the small molecule refers to the location of those parts only and does not necessarily limit the structure or location of the entire polypeptide(s) that comprises them.

The polypeptides described herein can comprise signaling domains. e.g., first and second signaling domains. By first and second in this context, it is indicated that the signaling domains are not identical. Signaling domains are those capable of receiving a signal (e.g., by interaction with an upstream signaling binding partner, either via direct binding or binding of a different domain that then causes steric alterations in the polypeptide) and transmitting that signal to a further downstream signaling partner (e.g., by interacting with a downstream signaling partner or target, altering the structure of the polypeptide to modulate interaction with a downstream signaling partner or target, or enzymatic action (e.g., kinase activity). Options for signaling domains, include intracellular signaling domains, extracellular signaling domains, CAR signaling domains, Notch domains, etc, are provided herein.

In one version of the present technology, the domain that binds to the small molecule, e.g., (the biotinylamide-binding domain) is present on a cell surface receptor polypeptide, and the small molecule (e.g., biotinylamide) is used in one or more other molecules to control the activity of the cell surface receptor polypeptide (see FIG. 1A for an illustrative embodiment). Accordingly, in one aspect of any of the embodiments provided herein is a cell surface receptor polypeptide comprising an extracellular domain that binds specifically to the small molecule (e.g., a biotinylamide).

A cell surface receptor polypeptide comprises, minimally, an extracellular domain and either a transmembrane domain or membrane-embedded domain. Transmembrane domain and membrane-embedded domains sequence are know for a number of different proteins, as are general secondary structures that can be engineered de novo to form such domains, e.g., a single alpha helix will form such a domain without regard to the particular primary amino acid sequence.

In some embodiments of any of the aspects, the cell surface receptor polypeptide further comprises an intracellular signaling domain. The intracellular signaling domain can be selected depending on the particular activity or signaling cascade the user wishes to influence. A variety of such signaling domains are known in the art and readily selected based on the user's preference.

By way of non-limiting example, the intracellular signaling domain can be a tyrosine kinase intracellular signaling domain. Tyrosine kinase intracellular signaling domains are activated by dimerization. Use of the methods and compositions described herein for dimerization is discussed elsewhere herein, but briefly, this can be accomplished with anti-biotinamide and bis-biotinamide to cause autophosphorylation and downstream cell signaling. An exemplary tyrosine kinase intracellular signaling domain is the EGFR intracellular domain which would permit user control of cell proliferation with bis-biotinamide. Sequences and structures for tyrosine kinase intracellular signaling domains are known in the art and readily determined by one of ordinary skill in the art.

A further non-limiting example is the use of CRISPR compatible Cas enzymes, e.g., Cas9 or dCas9, as part of the intracellular signaling domain. Activation can result in release of Cas9/dCas9 from the cell membrane, to then translocate to the nucleus for its mode of action, dCas9 can be fused to transcriptional activators to promote activation of target genes. Activator or repressor domains binding hairpin-modified sgRNAs could be released such that they can associate with dCas9 complexes in the nucleus to regulate gene expression. For more discussion of such an approach to Cas9/CRISPR, see, e.g., Zalatan et a. Cell 2015 160:339-350, which is incorporated by reference herein in its entirey. Sequences and structures for Cas enzymes are known in the art and readily determined by one of ordinary skill in the art.

In some embodiments of any of the aspects, the intracellular signaling domain is a nuclear-acting signaling domain. As used herein, a nuclear-acting signaling domain is a domain that in its endogenous form, is translocated to the nucleus upon stimulation or activation, wherein it interacts with one or more targets or signaling partners in the nucleus to propagate the signal. In some embodiments of any of the aspects, the intracellular domain is cleaved upon stimulus to permit the translocation. In some embodiments of any of the aspects, a nuclear-acting signaling domain comprises one or more of: a DNA-binding domain, a nuclear localization signal, a recombination binding protein-J-associated molecule (RAM) domain, and an ankyrin domain or ankyrin repeats. Sequences and structures of such domains are known in the art, see, e.g., Gordon et al. Journal of Cell Science 2008 121:3109-3119, which is incorporated by reference herein in its entirety. In some embodiments of any of the aspects, a nuclear-acting signaling domain comprises a DNA-binding domain.

As used herein, the term "DNA binding domain" (DBD) refers to an independently folded protein domain that contains at least one structural motif that recognizes double- or single-stranded DNA. A DBD can recognize a specific DNA sequence (a recognition sequence or DNA binding motif (DBM) or have a general affinity to DNA. Some DNA-binding domains may also include nucleic acids in their folded structure. Examples for DBDs include the helix-turn-helix motif, the zinc finger (ZF) domain, the basic leucine zipper (bZIP) domain, the winged helix (WH) domain, the winged helix-turn-helix (wHTH) domain, the High Mobility Group box (HMG)-box domains, White-Opaque Regulator 3 domains and oligonucleotide/oligosaccharide folding domains. The helix-turn-helix motif is commonly found in repressor proteins and is about 20 amino acids long. The zinc finger domain is generally between 23 and 28 amino acids long and is stabilized by coordinating zinc ions with regularly spaced zinc-coordinating residues (either histidines or cysteines).

The term "zinc finger" or "ZF" refers to a protein having DNA binding domains that are stabilized by zinc. The individual DNA binding domains are typically referred to as "fingers." A zinc finger protein has at least one finger, typically two fingers, three fingers, or six fingers. Each finger binds from two to four base pairs of DNA, typically three or four base pairs of DNA (the "subsite"). A zinc finger protein binds to a nucleic acid sequence called a target site. Each finger typically comprises approximately 30 amino acids as a zinc-chelating, DNA-binding subdomain. An exemplary motif characterizing one class of these proteins (C2H2 class) is -Cys-(X)2-4-Cys-(X)12-His-(X)3-5-His (where X is any amino acid) (SEQ ID NO: 61). Studies have demonstrated that a single zinc finger of this class consists of an alpha helix containing the two invariant histidine residues coordinated with zinc along with the two cysteine residues of a single beta turn (see, e.g., Berg & Shi, Science 271:1081-1085 (1996)).

In some embodiments of any of the aspects, the intracellular domain comprises a Notch receptor signaling domain (or Notch intracellular domain (NICD)). In some embodiments of any of the aspects, the intracellular domain comprises the intracellular portion of the Notch core. In some embodiments of any of the aspects, the polypeptide or receptor described herein comprises the Notch core. The Notch core is a conserved segment founding in SynNotch proteins. It is derived from natural Notch and comprises the Negative Regulator Region (NRR) and Notch TMD. Synthetic ligand binding domain and intracellular domains are fused to this core region in order to generate SynNotch proteins. The Notch core sequence and structure are known in the art, see, e.g., Morsut et al. Cell 2016 164:780-791, which is incorporated by reference herein in its entirety. Human Notch protein sequences, structures, and signaling activities are known in the art, see, e.g., Maillard et la. Annual Review of Immunology 2005 23:945-974, which is incorporated by reference herein in its entirety.

In some embodiments of any of the aspects, the intracellular signaling and/or transmembrane domain is cleaved at the S3 position of synNotch in order to release the intracellular signaling domain from the receptor and allow it to translocate in the cell.

In some embodiments of any of the aspects, the intracellular signaling domain comprises a transcriptional activator. The term "transcriptional activator" refers to a polypeptide or peptide that binds to promoters and recruits RNA polymerase to directly initiate transcription. Transcriptional activators typically bind nearby to transcriptional promoters and recruit RNA polymerase to directly initiate transcription. Repressors bind to transcriptional promoters and sterically hinder transcriptional initiation by RNA polymerase. Other transcriptional regulators serve as either an activator or a repressor depending on where it binds and cellular conditions. Transcriptional regulators for use in accordance with the invention include any transcriptional regulator described herein or known to one of ordinary skill in the art. Examples of genes encoding transcriptional regulators that may be used in accordance with the invention include, without limitation, those regulators provided in Table 63 of U.S. Patent Application No. 2012/0003630, which is incorporated herein in its entirety by reference. In some embodiments of any of the aspects, the transcriptional activator can be VP64, VP64-P65, VPR, or p65.

In some embodiments of any of the aspects, either the first or second small molecule controlled polypeptide of a synthetic signaling system comprises an intracellular signaling domain comprising a transcriptional activator and the other small molecule controlled polypeptide comprises an intracellular signaling domain comprising a DNA binding domain.

In some embodiments of any of the aspects, the cell surface receptor polypeptide is a chimeric antigen receptor and comprises a CAR intracellular signaling domain. As used herein, "chimeric antigen receptor" or "CAR" refers to an artificially constructed hybrid polypeptide comprising an antigen or target-binding domain (e.g. an antigen-binding portion of an antibody (e.g. a scFv)) linked to a cell signaling and/or cell activation domain. The CAR cell signaling and/or cell activation domain both refer to a "CAR intracellular signaling domain" as that term is used herein. In some embodiments of any of the aspects, the cell-signaling domain can be a T-cell signaling domain. In some embodiments of any of the aspects, the cell activation domain can be a T-cell activation domain. CARs have the ability to redirect the specificity and reactivity of T cells and other immune cells toward a selected target in a non-MHC-restricted manner, e.g., by exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells. CARs advantageously do not dimerize with endogenous T-cell receptor (TCR) alpha and beta chains. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fabs (instead of from an antibody. e.g., obtained from Fab libraries), in various embodiments, this scFv is fused to a transmembrane domain and then to an intracellular signaling domain. The scFv can be a domain that binds specifically to a biotinylamide, as described above herein.

"First-generation" CARs include those that solely provide CD3zeta signals upon antigen binding, "Second-generation" CARs include those that provide both costimulation (e.g. CD28 or CD 137) and activation (CD3Q. "Third-generation" CARs include those that provide multiple costimulation (e.g. CD28 and CD 137) and activation (CO3Q). Further discussion of CARs can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety. "Fourth generation" CARs (also known as TRUCKs or armored CARs), further comprises factors that enhance T cell expansion, persistence, and anti-tumoral activity such as comprise cytokines, such is IL-2, IL-5, IL-12 and co-stimulatory ligands; see e.g., Chmielewski M. Abken H (2015). "TRUCKs: the fourth generation of CARs". Expert Opinion on Biological Therapy. 15 (8): 1145-1154; which is incorporated by reference herein in its entirety In some embodiments of any of the aspects, the intracellular signaling domain can be a T-cell activation domain. In some embodiments of any of the aspects, the intracellular signaling domain is a signaling domain from a protein selected from the group consisting of: TCRζ, FcRγ, FcRβ, CD3γ, CD3δ, CD3ε, CD3ζ, CD22, CD79a, CD79b, CD66d, CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, ZAP70, and 41BB.

In some embodiments of any of the aspects, the intracellular signaling domain comprises an intracellular CD28, 4-1BB, and/or CD3ζ signaling domain. In some embodiments of any of the aspects, the intracellular signaling domains comprises intracellular CD28, 4-1 BB, and CD3ζ signaling domains. In some embodiments of any of the aspects, the intracellular domain comprises a CAR stimulatory domain and/or a CAR co-stimulatory domain.

CAR stimulatory domains regulate primary activation of the TCR complex either in a stimulatory way. CAR stimulatory domains that act in a stimulatory manner may contain signaling motifs which are known as immunoreceptor tyrosine-based activation motifs or ITAMs. Illustrative examples of ITAM containing CAR stimulatory domains that are of particular use in the invention include those derived from TCRζ, FcRγ, FcRβ, CD3γ, CD3δ, CD3ε, CD3ζ, CD22, CD79a. CD79b, and CD66d. In some embodiments of any of the aspects, the CAR stimulatory domain is a CD3ζ signaling domain.

As used herein, the term, "co-stimulatory signaling domain," or "CAR co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT. NKD2C SLP76, TRIM, and ZAP70. In one embodiment, a polypeptide comprises one or more CAR co-stimulatory signaling domains selected from the group consisting of CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70 signaling domains. In some embodiments of any of the aspects, the CAR co-stimulatory domain is a CD28 signaling domain.

Also contemplated herein are embodiments of the synthetic signaling systems described herein that comprise "split CARs." In one aspect of any of the embodiments, the first small molecule-controlled signaling polypeptide comprises the first small molecule-controlled signaling polypeptide comprises a first signaling domain comprising an intracellular CAR stimulatory domain; and the small molecule acceptor peptide (and/or small molecule) and the second small molecule-controlled signaling polypeptide comprises: a signaling domain comprising an extracellular domain that binds specifically to a target; a transmembrane domain; and the domain that binds specifically to a small molecule. Alternatively, in one aspect of any of the embodiments, the the first small molecule-controlled signaling polypeptide comprises a signaling domain comprising an extracellular domain that binds specifically to a target; a transmembrane domain; and the small molecule acceptor peptide (and/or small molecule) and the second small molecule-controlled signaling polypeptide comprises a first signaling domain comprising an intracellular CAR stimulatory domain; and the domain that binds specifically to the small molecule.

When a member of a split CAR embodiment is not specified to have a transmembrane domain, it can be is cytosolic; and/or is not directly tethered to the membrane. Alternatively, in some embodiments of the split CAR aspects, a small molecule-controlled signaling polypeptide can further comprise a transmembrane or membrane-tethering domain. A membrane-tethering domain can be, e.g, the membrane-tethering domain of a naturally-occurring protein that is tethered to the membrane and does not comprise an extracellular domain, or an abbreviated transmembrane domain that does not protrude extracellularly.

Either member of a split CAR embodiment can further comprise a CAR co-stimulatory domain. In some embodiments of any of the aspects, either member of a split CAR embodiments can further comprise a CAR stimulatory domain. In some embodiments of any of the aspects, one member of a split CAR embodiments does not comprise a CAR stimulatory domain. In some embodiments of any of the aspects, one member of a split CAR embodiments does not comprise a CAR co-stimulatory domain.

In some embodiments of any of the aspects, both the first and second signaling domains are intracellular signaling domains. In some embodiments of any of the aspects, both the first and second small molecule-controlled polypeptides are intracellular polypeptides. In some embodiments of any of the aspects, one of the first and second small molecule-controlled polypeptides is an intracellular polypeptide and the other is a transmembrane polypeptide. In some embodiments of any of the aspects, the second small molecule-controlled signaling polypeptide comprises, from N-terminus to C-terminus: an extracellular domain that binds specifically to the small molecule; a transmembrane domain; and an intracellular signaling domain.

In some embodiments of any of the aspects, both the first or second small molecule controlled polypeptide of a synthetic signaling system are intracellular polypeptides, one of the small molecule-controlled polypeptides comprises an intracellular signaling domain comprising a transcriptional activator and the other small molecule controlled polypeptide comprises an intracellular signaling domain comprising a DNA binding domain.

A small molecule (e.g., a biotinylamide) present on a molecule can be added by chemical synthesis, e.g., during in vitro peptide synthesis, or as a modification to a peptide produced in vivo or in a cell (e.g., a recombinant cell). For example, biotinyl-glycine and biotinyl-lysine are commonly used in peptide synthesis and such approaches can be readily adapted to include a biotinylamide in peptide synthesis. Similar systems are know for lipoic acid (see, e.g., Cohen et al. Chembiochem 2012 13:888-894; which is incorporated by reference herein in its entirety). If the molecule is a peptide, or comprises a peptide, the use of a small molecule acceptor peptide can facilitate directed addition of the small molecule after formation of the peptide. A small molecule acceptor peptide is a peptide sequence which is recognized by a small molecule ligase chosen by the user and to which the ligase can conjugate the small molecule. Accordingly, the sequence of the small molecule acceptor peptide can vary depending on the ligase selected. In some embodiments, the small molecule acceptor peptide is a biotin acceptor peptide. By way of example, suitable biotin acceptor peptide sequences are known in the art for many biotin ligases. By way of non-limiting example:

| Biotin Ligase | Biotin Acceptor Peptide sequences: | SEQ ID NO: | For more detail, see: |
|---|---|---|---|
| E. coli birA | GLNDIFEAQKIEWH | 100 | Schatz et al. Bio/Technology 1993 11:1138-1143 |
| | $X_1X_2X_3X_4X_5X_6X_7X_8X_9KX_{11}X_{12}X_{13}X_{14}$<br>$X_1$ = T, H, G, D, P, S, M, or L<br>$X_2$ = S, L, D, V, W, M, E, or T<br>$X_3$ = S, P, L, K, D, T, W, N, H A, or R<br>$X_4$ = A, M, K, T, N, G, D, E, P<br>$X_5$ = I, P, L, or T<br>$X_6$ = F or L<br>$X_7$ = D, R, E, L, N, A, or T<br>$X_8$ = A, S, or G<br>$X_9$ = M, Q, or T<br>$X_{11}$ = M or T<br>$X_{12}$ = V, E, L, M, T, Y, Q or D<br>$X_{13}$ = W, V, F, L, Y, or Q<br>$X_{14}$ = I, Y, H, V, S, L, or W | 101 | Schatz et al. Bio/Technology 1993 11:1138-1143 |
| | $X_1X_2X_3X_4X_5KX_7$<br>$X_1$ = L, I, T, M, or F<br>$X_2$ = F, L, or M<br>$X_3$ = E or D<br>$X_4$ = A, G, or S<br>$X_5$ = M, Q, or L<br>$X_7$ = M or V | 102 | Schatz et al. Bio/Technology 1993 11:1138-1143 |
| | $X_1X_2X_3X_4X_5KX_7$<br>$X_1$ = I, N, V, T, or M<br>$X_2$ = F or L<br>$X_3$ = E, D or A<br>$X_4$ = A, S, or D<br>$X_5$ = M, Q, or A<br>$X_7$ = M or I | 103 | Schatz et al. Bio/Technology 1993 11:1138-1143 |
| | $LX_2X_3QKX_6X_7X_8$<br>$X_2$ = H, N, or S<br>$X_3$ = A, S, or T<br>$X_6$ = I or V<br>$X_7$ = E, L, or Y<br>$X_8$ = W, L, or M | 104 | Schatz et al. Bio/Technology 1993 11:1138-1143 |

-continued

| Biotin Ligase | Biotin Acceptor Peptide sequences: | SEQ ID NO: | For more detail, see: |
|---|---|---|---|
| | $LX_1X_2IX_4X_5X_6X_7X_8X_9X_{10}X_{11}X_{12}$<br>$X_1$ = any amino acid<br>$X_2$ = any amino acid except<br>L, V, I, W, F, or Y<br>$X_4$ = F or L<br>$X_5$ = E or D<br>$X_6$ = A, G, S, or T<br>$X_7$ = Q or M<br>$X_8$ = K<br>$X_9$ = I, M, or V<br>$X_{10}$ = E, L, V, Y, or I<br>$X_{11}$ = W, Y, V, F, L, or I<br>$X_{12}$ = any amino acid except D and E | 105 | Beckett et al. Protein Science 1999 8:921-9 |
| | $LX_1X_2IX_4X_5X_6X_7X_8X_9X_{10}X_{11}X_{12}$<br>$X_1$ = any amino acid<br>$X_2$ = any amino acid except<br>L, V, I, W, F, or Y<br>$X_4$ = F or L<br>$X_5$ = E or D<br>$X_6$ = A, G, S, or T<br>$X_7$ = Q or M<br>$X_8$ = K<br>$X_9$ = I, M, or V<br>$X_{10}$ - E, L, V, Y, or I<br>$X_{11}$ = W, Y, V, F, L, or I<br>$X_{12}$ = R or H | 106 | Beckett et al. Protein Science 1999 8:921-9 |
| | LGGIFEAMKMELRD | 107 | Beckett et al. Protein Science 1999 8:921-9 |
| | LFLHDFLNAQKVELYPVTSSG | 108 | Beckett et al. Protein Science 1999 8:921-9 |
| | MAGGLNDIFEAQKIEWHEDTGGS | 109 | Beckett et al. Protein Science 1999 8:921-9 |
| | GLNDIFEAQKIEWH | 110 | Beckett et al. Protein Science 1999 8:921-9 |
| S. cerevisiae biotin ligase | TTNWVAQAFKMTFDP | 111 | Chen et al. J Am Chem Soc 2007 129:6619-25 |
| | $X_1X_2X_3X_4X_5X_6X_7X_8X_9KMTFX_{14}X_{15}$<br>$X_1$ = T, S, E, Q, D, N, or A<br>$X_2$ = T, P, W, T, H, Y, I, Q, or P<br>$X_3$ = N, S, E, A, T, F, G, Y<br>$X_4$ = W, H, D, H, S, or P<br>$X_5$ = V, L, D, or G<br>$X_6$ = A, R, F, L, or P<br>$X_7$ = Q, E, P, T, Y, R, N, S<br>$X_8$ = A, L, or P<br>$X_9$ = F or M<br>$X_{14}$ = D, S, T, or H<br>$X_{15}$ = P, R, K, S, T, or G | 112 | Chen et al. J Am Chem Soc 2007 129:6619-25 |
| | $X_1X_2X_3X_4X_5X_6X_7AX_9KMTFX_{14}X_{15}$<br>$X_1$ = T, S, E, Q, D, N, or A<br>$X_2$ = T, P, W, T, H, Y, I, Q, or P<br>$X_3$ = N, S, E, A, T, F, G, Y<br>$X_4$ = W, H, D, H, S, or P<br>$X_5$ = V, L, D, or G<br>$X_6$ = A, R, F, L, or P<br>$X_7$ = Q, E, P, T, Y, R, N, S<br>$X_9$ = F or M<br>$X_{14}$ = D, S, T, or H<br>$X_{15}$ = P, R, K, S, T, or G | 113 | Chen et al. J Am Chem Soc 2007 129:6619-25 |

-continued

| Biotin Ligase | Biotin Acceptor Peptide sequences: | SEQ ID NO: | For more detail, see: |
|---|---|---|---|
| | $X_1X_2X_3X_4X_5X_6X_7$AMKMTF$X_{14}X_{15}$<br>$X_1$ = T, S, E, Q, D, N, or A<br>$X_2$ = T, P, W, T, H, Y, I, Q, or P<br>$X_3$ = N, S, E, A, T, F, G, Y<br>$X_4$ = W, H, D, H, S, or P<br>$X_5$ = V, L, D, or G<br>$X_6$ = A, R, F, L, or P<br>$X_7$ = Q, E, P, T, Y, R, N, S<br>$X_{14}$ = D, S, T, or H<br>$X_{15}$ = P, R, K, S, T, or G | 114 | Chen et al. J Am Chem Soc 2007 129:6619-25 |
| | $X_1X_2X_3X_4X_5X_6X_7X_8X_9$KM$X_{12}$F$X_{14}X_{15}$<br>$X_1$ = T, S, E, Q, D, N, or A<br>$X_2$ = T, P, W, T, H, Y, I, Q, or P<br>$X_3$ = N, S, E, A, T, F, G, Y<br>$X_4$ = W, H, D, H, S, or P<br>$X_5$ = V, L, D, or G<br>$X_6$ = A, R, F, L, or P<br>$X_7$ = Q, E, P, T, Y, R, N, S<br>$X_8$ = A, L, or P<br>$X_9$ = F or M<br>$X_{12}$ = T or E<br>$X_{14}$ = D, S, T, or H<br>$X_{15}$ = P, R, K, S, T, or G | 115 | Chen et al. J Am Chem Soc 2007 129:6619-25 |

Each of the foregoing references is incorporated by reference herein in its entirety. Additional biotin ligases and corresponding biotin acceptor peptides are known in the art. In some embodiments of any of the aspects, the biotin acceptor peptide has the sequence of one of SEQ ID NOs: 100-115. In some embodiments of any of the aspects, the biotin acceptor peptide comprises the sequence of one of SEQ ID NOs: 100-115. In some embodiments of any of the aspects, the biotin acceptor peptide comprises a sequence having at least 80%, 85%, 90%, or 95% sequence identity to the sequence of one of SEQ ID NOs: 100-115. In some embodiments of any of the aspects, the biotin acceptor peptide comprises a sequence having at least 80%, 85%, 90%, or 95% sequence identity to the sequence of one of SEQ ID NOs: 100-115 and retains the wild-type activity, e.g., serves as a substrate for biotin ligase. In some embodiments of any of the aspects, the biotin acceptor peptide comprises a sequence having at least 95% sequence identity to the sequence of one of SEQ ID NOs: 100-115 and retains the wild-type activity, e.g., serves as a substrate for biotin ligase.

In some embodiments of any of the aspects, the small molecule acceptor polypeptide (and/or small molecule) is located between a transmembrane and/or membrane-tethering domain and any other intracellular domains. In some embodiments of any of the aspects, the small molecule acceptor polypeptide (and/or small molecule) is located between multiple other intracellular domains. In some embodiments of any of the aspects, a polypeptide can comprise multiple copies or iterations of the small molecule acceptor polypeptide (and/or small molecule).

In some embodiments of any of the aspects, a first and/or second small molecule-controlled polypeptide can further comprise a protease, e.g., a repressible protease. In some embodiments of any of the aspects the protease is NS3. Repressible proteases can be repressed by contacting the polypeptide with a repressor molecule, e.g., in the case of NS3, a suitable repressor is grazoprevir. When sufficient repressor is not present, the protease will activate and cleave the polypeptide which it is a part of. Accordingly, in one aspect of any of the embodiments, provided herein is a method of controlling signaling or activity of a first cell comprising a synthetic signaling system comprising at least one protease, the method comprising contacting the first cell with an agent that inhibits the protease (e.g., grazoprevir) to permit the signaling or activity of the first cell. Such repressible proteases and their repressors are known in the art and described in, e.g., International Patent Publication WO 2020/232366, which is incorporated by reference herein in its entirety.

Figure 10:
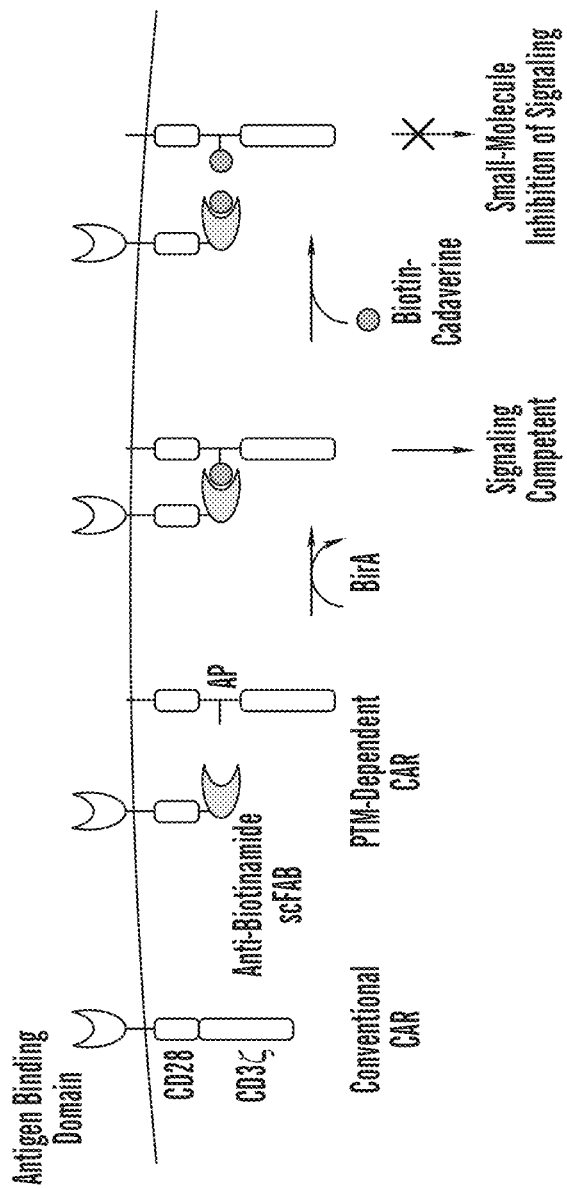
FIG. 10 depicts schematics of different molecules. From left to right are depicted: 1. A conventional CAR (2nd generation) utilizes a CD3ζ Stimulatory Domain and a CD28 Costimulatory Domain to induce T-Cell signaling in response to antigens directed by the antigen binding domain. 2. One embodiment described herein employs a split CAR structure with the Stimulatory Domain fused to a signaling-deficient membrane protein. In this design, the AntiBiotinamide scFAB is fused to one portion of the CAR that includes the antigen binding domain, and the biotin acceptor peptide (AP) is fused to the other which includes the stimulatory domain. 3. When BirA is expressed in the T-Cell, either through transcriptional induction or other chemical induction methods, the AP is biotinylated—leading to binding of the two parts of the CAR. In this configuration, the CAR is signaling competent and can respond to antigens 4. The use of membrane-permeant biotinamide-containing small molecules will competitively bind to the scFAB, leading to disruption of the two parts of the CAR. In this configuration, the CAR is again no longer signaling competent.

An exemplary embodiment of such cell surface receptor split-CAR polypeptides is depicted in FIG. 10. A split CAR structure is depicted, with the Stimulatory Domain fused to a signaling-deficient membrane protein. In this design, the AntiBiotinamide scFAB is fused to one portion of the CAR that includes the antigen binding domain, and the biotin acceptor peptide (AP) is fused to the other which includes the stimulatory domain. When biotin ligase is expressed in the T-Cell, either through transcriptional induction or other chemical induction methods, the AP is biotinylated—leading to binding of the two parts of the CAR. In this configuration, the CAR is signaling competent and can respond to antigens. The use of membrane-permeant biotinamide-containing small molecules will competitively bind to the scFAB, leading to disruption of the two parts of the CAR. In this configuration, the CAR is again no longer signaling competent. This design is beneficial because it offers rapid chemically induced changes in the ability for the CAR to signal. CARs often risk toxicity or off-target effects, so it is becoming increasingly important to be able to control cellular signaling through the use of safe and rapidly acting small molecules.

Other designs include the switching the orientation of the scFAB and the AP, such that the AP is on the Antigen Binding Domain containing receptor, and the scFAB is on the Stimulatory Domain Receptor. It is also possible to use the scFAB and AP on the extracellular side of the receptor to accomplish similar effects. This would permit the use of cell-impermeant small molecules such as biocytin. Another possibility is for the co-stimulatory domain to not be tethered to the membrane, but instead be a cytosolic protein.

In embodiments where the domain that binds specifically to the small molecule (e.g., a biotinylamide) is found in a cell surface receptor polypeptide, the activity of the cell surface receptor polypeptide can be controlled by the presence and arrangement of the small molecules (e.g., biotinylamide molecules). When the domain that binds specifically to a small molecule (e.g., biotinylamide) binds to a small molecule that is not soluble, e.g., is coupled to enough mass to exert significant force on the cell surface receptor polypeptide, the cell surface receptor polypeptide will be activated. Conversely, if the domain that binds specifically to a small molecule binds to a small molecule that is soluble, e.g., is not coupled to enough mass to exert significant force on the cell surface receptor polypeptide, the cell surface receptor polypeptide will not be activated. At sufficient quantities, a soluble small molecule can prevent or decrease binding of non-soluble small molecules, thereby providing tunable activation of the cell surface receptor polypeptide.

Accordingly, in one aspect of any of the embodiments, provided herein is a system comprising a) a cell surface receptor polypeptide comprising an extracellular domain that binds specifically to a small molecule, and b) one or both of: i) a surface-attached molecule comprising a small molecule acceptor peptide conjugated or ligated to the small molecule (and optionally a binding domain specific for a target) and ii) a soluble molecule comprising a small molecule acceptor peptide (and/or small molecule). In one aspect of any of the embodiments, provided herein is a system comprising a) a cell surface receptor polypeptide comprising an extracellular domain that binds specifically to a small molecule, and b) one or both of: i) a surface-attached molecule conjugated or ligated to a small molecule (and optionally a binding domain specific for a target) and ii) a soluble molecule comprising a small molecule acceptor peptide (and/or small molecule). In some embodiments of any of the aspects, the cell surface receptor polypeptide further comprises an intracellular signaling domain. In some embodiments of any of the aspects, the cell surface receptor polypeptide is provided in/on a first cell. In one aspect of any of the methods, provided herein is a method of controlling signaling or activity of a first cell comprising a cell surface receptor polypeptide comprising an extracellular domain that binds specifically to a small molecule, the method comprising: a) contacting the first cell with a surface-attached molecule comprising a small molecule acceptor peptide (and/or small molecule) to induce the signaling or activity of the first cell (the surface-attached molecule optionally further comprising a binding domain specific for a target), and/or b) contacting the first cell with a soluble molecule comprising a small molecule acceptor peptide (and/or small molecule) to inhibit the signaling or activity of the first cell.

A surface-attached molecule or polypeptide is present in, bound to, or conjugated to a surface, e.g., to provide sufficient mass to activate the cell surface receptor polypeptide upon binding with the cell surface receptor polypeptide. In some embodiments of any of the aspects, binding can be non-covalent, e.g., by hydrogen, electrostatic, or van der Waals interactions, however, binding may also be covalent. The term "conjugated" refers to the attachment of at least two entities to form one entity. The joining of the two entities can be direct (e.g., via covalent or non-covalent bonds) or indirect (e.g., via linkers etc.). Thus, conjugation can be by means of linkers, chemical modification, peptide linkers, chemical linkers, covalent or non-covalent bonds, or protein fusion or by any means known to one skilled in the art. The joining or conjugation can be permanent or reversible.

A surface can include a cell surface (e.g., of the first cell or a second cell), a lipid bilayer, or a solid surface. In some embodiments of any of the aspects, a lipid bilayer surface can be a liposome. In some embodiments of any of the aspects, the surface is a solid surface or solid support. The solid surface can be e.g., beads (such as magnetic beads, polystyrene beads, or gold beads); a chip; a cell culture plate, dish, well; a microfluidic device; a filter; affinity column; cavity; channel; tube; resin; fiber; sheet; biocompatible polymer or material; or the like.

A surface can also include a nanocarrier. For example, various nanocarriers for targeting to cancer tumors (e.g., via the enhanced permeability and retention effect) are known in the art and can include but are not limited to PLGA nanoparticles, poly(carboxyphenoxypropane/sebacic acid), poly(glycerol monsteratate-co-caprolactone), and the like. Such nanocarriers and their use are described in the art, e.g., Rosenblum et al. Nature Communications 2018 9:1410; which is incorporated by reference herein in its entirety.

Surface-attached molecules can be attached by any suitable chemistry, including bioorthogonal chemistries. Exemplary biorthogonal chemistries are described in Devaraj. ACS Central Science 2018 4:952-9; which is incorporated by reference herein in its entirety. In some embodiments of any of the aspects, the small molecule of the surface-attached molecule can be is tetrazine-functionalized and ligated to immobilized trans-cyclooctene (TCO).

As used herein, the term "bead" refers to a microparticle of any design or construction, but preferably a microparticle that is about the size of a cell or smaller. While cell sizes vary according to cell type, the bead (microparticles) can be of any such size or smaller, e.g. nanoscale in size. In some embodiments of any of the aspects, the beads or particles can range in size from 1 nm to 1 mm. In some embodiments of any of the aspects, the beads can be about 250 nm to about 250 μm in size.

Suitable materials for a solid surface include, without limitation, a synthetic polymer, biopolymer, latex, or silica. Such materials are well known in the art. For example, the use of beads and/or particles is known in the art and described, e.g. magnetic bead and nano-particles are well known and methods for their preparation have been described in the are art, for example in U.S. Pat. Nos. 6,878,445; 5,543,158; 5,578,325; 6,676,729; 6,045,925 and 7,462,446, and U.S. Pat. Pub. Nos.: 2005/0025971; 2005/0200438; 2005/0201941; 2005/0271745; 2006/0228551; 2006/0233712; 2007/01666232 and 2007/0264199, contents of all of which are herein incorporated by reference in their entirety. Magnetic microbeads are easily and widely available commercially, with or without functional groups, e.g., from Dynal Inc. of Lake Success, N. Y.; PerSeptive Diagnostics, Inc. of Cambridge, Mass. Invitrogen Corp. of Carlsbad, Calif.; Cortex Biochem Inc. of San Leandro, Calif.; and Bangs Laboratories of Fishers, Ind.

In some embodiments of any of the aspects, the surface-attached molecule or polypeptide is not soluble.

In some embodiments of any of the aspects, the surface-attached molecule or polypeptide can further comprise a binding domain specific for a target. In some embodiments of any of the aspects, a binding domain specific for a target can comprise an aptamer, antibody reagent, or antigen-binding portion thereof, polypeptide reagent, or a small molecule. Antibody reagents that are therapeutic and/or specific for any particular target antigen are readily selected by one of skill in the art from known antibody reagents, e.g. from FDA-approved therapeutic antibody reagents and/or commercially available antibody reagents which are listed in catalogs according to their target specificity.

A suitable target can be a disease marker, or a marker specific to a cell type that the user wishes the first cell to act upon, or act only in the presence of. In some embodiments of any of the aspects, the marker is found on or is specific to a second cell or second cell type. Markers are commonly cell-surface markers. "Marker" refers to an expression product, e.g., nucleic acid or polypeptide which is differentially present in a sample taken from subjects having having a condition (e.g., cancer), as compared to a comparable sample taken from control subjects (e.g., a healthy subject) or which is which is differentially present in specific cell type as compared to a comparable sample taken from other cell types. The term "biomarker" is used interchangeably with the term "marker."

In some embodiments of any of the aspects, the second cell or second cell type is a cancer cell. In such embodiments, the first cell, e.g., the cell comprising a cell surface receptor polypeptide which is a CAR, can be an immune cell, e.g., a T cell. Such embodiments are suited for methods of immunotherapy, e.g., by permitting control or tunability of a CAR-T cell.

The soluble molecule comprising a small molecule can further comprise a polymer, a dendrimer, a nanoparticle, a polypeptide, an antibody, or antibody reagent. Suitable small molecules comprising a biotinylamide include bis-biotinamide and des-thio-biotinamide, and multivalent biotinamides (e.g., trivalent or tetravalent biotinamides). The small molecule (e.g., biotinylamide) can be bound, attached, or conjugated to proteins and other macromolecules to permit targeting to specific locations and/or to tune the half-life of the soluble molecule in vivo. Exemplary peptides or polypeptides include bovine scrum albumin (BSA).

A polymer can be, e.g., a biocompatible polymer. A biocompatible polymer refers to materials which do not have toxic or injurious effects on biological functions. Biocompatible polymers include natural or synthetic polymers. Examples of biocompatible polymers include, but are not limited to, collagen, poly(alpha esters) such as poly(lactate acid), poly(glycolic acid), polyorthoesters and polyanhydrides and their copolymers, polyglycolic acid and polyglactin, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, polyglactin, or copolymers or physical blends of these materials. In some embodiments of any of the aspects, the polymer is polyethylene glycol (PEG). For examples, 4-arm and 8-arm biotin PEG is available commercially from Creative PEGWorks Chapell Hill, N.C. (Cat. No. PLS-2050 through PLS-2057, PSB-3363 through PSB-3369, PSB-3435, PJK-1900 though PJK-1904, PJK-1930 through PJK-1949, PJK-1970 through PJK-1974, PJK-1915 through PJK-1919, PBL-8161 thorugh PBL-8165. PLS-9950 through PLS-9953. PHB-3931 through PHB-3935, PSB-4201 through PSB-4204, PSB-891 through PSB-893, and PBL-9001 through PBL-9005).

As the size of the soluble molecule increases, greater doses should be used to achieve the same effect on the signaling activity of the first cell.

In the methods described herein, the contacting steps a) and b) can be performed in the alternative, in sequence (either order), in an overlapping manner, concurrently, consecutively, or any combination of the foregoing over time. These different approaches, depending on the half-life of the control molecules and their relative concentrations, permit tunability and control of the time in which the signal persists.

In embodiments where the first cell comprises a first small molecule-controlled signaling polypeptide comprising a domain that binds specifically to the small molecule (e.g., a biotinylamide) and a second small molecule-controlled signaling polypeptide comprising a signaling domain, the interaction of the two small molecule-signaling polypeptides (and therefore the signaling or activity of the first cell) can be inhibited by contacting the cell with a further molecule comprising a domain that binds specifically to the small molecule. Suitable domains that bind specifically to a small molecule are described elsewhere herein and can include an antibody, an antibody reagent, or a cell-permeant antibody (e.g., scFv or scFab). In some embodiments of any of the aspects, the further molecule comprising a domain that binds specifically to the small molecule is an antibody or antibody reagent that is surface-attached or expressed on the surface of a second cell.

Signaling or activity of a first cell described herein can also be inhibited by contacting the cell with an inhibitor of one or more of the signaling domains. By way of non-limiting example, Notch signaling domains are inhibited by DLL1 and DLL4. Accordingly, a first cell can be contacted with a polypeptide comprising a DLL1 and/or DLL4 polypeptide or protein. In some embodiments of any of the aspects, the polypeptide comprising a DLL 1 and/or DLL4 polypeptide or protein can further comprise a domain that binds specifically to the small molecule, e.g., to strengthen binding to the target and/or to compete against a first or second small molecule-controlled polypeptide for binding to small molecule, depending on the specific arrangement of first and/or second small molecule-controlled polypeptides.

In some embodiments of the methods described herein, the signaling or activity of the first cell is immune response-promoting signaling or activity. As used herein, an "immune response" refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus (e.g., to an a disease, an antigen, or healthy cells, e.g., in the case of autoimmunity). In some embodiments of the aspects described herein, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response. Stimulation of an immune response refers to an induction or increase of the immune response. Suppression of an immune response refers to an elimination or decrease of the immune response.

An immune response can be the development in a subject of a humoral and/or a cell-mediated immune response to a target. For purposes of the present invention, a "humoral immune response" is an antibody-mediated immune response and involves the induction and generation of antibodies that recognize and bind with some affinity for the antigen, while a "cell-mediated immune response" is one mediated by T-cells and/or other white blood cells. A "cell-mediated immune response" is elicited by the presentation of antigenic epitopes in association with Class I or Class II molecules of the major histocompatibility complex (MHC), CD1 or other non-classical MHC-like molecules. This activates antigen-specific CD4+T helper cells or CD8+ cytotoxic lymphocyte cells ("CTLs"). CTLs have specificity for peptide antigens that are presented in association with proteins encoded by classical or non-classical MHCs and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide or other antigens in association with classical or non-classical MHC molecules on their surface. A "cell-mediated immune response" also refers to the production of cytokines, chemokines and other such molecules produced by activated T-cells and/or other white blood cells, including those derived from CD4+ and CD8+ T-cells. Immune responses can be detected by a variety of methods known to those skilled in the art, including but not limited to, antibody production, cytotoxicity assay, proliferation assay, cytokine release assays, lymphoproliferation (lymphocyte activation) assays, CTL cytotoxic cell assays, by assaying for T-lymphocytes specific for the antigen in a sensitized subject, or by measurement of cytokine production by T cells. Such assays are well known in the art. See, e.g., Erickson et al. (1993) J. Immunol. 151:4189-4199; and Doe et al. (1994) Eur. J. Immunol. 24:2369-2376.

A cell can be any cell, for example, any mammalian cell, e.g., a human cell. In some embodiments of any of the aspects, a cell is a dendritic cell, regulatory T cell, or effector T cell.

In some embodiments of any of the aspects, the first cell is an immune cell. In some embodiments of any of the aspects, the first cell is a T cell e.g., a regulatory or effector T cell. In some embodiments of any of the aspects, the first cell is a CAR-T cell and/or engineered cell.

In some embodiments of any of the aspects, the second cell is a diseased cell. In some embodiments of any of the aspects, the diseased cell is a cancer cell. In some embodiments of any of the aspects, the diseased cell can be an infected cell, or a pathogen, e.g., the diseased cell can be infected with a bacterial, fungal, or viral pathogen or be a bacterial or fungal pathogen. Use of CAR-Ts in such applications is described in more detail at, e.g., Seif et al. Font. Immunol. 2019 10:2711, which is incorporated by reference herein in its entirety.

In some embodiments of any of the aspects, the binding domain specific for a target binds a marker on the surface of a diseased cell. In some embodiments of any of the aspects, the binding domain specific for a target binds a marker specific to diseased cells. In some embodiments of any of the aspects, the binding domain specific for a target binds a marker on the surface of an infected cell. In some embodiments of any of the aspects, the binding domain specific for a target binds a marker specific to infected cells. In some embodiments of any of the aspects, the binding domain specific for a target binds a marker on the surface of a pathogen. In some embodiments of any of the aspects, the binding domain specific for a target binds a marker specific to a pathogen.

As used herein, the term "target" refers to a biological molecule (e.g., peptide, polypeptide, protein, lipid, carbohydrate) to which a domain or moiety can selectively bind. The target can be, for example, an intracellular target (e.g., an intracellular protein target) or a cell surface target (e.g., a membrane protein, a receptor protein) or an extracellular matrix (e.g., collagen). In some embodiments of any of the aspects, a target is a cell surface target, such as a cell surface protein. By binding to a particular target, the binding domain specific for the target localizes the polypeptide and/or cell which is is part of or bound to, to the target molecule.

In some embodiments of any of the aspects, target is a receptor, extracellular matrix protein, extracellular protein, ion channel, transporter, peptide, polypeptide, nucleic acid, or microorganism. Targets for various cell types and diseases are well known in the art. Further suitable targets are known in the art, e.g., see Gross et al. Annu Rev Pharmacol Toxicol 2016 56:59-83; which is incorporated by reference herein in its entirety. By way of further non-limiting example, suitable targets on cancer cells can include ErbB family receptors, transforming growth factor beta (TGF-β) family receptors, cluster of differentiation 52 (CD52), programmed death-ligand 1 (PD-L1), vascular endothelial growth factor receptor 1 (VEGFR 1), vascular endothclial growth factor receptor 2 (VEGFR2), vascular endothelial growth factor receptor3 (VEGFR3), platelet-derived growth factor receptor beta (PDGFRβ), abelson murine leukemia viral oncogene (ABL), cluster of differentiation 19 (CD19), cluster of differentiation 3 (CD3), mitogen-activated protein kinase kinase (MEK), programmed cell death protein 1 (PD-1), and/or cluster of differentiation 20 (CD20).

In some embodiments of the methods described herein, the method comprises a method of immunotherapy, e.g., treating a subject in need of immunotherapy or in need of treatment for cancer. As used herein, the term "immunotherapy" refers to any chemical or biological agent with therapeutic usefulness in the treatment of diseases characterized by abnormal cell growth by promoting, preserving, or increasing the activity of immune cells. Immunotherapies include immune checkpoint inhibitors, T-cell transfer therapy (e.g., CAR-T therapies), antibody therapies, treatment vaccines, and immune system modulators.

In embodiments relating to treatment, the method can comprise, prior the contacting step(s), administering the first cell to the subject. In embodiments relating to treatment, the method can comprise, prior to one or more of the contacting steps, one or more steps of administering a cell, polypeptide, molecule, or other composition specified in the method to the subject. In embodiments relating to treatment, the contacting step(s) can comprise administering a cell, polypeptide, molecule, or other composition specified in the contacting step to the subject, such that the contact of the two entities occurs in the subject. In embodiments relating to treatment, each composition specified can be administered in sequence (either order), in an overlapping manner, concurrently, consecutively, or any combination of the foregoing over time. Administration of any composition can be repeated as needed to increase or sustain a desired response or effect.

The methods and compositions described herein can also be applied to tissue regeneration and/or tissue engineering applications. By using the approaches described herein to control growth, proliferation, and/or differentiation of the first cell, tissue growth in vivo or in vitro can be controlled. This control can be temporal and/or spatial. e.g., by providing a scaffold coated with mone of more the molecules and compositions described herein that interact with the first cell. Such approaches can include application of growth factors, allografts, cell-based therapies, gene-based therapies, scaffolds, scaffold implantation, and the like to control or direct the design, construction, modification, and growth of living tissue using biomaterials, cells, and factors alone and in combination. Appropriate cells, growth factors, differentiation factors, scaffolds, and the like are well known in the art for a variety of tissue types and are readily selected by a user of ordinary skill in the art based on the identity of the desired tissue type.

In some embodiments of any of the aspects, the signaling or activity of the first cell is tissue generation or regeneration promoting signaling or activity. In some embodiments of any of the aspects, the method described herein is a method of in vitro or in vivo tissue engineering. In some embodiments of any of the aspects, the surface-attached molecule or polypeptide is attached to a tissue engineering scaffold. Signaling pathways and modulation thereof, as well as scaffolding, to promote tissue regeneration or generation, or tissue engineering are known in the art, see e.g., Davis et al. Biochem Soc Trans 2016 44:696-701, which is incorporated by reference herein in its entirety.

In embodiments relating to tissue generation or regeneration, the intracellular signaling domain can comprise the signaling domain and/or the intracellular domain of a cadherein, e.g., E-cadherein (e.g., NCBI Gene ID 999), P-cadherein (e.g., NCBI Gene ID 1001); or MyoD (e.g., NCBI Gene ID 4654).

In some embodiments of any of the aspects, the signaling or activity of the first cell is reprogramming signaling or activity, e.g., to create or induce an iPSC. In embodiments relating to iPSCs, the intracellular signaling domain can comprise the signaling domain and/or the intracellular domain of a Yamanaka factor. Yamanaka factors are known in the art and include Myc, Oct3/4, Sox2, and Klf4). Further discussion of Yamanka factors can be found, e.g., at Yamanaka et al. Cell 2006 126:663-76, which is incorporated by reference herein in its entirety.

Further examples of proteins suitable for use in an intracellular signaling domain as described herein can be found in, e.g., Nakajim et al., Keio J Med 201160:47-55, which is incorporated by reference herein in its entirety.

In a second version of the present technology, the small molecule (e.g., biotinylamide) is present on a cell surface receptor polypeptide, and a domain that binds specifically to the small molecule is used in one or more other molecules to control the activity of the cell surface receptor polypeptide (see FIG. 3A for an illustrative embodiment). Accordingly, in one aspect of any of the embodiments, described herein is a first polypeptide comprising i) an extracellular small molecule acceptor peptide (and/or small molecule), and ii) a first intracellular signaling domain. In some embodiments of any of the aspects, the first polypeptide further comprises iii) an extracellular target-binding domain. The second version of the present technology can be used for the same purposes as described above herein, e.g., for treatment or tissue engineering. Methods of applying the second version of the present technology for such purposes are described in detail below.

Systems relevant to this second version of the present technology are also provided. For example, in one aspect of any of the embodiments, described herein is a system comprising a first polypeptide comprising i) an extracellular small molecule acceptor peptide (and/or small molecule), and ii) a first intracellular signaling domain; and a second polypeptide comprising: i) an extracellular domain that binds specifically to the small molecule. In some embodiments of any of the aspects, the second polypeptide further comprises ii) a second intracellular signaling domain. In some embodiments of any of the aspects, the first polypeptide further comprises iii) an extracellular target-binding domain.

In some embodiments of any of the aspects, either or both of the first and the second polypeptides is a CAR. In some embodiments of any of the aspects, either or both of the first and the second intracellular signaling domains comprise one or more of an intracellular CD28, 4-1BB, and/or CD3ζ signaling domain. In some embodiments of any of the aspects, either or both of the first and the second intracellular signaling domains comprise each of: intracellular CD28, 4-1BB, and CD3ζ signaling domains.

The systems relating to the second version of the technology described herein can be controlled using the general principles discussed throughout the disclosure. For example, in one aspect of any of the embodiments, provided herein is a method of controlling signaling or activity of a first cell comprising a first polypeptide comprising i) an extracellular small molecule acceptor peptide (and/or small molecule), and ii) a first intracellular signaling domain, the method comprising a) contacting the first cell with a soluble small molecule comprising a small molecule acceptor peptide (and/or small molecule) to inhibit the signaling or activity of the first cell and/or b) contacting the first cell with a surface-attached second polypeptide comprising: i) an extracellular domain that binds specifically to the small molecule. In some embodiments of any of the aspects, the surface-attached second polypeptide is expressed on the surface of a second cell.

In some embodiments of any of the aspects described herein, the receptors and polypeptides described herein can include sequences from dimerizing receptors, e.g., tyrosine kinases, to provide even further control over the system. The dimer pair can be a homodimer or heterodimer, e.g., if it is a heterodimer pair, the second member of the pair can be a wild-type receptor or a further engineered polypeptide. The disruption of the dimer pair can be controlled via the interactions described herein, additional drugs specific to the dimer interaction, or by cleaving domains necessary for the dimerization.

In one aspect of any of the embodiments, provided herein is a nucleic acid or set of nucleic acids encoding one or more of the polypeptide(s), receptor(s), and/or system(s) described herein. The nucleic acid(s) can be provided, e.g., in a vector, a genome, or a cell. In some embodiments of any of the aspects, the nucleic acid(s) are operably connected to a promoter and/or other expression control elements (e.g., enhancers or repressors).

In one aspect of any of the embodiments, provided herein is a cell or set of cells comprising one or more of the nucleic acids, polypeptides, receptors, and/or systems described herein. In some embodiments of any of the aspects, one or more of the cells are engineered cells. In some embodiments of any of the aspects, one or more of the cells are immune cells, e.g., T cells.

In embodiments relating to a cell comprising a polypeptide or receptor with a biotin acceptor polypeptide, the cell can further comprise or encode a biotin ligase, e.g., a bacterial biotin ligase, for ligating a biotinylamide to the biotin acceptor polypeptide. In some embodiments of any of the aspects, the biotin ligase can be *E. coli* biotin ligase (birA), e.g., NCBI Gene ID: 948469 or 914965. Expression of an exogenous biotin ligase can be controlled by use of an inducible or repressible promoter to provide further control of the systems and methods described herein. For example, when biotin ligase is not expressed, the polypeptide or receptor with a biotin acceptor polypeptide will not be able to interact with other molecules comprising a domain that binds specifically to a biotinylamide. Conversely, when biotin ligase is expressed, the polypeptide or receptor with a biotin acceptor polypeptide will be able to interact with other molecules comprising a domain that binds specifically to a biotinylamide. Inducible and repressible promoters allow the expression of the polypeptide to be increased or decreased as desired and are in contrast to constitutive promoters. In some embodiments of any of the aspects, the inducible promoter is TRE3G.

In embodiments where the small molecule ligase is controlled by an inducible promoter, the signaling of a first cell comprising the gene encoding the ligase can be permitted or induced by contacting the first cell with an agent that induces transcription from the inducible promoter. For example, the inducible promoter TRE3G can be induced by rtTA-3. Other examples of inducible (or conversely, repressible promoters) are known in the art.

In some embodiments of any of the aspects, the biotin ligase is targeted to the endoplasmic reticulum, the cell surface, the cytoplasm, and/or or the golgi. In some embodiments of any of the aspects, the biotin ligase is targeted to the endoplasmic reticulum. Methods of targeting a protein to one or more desired intraceullar compartments, e.g, by provising of signal peptides, is well known in the art.

In some embodiments of any of the aspects, any of the domains or sequences described herein can be human or humanized. For example, the human biotin ligase gene is known. e.g., NCBI Gene ID: 3141 along with its mRNA (e.g., NCBI Ref Seqs: NM_000411.8 (SEQ ID NO: 118), NM_001242784.3 (SEQ ID NO: 119), NM_001242785.2 (SEQ ID NO: 120), NM_001352514.2 (SEQ ID NO: 121), NM_001352515.2 (SEQ ID NO: 122), NM_001352516.2 (SEQ ID NO: 123), NM_001352517.1 (SEQ ID NO: 124), NM_001352518.2 (SEQ ID NO: 125)) and polypeptide sequences (e.g., NCBI Ref Seqs: NP_000402.3 (SEQ ID NO: 126), NP_001229713.1 (SEQ ID NO: 127), NP_001229714.1 (SEQ ID NO: 128), NP_001339443.1 (SEQ ID NO: 129), NP_001339444.1 (SEQ ID NO: 130), NP_001339445.1 (SEQ ID NO: 131), NP_001339446.1 (SEQ ID NO: 132), NP_001339447.1 (SEQ ID NO: 133). In some embodiments of any of the aspects, the biotin ligase can have a sequence of any of SEQ ID NOs: 126-133, or be encoded by a nucleic acid sequence having the sequence of any of SEQ ID NOs: 118-125. Human sequences of other proteins or nucleic acids described herein are readily identified by one of ordinary skill in the art by searching the NCBI database for the name of the protein or gene, selecting the "Homology", "Orthologs", or "HomoloGene" links/sections, and then selecting the entry for *Homo sapiens*. Alternatively, the sequence can be used to run a BLAST search, and the *Homo sapiens* sequence with the highest degree of homology can be selected.

The term "constitutively active promoter" refers to a promoter of a gene which is expressed at all times within a given cell. Exemplary promoters for use in mammalian cells include cytomegalovirus (CMV) and the like. The term "inducible promoter" refers to a promoter of a gene which can be expressed in response to a given signal, for example addition or reduction of an agent. Non-limiting examples of an inducible promoter are promoters that are regulated in a specific tissue type, a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard, Proc. Natl. Acad. Sci. USA 89:5547, 1992, and Paillard, Human Gene Therapy 9:983, 1989; each of which are incorporated by reference herein in its entirety). In some embodiments of any of the aspects, expression of the polypeptide can be precisely regulated, for example, by using an inducible regulatory sequence that is sensitive to certain physiological regulators, e.g., circulating glucose levels, or hormones (Docherty et al., 1994, FASEB J. 8:20-24). Such inducible expression systems, suitable for the control of expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the polypeptide.

In some embodiments of any of the aspects, a nucleic acid as described herein can comprise a viral vector or viral genome encoding one or more of the proteins described herein (e.g., a receptor, CAR, or birA protein). In some embodiments of any of the aspects, a nucleic acid as described herein can be provided by providing a virus or virion or viral particle comprising a nucleic acid encoding one or more of the proteins described herein (e.g., a receptor, CAR, or birA protein). Accordingly, In some embodiments of any of the aspects, a cell described herein can comprise a viral vector, viral genome, virus, virion, or viral particle comprising such a protein and/or nucleic acid.

In some embodiments of any of the aspects described herein, where a small molecule would be connected to, ligated to, or interacting with two different molecules, e.g., in the case of a surface-attached small molecule, the systems and methods relate to a multi-small molecule composition in which a first small molecule and second small molecule are conjugated, ligated, or otherwise associated with each other (e.g., by being conjugated to the same scaffold molecule). One molecule that interacts with the multi-small molecule compositions interacts with the first small molecule and the second molecule that interacts with a small molecule interacts with the second small molecule. By way of non-limiting example, exemplified herein is the use of biotin-FITC as a small-molecule linker (multi-small molecule composition) with the ability to induce trans-cellular signaling. In this coculture system, a first cell expressed an anti-FITC Synthetic Notch, which can bind one end of the biotin-FITC, and the second cell expresses an anti-biotin ligand (as described elsewhere herein), which binds the other end of the multi-small molecule composition. The signaling capacity of such a system is concentration dependent—low concentrations do not induce signaling, and high concentrations lead to lower signaling due to the ability of soluble ligand to act as a competitive inhibitor. It is further contemplated herein that multi-small molecule compositions comprising third, fourth, or more small molecules and cognate polypeptides/molecules as described herein can be constructed and used as described herein, e.g., to activate multiple signaling pathways with a single controller (the multi-small molecule composition).

In some embodiments of any of the aspects, the methods described herein relate to treating a subject having or diagnosed as having cancer with a composition or system as described herein. Subjects having cancer can be identified by a physician using current methods of diagnosing cancer. Symptoms and/or complications of cancer which characterize these conditions and aid in diagnosis are well known in the art and include but are not limited to, for example, in the case of breast cancer a lump or mass in the breast tissue, swelling of all or part of a breast, skin irritation, dimpling of the breast, pain in the breast or nipple, nipple retraction, redness, scaliness, or irritation of the breast or nipple, and nipple discharge. Tests that may aid in a diagnosis of, e.g. breast cancer include, but are not limited to, mammograms, x-rays, MRI, ultrasound, ductogram, a biopsy, and ductal lavage. A family history of cancer or exposure to risk factors for cancer (e.g. smoke, radiation, pollutants, BRCA1 mutation, etc.)

The compositions and methods described herein can be administered to a subject having or diagnosed as having cancer. In some embodiments of any of the aspects, the methods described herein comprise administering an effective amount of compositions described herein to a subject in order to alleviate a symptom of a cancer. As used herein, "alleviating a symptom" of a cancer is ameliorating any condition or symptom associated with the cancer. As compared with an equivalent untreated control, such reduction is by at least 5%, 10%. 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic. In some embodiments of any of the aspects, the administration is subcutaneous.

The term "effective amount" as used herein refers to the amount of at least one chimeric molecule needed to alleviate at least one or more symptom of the disease or disorder, and relates to a sufficient amount of pharmacological composition to provide the desired effect. The term "therapeutically effective amount" therefore refers to an amount of at least one chimeric molecule that is sufficient to provide a particular anti-cancer effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient(s), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for immune activity, among others. The dosage can be determined by a physician and adjusted, as necessary, to suit observed effects of the treatment.

Effective amounts, toxicity, and therapeutic efficacy can be determined by standard pharmaceutical procedures in cell cultures or experimental animals, e.g., for determining the minimal effective dose and/or maximal tolerated dose. The dosage can vary depending upon the dosage form employed and the route of administration utilized. A therapeutically effective dose can be estimated initially from cell culture assays. Also, a dose can be formulated in animal models to achieve a dosage range between the minimal effective dose and the maximal tolerated dose. The effects of any particular dosage can be monitored by a suitable bioassay, e.g., assay for tumor growth and/or size among others. The dosage can be determined by a physician and adjusted, as necessary, to suit observed effects of the treatment.

In some embodiments of any of the aspects, the technology described herein relates to a pharmaceutical composition comprising a molecule, polypeptide, receptor, cell, or system, as described herein, and optionally a pharmaceutically acceptable carrier. In some embodiments of any of the aspects, the active ingredients of the pharmaceutical composition comprise a molecule, polypeptide, receptor, cell, and/or system, as described herein. In some embodiments of any of the aspects, the active ingredients of the pharmaceutical composition consist essentially of a molecule, polypeptide, receptor, cell, and/or system, as described herein. In some embodiments of any of the aspects, the active ingredients of the pharmaceutical composition consist of a molecule, polypeptide, receptor, cell, and/or system, as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin. HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier". "pharmaceutically acceptable carrier" or the like are used interchangeably herein. In some embodiments of any of the aspects, the carrier inhibits the degradation of the active agent(s) as described herein.

In some embodiments of any of the aspects, the pharmaceutical composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to. DUROS®-type dosage forms and dose-dumping.

Suitable vehicles that can be used to provide parenteral dosage forms of a molecule, polypeptide, receptor, cell, or system as disclosed within are well known to those skilled in the art. Examples include, without limitation; sterile water; water for injection USP; saline solution; glucose solution; aqueous vehicles such as but not limited to, sodium chloride injection, Ringer's injection, dextrose Injection, dextrose and sodium chloride injection, and lactated Ringer's injection water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a composition as disclosed herein can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21-st Ed., Lippincott. Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments of any of the aspects, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.; 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to. pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 Bi; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, the molecule, polypeptide, receptor, cell, or system, described herein is administered as a monotherapy, e.g., another treatment for the disease is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azascrine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylomithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

In certain embodiments, an effective dose of a composition comprising a molecule, polypeptide, receptor, cell, and/or system as described herein can be administered to a patient once. In certain embodiments, an effective dose of a composition comprising a molecule, polypeptide, receptor, cell, and/or system as described herein can be administered to a patient repeatedly. For systemic administration, subjects can be administered a therapeutic amount of a composition, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments of any of the aspects, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. cancer cell growth, by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient(s). The desired dose or amount of activation can be administered at one time or divided into subdoses, e.g., 2-4 subdoses and administered over a period of time, e.g., at appropriate intervals through the day or other appropriate schedule. In some embodiments of any of the aspects, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks. 1 month, 2 months, 3 months. 4 months. 5 months, or 6 months, or more. A composition comprising a molecule, polypeptide, receptor, cell, and/or system as described herein can be administered over a period of time, such as over a 5 minute, 10 minute, 15 minute, 20 minute, or 25 minute period.

The dosage ranges for the administration of composition as described herein, according to the methods described herein depend upon, for example, the form of the composition, its potency, and the extent to which symptoms, markers, or indicators of a condition described herein are desired to be reduced, for example the percentage reduction desired for cancer cell growth or the extent to which, for example, immune responses are desired to be induced. The dosage should not be so large as to cause adverse side effects, such as autoimmunity. Generally, the dosage will vary with the age, condition, and sex of the patient and can be determined by one of skill in the art. The dosage can also be adjusted by the individual physician in the event of any complication.

The efficacy of a composition in, e.g. the treatment of a condition described herein, or to induce a response as described herein (e.g. cancer) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. immune response induction. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. immune responses). It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g. T cell activity.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments of any of the aspects. "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased". "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species. e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms. "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease, e.g., cancer. A subject can be male or female.

A subject can be one who has been previously diagnosed with or identified as suffering from or having a condition in need of treatment (e.g., cancer) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer, cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. The terms also refer to fragments or variants of the polypeptide that maintain at least 50% of the activity or effect, of the full length polypeptide. Conservative substitution variants that maintain the activity of wildtype proteins will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants, fragments, and/or fusion proteins can be tested for activity, for example, by administering the variant to an appropriate animal model of, e.g., cancer, as described herein.

In some embodiments of any of the aspects, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of the wildtype, e.g. 110%. 125%, 150%, 175%, 200%. 500%, 1000% or more.

One method of identifying amino acid residues which can be substituted is to align, for example, the human sequence to a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp or BLASTn (available on the world wide web at blast.ncbi.nlm.nih.gov), with default parameters set.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as lie, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. activity and specificity of a native or reference polypeptide is retained.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure.

Amino acids can be grouped according to similarities in the properties of their side chains (in A. L. Lehninger, in Biochemistry, second ed., pp. 73-75, Worth Publishers, New York (1975)); (1) non-polar: Ala (A), Val (V), Leu (L), Ile (I), Pro (P), Phe (F), Trp (W), Met (M); (2) uncharged polar; Gly (G), Ser (S), Thr (T), Cys (C), Tyr (Y), Asn (N), Gn (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, le; (2) neutral hydrophilic: Cys, Ser, Thr, Asn, Gin; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gin or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu. Typically conservative substitutions for one another also include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton. Proteins (1984)).

In some embodiments of any of the aspects, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments of any of the aspects, the polypeptide described herein can be a variant of a sequence described herein. In some embodiments of any of the aspects, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

In some embodiments of any of the aspects, a polypeptide can comprise one or more amino acid substitutions or modifications. In some embodiments of any of the aspects, the substitutions and/or modifications can prevent or reduce proteolytic degradation and/or prolong half-life of the polypeptide in a subject. In some embodiments of any of the aspects, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002): and/or Fc fragments (Ashkenazi and Chamow, 1997). The references in the foregoing paragraph are incorporated by reference herein in their entireties.

In some embodiments of any of the aspects, a polypeptide as described herein can comprise at least one peptide bond replacement. A polypeptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments of any of the aspects, a polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments of any of the aspects, a polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments of any of the aspects, a polypeptide can be modified, e.g. by addition of a moiety to one or more of the amino acids that together comprise the peptide. In some embodiments of any of the aspects, a polypeptide as described herein can comprise one or more moiety molecules, e.g. 1 or more moiety molecules per polypeptide, 2 or more moiety molecules per polypeptide, 5 or more moiety molecules per polypeptide, 10 or more moiety molecules per polypeptide or more moiety molecules per polypeptide. In some embodiments of any of the aspects, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments of any of the aspects, an end-capping modification can comprise acetylation at the N-terminus, N-terminal acylation, and N-terminal formylation. In some embodiments of any of the aspects, an end-capping modification can comprise amidation at the C-terminus, introduction of C-terminal alcohol, aldehyde, ester, and thioester moieties. The half-life of a polypeptide can be increased by the addition of moieties, e.g. PEG, albumin, or other fusion partners (e.g. Fc fragment of an immunoglobin).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002, Braman "In Vitro Mutagenesis Protocols" Springer, 2004; and Rapley "The Nucleic Acid Protocols Handbook" Springer 2000: which are herein incorporated by reference in their entireties. In some embodiments of any of the aspects, a polypeptide as described herein can be chemically synthesized and mutations can be incorporated as part of the chemical synthesis process.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies. Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

Antibodies and/or antibody reagents can include an immunoglobulin molecule, a monoclonal antibody, a chimeric antibody, a CDR-grafted antibody, a humanized antibody, a fully human antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

As used herein, the term "nanobody" or single domain antibody (sdAb) refers to an antibody comprising the small single variable domain (VHH) of antibodies obtained from camelids and dromedaries. Antibody proteins obtained from members of the camel and dromedary (*Camelus baclrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994: which is incorporated by reference herein in its entirety).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998: see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62: and Lauwercys, M. et al. 1998 EMBO J. 17: 3512-3520: each of which is incorporated by reference herein in its entirety. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins. i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in camelid nanobodies being extremely thermostable, stable to extreme pH and to proteoytic digestion, and poorly antigenic. See U.S. patent application 20040161738 published Aug. 19, 2004; which is incorporated by reference herein in its entirety. These features combined with the low antigenicity to humans indicate great therapeutic potential.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments of any of the aspects, the expression of a biomarker(s), target(s), or gene/polypeptide described herein is/are tissue-specific. In some embodiments of any of the aspects, the expression of a biomarker(s), target(s), or gene/polypeptide described herein is/are global. In some embodiments of any of the aspects, the expression of a biomarker(s), target(s), or gene/polypeptide described herein is systemic.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

In some embodiments of any of the aspects, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the nucleic acid or polypeptide described herein is exogenous. In some embodiments of any of the aspects, the nucleic acid or polypeptide described herein is ectopic. In some embodiments of any of the aspects, the nucleic acid or polypeptide described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

In some embodiments of any of the aspects, a nucleic acid described herein is comprised by a vector. In some of the aspects described herein, a nucleic acid as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of nonessential viral genes. The vector and/or particle may be utilized for the purpose of transferring any nucleic acids into cells either in vitro or in vivo. Numerous forms of viral vectors are known in the art.

It should be understood that the vectors described herein can, In some embodiments of any of the aspects, be combined with other suitable compositions and therapies. In some embodiments of any of the aspects, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with, e.g., cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments of any of the aspects, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments of any of the aspects, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers. 2014 (ISBN-1449659055); Michael Richard Green and Joseph Sambrook. Molecular Cloning: A Laboratory Manual, 4th ed., Cold Spring Harbor Laboratory Press, Cold Spring Harbor, N.Y., USA (2012) (ISBN 1936113414): Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005: and Current Protocols in Immunology (CPI) (John E. Coligan, ADA M Kruisbeek, David H Margulies, Ethan M Shevach, Warren Strobe, (eds.) John Wiley and Sons, Inc. 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). An alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An "alkenyl" is an unsaturated alkyl group is one having one or more double bonds bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), and the higher homologs and isomers.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Exemplary aryl and heteroaryl groups include, but are not limited to, phenyl, 4-nitrophenyl, 1-naphthyl, 2-naphthyl, biphenyl, 4-biphenyl, pyrrole, 1-pyrrolyl, 2-pyrrolyl, 3-pyrrolyl, pyrazole, 3-pyrazolyl, imidazole, imidazohyl, 2-imidazolyl, 4-imidazolyl, benzimidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, thiazolyl, 2-thiazolyl, 4-thiazolyl, 5-thiazolyl, 2-furyl, 3-furyl. 2-thienyl, 3-thienyl, pyridine. 2-pyridyl, naphthyridinyl, 3-pyridyl, 4-pyridl, benzophenonepyridyl, pyridazinyl, pyrazinyl, 2-pyrimidyl, 4-pyrimidyl, pyrimidinyl, 5-benzothiazolyl, purinyl, 2-benzimidazolyl, indolyl, 5-indolyl, quinoline, quinolinyl, 1-isoquinolyl, 5-isoquinolyl, 2-quinoxalinyl, 5-quinoxalinyl, 3-quinoll, 6-quinolyl, furan, furyl or furanyl, thiophene, thiophenyl or thienyl, diphenylether, diphenylamine, and the like.

The term "optionally substituted" means that the specified group or moietyis unsubstituted or is substituted with one or more (typically 1, 2, 3, 4, 5 or 6 substituents) independently selected from the group of substituents listed below in the definition for "substituents" or otherwise specified. The term "substituents" refers to a group "substituted" on a substituted group at any atom of the substituted group. Suitable substituents include, without limitation, halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A cell surface receptor polypeptide comprising i) an extracellular domain that binds specifically to a biotinylamide.
2. The polypeptide of paragraph 1, wherein the domain that binds specifically to a biotinylamide is an antibody or antibody reagent.
3. The polypeptide of paragraph 2, wherein the antibody reagent is a scFv.
4. The polypeptide of any of paragraphs 2-3, wherein the antibody reagent comprises the 6 CDRs of SEQ ID NOs: 4-9.
5. The polypeptide of any of paragraphs 2-4, wherein the antibody reagent comprises SEQ ID NOs: 1 and 2.
6. The polypeptide of any of paragraphs 2-4, wherein the antibody reagent comprises amino acids 1-119 of SEQ ID NO: 1 and amino acids 1-117 of SEQ ID NO: 2.
7. The polypeptide of any of paragraphs 2-4, wherein the antibody reagent comprises amino acids 1-119 of SEQ ID NO: 1 and amino acids 1-117 of SEQ ID NO: 2, joined by a peptide linker.
8. The polypeptide of paragraph 7, wherein the peptide linker comprises SEQ ID NO: 3.
9. The polypeptide of any of paragraphs 1-8, wherein the domain that binds specifically to a biotinylamide binds specifically to biotinamide, biocyntinamide, and/or biocytin.
10. The polypeptide of any of paragraphs 1-9, wherein the domain that binds specifically to a biotinylamide does not bind to biotin.
11. The polypeptide of any of paragraphs 1-8, wherein the domain that binds specifically to a biotinylamide binds specifically as compared to binding of the domain with biotin.
12. The polypeptide of any of paragraphs 1-8, wherein the domain that binds specifically to a biotinylamide binds specifically to biotin lacking its carboxylic acid group as compared to binding of the domain with biotin.
13. The polypeptide of any of paragraphs 1-12, further comprising ii) an intracellular signaling domain.
14. The polypeptide of paragraph 13, wherein the intracellular signaling domain is a nuclear-acting signaling domain.
15. The polypeptide of paragraph 14, wherein the nuclear-acting signaling domain comprises a DNA-binding domain.
16. The polypeptide of any of paragraphs 13-15, wherein the signaling domain comprises a Notch receptor signaling domain.
17. The polypeptide of paragraph 16, wherein the Notch receptor signaling domain comprises the Notch core.
18. The polypeptide of any of paragraphs 13-15, wherein the intracellular signaling domain comprises a transcriptional activator.
19. The polypeptide of paragraph 18, wherein the transcriptional activator is GAL4-VP64.
20. The polypeptide of any of paragraphs 1-13, wherein the polypeptide is a chimeric antigen receptor (CAR) comprising the domain that binds specifically to a biotinylamide and an intracellular signaling domain.
21. The polypeptide of paragraph 20, wherein the intracellular signaling domain comprises an intracellular CD28, 4-1BB, and/or CD3ζ signaling domain.
22. The polypeptide of paragraph 20, wherein the intracellular signaling domains comprises intracellular CD28, 4-1BB, and CD3ζ signaling domains.
23. A system comprising a) the cell surface receptor polypeptide of any of paragraphs 1-22 and b) one or both of:
  i) a surface-attached molecule comprising:
    A, a binding domain specific for a target; and
    B. a biotinylamide and/or a biotin acceptor peptide; and
  ii) a soluble molecule comprising a biotinylamide and/or a biotin acceptor peptide.
24. The system of paragraph 23, wherein the soluble molecule is a small molecule or an antibody or antibody reagent.
25. A method of controlling signaling or activity of a first cell comprising the system of any of paragraphs 23-24, the method comprising:
  a. contacting the first cell with a surface-attached molecule comprising:
    i. a binding domain specific for a target; and
    ii. a biotinylamide and/or a biotin acceptor peptide to induce the signaling or activity of the first cell; and/or
  b. contacting the first cell with a soluble molecule comprising a biotinylamide and/or a biotin acceptor peptide to inhibit the signaling or activity of the first cell.
26. The system or method of any of paragraphs 23-25, wherein the surface-attached molecule is bound or conjugated to the first cell, a second cell, a lipid bilayer surface, or a solid surface.
27. The system or method of paragraph 26, wherein the solid surface is a bead.
28. The system or method of paragraph 26, wherein the lipid bilayer surface is a liposome.
29. The system or method of paragraph 28, wherein the surface-attached molecule is not soluble.
30. The system or method of any of paragraphs 23-29, wherein the surface-attached molecule further comprises a binding domain specific for a target.
31. The system or method of any of paragraphs 23-31, wherein the target is a cell-surface marker on a second cell and the first cell is an immune cell.
32. The system or method of paragraph 31, wherein the second cell is a cancer cell.
33. The system or method of any of paragraphs 23-32, wherein the soluble molecule comprises or is bis-biotinamide.
34. The system or method of any of paragraphs 23-33, wherein the soluble molecule comprises a peptide.
35. The system or method of any of paragraphs 23-34, wherein the soluble molecule comprises a peptide conjugated to a biotinylamide.
36. The system or method of any of paragraphs 34-35, wherein the peptide comprises bovine sersum albumin (BSA).
37. The system or method of any of paragraphs 23-36, wherein the soluble molecule comprises a polymer conjugated to a biotinylamide.
38. The system or method of paragraph 37, wherein the polymer is polyethylene glycol (PEG).
39. The method of any of paragraphs 25-38, wherein the signaling or activity of the first cell is immune-promoting signaling or activity.
40. The method of any of paragraph 39, wherein the first cell is an immune cell.
41. The method of any of paragraphs 39-40, wherein the second cell is a diseased cell.
42. The method of paragraph 39-41, wherein the first cell is a T cell and the binding domain specific for a target binds a marker on the surface of a diseased cell.
43. The method of paragraph 39-40, wherein the first cell is a T cell and the binding domain specific for a target binds a marker specific to diseased cells.
44. The method of any of paragraphs 4143, wherein the diseased cells are cancer cells.
45. The method of any of paragraphs 39-44, wherein the method is a method of treating a subject in need of immunotherapy.
46. The method of paragraph 45, wherein the method comprises, prior to the contacting step of a), administering the first cell to the subject.
47. The method of any of paragraphs 45-46, wherein the method comprises, prior to the contacting step of a), administering a molecule comprising:
  i. a binding domain specific for a target; and
  ii. a biotinylamide and/or a biotin acceptor peptide
  such that it attaches to a surface in the subject, or is administered already attached to a surface, thereby providing the surface-attached molecule.
48. The method of any of paragraphs 45-47, wherein the method comprises, prior to the contacting step of b), administering the soluble molecule.
49. The method of any of paragraphs 25-38, wherein the signaling or activity of the first cell is tissue generation or regeneration promoting signaling or activity.
50. The method of paragraph 49, wherein the method is a method of in vitro or in vivo tissue engineering.
51. The method of any of paragraphs 49-50, wherein the surface-attached molecule is attached to a tissue engineering scaffold.
52. A first polypeptide comprising i) an extracellular biotinylamide and/or a biotin acceptor peptide and ii) a first intracellular signaling domain.

53. The first polypeptide of paragraph 52, further comprising iii) an extracellular target-binding domain.
54. The first polypeptide of any of paragraphs 52-53, wherein the first intracellular signaling domain comprises intracellular CD28, 4-1BB, and/or CD3ζ signaling domains.
55. The first polypeptide of any of paragraphs 52-53, wherein the first intracellular signaling domain comprises intracellular CD28, 4-1BB, and CD3ζ signaling domains.
56. The polypeptide of any of paragraphs 52-53, wherein the intracellular signaling domain is a nuclear-acting signaling domain.
57. The polypeptide of paragraph 56, wherein the nuclear-acting signaling domain comprises a DNA-binding domain.
58. The polypeptide of any of paragraphs 56-57, wherein the signaling domain comprises a Notch receptor signaling domain.
59. The polypeptide of paragraph 58, wherein the Notch receptor signaling domain comprises the Notch core.
60. The polypeptide of any of paragraphs 56-58, wherein the intracellular signaling domain comprises a transcriptional activator.
61. The polypeptide of paragraph 60, wherein the transcriptional activator is GAL4-VP64.
62. A system comprising the first polypeptide of any of paragraphs 52-61 and a second polypeptide comprising: i) an extracellular domain that binds specifically to a biotinylamide and ii) a second intracellular signaling domain.
63. The polypeptide or system of any of paragraphs 52-62, wherein the first and/or second polypeptide is a CAR.
64. The system of any of paragraphs 62-63, wherein the domain that binds specifically to a biotinylamide is an antibody or antibody reagent.
65. The system of paragraph 64, wherein the antibody reagent is a scFv.
66. The system of any of paragraphs 64-65, wherein the antibody reagent comprises the 6 CDRs of SEQ ID NOs: 4-9.
67. The system of any of paragraphs 64-65, wherein the antibody reagent comprises SEQ ID NOs: 1 and 2.
68. The system of any of paragraphs 64-65, wherein the antibody reagent comprises amino acids 1-119 of SEQ ID NO: 1 and amino acids 1-117 of SEQ ID NO: 2.
69. The system of any of paragraphs 64-65, wherein the antibody reagent comprises amino acids 1-119 of SEQ ID NO: 1 and amino acids 1-117 of SEQ ID NO: 2, joined by a peptide linker.
70. The system of paragraph 69, wherein the peptide linker comprises SEQ ID NO: 3.
71. The system of any of paragraphs 62-70, wherein the domain that binds specifically to a biotylamide binds specifically to biotinamide, biocyntinamide, and/or biocytin.
72. The system of any of paragraphs 62-70, wherein the domain that binds specifically to a biotinylamide does not bind to biotin.
73. The system of any of paragraphs 62-70, wherein the domain that binds specifically to a biotinylamide binds specifically as compared to binding of the domain with biotin.
74. The system of any of paragraphs 62-70, wherein the domain that binds specifically to a biotinylamide binds specifically to biotin lacking its carboxylic tail as compared to binding of the domain with biotin.
75. The polypeptide or system of any of paragraphs 52-74, wherein the first and/or second intracellular signaling domain comprises an intracellular CD28, 4-1BB, and/or CD3ζ signaling domain.
76. The polypeptide or system of any of paragraphs 52-74, wherein the first and/or second intracellular signaling domain comprises intracellular CD28, 4-1BB, and CD3ζ signaling domains.
77. A method of controlling signaling or activity of a first cell comprising the system of any of paragraphs 62-77, the method comprising:
   a. contacting the first cell with a soluble small molecule comprising a biotinylamide and/or a biotin acceptor peptide to inhibit the signaling or activity of the first cell.
78. The method of paragraph 77, wherein the soluble small molecule is bis-biotinamide.
79. The method of any of paragraphs 77-78, wherein the signaling or activity of the first cell is immune-promoting signaling or activity.
80. The method of any of paragraph 79, wherein the first cell is an immune cell.
81. The method of paragraph 80, wherein the first cell is a T cell and the extracellular target-binding domain binds a marker on the surface of a diseased cell.
82. The method of paragraph 80, wherein the first cell is a T cell and the extracellular target-binding domain binds a marker specific to a diseased cell.
83. The method of any of paragraphs 81-82, wherein the diseased cell is a cancer cell.
84. The method of any of paragraphs 79-83, wherein the method is a method of treating a subject in need of immunotherapy.
85. The method of paragraph 84, wherein the method comprises a first step of administering the first cell to the subject.
86. The method of any of paragraphs 77-78, wherein the signaling or activity of the first cell is tissue generation or regeneration promoting signaling or activity.
87. The method of paragraph 86, wherein the method is a method of in vitro or in vivo tissue engineering.
88. A nucleic acid or set of nucleic acids encoding the receptor, polypeptide, or system of any of paragraphs 1-76.
89. A cell or set of cells comprising or encoding the receptor, polypeptide, system, or nucleic acid of any of paragraphs 1-76 and 88.
90. The cell of paragraph 89, further comprising or encoding biotin ligase.
91. The cell of paragraph 90, wherein the biotin ligase is *E. coli* biotin ligase.

Some embodiments of the technology described herein can be defined according to any of the following numbered paragraphs:

1. A first small molecule-controlled signaling polypeptide comprising:
   a. a small molecule acceptor peptide and/or a small molecule; and
   b. at least a first signaling domain.
2. A second small molecule-controlled signaling polypeptide comprising:
   a. an domain that binds specifically to a small molecule; and
   b. at least a second signaling domain.

3. A synthetic signaling system comprising:
   a. a first small molecule-controlled signaling polypeptide of paragraph 1 and a second small molecule-controlled signaling polypeptide of paragraph 2
   b. a first small molecule-controlled signaling polypeptide of paragraph 1 and a polypeptide comprising a domain that binds specifically to a small molecule: or
   c. a second small molecule-controlled signaling polypeptide and a polypeptide comprising a small molecule acceptor peptide and/or a small molecule.
4. The polypeptide or system of any of paragraphs 1-3, wherein the second small molecule-controlled signaling polypeptide comprises:
   i) a signaling domain comprising an extracellular domain that binds specifically to a target;
   ii) a transmembrane domain; and
   iii) the domain that binds specifically to a small molecule.
5. The polypeptide or system of any of paragraphs 1-3, wherein the first small molecule-controlled signaling polypeptide comprises:
   i) a signaling domain comprising an extracellular domain that binds specifically to a target;
   ii) a transmembrane domain; and
   iii) the small molecule acceptor peptide and/or the small molecule.
6. The polypeptide or system of paragraph 4 or 5, wherein the first or second small molecule-controlled signaling polypeptide does not comprise a CAR stimulatory domain.
7. The polypeptide or system of any of paragraphs 4-6, wherein the first or second small molecule-controlled signaling polypeptide does not comprise a CAR co-stimulatory domain.
8. The polypeptide or system of paragraph 7, wherein the first or second small molecule-controlled signaling polypeptide comprises a CAR stimulatory or co-stimulatory domain.
9. The polypeptide or system of any of paragraphs 1-8, wherein the first small molecule-controlled signaling polypeptide comprises:
   a. a first signaling domain comprising an intracellular CAR stimulatory domain; and
   b. the small molecule acceptor peptide and/or the small molecule.
10. The polypeptide or system of any of paragraphs 1-8, wherein the second small molecule-controlled signaling polypeptide comprises:
   a. a first signaling domain comprising an intracellular CAR stimulatory domain; and
   b. the domain that binds specifically to a small molecule.
11. The polypeptide or system of paragraph 9 or 10, wherein the first or second small molecule-controlled signaling polypeptide further comprises a transmembrane or membrane-tethering domain.
12. The polypeptide or system of any of paragraphs 9-10, wherein the first or second small molecule-controlled signaling polypeptide does not comprise a transmembrane domain; is cytosolic; and/or is not directly tethered to the membrane.
13. The polypeptide or system of any of paragraphs 9-12, wherein the first small molecule-controlled signaling polypeptide further comprises a CAR co-stimulatory domain.
14. The polypeptide or system of any of the preceding paragraphs, wherein the CAR stimulatory domain is a CD3, signaling domain.
15. The polypeptide or system of any of the preceding paragraphs, wherein the CAR co-stimulatory domain is a CD28 signaling domain.
16. The synthetic signaling system of paragraph 3, wherein the first small molecule-controlled signaling polypeptide is according to paragraph 9 and the second small molecule-controlled signaling polypeptide is according to paragraph 4.
17. The synthetic signaling system of paragraph 3, wherein the first small molecule-controlled signaling polypeptide is according to paragraph 5 and the second small molecule-controlled signaling polypeptide is according to paragraph 10.
18. The polypeptide or system of any of the preceding paragraphs, wherein i) the domain that binds specifically to a small molecule and/or ii) the small molecule acceptor peptide and/or the small molecule are extracellular.
19. The polypeptide or system of any of the preceding paragraphs, wherein i) the domain that binds specifically to a small molecule and/or ii) the small molecule acceptor peptide and/or the small molecule are intracellular.
20. The polypeptide or system of any of paragraphs 1-3, wherein the first and second small molecule-controlled polypeptides are intracellular.
21. The polypeptide or system of paragraph 20, wherein the first and second signaling domains are intracellular signaling domains.
22. The polypeptide or system of any of paragraphs 1-3, wherein the second small molecule-controlled signaling polypeptide comprises, from N-terminus to C-terminus:
   i) an extracellular domain that binds specifically to the small molecule;
   ii) a transmembrane domain;
   iii) and an intracellular signaling domain.
23. The system of any of paragraphs 3-22, wherein the small molecule acceptor peptide accepts a first small molecule or the small molecule is a first small molecule, the domain that binds specifically to a small molecule binds specifically to a second small molecule; and the system further comprises a multi-small molecule composition comprising the first and second small molecules conjugated or linked to each other.
24. The polypeptide or system of any of the preceding paragraphs, wherein the small molecule is biotin, a biotinylamide, fluorescein, digoxigenin, or fluorescein isothiocyanate (FITC); or the first and second small molecule are each selected independently from biotin, a biotinylamide, fluorescein, digoxigenin, and fluorescein isothiocyanate (FITC).
25. The polypeptide or system of any of the preceding paragraphs, wherein the domain that binds specifically to a small molecule is an antibody or antibody reagent.
26. The polypeptide or system of paragraph 25, wherein the antibody reagent is a scFv.
27. The polypeptide or system of paragraph 25, wherein the antibody reagent is a scFab.
28. The polypeptide or system of any of paragraphs 25-27, wherein the small molecule, the first small molecule, or the second small molecule is biotin or a biotinylamide and the antibody reagent comprises the 6 CDRs of SEQ ID NOs: 4-9.

29. The polypeptide or system of any of paragraphs 25-27, wherein the small molecule, the first small molecule, or the second small molecule is biotin or a biotinylamide and the antibody reagent comprises SEQ ID NOs: 1 and 2.
30. The polypeptide or system of any of paragraphs 25-27, wherein the small molecule, the first small molecule, or the second small molecule is biotin or a biotinylamide and the antibody reagent comprises amino acids 1-119 of SEQ ID NO: 1 and amino acids 1-117 of SEQ ID NO: 2.
31. The polypeptide or system of any of paragraphs 25-27, wherein the small molecule, the first small molecule, or the second small molecule is biotin or a biotinylamide and the antibody reagent comprises amino acids 1-119 of SEQ ID NO: 1 and amino acids 1-117 of SEQ ID NO: 2, joined by a peptide linker.
32. The polypeptide or system of paragraph 31, wherein the peptide linker comprises SEQ ID NO: 3.
33. The polypeptide or system of any of paragraphs 24-32, wherein the domain that binds specifically to a biotinylamide binds specifically to biotinamide, biocyntinamide, and/or biocytin.
34. The polypeptide or system of any of paragraphs 24-33, wherein the domain that binds specifically to a biotinylamide does not bind to biotin.
35. The polypeptide or system of any of paragraphs 24-33, wherein the domain that binds specifically to a biotinylamide binds specifically as compared to binding of the domain with biotin.
36. The polypeptide or system of any of paragraphs 24-33, wherein the domain that binds specifically to a biotinylamide binds specifically to biotin lacking its carboxylic acid group as compared to binding of the domain with biotin.
37. The polypeptide or system of any of the preceding paragraphs, wherein either the first or second small molecule-controlled polypeptide comprises an intracellular signaling domain.
38. The polypeptide or system of paragraph 37, wherein the signaling domain comprises a Notch receptor signaling domain.
39. The polypeptide or system of paragraph 38, wherein the polypeptide or system comprises a Notch core, the Notch core comprising a Notch receptor signaling domain.
40. The polypeptide or system of any of paragraphs 38-39, wherein the polypeptide comprising a Notch receptor signaling domain has a transmembrane domain and an extracellular small molecule acceptor peptide and/or the small molecule.
41. The polypeptide or system of paragraph 37, wherein the intracellular signaling domain comprises a transcriptional activator.
42. The polypeptide or system of paragraph 41, wherein the transcriptional activator is GAL4-VP64.
43. The polypeptide or system of paragraph 37, wherein the intracellular signaling domain is a nuclear-acting signaling domain.
44. The polypeptide or system of paragraph 43, wherein the nuclear-acting signaling domain comprises a DNA-binding domain.
45. The system of paragraph 43 or 44, wherein the other small molecule-controlled polypeptide of the system comprises a DNA binding domain and both the first and second small molecule-controlled polypeptides are intracellular.
46. The polypeptide or system of any of the preceding paragraphs, wherein the first or second small molecule-controlled polypeptide further comprises a protease.
47. The polypeptide or system of paragraph 46, wherein the protease is NS3.
48. A polypeptide or system of any of the preceding paragraphs, further comprising one or more of:
    a surface-attached molecule comprising a binding domain specific for a target; and a small molecule acceptor peptide and/or a small molecule;
    a soluble molecule comprising a small molecule acceptor peptide and/or a small molecule; and
    a multi-small molecule composition comprising the first and second small molecules conjugated or linked to each other.
49. The polypeptide or system of paragraph 48, wherein the soluble molecule comprises a small molecule and an antibody or antibody reagent.
50. A nucleic acid or set of nucleic acids encoding the polypeptide or system of any of paragraphs 1-49.
51. A cell or set of cells comprising the polypeptide or system of any of the preceding paragraphs.
52. A cell or set of cells comprising a nucleic acid encoding the polypeptide or system of any of the preceding paragraphs.
53. The cell or set of cells of any of paragraphs 51-52, wherein the small molecule, first small molecule, or second small molecule is biotin or a biotinylamide and the cell further comprises a nucleic acid encoding biotin ligase
54. The cell or set of cells of paragraph 53, wherein the biotin ligase is targeted to the endoplasmic reticulum, the cell surface, the cytoplasm, and/or the golgi.
55. The cell or set of cells of paragraph 53, wherein the biotin ligase is targeted to the endoplasmic reticulum.
56. The cell or set of cells of any of paragraphs 53-55, wherein the nucleic acid encoding the biotin ligase further comprises an inducible promoter operably linked to the sequence encoding the biotin ligase.
57. The cell or set of cells of paragraph 56, wherein the inducible promoter is TRE3G.
58. A method of controlling signaling or activity of a first cell comprising the system of any of the preceding paragraphs, the method comprising:
    a. contacting a first cell comprising a system of paragraphs 22-23 with a soluble molecule comprising a small molecule acceptor peptide and/or the small molecule to inhibit the signaling or activity of the first cell;
    b. contacting a first cell comprising a system of any of paragraphs 5, 10, or 17-23 with a further molecule comprising a domain that binds specifically to the small molecule to inhibit the signaling or activity of the first cell; or
    c. contacting the first cell with an agent that inhibits the protease of paragraph 46 or 47 to permit the signaling or activity of the first cell;
    d. contacting the first cell with an agent that induces the inducible promoter of paragraph 56 or 57 to permit the signaling or activity of the first cell; and/or
    e. contacting a first cell comprising the system of paragraph 22 or 23 with a surface-attached molecule comprising a small molecule acceptor peptide conjugated to the small molecule and/or the small molecule,
        to induce the signaling or activity of the first cell; and/or f. expressing in a first cell comprising the system of any of paragraphs 38-40, an inhibitor polypeptide comprising a DLL1 or DLL4 polypeptide.
59. The method of paragraph 58, wherein the soluble molecule comprises or is bis-biotinamide.
60. The method of paragraph 58 or 59, wherein the soluble molecule is cell permeant.
61. The method of any of paragraphs 58-60, wherein the soluble molecule comprises a peptide or small molecule.
62. The method of any of paragraphs 58-61, wherein the soluble molecule comprises a peptide conjugated to a small molecule.
63. The method of any of paragraphs 61-62, wherein the peptide comprises bovine serum albumin (BSA).
64. The method of any of paragraphs 58-63, wherein the soluble molecule comprises a polymer conjugated to a small molecule.
65. The system or method of paragraph 64, wherein the polymer is polyethylene glycol (PEG).
66. The system or method of any of paragraphs 58-65, wherein the soluble molecule is tetarazine-functionalized.
67. The method of paragraph 58, wherein the further molecule comprising a domain that binds specifically to the small molecule is an antibody, antibody reagent, or a cell permeant antibody reagent.
68. The method of paragraph 58, wherein the further molecule comprising a domain that binds specifically to the small molecule is an antibody or antibody reagent that is surface-attached or expressed on the surface of a second cell.
69. The method of paragraph 58, wherein the agent that inhibits the protease is grazoprevir.
70. The method of paragraph 69, wherein the inducible promoter is TRE3G and the agent is rtTA-3.
71. The method of any of the preceding paragraphs, wherein the surface-attached molecule is bound or conjugated to the first cell, a second cell, a lipid bilayer surface, or a solid surface.
72. The method of paragraph 71, wherein the solid surface is a bead.
73. The method of paragraph 71, wherein the lipid bilayer surface is a liposome.
74. The method of any of paragraphs 58 and 71-73, wherein the surface-attached molecule is not soluble.
75. The method of any of paragraphs 58 and 71-74, wherein the surface-attached molecule further comprises a binding domain specific for a target.
76. The method of any of paragraphs 58 and 71-75, wherein the small molecule of the surface-attached molecule is tetrazine-functionalized and ligated to immobilized trans-cyclooctene (TCO).
77. The method of paragraph 58, wherein the inhibitor polypeptide comprising a DLL 1 or DLL4 polypeptide further comprises a domain that binds specifically to the small molecule, first small molecule, or second small molecule.
78. The polypeptide, system, or method of any of the preceding paragraphs, wherein the target is a cell-surface marker on a second cell and the first cell is an immune cell.
79. The polypeptide, system or method of paragraph 78, wherein the second cell is a cancer cell.
80. The method of any of paragraphs 78 or 79, wherein the signaling or activity of the first cell is immune-promoting signaling or activity.
81. The method of any of paragraph 80, wherein the first cell is an immune cell.
82. The method of any of paragraphs 78-81, wherein the second cell is a diseased cell.
83. The method of paragraph 81, wherein the first cell is a T cell and the binding domain specific for a target binds a marker on the surface of a diseased cell.
84. The method of paragraph 81, wherein the first cell is a T cell and the binding domain specific for a target binds a marker specific to diseased cells.
85. The method of any of paragraphs 83-84, wherein the diseased cells are cancer cells.
86. The method of any of paragraphs 78-85, wherein the method is a method of treating a subject in need of immunotherapy.
87. The method of paragraph 86, wherein the method comprises, prior to the contacting step, administering the first cell to the subject.
88. The method of any of paragraphs 58-87, wherein the method comprises, prior to the contacting step of e), administering a molecule comprising:
  i. a binding domain specific for a target; and
  ii. a small molecule acceptor peptide and/or a small molecule
  such that it attaches to a surface in the subject, or is administered already attached to a surface, thereby providing the surface-attached molecule.
89. The method of any of paragraphs 58-88, wherein the method comprises, prior to the contacting step of b), administering the soluble molecule.
90. The method of any of paragraphs 58-89, wherein the signaling or activity of the first cell is tissue generation or regeneration promoting signaling or activity.
91. The method of paragraph 90, wherein the method is a method of in vitro or in vivo tissue engineering.
92. The method of any of paragraphs 90-91, wherein the surface-attached molecule is attached to a tissue engineering scaffold.

Some embodiments of the technology described herein can be defined according to any of the following numbered paragraphs:
1. A synthetic signaling system comprising:
  a. a first small molecule-controlled signaling polypeptide comprising i) a small molecule acceptor peptide or a small molecule and ii) at least a first signaling domain; and a second small molecule-controlled signaling polypeptide comprising i) a domain that binds specifically to a small molecule and ii) at least a second signaling domain;
  b. a first small molecule-controlled signaling polypeptide comprising i) a small molecule acceptor peptide or a small molecule and ii) at least a first signaling domain; and a polypeptide comprising a domain that binds specifically to the small molecule; or
  c. a second small molecule-controlled signaling polypeptide comprising i) a domain that binds specifically to a small molecule and ii) at least a second signaling domain and a polypeptide comprising a small molecule acceptor peptide or a small molecule.
2. The system of paragraph 1, wherein the first small molecule-controlled signaling polypeptide comprises:
  a. a first signaling domain comprising an intracellular CAR stimulatory domain; and
  b. the small molecule acceptor peptide or the small molecule; and/or the second small molecule-controlled signaling polypeptide comprises:

i) a signaling domain comprising an extracellular domain that binds specifically to a target;
ii) a transmembrane domain; and
iii) the domain that binds specifically to a small molecule.
3. The system of paragraph 1, wherein the first small molecule-controlled signaling polypeptide comprises:
iv) a signaling domain comprising an extracellular domain that binds specifically to a target;
v) a transmembrane domain; and
vi) the small molecule acceptor peptide or the small molecule; and/or
wherein the second small molecule-controlled signaling polypeptide comprises:
a. a first signaling domain comprising an intracellular CAR stimulatory domain; and
b. the domain that binds specifically to the small molecule.
4. The system of paragraph 1, wherein the first or second small molecule-controlled signaling polypeptide comprises a CAR stimulatory or co-stimulatory domain.
5. The system of paragraph 4, wherein the CAR stimulatory domain is a CD3ζ signaling domain.
6. The system of paragraph 4, wherein the CAR co-stimulatory domain is a CD28 signaling domain.
7. The system of paragraph 1, wherein i) the domain that binds specifically to the small molecule and/or ii) the small molecule acceptor peptide or the small molecule are extracellular.
8. The system of paragraph 1, wherein i) the domain that binds specifically to the small molecule and/or ii) the small molecule acceptor peptide or the small molecule are intracellular.
9. The system of paragraph 1, wherein the first and second small molecule-controlled polypeptides are intracellular.
10. The system of paragraph 9, wherein the first and second signaling domains are intracellular signaling domains.
11. The system of paragraph 1, wherein the small molecule is biotin, a biotinylamide, fluorescein, digoxigenin; or fluorescein isothiocyanate (FITC).
12. The system of paragraph 1, wherein the domain that binds specifically to the small molecule is an antibody or antibody reagent.
13. The system of paragraph 1, wherein the signaling domain comprises a Notch receptor signaling domain.
14. The system of paragraph 13, wherein the polypeptide or system comprises a Notch core, the Notch core comprising a Notch receptor signaling domain.
15. The system of paragraph 1, wherein the signaling domain comprises a transcriptional activator.
16. The system of paragraph 1, wherein the signaling domain is a nuclear-acting signaling domain.
17. The system of paragraph 16, wherein the nuclear-acting signaling domain comprises a DNA-binding domain.
18. The system of paragraph 1, further comprising one or both of:
a surface-attached molecule comprising a binding domain specific for a target, and a small molecule acceptor peptide a small molecule; and
a soluble molecule comprising a small molecule acceptor peptide or a small molecule.
19. A cell or set of cells comprising a nucleic acid encoding the system of paragraph 1.

20. The cell or set of cells of paragraph 19, wherein the small molecule is biotin or a biotinylamide and the cell further comprises a nucleic acid encoding biotin ligase
21. A method of treating a subject in need of immunotherapy, the method comprising administering to the subject a first immune cell comprising the system of paragraph 1.
22. The method of paragraph 21, wherein one of the small molecule-controlled signaling polypeptides comprises an extracellular binding domain that binds specifically to a target, wherein the target is a cell surface marker specific to cancer cells or found on the surface of a cancer cell.
23. The method of paragraph 21, wherein the immune cell is a T cell.

EXAMPLES

Example 1

Described herein are cell surface receptors containing an anti-biotinamide antibody fragment, which allows binding to biotinylated proteins without binding to biotin present in cell culture media and human serum. The invention includes an anti-biotinamide synthetic Notch receptor, which is able to bind biotinylated proteins to create specified cellular signaling outputs, as well as an anti-biotinamide chimeric antigen receptor, which is able to stimulate T cell receptor pathways, leading to T cell activation. Biotinylation is a common modification to antibodies, and the use of these modified antibodies in conjunction with the anti-biotinamide receptors allows for targeting of diverse functional groups, while having a universal receptor expressing cell. Additionally, further control of cell signaling is often needed, and this form of receptor allows the use of biotin-based small molecules as competitive inhibitors to prevent and reverse binding and therefore prevent cell signaling. This work demonstrates a method to achieve enhanced temporal control of cellular signaling, which is needed in therapies such as CAR-T.

For example, in the case of the anti-biotinamide synthetic Notch receptor, the protein coding sequence of anti-biotinamide single chain variable fragment can be fused to the protein coding sequence of a synthetic Notch receptor (Notch core, and the transcriptional activator, GAL4-VP64). For the chimeric antigen receptor, the antibody fragment can instead be fused to the coding sequence of a chimeric antigen receptor (CD28, 4-1BB, and CD3ζ signaling domain). This DNA can be transfected or transduced in mammalian cells, and the signaling ability can be analyzed through a corresponding promoter (UAS for Notch and NFAT for CAR). These cells can be cocultured by mixing with target cells, with activation being determined by expression of a reporter gene. Inhibition can analyzed through the addition of small molecules to the coculture and the expression of a reporter gene. Addition of biotinylated antibodies can also be added to this cell mix.

Additional ideas and constructs related to the invention are as follows. The development of a CAR that is biotinylated and only has one intracellular co-stimulatory domain. The CAR binds to a synthetic cell surface protein with an anti-biotinamide extracellular region and the other intracellular co-stimulatory domain. This allows CAR signaling, but when bis-biotinamide is added, the co-stimulatory domains are separated and signaling is prevented. This has the benefit of being reversible and can be modulated with inert (biotin-based) and cell-inpermeant molecules.

Different intracellular domains can be used for the cell-surface receptors to extend the signaling to different outputs. Some level of difference in sequence identity can be tolerated by the anti-biotinamide antibody fragment.

Example 2: Engineering a Synthetic Post-Translational Modification Signaling Stem Via Enzyme Mediated Biotinylation Post-translational modifications of proteins are an essential way that cells create diversity in protein function. In intercellular signaling, post-translational modifications such as the glycosylation of receptors and ligands allow for fine tuning of their affinity. Here, we present an analogous synthetic method for post-translational control of eukaryotic receptor activity via orthogonal biotin-based post-translational modifications. We show that the fusion of a small biotin accepting peptide to the N-terminus of synthetic Notch receptors can be biotinylated by endoplasmic reticulum retained E. coli biotin ligase, and thus functionalized to respond to biotin-binding molecules. We demonstrate that this system can be applied to cell—cell interactions through the development of a biotinamide specific cell surface ligand, and that the expression levels of biotin ligase can affect the extent of activation of target genes. Finally, we extend the toolset of biotin-based receptors to include a biotin-binding synthetic Notch system that can respond to the synthetic post-translational modification.

Cells that express similar levels of surface proteins can display divergent signaling patterns. This behavior in certain situations can be attributed to the diversity in protein post-translational modifications (PTMs) that these receptors undergo while being trafficked through the secretory pathway. The addition of these small chemical groups to amino acid side chains is accomplished through various enzymes which can act both selectively and non-selectively for their substrate proteins, and these PTMS of cell surface receptors have been shown to impact the affinity of the receptors for their associated ligands. The presence or absence of PTM enzymes has been seen to alter the downstream gene expression due to receptor activation. In order to explore the underlying design principles of receptor PTMs, it would be useful to develop a synthetic system that could establish and read post-translational modification states without interfering any native pathways.

A post-translational modification that affects many proteins in the secretory pathway and the extracellular space is glycosylation. Various glycans can be attached and elongated on proteins, which can impact the structure and function of the extracellular protein. The expression of the glycosyltransferase Fut8, which adds a fucosyl group to the innermost GlcNAc residue of N-linked oligosaccharides, has been shown to increase the fucosylation of Epidermal Growth Factor Receptor. This post-translational modification of the receptor has been implicated in increased affinity for the Epidermal Growth Factor ligand, and as a result, increased auto-phosphorylation and downstream signaling1. Additionally, it has been seen that inhibition of Golgi α-mannosidase IA and IB, an enzyme which trims the first mannose residues in N-linked oligosaccharides, causes a lowered affinity of the fibronectin receptor Integrin alpha-5/beta-1 for fibronectin and associated peptides. This indicates that full processing of post-translational modifications is necessary for binding of the receptor and attachment of cells to fibronectin substrates2. It has been noted by several groups that the glycosylation profiles of antibodies can affect the affinity of the antibody for different Fc receptors, as well as modulating anti-inflammatory activity3,4.

An additional receptor which has its function largely influenced by post-translational modifications is the Notch receptor. Notch signaling occurs through the binding of the Notch receptor protein to its associated cell-surface ligands, Delta or Jagged, on opposing cells5. This binding triggers a force-responsive unbinding of the Notch Regulatory Region, and the downstream release of its intracellular domain, a transcription factor6-8. In humans, there are four 134 forms of Notch and five main cell-surface ligands, yet through Notch signaling, organisms are able to give rise to a large number of distinct signaling states9. An important and outstanding question in the field is how these relatively few proteins can have such divergent properties. One way in which this is done is through the use of post-translational modifying enzymes. In mammals, Notch is modified on its way through the secretory pathway with various sugar groups10-13. Various Fringe glycosyltransferases have been found to add different types of sugar groups to the receptors in one cell and the ligands in another, and their expression level can impact the extent and diversity of the glycosyl groups. This in turn, has been shown to have large effects on the binding of Notch to its different ligands14, which can change its signaling capabilities.

The complexity of glycosylation states and the promiscuity of natural enzymes can create difficulty in understanding the principles which underlie PTM-based signaling. Instead, we aimed to develop an orthogonal system of PTMs in cellular signaling, in which the enzyme and the chemical modification have no influence on native biological processes. The functional parts of this orthogonal post-translational modification could then be programmed, and their effects on cellular signaling could be studied.

In order to first develop this orthogonal post-translational modification in mammalian cells, we examined the properties of E. coli biotin ligase (BirA), which is a protein that enzymatically activates biotin to form a biotinyl 5'-adenylate and binds the biotin to Biotin Carboxyl Carrier Protein. Although 75 amino acids of the natural substrate are required for efficient biotin transfer, a minimal substrate of BirA-catalyzed biotin transfer has been developed that is only 14 amino acids15. The minimal biotin accepting peptide (AP) can be fused to proteins and has been 155 commonly done for purification of biomolecules, such as antibodies. Other groups have shown that biotin ligase can be used to tag surface proteins for visualization16,17. The orthogonality of this biotin ligase in mammalian cells offers the ability to develop biotin into a synthetic PTM.

Results

E. coli Biotin Ligase (BirA) Engmatically Bitinylates Synthetic Receptor

Figure 1B:
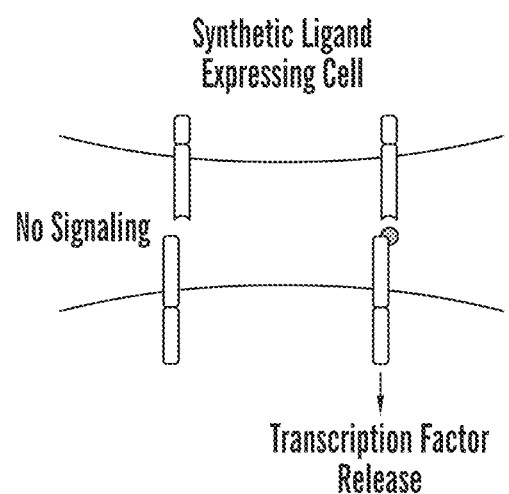

In order to develop an extracellular-based receptor signaling system, we first looked to develop a synthetic Notch18 due to its relatively direct mechanism of signal transduction. The synthetic receptor contains an extracellular myc epitope tag, an anti-GFP nanobody19, the mouse Notch core region, and an intracellular C-terminal Gal4-VP64 transcriptional activator. We then fused biotin AP between the myc tag and the anti-GFP nanobody to form the acceptor peptide synthetic Notch (apSyN). We co-express the receptor with an endoplasmic reticulum-retained E. coli biotin ligase (BirA-ER). This enzyme contains an N-terminal murine Igκ leader sequence20 for enhanced sorting to the secretion pathway and a C-terminal KDEL tag21 (SEQ ID NO: 117) for retention in the endoplasmic reticulum, where it is able to biotinylate acceptor peptides in the secretion pathway. As the apSyN traffics through the endoplasmic reticulum on its way to the cell surface, we expect the receptor to be biotinylated by BirA-ER17171 (FIGS. 1A-1B).

Figure 1C:
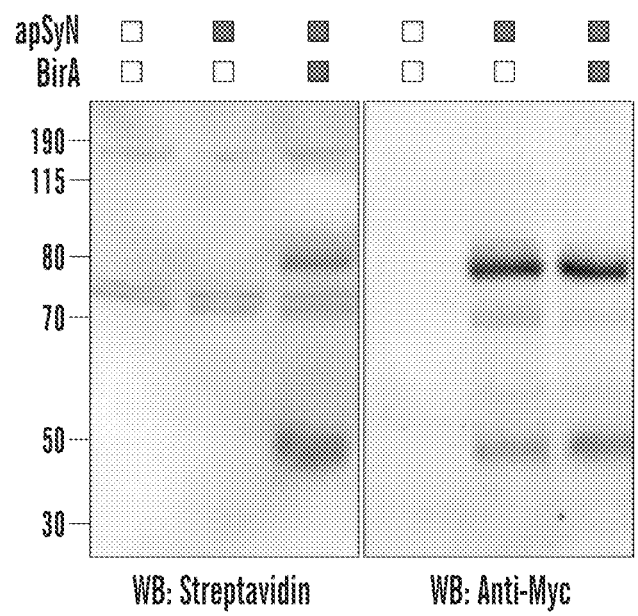

BirA-ER must be selective for the biotin acceptor peptide in order for biotin to function as an orthogonal post-translational modification. We have determined the specificity of endoplasmic reticulum-retained BirA-ER by expressing the apSyN with or without BirA-ER in mammalian cells. We then performed a Western blot by lysing the cells and probing the blot with Streptavidin-HRP (FIG. 1C). Two additional bands corresponding to the full-length and the S Furin-processed synthetic Notch were found when probing with Streptavidin-HRP. Because the synthetic Notch was also tagged with a myc tag, when probed with an anti-myc antibody, the corresponding bands were found with and without biotin ligase. The only novel biotinylated bands when the cells expressed BirA-ER correspond to the apSyN indicating that BirA-ER is specific for the biotin acceptor peptide and do not biotinylate any additional native proteins to any appreciable degree. The background biotin bands in both cases correspond to endogenous biotinylated proteins-propionyl-CoA carboxylase (74 kDa), 3-methylcrotonyl-CoA carboxylase (75 kDa), and pyruvate carboxylase (127 kDa)22.

Figure 1E:
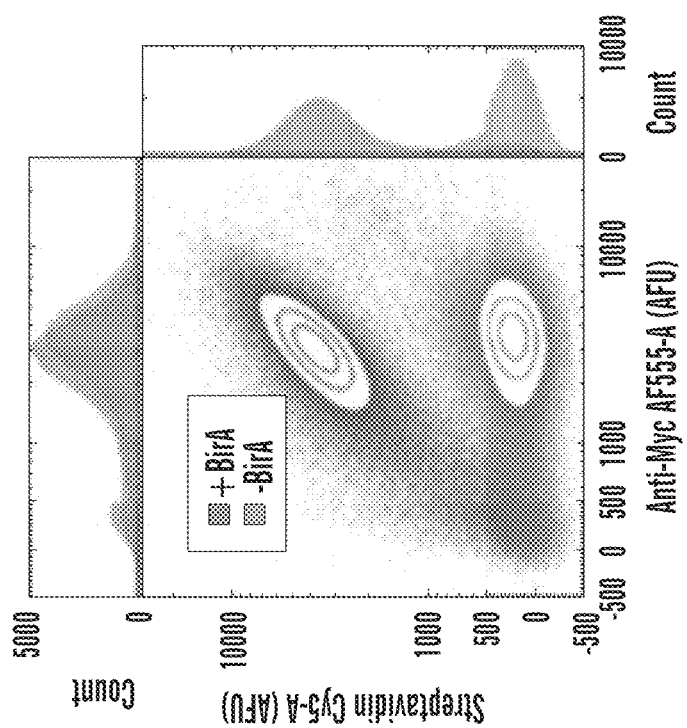
Figure 1D:
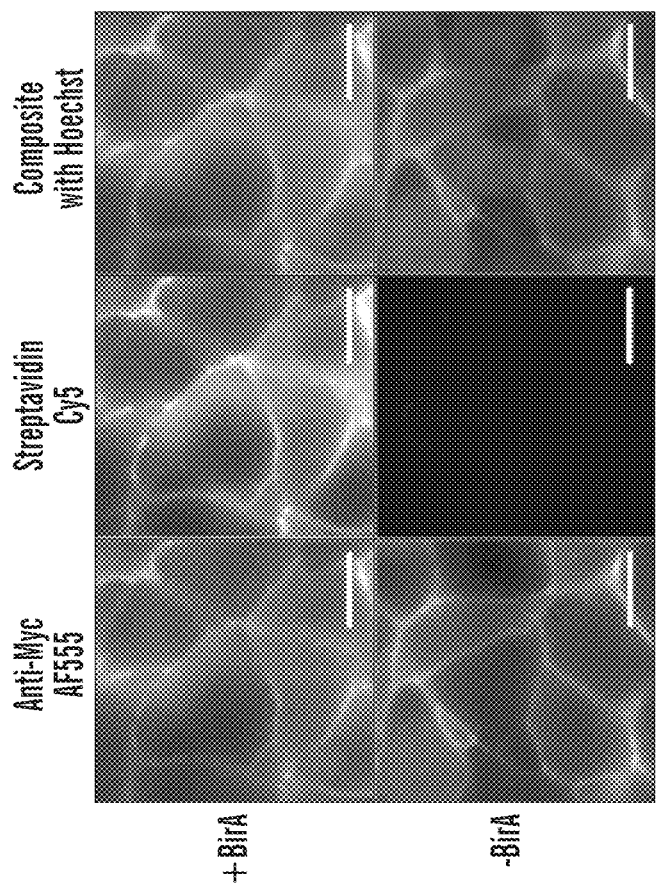

Because synthetic Notch signaling is dependent on the cell surface localization of the receptor, we next determined if the expression of BirA-ER impacted the ability of the receptor to localize properly. To accomplish this, we first created a HEK293FT cell line that stably expressed the apSyN and was subsequently transduced to express BirA-ER. We probed the cell surface of the two synthetic Notch expressing cell lines with an anti-myc antibody as well as a dye-conjugated Streptavidin and examined surface localization with epifluorescent microscopy and flow cytometry (FIG. 1D-1E). Using the myc-tag, we were able to see localization of the receptor at the surface in both cases. However, there was only cell-surface localization of biotin when the cell line is co-expressed BirA-ER. Additionally, the co-expression of BirA-ER did not impact cell-surface localization as both cell lines had similar levels of myc present on the surface.

Figure 2C:
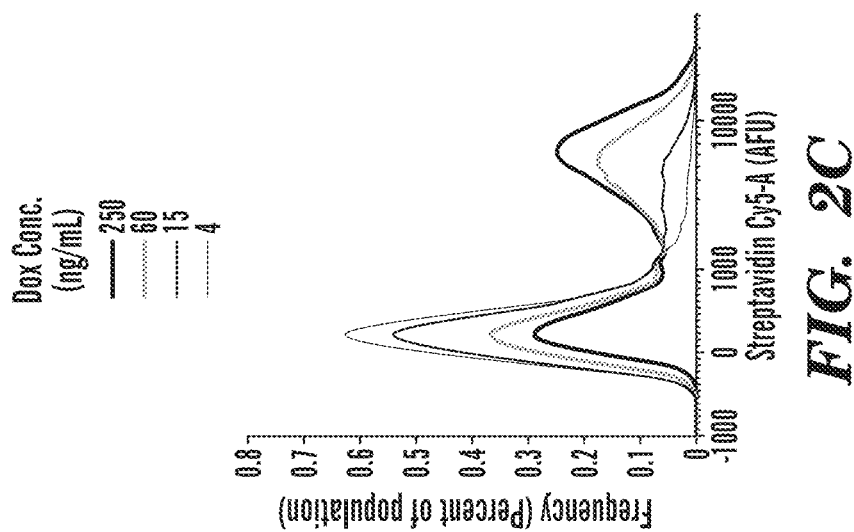
Figure 2B:
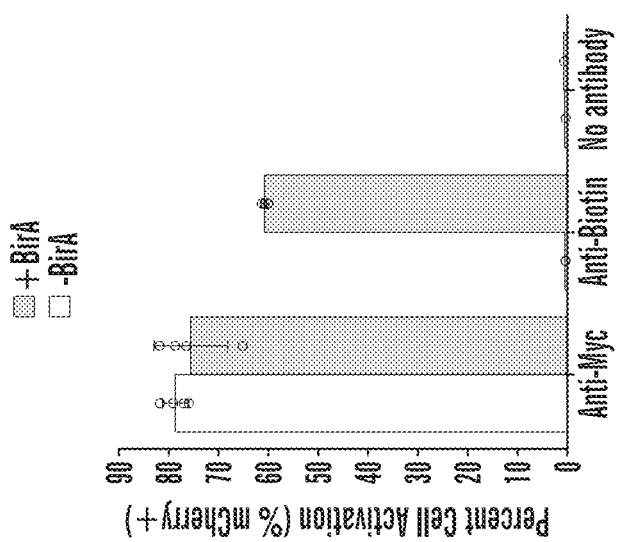
Figure 2A:
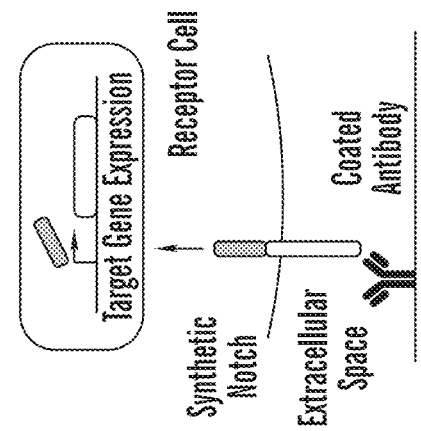
Figure 5A:
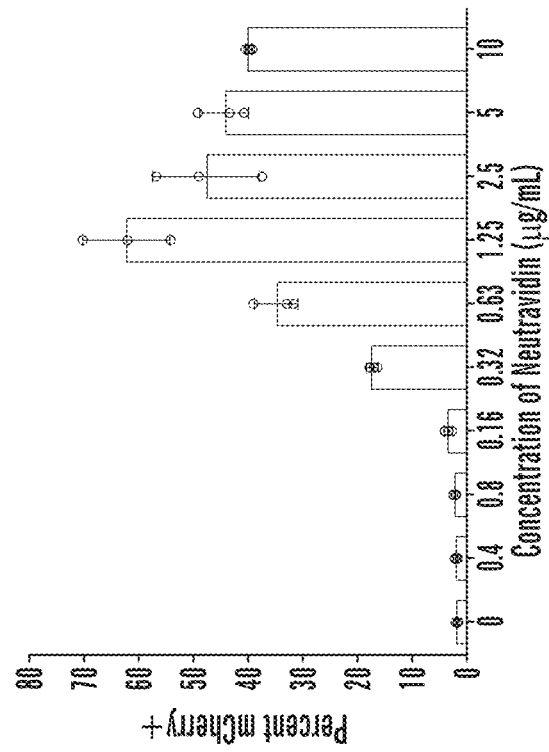
FIGS. 5A-5C.
Figure 5B:
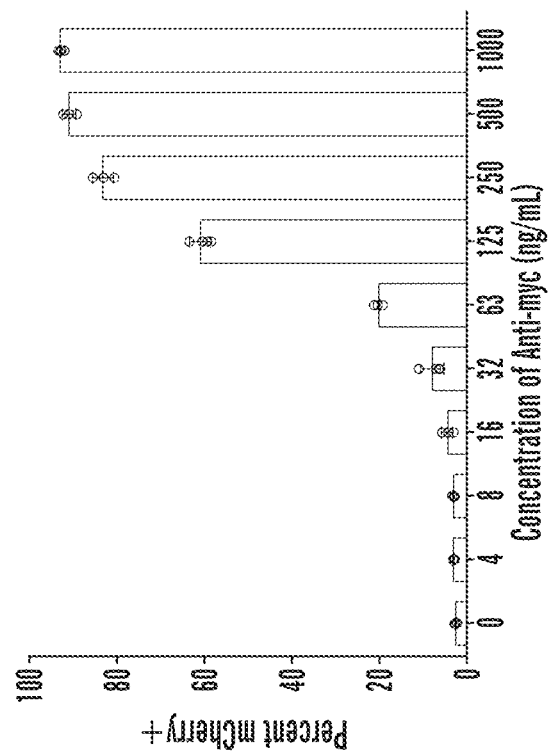
Figure 5C:
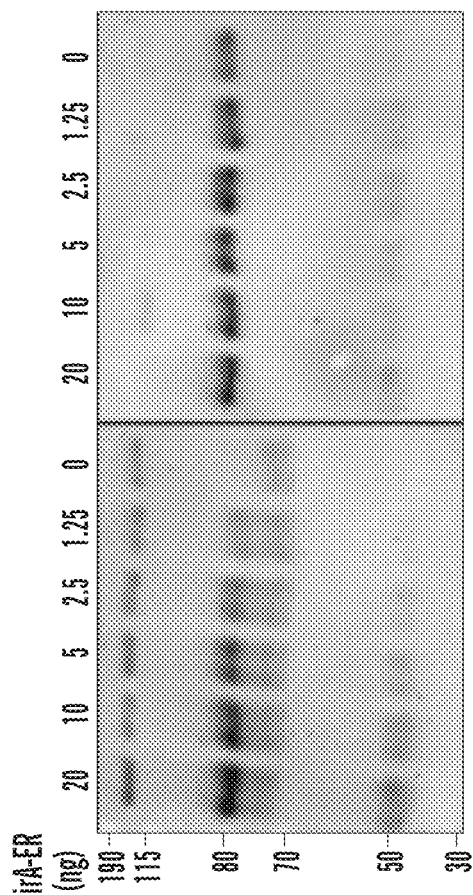

Post-Translational Biotinylation of apSyN Via BirA-ER Regulates Activation by Biotin Binding Molecules Synthetic Notch constructs are useful because they are able to direct extracellular cues to an intracellular output. In order to determine if the apSyN could undergo predicted signaling mechanics of extracellular binding and intracellular domain release based on the presence of the PTM, we used an established Notch signaling assay23 (FIG. 2A). Synthetic Notch expressing 202 cell lines, which have a genome-integrated fluorescent reporter (UAS:H2B-mCherry), were plated on wells coated with Notch binding substrates, and Notch activation was measured by the expression of mCherry. Avidin is an attractive choice to activate biotin-based substrates, but biotin is present in cell culture media in small amounts, which would bind to the plated avidin and may confound signaling results (FIG. 5B). We instead interrogated the signaling capabilities by coating tissue culture wells with an anti-Biotin antibody that is specific for biotinamide24. Receptor expressing cells which co-expressed BirA-ER displayed higher expression of mCherry than those that did not express BirA-ER (FIG. 2B). We also used an anti-myc antibody, and saw that it triggered apSyN activation regardless of the expression of BirA-ER. The dose-response curve of the system showed a maximum percent of receptor activation at 500 ng/mL of anti-myc antibody in PBS and 550 ng/mL of anti-Biotin antibody in PBS (FIG. 5A). Finally, to confirm that reporter activation was due to the expected pathway, we used a Notch pathway inhibitor, DAPT, which inhibits γ-secretase, a protease that cleaves the transmembrane domain of Notch releasing its transcription factor. DAPT ablated mCherry expression in all cases.

Next, we aimed to demonstrate further control of synthetic Notch activation by expressing BirA-ER under the control of a doxycycline inducible promoter. There have been several systems developed, but we used the TRE3G promoter and its activator Tet-On 3G due to the reported low basal levels of gene expression and high dynamic range25. The HEK293FT-based cell line includes a fluorescent reporter, a constitutively active apSyN and a doxycycline inducible BirA-ER. We first interrogated the ability to control the biotinylation of the apSyN through flow cytometry. We cultured this cell line in differing concentrations of doxycycline, and probed with a dye-conjugated Streptavidin before analyzing cell fluorescence by flow cytometry (FIG. 2C). We saw a correlation of doxycycline concentration with the overall biotinylation state of the cell population. To determine if this increase in biotinylation correlated with increased activation, we also plated this cell line on surface-coated anti-Biotin antibody with different levels of doxycycline, and analyzed the downstream fluorescent reporter activation (FIG. 2D). We saw an increased number of cells with activated reporter as we increased doxycycline concentration.

To demonstrate the ability to control biotinylation state through other drug inducible methods, we targeted the TRE3G promoter with a grazoprevir inducible transcription factor. Several groups, including our own26 have shown the benefits of using the Hepatitis C virus nonstructural protein 3 as a ligand inducible connection27 (FIGS. 2E-2F). In this study, we used a fusion protein that contains an N-terminal TetR which will bind the TRE3G promoter region, the NS3 ligand inducible connection, and a C-terminal VP64 transcriptional activator domain. This construct was transfected into the TRE3G: BirA-ER cell line, plated on wells coated with anti-Biotin antibody, and cultured in the presence or absence of 5 µM grazoprevir. Only cells cultured with grazoprevir expressed BirA-ER, and therefore activated due to the anti-Biotin antibody.

Cells with apSyN can Respond Differently to Cues on Target Cells Based on the Presence of BirA The next goal of this study was to extend the control of PTMs to cell-cell signaling contexts. In order to accomplish this, it was necessary to develop a cell line that is able to selectively bind to the biotinylated synthetic Notch (FIG. 3A). As stated earlier, it would be preferable for the ligand to have low affinity for free biotin so as to not be required to use modified media. For this reason, we developed a single chain variable fragment based on a biotinamide-specific antibody24. This antibody does not bind to free biotin but binds to biotin with an amide linker. In order to accomplish this, we fused the variable heavy and light regions with a long flexible peptide. To target the ligand to the membrane, we used an N-terminal murine Igκ leader sequence20 and a transmembrane domain from the platelet-derived growth factor receptor. Additionally, the extracellular region has an HA and a SNAP tag for imaging. Finally, to promote the endocytosis necessary for mechanosensitive Notch signaling, we used a C-terminal rat Delta intracellular domain. We transduced a HEK293FT cell line that constitutively expressed this construct.

We then examined the ability of the anti-Biotin ligand expressing cell line to activate the apSyN cells in two ways. In order to differentiate the two different cell lines, we virally transduced the receptor-expressing cell line with a nuclear localized blue fluorescent protein and probed the SNAP-tag of ligand-expressing cells with a benzylguanine dye. We mixed the two cell lines and plated them in a cell culture dish. We then captured images of representative locations where the two cell types interacted and examined the nuclear mCherry expression (FIG. 3B). We saw that only when the receptor cell line is co-expressing BirA-ER and in contact with ligand expressing cells, was there receptor activation and downstream mCherry expression.

Figure 3D:
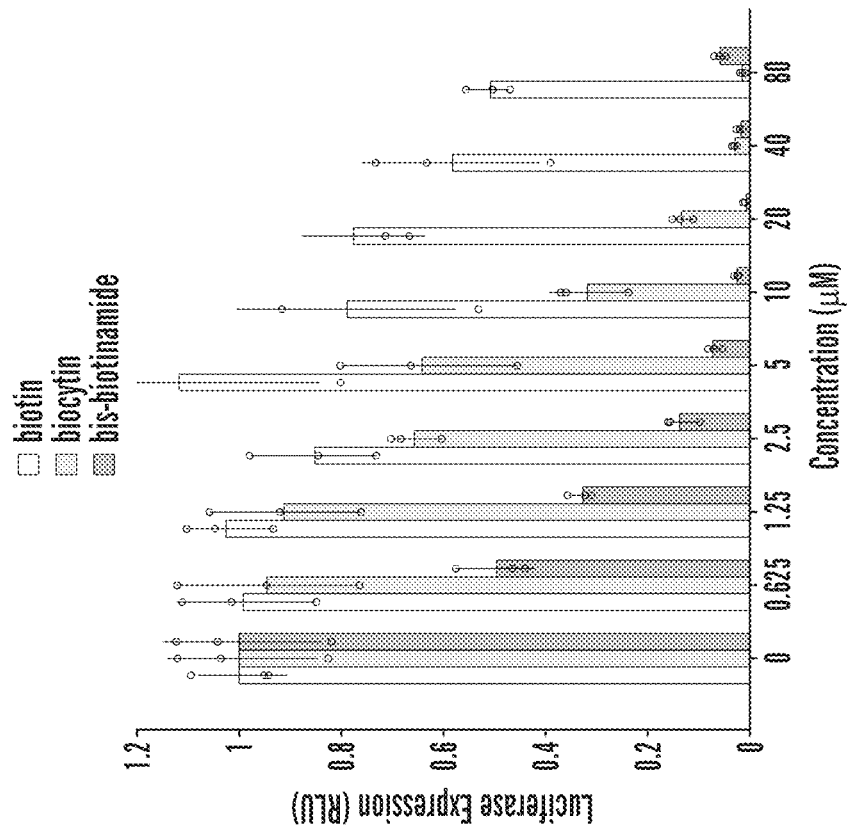
Figure 3C:
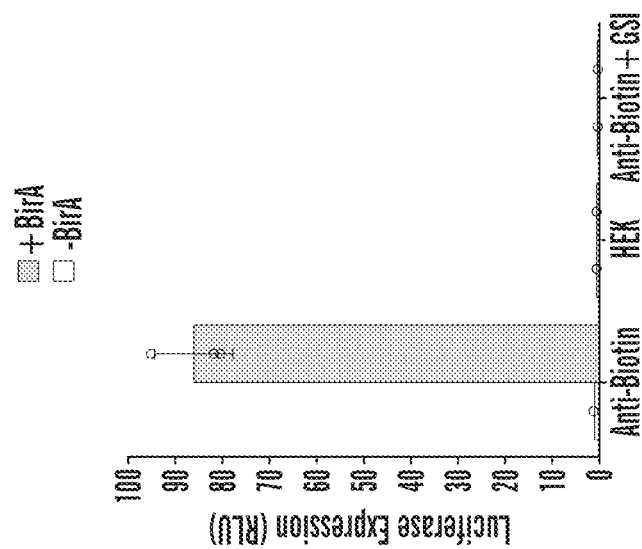

To examine this behavior more quantitatively, we used an established luciferase-based coculture assay28. Receptor cells were transfected with a luciferase reporter plasmid, and ligand expressing cells were added the next day. Finally cells were lysed after one day of coculturing to examine the luminescence due to luciferase expression (FIG. 3C). Only apSyN cells which coexpressed BirA-ER were able to activate and express Luciferase due to the anti-Biotin ligand expressing cells.

We also saw a similar ability to control activation with small molecules in this coculture assay. The previously used γ-secretase inhibitor, DAPT, non-specifically inhibits all Notch activity (synthetic and endogenous) as well as other intramembrane cleavage events such as amyloid precursor protein. We sought to develop an inhibition method that is specific for this pathway and therefore allow for additional control of signaling without disrupting native pathways. In order to accomplish this, we looked to competitively inhibit binding of the antibody fragment with three molecules: biotin, biocytin, and bis-biotinamide (FIG. 3D). Although biotin had limited impact on cell signaling as expected due to the decreased affinity of the single chain variable fragment for free biotin, biocytin was able to inhibit cell signaling to some degree. Bis-biotinamide, with two biotin groups attached with a linker, had an increased ability to inhibit cell activation due to the increased apparent affinity of cooperative binding. We used the previously established coculture assay while culturing cells in different concentrations of the described molecules and then analyzed the corresponding luciferase expression.

Figure 3F:
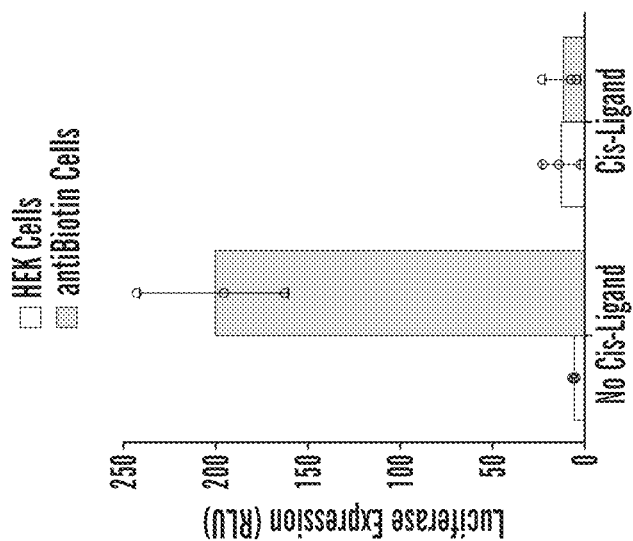
Figure 3E:
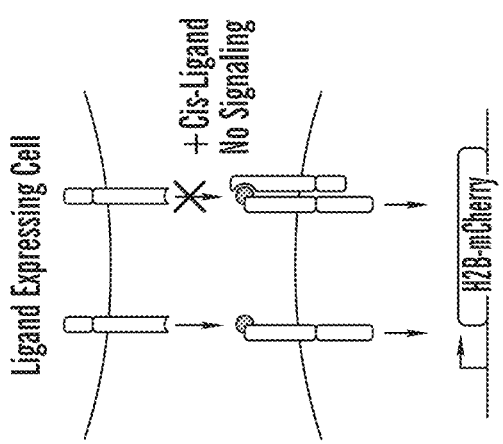

Finally, we aimed to develop a genetically-encoded inhibitor of the biotinylation-dependent signaling. Notch signaling has been shown to be inhibited by the expression of an associated ligand, DLL 1 or DLL4, in the receptor expressing cell. We expressed an Anti-Biotin ligand in the receptor expressing cells and observed decreased activation in coculture assays when compared to cells without the cis-ligand (FIG. 3F).

Post-Translational Biotinylation of Secreted Proteins

Figure 6B:
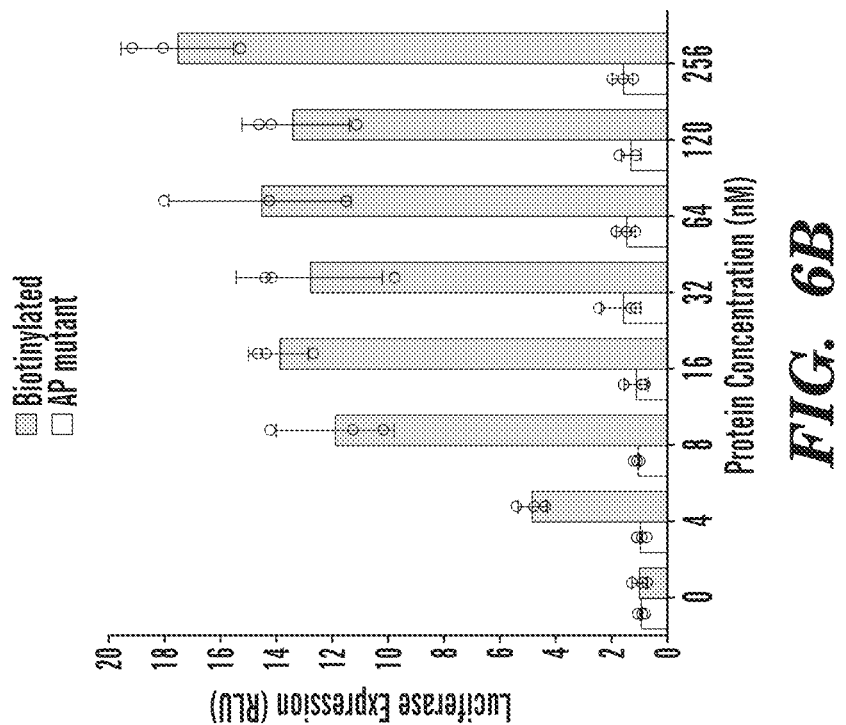
FIGS. 6A-6B.
Figure 6A:
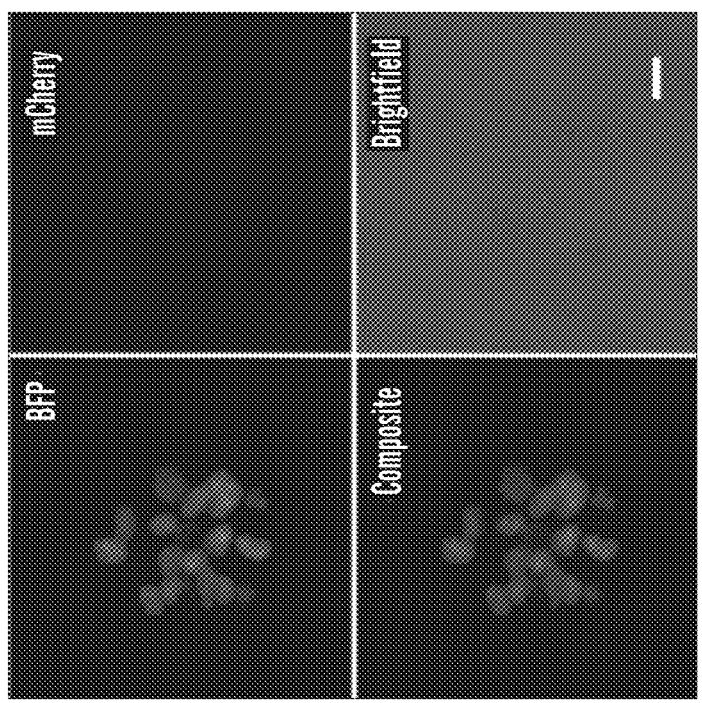

We next investigated whether we could control the PTMs of secreted proteins to modulate the signaling capabilities of two separate cell lines. It has been noted by several groups that the glycosylation profiles of antibodies can affect the affinity of the antibody for different Fc receptors, as well as modulating anti-inflammatory activity3,4. To recapitulate this mechanism in a synthetic system, we first determined whether soluble factors could act as a bridge between the receptor expressing cells and ligand expressing cells. To accomplish this, we expressed green fluorescent protein that had been tagged with either the biotin acceptor peptide (GFP-AP*) or a mutant form that cannot be modified (GFP-APmut) in an E. coli strain containing an PTG inducible BirA construct. After purifying the resulting proteins, we used the luciferase-based coculture method to analyze the effect on cellular signaling. The apSyN construct contains an anti-GFP nanobody, and the anti-biotinamide ligand allows for binding to biotin. We hypothesized, that when these two cell types were cultured together, GFP-AP* could promote signaling. Increased concentrations of biotinylated GFP increased cell activation, while GFP-APmut had little effect on activation at any concentration we tested (FIG. 6B). This indicated that biotinylated soluble factors could act as a bridge between synthetic receptor and ligand expressing cells.

We next looked to develop a mammalian cell line that secretes GFP-AP which would allow for the dependence on BirA-ER for biotinylation. The construct for the secreted GFP contains an N-terminal murine Igκ leader sequence20, a FLAG tag, and a C-terminal biotin acceptor peptide. We characterized the ability of the cell line to secrete GFP-AP* by harvesting the spent media of cells that were cultured at different seeding concentrations. We hypothesized that increased concentration of cells producing GFP-AP* would give an increased concentration of the biotinylated protein and would then be able to more effectively promote signaling between the receptor and ligand expressing cell lines. We performed a Western blot of the spent media probing with Streptavidin and an anti-FLAG antibody and were able to see the corresponding increases in protein concentration.

Finally, we aimed to demonstrate the ability of this secretion cell line to direct cell-cell signaling of two different receptor and ligand expressing cell lines without direct contact. This three cell type system mirrors some native signaling processes, where a modified antibody is able to bridge an antigen-presenting cell and the Fc receptor of immune cells4. We accomplished this by using a specialized cell culture platform that has distinct separation of different cell types, while sharing the media. One well of the system contained cells that secrete GFP-AP with or without BirA-ER expression. The other well contained a mixture of anti-GFP synthetic Notch receptor cells and anti-Biotin ligand expressing cells. Only when the secreted GFP-AP was biotinylated were the receptor and ligand cell lines able to interact and direct downstream reporter activation.

Biotin Binding Synthetic Receptors can be Inhibited by Soluble Ligand

In order to expand the capabilities of a biotin-based synthetic signaling toolkit, we worked to establish a synthetic Notch system based on the anti-biotinamide scFv described above (FIG. 4A). This scFv has several benefits to traditional avidin-based technologies. The antibody is able to preferentially bind to biotin that has lost its carboxylic acid tail. The antibody has two key aspartic acid residues (D31 and D52) that are compatible with a linker, but repel the carboxylic acid tail of biotin. Biotin is present at low concentrations in serum, so this biocytinamide-specific binding molecule allows for preferential binding to the ligand of interest. We fused the antiBiot scFv to the synthetic Notch core with a GAL4-VP64 transcriptional activator and created a stable cell line in the same GAL4 dependent fluorescent reporter line as before.

Figure 7D:
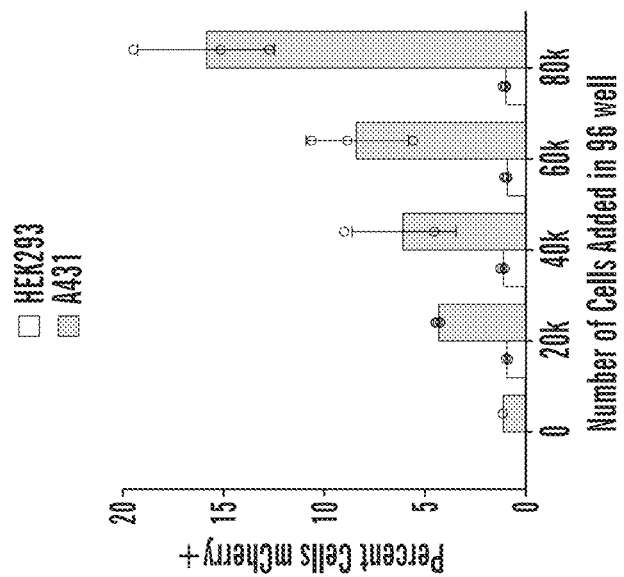

We first asked if this synthetic receptor cell line could activate to various ligands coated on a 96 well plate. The antiBiot synthetic Notch had a typical dose response curve to biotin-BSA, with maximal activation at around 5 nM of conjugated biotin (FIG. 4B). We tested several additional substrates including desthiobiotin conjugated BSA, which has a lower affinity for avidins, as well as a Biotinidase resistant form of biotin (FIG. 7A). Biotinidase is an enzyme secreted into serum that cleaves biotin from conjugated proteins. All substrates displayed similar ability to activate the antiBiot synthetic Notch when normalized to the concentration of the conjugated hapten. Several groups have seen that using soluble ligand is a way to prevent cell activation through binding to the antigen binding region of Notch18. We used biotin and biocytin, and we found that biocytin was able to turn off the system when introduced at the time of plating. Biocytin lowered activation at 3 μM (FIG. 4D and FIG. 7B).

In order to increase the sensitivity of the system, we looked at desthiobiotin, which in avidin-based systems has a binding constant 106 fold less than biotin. In order to accomplish this, we conjugated desthiobiotin to BSA through an NHS ester-amine reaction. When antiBiot synthetic Notch was stimulated with this molecule, the system again had a typical dose curve.

Using a biotin linked to a photocleavable domain and chemically conjugated to BSA with an NHS ester-amine reaction, we again stimulated antiBiot synthetic Notch cells with this molecule and saw a dose response similar to biotin and desthiobiotin. We then plated the ligand as before, but we exposed the plate to differing times of 300-350 nm light either from a UV lamp or through the Zeiss G 365 Filter on an epifluorescent microscope to release plated biotin. From this, we saw illumination time dependent levels of activation. Photopatterning can be achieved by applying a photomask, and plated cells only activate on locations that were not illuminated.

Antibody Fragments can be Biotinylated to Promote Activation to Target Ligands

Figure 7C:
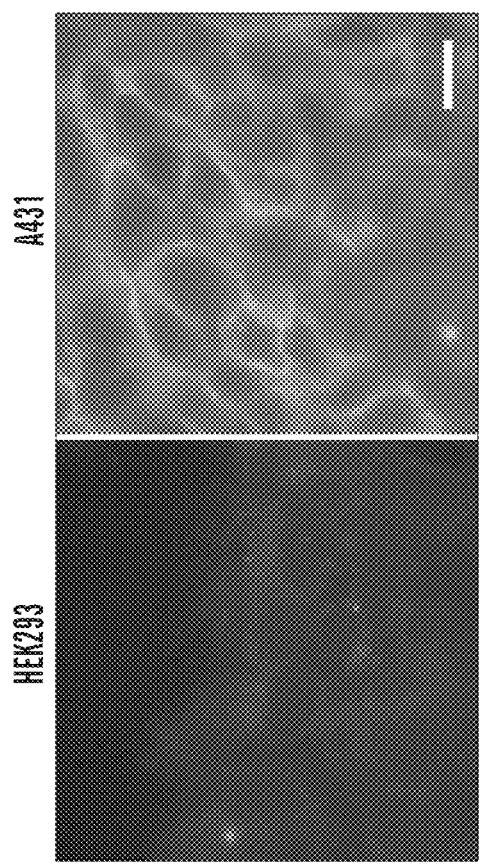
Figure 8C:
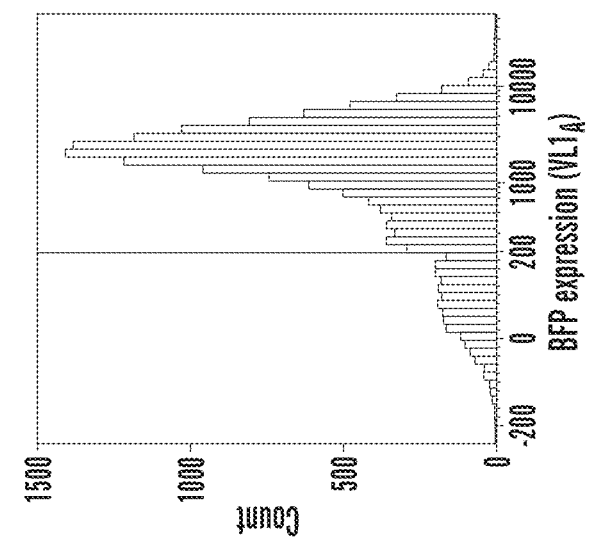
FIGS. 8A-8C depict flow cytometry gating schemes.
Figure 8B:
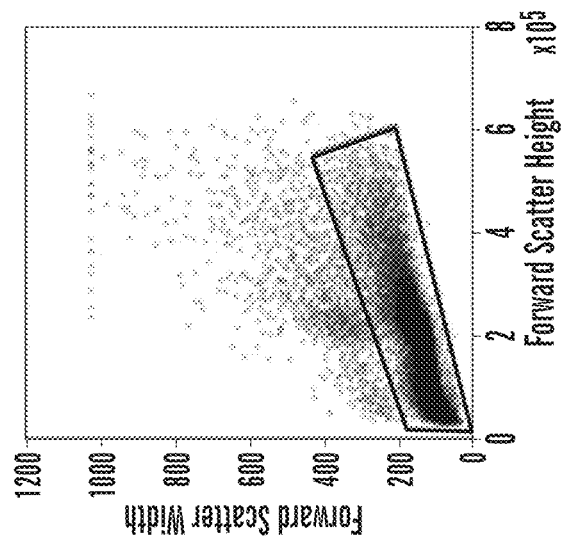
Figure 8A:
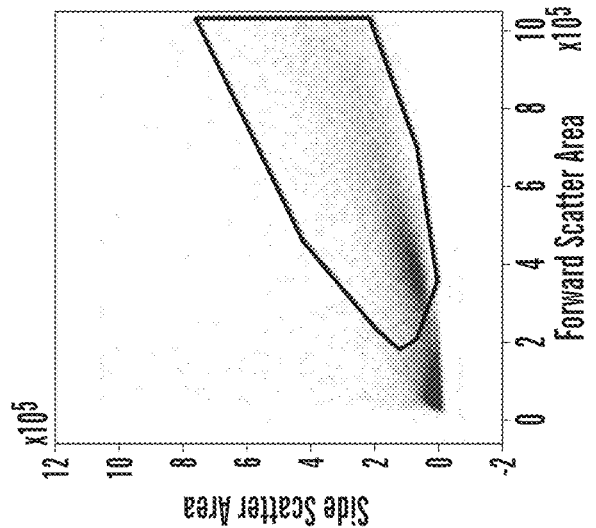

Similarly to controlling cellular signaling with a biotinylated form of a fluorescent protein, we looked to determine if we could use the same concept to promote signaling from endogenous targets. In order to do this, we utilized a nanobody for the Endothelial Growth Factor Receptor. This receptor, which is commonly upregulated in cancer, accomplishes signaling by binding the Endothelial Growth Factor, leading to autophosphorylation and downstream signaling. The nanobody that we used. EgA1, has been shown to decrease signaling through this pathway by binding to the receptor and promoting a conformational change preventing Endothelial Growth Factor binding29,30. We first expressed a Synthetic Notch with EgA1 as its extracellular binding domain, and observed that in coculture assays, the cell line was able to activate to A431 cells, a line that overexpresses EGFR, while was not able to activate to HEK293FT cells (FIG. 7C).

We expressed a secreted form of the nanobody with a fused biotin acceptor peptide in cell lines expressing the BirA-ER. From epifluorescence microscopy, we were able to see that the secreted nanobody bound to EGFR. Additionally, when spent media from cells secreting the nanobody were added to cocultures between the antiBiot synthetic Notch and A431 cells, which overexpress EGFR, we were able to see increased receptor activation. The control of biotin ligase in this system can change the secreted nanobody's function from inhibitory to promoting specific target gene activation.

Discussion

Together, these results represent a biotin-based system for synthetic signaling in mammalian cells. Synthetic post-translational modifications were accomplished by leveraging the enzymatic capabilities of *E. coli* biotin ligase, applying a biotinamide specific antibody, and utilizing chemical and photochemical control to achieve a highly sensitive system for synthetic biology. This set of tools can be used to probe the complexity of post-translational modifications in receptor biology, as well as aid in the creation of new receptors for immunotherapy.

We have developed a synthetic system of extracellular signaling that requires PTMs. The diversity of native Notch signaling is partially due to the diversity in possible glycosylation states of both the receptor and the ligand. This work demonstrates the ability to extend this diversity of signaling states to synthetic receptor systems. Through controlling not only the expression of the receptor, but also the modifying enzyme, it is possible to modulate the receptor's signaling capabilities. This study demonstrates a platform for studying these effects in a synthetic co-culture system. Additionally, the use of PTMs in secreted proteins mimic the natural signaling capabilities of antibodies, where depending on the glycosylation state of the antibody, different levels of response occur. For fucosylation, this occurs through the change in affinity for the Fc receptor, but other changes exist for different glycosylation states such as sialylation. The engineered synthetic platform for installing PTMs to secreted proteins enables us the opportunity to study how modified paracrine factors can influence juxtacrine signaling.

Methods

Plasmid Construction

Standard cloning procedures were used in the generation of all DNA constructs. DNA 400 fragments were amplified with Phusion™ High-Fidelity DNA polymerase (New England Biolabs), and Gibson assembly was accomplished using the NEBuilder HiFi DNA Assembly master mix (New England Biolabs). New England Biolabs restriction enzymes were used to digest DNA, and T4 DNA Ligase (New England Biolabs) was used for ligation. The pDisplay-BirA-ER construct (Addgene #20856) and the pLV-EBFP2-nuc construct (Addgene #36085) are available from Addgene.

Mammalian Cell Culture

Mammalian cell lines were cultured in a humidified incubator maintained at 37° C. with 5% CO2. HEK293FT cells (Thermo Fisher) were cultured in DMEM with 10% FBS supplemented with on essential amino acids (Life Technologies), Glutamax (Life Technologies), and G418 (500 μg/mL; Invitrogen). Stable cell lines with resistance markers were maintained in Zeocin (100 μg/mL; Invitrogen), Puromycin (500 ng/mL; Invitrogen), Hygromycin B (75 μg/mL; Invitrogen), or Blasticidin (10 μg/mL; Invitrogen).

DNA Transfection

DNA transfections were carried out with Lipofectamine 3000 Reagent (Thermo Fisher) according to the manufacturer's instructions. For coculture assays, luciferase reporter plasmids were reverse transfected into synthetic Notch receiver cells.

Stable Cell Line Generation

HEK293FT cells were grown in 6-well plates and cotransfected with lentivirus packaging and envelope plasmids (VSV-G and psPAX2) in addition to plasmids containing the gene of interest. Supernatant was collected 24 hr and 48 hr after, spun down to remove cell debris, and filtered with a 0.45 μm filter. The media containing lentivirus was then added to cell lines for 48 hr. The appropriate antibiotic was added for ten days, and single clones were isolated via limited dilution. For cell lines established with a pcDNA3.1 vector, cells were transfected with linearized DNA, and 48 hr post-transfection, antibiotic and limited dilution protocols were performed as above.

Western Blots

Cell lysates were prepared by direct lysis in RIPA Lysis and Extraction Buffer (Thermo), and denaturing polyacrylamide gel electrophoresis was accomplished with NuPAGE (Thermo Fisher). Proteins were transferred to membranes for probing with Streptavidin-HRP and anti-myc. Detection of the labeled antigens was done by chemiluminescence via the SuperSignal™ West Pico PLUS Chemiluminescent Substrate (Pierce).

Fluorescence Microscopy

Cells were imaged by epifluorescence microscopy after having been plated on 8-well Optically Clear Plastic Bottom slides (Ibidi) coated with Fibronectin. During imaging, cells were maintained in PBS or standard culture media. For immunofluorescent staining of fixed cells, cells were fixed for 10 min at room temperature with paraformaldehyde (4% v/v in PBS from 16% solutions purchased from Thermo Fisher) and rinsed with PBS. Cells were blocked with a BSA solution (5% in PBS) before being incubated with fluorophore conjugated streptavidin or antibody. Images were acquired with ZEN™ imaging software (Zeiss). Image files were processed with a custom MATLAB™ (Mathworks) script in order to adjust contrast uniformly across experiments.

Plated Ligand Assay

Nontreated 96-well plates were coated with Fibronectin (5 ng/mL) and plated ligand in 50 µL PBS for 1-hr. Initial experiments were done with a serial dilution of ligand to determine working concentrations. The wells were rinsed three times with 200 µL PBS, and 40 k synthetic Notch receiver cells were plated in each well. Receptor activation was measured 24 hr post-plating via fluorescence microscopy or flow cytometry.

Flow Cytometry

Cells analyzed with an Attune NxT flow cytometer and were gated for living cells by scatter detection. The percent activation was determined by calculating the percentage of cells with mCherry expression levels above a certain threshold.

Coculture Luciferase Assay

The luciferase assay used for coculture studies was adapted from Gordon et al28. Synthetic Notch receiver cells were reverse transfected in a 96-well plate (50 k cells per well) with 9.9 ng of UAS:Firefly-Luciferase plasmid and 0.1 ng Nanoluc plasmid per well. 24 hr post-transfection, 80 k sender cells were added to each well. 48 hr post-transfection, cells were lysed (Nano-Glo Dual-Luciferase Reporter Assay System, Promega) and the luminescence was found following the manufacturer's instructions. Each well was normalized to the luminescence output of Nanoluc (transfection control).

Protein Conjugation

Bovine Serum Albumin was conjugated with desthiobiotin via an NHS ester/amine reaction. 75 µM BSA in bicarbonate buffer and 20% DMSO was mixed with 7.5 mM desthiobiotin succinimidyl ester (Click Chemistry Tools 1201) in ultra-dry DMSO in a 9:1 mixture on ice. The reaction proceeded for 1 hour at room temperature and went through 3 rounds of dialysis in PBS. The solution was diluted and filter sterilized. The final theoretical concentration after dilution of the desthiobiotin-BSA was 13.5M with a maximum of a 9:1 desthiobiotin to BSA concentration.

The reaction of photocleavable biotin (Click Chemistry Tools 1225) to BSA occurred in a similar reaction.

REFERENCES

1. Wang, X. et al. Core fucosylation regulates epidermal growth factor receptor-mediated intracellular signaling. *J. Biol. Chem.* 281, 2572-2577 (2006).
2. Akiyama, S. K., Yamada, S. S. & Yamada, K. M. Analysis of the role of glycosylation of the human fibronectin receptor. *J. Biol. Chem.* 264, 18011-18018 (1989).
3. Planinc. A. et al. Batch-to-batch N-glycosylation study of infliximab, trastuzumab and bevacizumab, and stability study of bevacizumab. *Eur. J. Hosp. Pharm.* 24, (2017).
4. Giddens, J. P., Lomino, J. V., DiLillo, D. J., Ravetch, J. V. & Wang, L. X. Site-selective chemoenzymatic glycoengineering of Fab and Fc glycans of a therapeutic antibody. *Proc. Natl. Acad. Sci. U.S.A.* 115, 12023-12027 (2018).
5. Bray, S. J. Notch signalling: A simple pathway becomes complex. *Nat. Rev. Mol. Cell Biol.* 7, 678-689 (2006).
6. Artavanis-Tsakona, S., Rand, M. D. & Lake, R. J. Notch signaling: cell fate control and signal transduction in development. *Science* (80-). 284, 770-776 (1999).
7. Vooijs. M., Schroeter, E. H., Pan, Y. Blandford, M. & Kopan. R. Ectodomain shedding and intramembrane cleavage of mammalian Notch proteins is not regulated through oligomerization. *J. Biol. Chem.* 279, 50864-50873 (2004).
8. Varnum-Finney, B. et al. Immobilization of Notch ligand, Delta-1, is required for induction of Notch signaling. *J. Cell Sci.* 113, 4313-4318 (2000).
9. Bray, S. J. Notch signalling in context. *Nat. Rev. Mol. Cell Biol.* 9, 722-735 (2016).
10. Kakuda, S. & Haltiwanger, R. S. Deciphering the Fringe-Mediated Notch Code: Identification of Activating and Inhibiting Sites Allowing Discrimination between Ligands. *Dev. Cell* 40, 193-201 (2017).
11. Panin, V. M. et al. Notch ligands are substrates for protein O-fucosyltransferase-1 and Fringe. *J. Biol. Chem.* 277, 29945-29952 (2002).
12. Haltiwanger, R. S. et al. Fringe is a glycosyltransferase that modifies Notch. *Nature* 406, 369-375 (2000).
13. Fleming R. J., Gu, Y. & Hukriede, N. A. Serrate-mediated activation of Notch is specifically blocked by the product of the gene fringe in the dorsal compartment of the *Drosophila* wing imaginal disc. *Development* 124, 2973-2981 (1997).
14. LeBon, L., Lee, T. V. Sprinzak, D., Jafar-Nejad, H. & Elowitz. M. B. Fringe proteins modulate Notch-ligand cis and trans interactions to specify signaling states. *Elife* 3, e02950 (2014).
15. Beckett, D., Kovaleva, E., Petter, S. & Schatz, P. J. A minimal peptide substrate in biotin holoenzyme synthetase-catalyzed biotinylation. *Protein Sci.* 8, 921-929 (1999).
16. Chen, I., Howarth, M., Lin, W. & Ting, A. Y. Site-specific labeling of cell surface proteins with biophysical probes using biotin ligase. *Nat. Methods* 2, 99-104 (2005).
17. Howarth, M., Takao, K., Hayashi, Y. & Ting, A. Y. Targeting quantum dots to surface proteins in living cells with biotin ligase. *Proc. Nat. Acad. Sci.* 102, 7583-7588 (2005).
18. Morsut, L. et al. Engineering Customized Cell Sensing and Response Behaviors Using Synthetic Notch Receptors. *Cell* 164, 780-791 (2016).
19. Fridy, P. C. et al. A robust pipeline for rapid production of versatile nanobody repertoires. *Nat. Methods* 11, 1253-1260 (2014).
20. Coloma, M. J., Hastings, A., Wims, L. A. & Morrison, S. L. Novel vectors for the expression of antibody molecules using variable regions generated by polymerase chain reaction. *J. Immunol. Methods* 152, 89-104 (1992).
21. Denecke, J., De Rycke, R. & Botterman, J. Plant and mammalian sorting signals for protein retention in the 22. Ingaramo, M. & Beckett, D. Selectivity in post-translational biotin addition to five human carboxylases. *J. Biol. Chem.* 287, 1813-1822 (2012).
23. Gordon, W. R. et al. Mechanical Allostery: Evidence for a Force Requirement in the Proteolytic Activation of Notch. *Dev. Cell* 33, 729-736 (2015).
24. Dengl, S. et al. Hapten-directed spontaneous disulfide shuffling: A universal technology for site-directed covalent coupling of payloads to antibodies. *FASEB J.* 29, 1763-1779 (2015).
25. Zhou, X., Vink, M., Klaver, B., Berkhout, B. & Das, A. T. Optimization of the Tet-On system for regulated gene expression through viral evolution. *Gene Ther.* 13, 1382-1390 (2006).
26. Tague. E. P., Dotson, H. L., Tunney, S. N., Sloas, D. C. & Ngo, J. T. Chemogenetic control of gene expression and cell signaling with antiviral drugs. *Nat. Methods* 15, 519-522 (2018).
27. Gao, X. J., Chong, L. S., Kim, M. S. & Elowitz, M. B. Programmable protein circuits in living cells. *Science (80-.).* 361, 1252-1258 (2018).
28. Gordon, W. R. et al. Mechanical Allostery: Evidence for a Force Requirement in the Proteolytic Activation of Notch. *Dev. Cell* 33, 729-736 (2015).
29. Hofman, E. G. et al. EGF induces coalescence of different lipid rafts. *J. Cell Sci.* 121, 2519-2528 (2008).
30. Schmitz, K. R., Bagchi, A., Roovers, R. C., Van Bergen En Henegouwen, P. M. P. & Ferguson. K. M. Structural evaluation of EGFR inhibition mechanisms for nanobodies/VHH domains. *Structure* 21, 1214-1224 (2013).

Example 3: A Genetically Encodable and Chemically Disruptible System for Synthetic Post-Translational Modification Dependent Signaling The use of post-translational modifications is essential to the complexity of signaling in higher organisms, yet the recapitulation of these signaling motifs in synthetic contexts has been limited due to the lack of well-defined post-translational modification modules. Described herein is a toolset of biotin-based signaling systems, which is advantageous in its orthogonality and specificity in mammalian cells. Provided are several use cases of this system in both extracellular and intracellular signaling pathways, highlighting the application of a binding protein specific for the modification. Finally, we present several small molecules which can augment signaling properties, either as agonists or antagonists. The genetically encodable tools described here represent methods to develop more complex signaling in synthetic pathways by mirroring those used in natural contexts.

Introduction

The development of synthetic multicellular systems requires an increasing level of control in designed signaling domains. As synthetic biology has advanced, numerous orthogonal tools for engineering cellular communication have been developed, often taking inspiration from natural signaling frameworks. Modules inspired by the Lefty-Nodal system[1], the cadherin system[2], receptor tyrosine kinases[3], and the Notch pathway[4-7] have demonstrated functional understanding of the proteins used to develop natural multicellular systems. In particular, the use of synthetic Notch receptors has proven successful in recapitulating many of the natural processes found in development[8,9]. However, there still exists a lack of tools to scale up the complexity of these initial designs.

One framework that has proven successful in natural contexts but has seen limited engineering in synthetic ones is the use of post-translational modifications (PTMs). PTMs add a crucial layer of fine-tuning and regulation of cellular processes. PTMs can provide an immediate response to cell cues to modulate protein function, including stability, protein-protein interactions, localization, and activity. In the context of Notch signaling, PTM of Notch signaling components serves as an essential layer of control that enables the diverse pleiotropic outcomes of Notch signaling in vivo[10-12]. Various studies have indicated indispensable roles for the modification of Notch ECDs, and the expression of glycosyltransferase genes is known to play an essential role in the spatiotemporal regulation of the signaling capacity and signaling outcomes of Notch receptors[13-15]. PTMs allow the Notch pathway to accomplish numerous distinct signaling states in different developmental settings.

Current designs which utilize PTMs in synthetic biology have primarily focused on protease-mediated networks or rewiring native PTM pathways. Although controlled protease activity has been demonstrated to be effective in enabling rapid changes in signaling[16,17], the use cases in which proteases can be used are limited to multi-domain proteins, and many proteases have off-target activity, limiting their orthogonality. Rewiring native PTM pathways has again been successful in generating rapid responses as well as leading to changes in phenotype as functional outputs[18]; however, the use of these domains is limited to already established networks, and these PTM systems are often based on phosphorylation[19], a chemical tag that is highly used and promiscuous in mammalian cells. The PTM toolset needs the elaboration of an orthogonal and highly specific small molecule tag for use in both extracellular and intracellular environments.

An ideal synthetic PTM-based signaling system would recapitulate the features of natural PTMs as well as exist within the context of natural occurring signaling pathways. It would be necessary for the synthetic PTM to be orthogonal: the novel PTM should not interact with any native proteins, the enzyme adding the modification should be specific for its designed target, and any synthetic binding protein against the modification should be selective for that modification. For these reasons, a biotin-based PTM system is ideal for constructing a synthetic signaling system. Groups have developed and optimized a small peptide that can be biotinylated by *E. coli* BirA[20] and have demonstrated its use in mammalian cells[21,22]. Furthermore, BirA has been effectively engineered for various purposes[23,24], such as proximity ligation. Our approach in expanding this tool for synthetic signaling capabilities is to generate systems that can respond to the biotin signal and to take inspiration from natural pathways.

Results

A Biotinylation-Sensitive Synthetic Notch

Figure 11C:
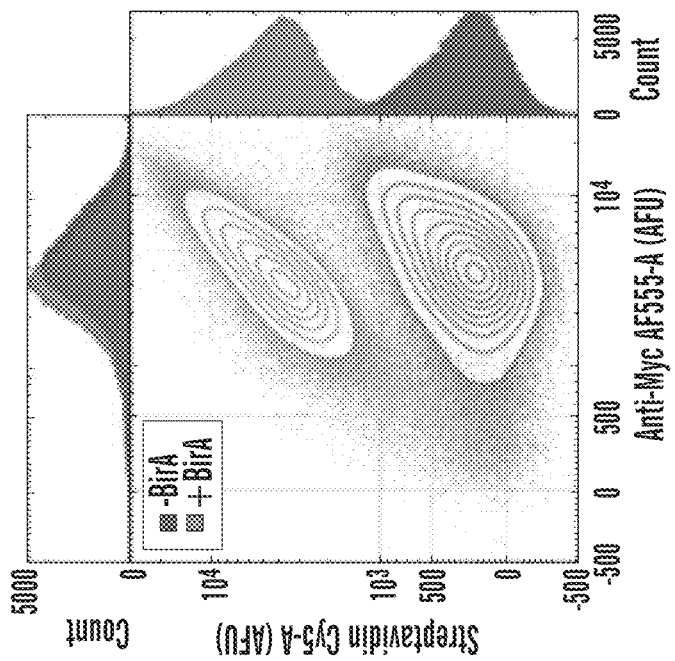
FIGS. 11A-11I demonstrate that BirA localized to the secretory pathway biotinylates biotin acceptor peptide fused receptors, and regulated expression of BirA leads to control of downstream processes.
Figure 11B:
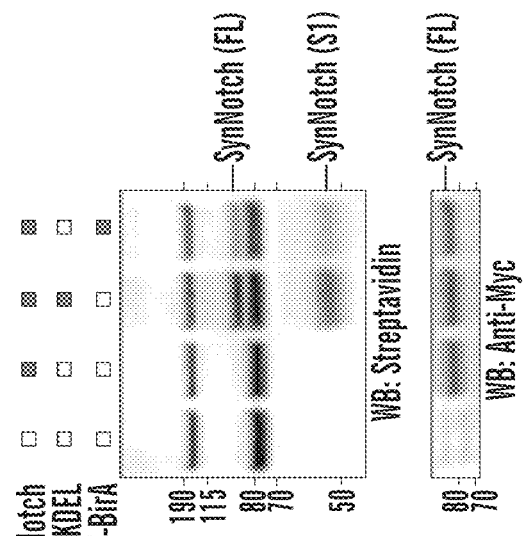
Figure 11A:
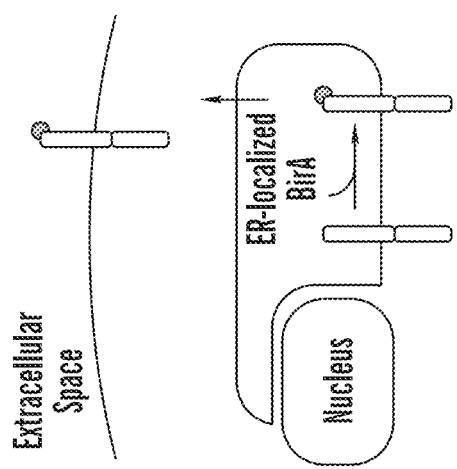

A biotinylation-sensitive synthetic Notch (SynNotch) was constructed by fusing the biotin acceptor peptide (AP) sequence to the extracellular region of an anti-GFP containing receptor, generating "AP-SynNotch." In this design, it was anticipated that the ligand-specificity of the receptor could be regulated in a post-translational manner, enabling its recognition of biotin-binding ligands following modification by BirA (FIG. 11A). In initial experiments, it was sought to confirm that AP-SynNotch could be selectively modified in cells containing luminal BirA constructs, and to verify that the receptor could be correctly processed and trafficked to the cell surface following its biotinylation. Immunoblot analyses of cells expressing either an endoplasmic reticulum (ER)-, or Golgi-targeted BirA (BirA-KDEL and GalT-BirA, respectively), showed highly-specific modification by BirA, with receptor components appearing as the only streptavidin-reactive bands beyond that of endogenously biotinylated proteins (FIG. 11B, FIGS. 15A-15B). Notably, signals corresponding to biotinylated versions of both the full-length (77 kDa) and S-cleaved (43 kDa) were observed. Thus, the post-translationally modified receptor can be correctly processed to its heterodimeric via furin-mediated cleavage within the Golgi[26]. Because more efficient biotinylation was observed using BirA-KDEL, as compared to GalT-BirA, we proceeded with the ER-localized enzyme in subsequent analyses.

Given that cell surface localization is a requirement in the detection of extracellular ligands, it was next asked whether biotinylated AP-SynNotch could be trafficked to the plasma membrane. Staining of non-permeabilized cells using dye-conjugated streptavidin (Cy5-SA) confirmed the presentation of biotinylated receptors on the surface of transfected HEK293 cells (FIG. 15C). In addition, dual labeling with a fluorescent anti-myc antibody (ms-anti-myc/anti-ms-AF555) displayed similar surface anti-myc reactivity between BirA-KDEL expressing and non-expressing cells (FIG. 1C, FIG. 15D). Thus, biotinylation did not appear to deter the trafficking efficiency of AP-SynNotch, as compared to its unmodified counterpart. These results, together with those described above, confirm that AP-SynNotch can be selectively and efficiently biotinylated, and that the modified receptor is correctly processed within the Golgi prior to its presentation at the plasma membrane.

Conditional Signaling in Response to a PTM-Specific Ligand

Figure 11D:
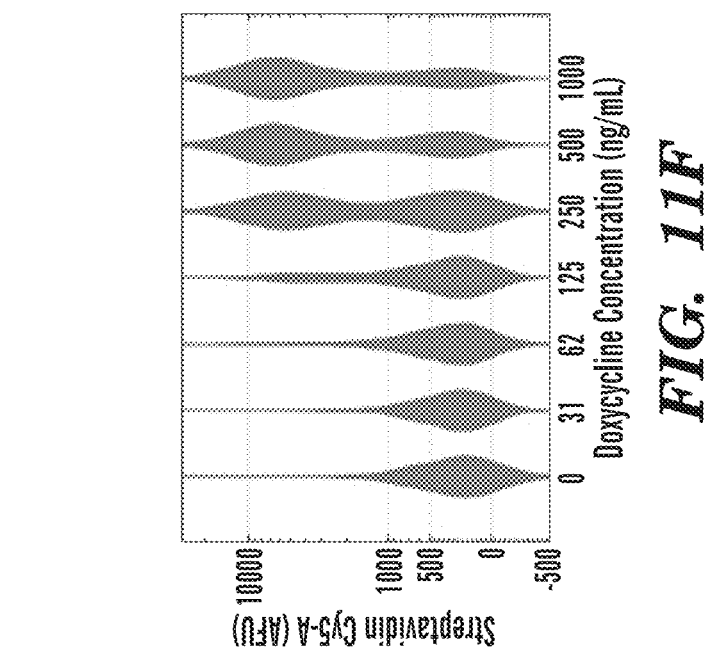

Next to be evaluated were the signaling properties of AP-SynNotch. Here, the activity of the receptor in response to different ligands was compared in cells with and without BirA-KDEL. Using a receptor containing a Gal4-VP64 ICD, the signaling activity of AP-SynNotch was measured in transfected HEK293 cells containing a stably-integrated reporter gene (UAS:H2B-mCherry). In order to stimulate receptor activation, transfected cells were grown on culture surfaces containing immobilized ligands, and reporter expression levels were measured the next day using flow cytometry (FIG. 11D).

Figure 11E:
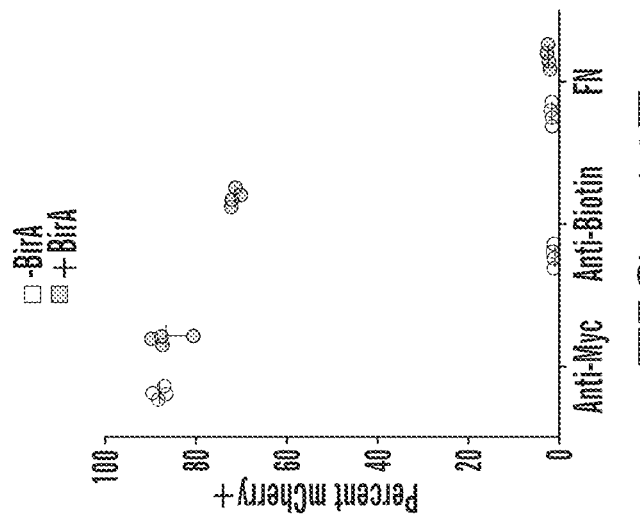

In control analyses, the background activity of modified and unmodified receptors were compared by measuring reporter levels from cells grown in ligand-uncoated wells. Quantification of H2B-mCherry indicated similar degrees of (background) reporter expression in both BirA-KDEL-expressing and non-expressing cells (FIG. 11E). Thus, biotinylation of AP-SynNotch did not appear to alter the quiescence of AP-SynNotch in the absence of synthetic ligands. To confirm the inducibility of the receptor, cells that were grown in the presence of anti-myc IgG (a positive control ligand) were also analyzed (FIG. 15E). Measurement of these cells revealed strong levels of signaling-induced reporter activity, with closely-matched H2B-mCherry levels between BirA-KDEL expressing and non-expressing cells. Thus, the coexpression of BirA-KDEL did not appear to inhibit, nor limit the inducibility of the receptor in response to a PTM-independent ligand.

In contrast to results obtained using anti-myc IgG, stimulation with a biotin-specific ligand (anti-biotin IgG) resulted in divergent responses between BirA-KDEL expressing and non-expressing cells (FIG. 11E, FIG. 15F). Cells that expressed BirA-KDEL exhibited strong signaling responses to the anti-biotin IgG ligand, eliciting reporter expression levels nearing that which was induced by stimulation with anti-myc IgG. Cells that lacked BirA-KDEL, however, exhibited only background amounts of H2B-mCherry, similar to levels that were expressed by ligand-untreated control cells. These result indicate that the coexpression of BirA-KDEL is able to confer new ligand-recognition capabilities to AP-SynNotch, permitting its detection of biotin-binding ligands in a PTM-dependent manner.

Control over Receptor PTM and Signaling Activity

In natural systems, the PTM of Notch receptors is tightly regulated in order to achieve precise developmental control over processes such as cell patterning, boundary formation, and tissue morphogenesis[27-29]. In certain systems, this regulation is achieved via dynamic and spatiotemporally-restricted expression of Notch-modifying glycosyltransferases[14,15] Seeking to gain similar control over AP-SynNotch, it was next asked whether regulated BirA-KDEL expression could be used to fine-tune the extent of biotinylation, and as a result, the signaling responses to biotin-binding ligands.

Figure 11F:
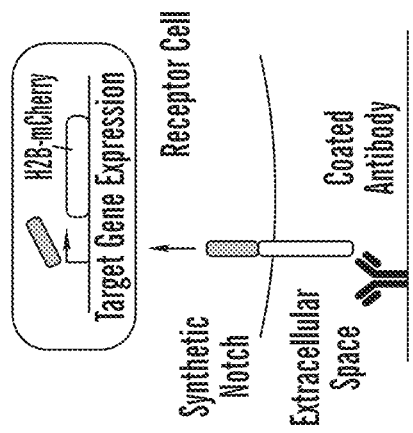
Figure 11I:
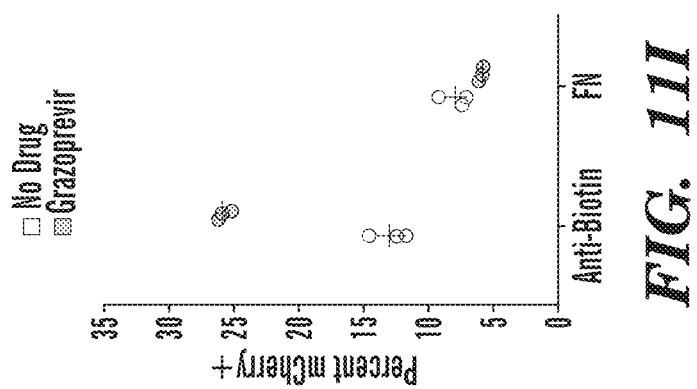
Figure 11H:
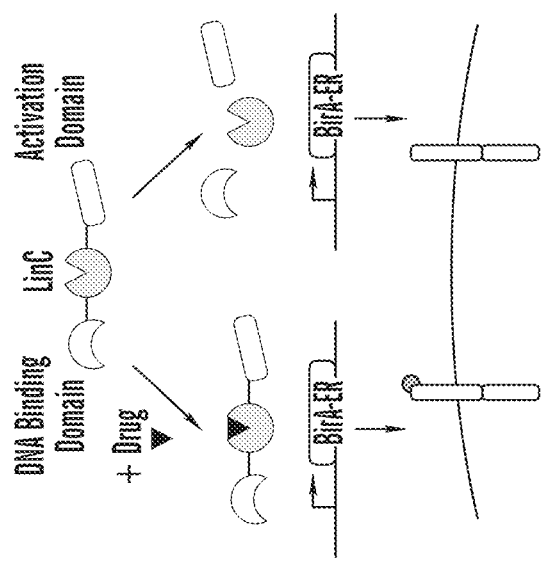
Figure 11G:
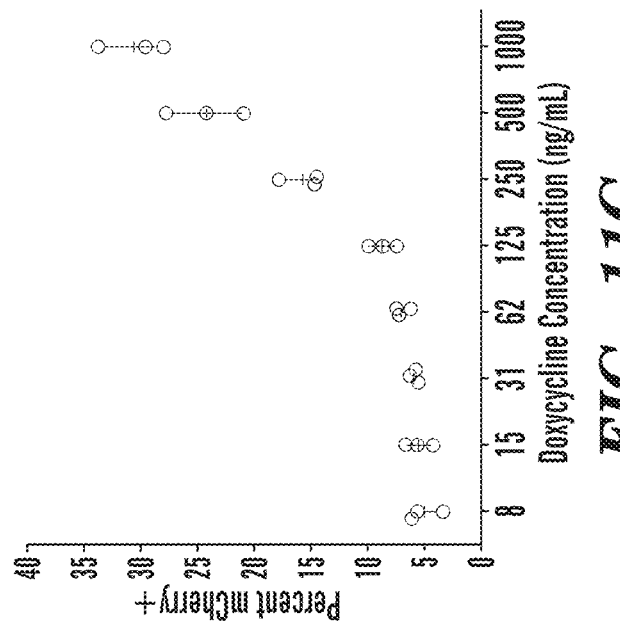
Figure 15G:
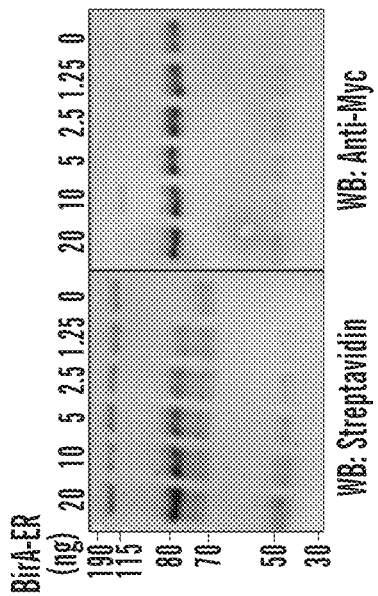
Figure 15F:
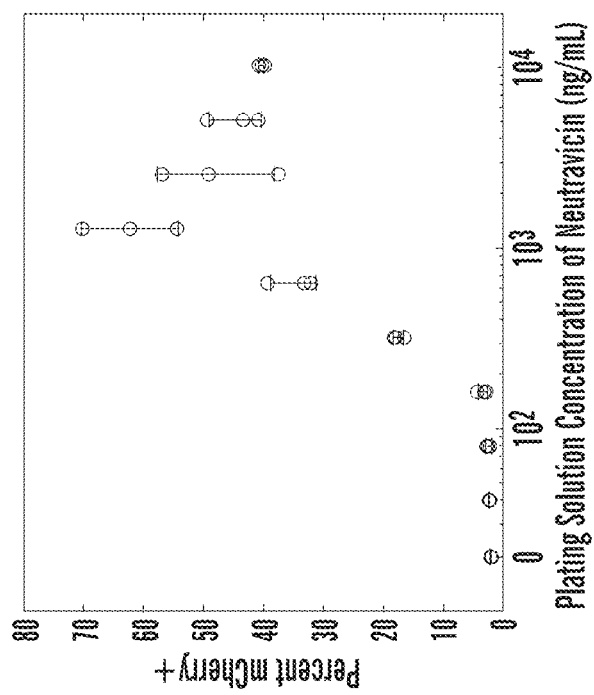

In an initial analysis, it was confirmed that graded levels of receptor biotinylation could be facilitated by varying the amount of BirA-KDEL plasmid used during transfection (FIG. 15G). Desiring to gain greater control, it was next asked whether similar fine-tuning could be achieved by tuning the expression of the ligase at the level of gene transcription. In order to examine this possibility, a stable cell line was generated in which a BirA-KDEL encoding gene was placed under the control of the TRE3G promoter. In cells where the tetracycline transactivator-3 (rtTA-3) was used to regulate TRE3G transcription, both the extent of AP-SynNotch modification, as well as its signaling capacity in response to anti-biotin IgG, could be tuned in a dose-dependent manner via treatment with doxycycline (FIG. 11F-11G).

In addition to rtTA-3, similar control was achieved using an inducible transcription using the LInC (for Ligand Inducible Connection) strategy. Here, a transcription factor that responds to treatment with viral protease inhibitors—specifically those targeting the NS3 cis-protease from Hepatitis C virus (HCV)—was exploited to achieve drug-control using grazoprevir, a clinically approved antiviral drug. Here, inhibition of the HCV NS3 protease by grazoprevir results in the preservation of a fusion protein in which NS3 is encoded between TetR and VP64 domains (TetR-NS3-VP64). Accordingly, treatment of cells with grazoprevir resulted in an elevation of signaling activity in response to anti-biotin IgG (FIG. 11H-11I). Together, these results demonstrate the ability to modulate PTM state and signaling capacity through controlled expression of BirA.

An Encodable Biotin-Binding Ligand Although IgG-coated surfaces provide a convenient way to quickly validate receptor designs, the goal in this work was to construct cell-cell signaling systems resembling those found in nature. Toward this end, an encodable biotin-binding ligand was sought, anticipating that such a protein could be combined with AP-SynNotch and BirA-KDEL to comprise a genetic toolkit for constructing synthetic pathways of intercellular communication. Hypothesizing that such a PTM-specific ligand could be generated by encoding a biotin-binding domain as a cell surface-bound protein, it was next sought to identify an encodable PTM-recognition element.

Given the one-to-one binding stoichiometry between natural ligands and Notch receptors, an ideal synthetic ligand would be able to recognize biotinylated AP-SynNotch via a monomeric biotin-binding domain. Although sequences based on streptavidin- and avidin-derived proteins were considered as PTM-recognition modules, the multivalency of these domains motivated the inventors to search for alternative biotin-binding sequences, especially those that could be readily encoded in a monomeric form. Previous work described an antibody with specificity for biotinamide, a derivative of biotin that is formed following its attachment to proteins. Because biotinamide is generated following the modification of AP, it was thus tested whether sequences from anti-biotinamide IgG could be used to create an encodable ligand.

Figures 12A, 12B, 12C:
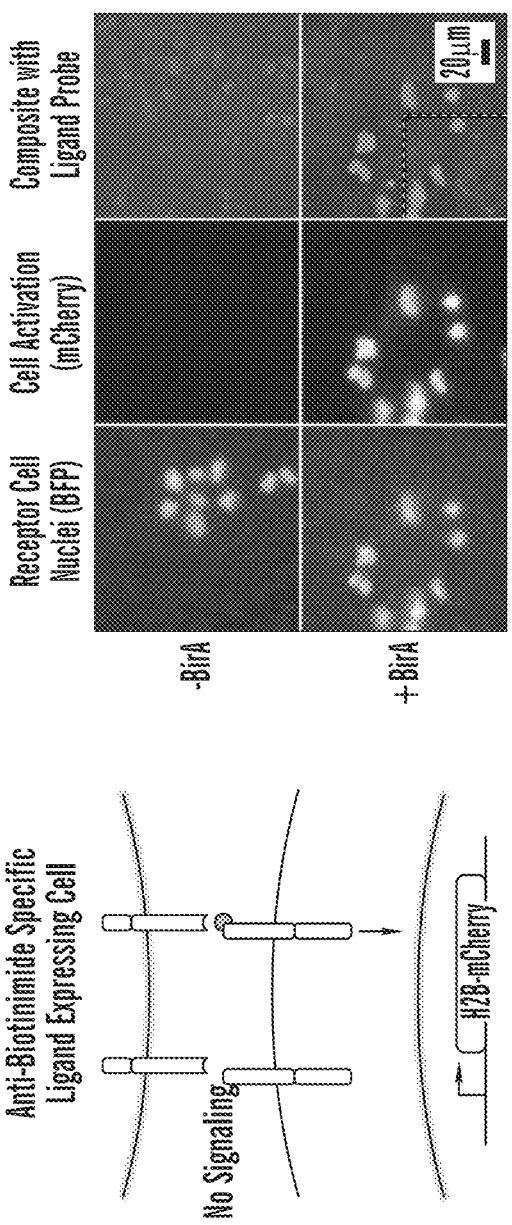
FIGS. 12A-12H demonstrate that Anti-Biotinamide specific ligand expressing cells activate only biotinylated receptor cells, and the signaling can be inhibited with genetically encoded constructs and small molecules.

To generate a monomeric biotin-binding domain, the anti-biotinamide IgG sequence was used to design a single-chain variable fragment (scFv). This sequence was then used to encode a biotin-binding ligand protein, which was created by linking the scFv to the transmembrane domain (TMD) from platelet-derived growth factor receptor (PDGFR), followed by the cytosolic fragment from the native Notch ligand Delta Like (DLL)-1. In addition to these components, a SNAP-tag domain was also included within the extracellular region of the protein, to permit its visualization using benzylguanine-containing dyes. The resulting sequence, dubbed "anti-bio-ligand," was then tested for its expression and signaling activity in mammalian cells (FIG. 12A).

To determine whether it could facilitate trans-cellular activation, anti-bio-ligand was used to generate a stable line of ligand-expressing "sender" cells. Direct labeling of the protein using a cell-impermeant SNAP-tag reactive dye (SNAP-Surface-AF647) confirmed the cell surface presentation of the ligand, and its detection within internalized punctae verified its ability to be retrieved from the plasma membrane (FIGS. 12B-12C). Thus, anti-bio-ligand satisfies the basic requirements of trans-activating ligands.

Figure 12F:
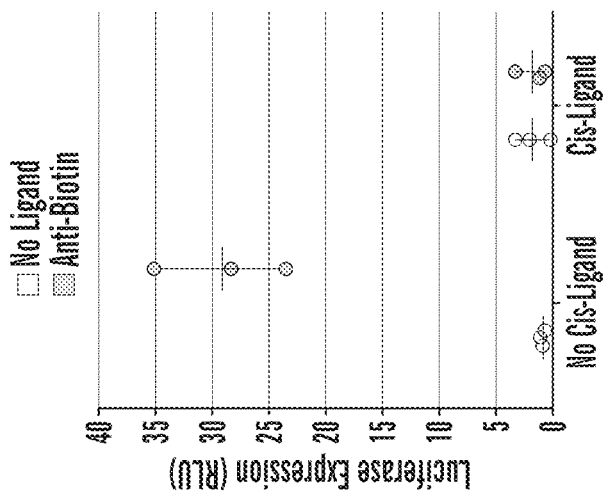
Figure 12E:
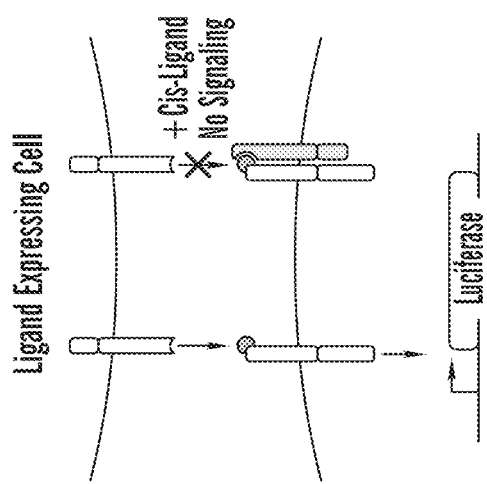
Figure 12D:
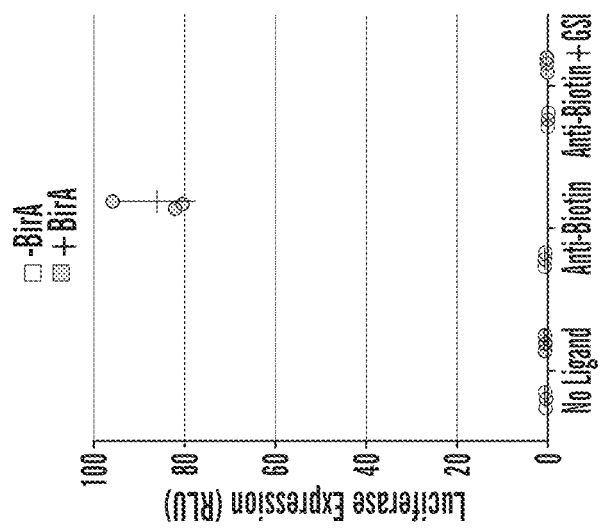
Figure 16A:
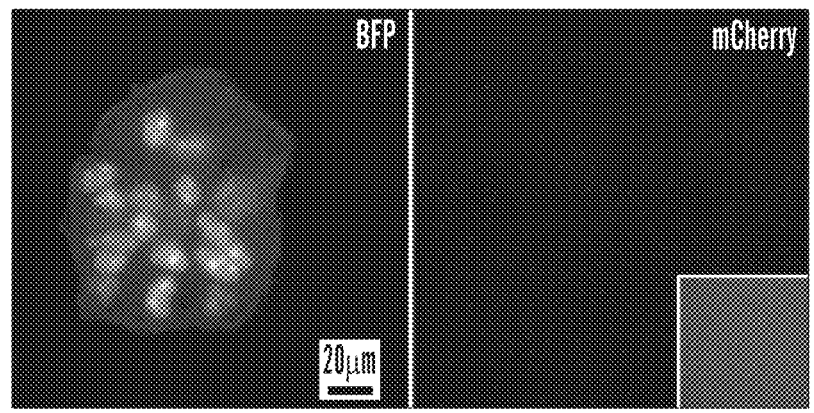
FIGS. 16A-16B demonstrate that a biotinamide-specific antibody fragment binds biotinylated proteins and can trigger activation of biotinylated AP-SynNotch when fused to a membrane protein.

Next, to confirm the trans-activating capability of the ligand, the ligand-expressing sender cells were combined with AP-SynNotch expressing "receiver" cells in a coculture assay. Here, the trans-cellular signaling activity was evaluated by inspecting receiver cells for the expression of a signaling (Gal4)-dependent reporter gene. Using receiver cells containing a fluorescence-based reporter construct (UAS:H2-mCherry), a spatial analysis was carried out in which cocultures were visually inspected using fluorescence microscopy. In order to distinguish between individual cell types, sender cells were labeled with a constitutive nuclear-BFP marker and sender cells were identified via ligand labeling with SNAP-Surface-AF647. In cocultures containing BirA-KDEL expressing receiver cells, strong H2B-mCherry expression was observed in areas where senders and receivers were positionally juxtaposed (FIGS. 12B-12C). Importantly, expression of the reporter protein was not detected in BirA-KDEL receivers grown alone (without senders), nor in cocultures in which receiver cells lacked BirA-KDEL expression (FIG. 12B, FIG. 16A). Additionally, luminescence-based analyses using receiver cells containing a firefly luciferase (fLuc)-based reporter construct (UAS:fLuc) provided quantitative verification of our fluorescence imaging results (FIG. 12D). Together, these data validate anti-bio-ligand as a signaling-competent and PTM-specific cell-based ligand.

PTM-Specific Cis-Inhibition

In natural systems, the signal-receiving capability of Notch can be genetically regulated via coincident expression of receptors and ligands by the same cell (i.e., "cis-inhibition"). In certain cases, the strength and specificity of natural cis-interactions is modulated via post-translational control[14]. Recognizing the utility of genetic modulation, it was next asked whether the signaling capacity of the AP-SynNotch could be controlled via binding to anti-bio-ligand in cis. To test this possibility, anti-bio-ligand was expressed in AP-SynNotch receivers and the signal-receiving capacity of the resulting cells was measured in a coculture with anti-bio-ligand senders (FIG. 12E). Quantification of reporter levels indicated that AP-SynNotch trans-signaling could be inhibited by the co-expression of anti-bio-ligand. (FIG. 12F). Thus, the expression of anti-bio-ligand can be used to block the signaling capacity of biotinylated receptors, providing a negative-regulatory mechanism that can be used to counteract the positive-regulation that is conferred via the inducible BirA-KDEL system described above.

Inhibition of Signaling Via Soluble Biotinamide Molecules

Figure 12G:
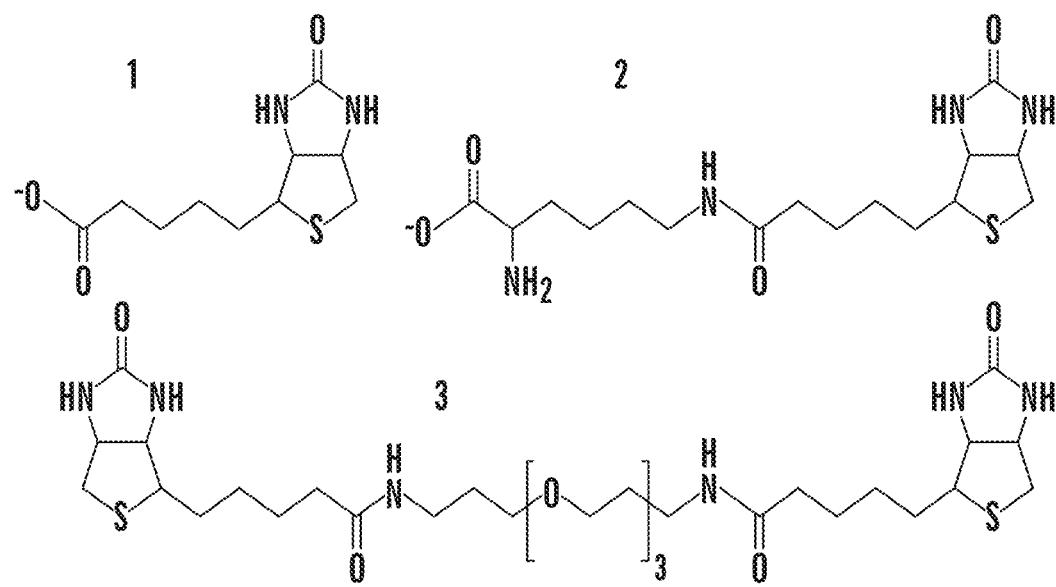
Figure 12H:
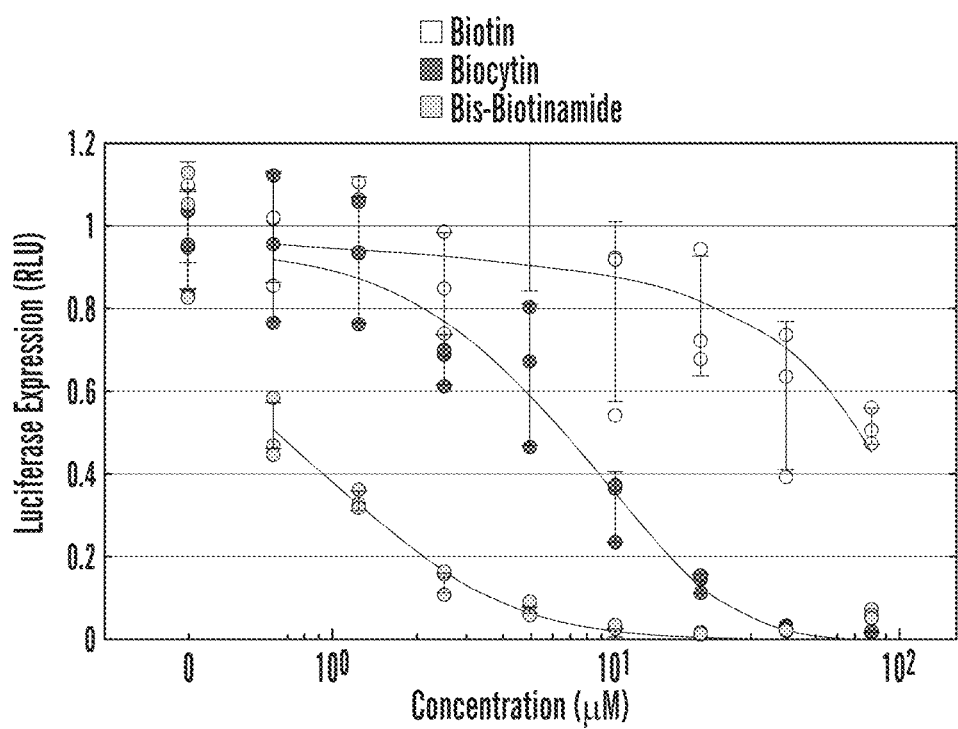

Tight-regulation is a requirement of cell-engineered systems in biomedical applications, and such control can be achieved by combining genetic strategies with external drug-control. Thus, it was next sought to design exogenous molecules that could be combined with the present encodable components in order to achieve versatile "chemogenetic" control. Soluble binding proteins can be used to block trans-cellular interactions between endogenous Notch receptors and ligands. It was tested whether soluble biotin-derived compounds could be used to competitively interact between our synthetic ligand and receptor (FIG. 12G). Although biotin (1) had limited impact on cell signaling as expected due to the decreased affinity of the single chain variable fragment for free biotin[30], biocytin (2) was able to inhibit cell signaling. Use of bis-biotinamide (3), in which two biotin units are connected via a short polyethylene glycol (PEG) linker, resulted in more potent inhibition as compared to that of biotinamide (FIG. 12F). In addition to their selective recognition by Anti-Biotinamide, the cell-impermeant nature of biocytin and bis-biotinamide offer the advantageous feature of limiting disruption/inhibition to cell-surface presented components.

Inducible Signaling with Bispecific Receptor Agonists

Figure 16B:
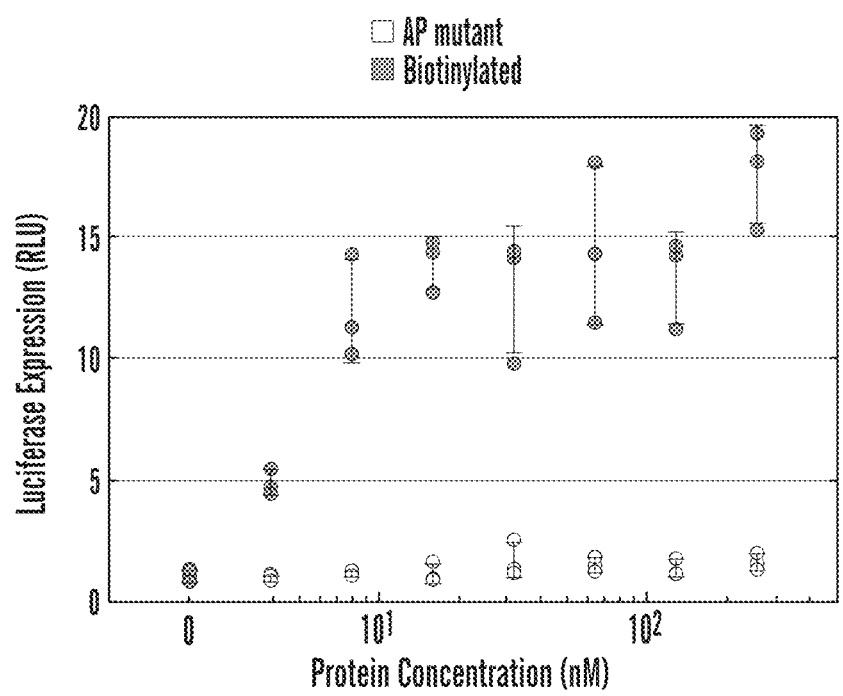

In addition to antagonizing AP-SynNotch, synthetic strategies in order to induce AP-SynNotch activation using exogenously administered molecules were also developed. Toward this end, two strategies were devised: in a first approach, a bispecific "bridge" protein was created that could be used to induce trans-cellular complexes between synthetic ligands and receptors. The addition of a purified, monobiotinylated GFP (GFP-biotin) to coculture mixtures induced signaling between senders and receivers, whereas reporter levels from mixtures treated with a non-biotinylated GFP resembled that of control (non-treated) cells (FIG. 16B).

Figure 13A:
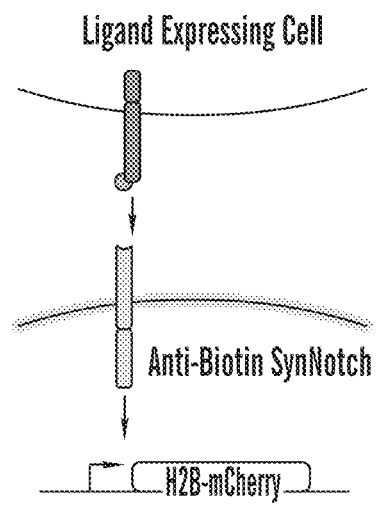
FIGS. 13A-13F demonstrate that An Anti-Biotinamide specific receptor binds and activates to biotinylated molecules, which can be triggered via a click reaction with tethered TCO.
Figure 13B:
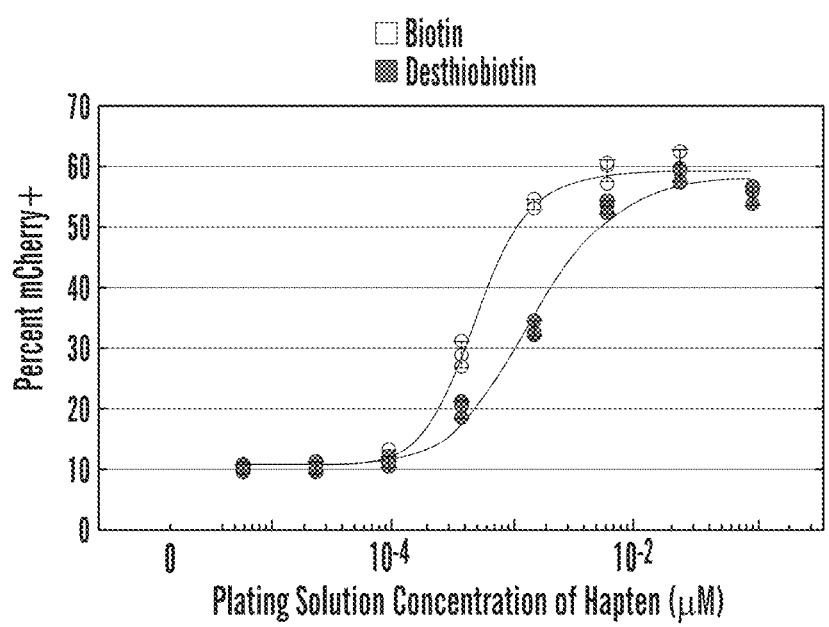
Figure 13C:
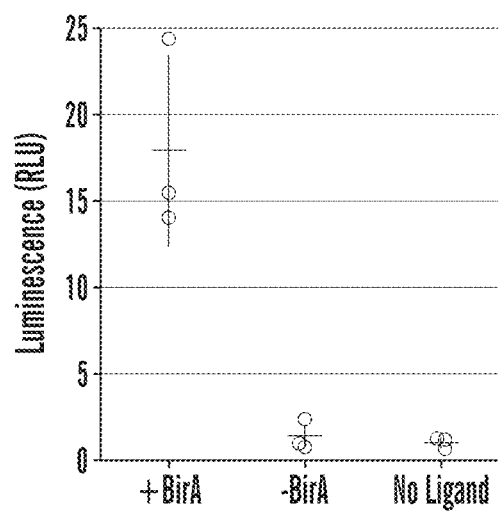
Figure 17A:
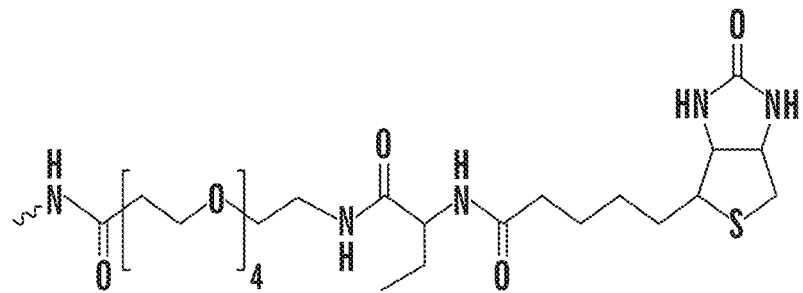
FIGS. 17A-17D demonstrate that a synthetic Notch against biotinamide can bind and activate to biotin-based substrates, and the interaction can be inhibited by biocytin.
Figure 17B:
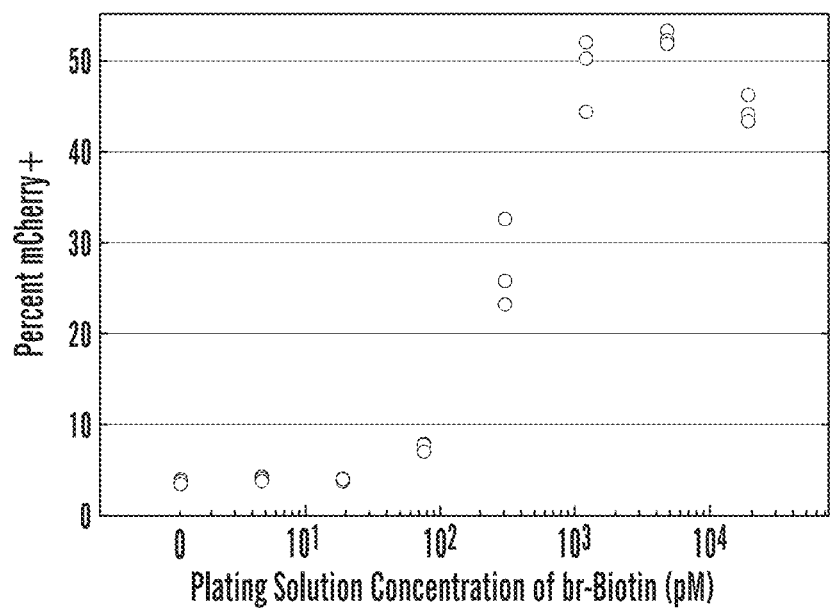
Figure 17C:
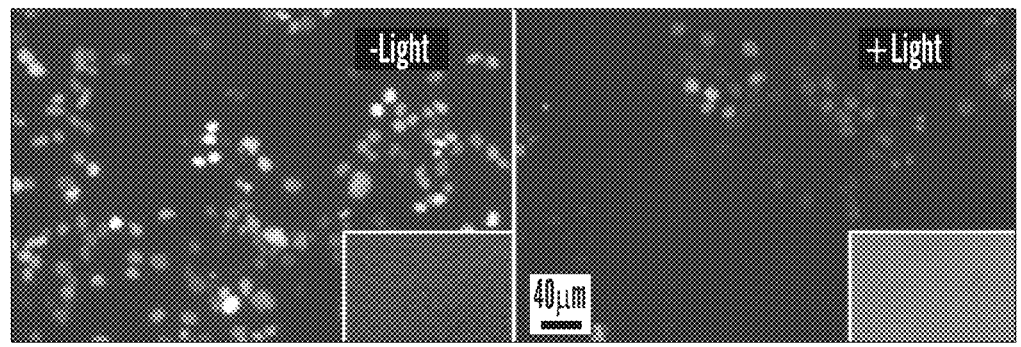
Figure 17D:
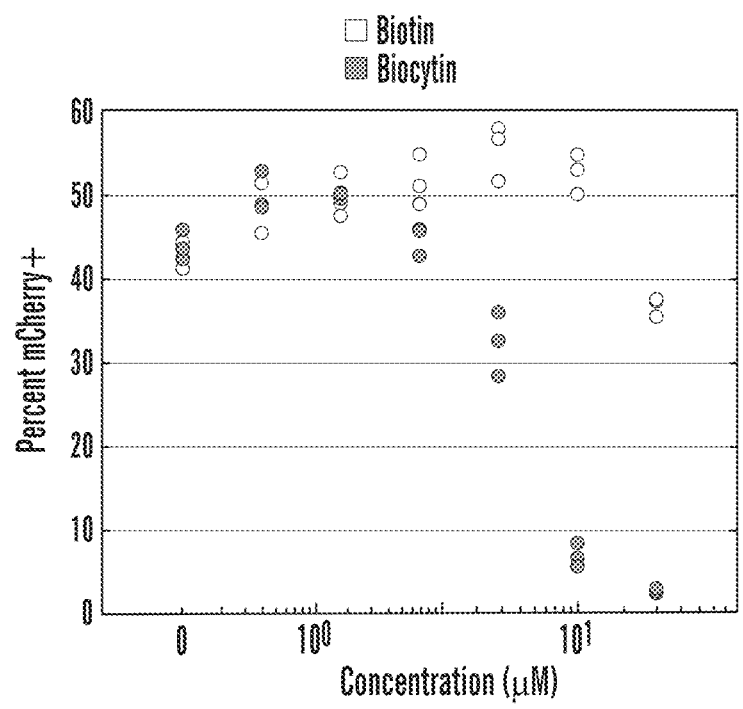

In a second approach, it was reasoned that the biotin-binding molecule could instead be fused as a SynNotch, rather than as a ligand. In this inverse orientation, the receptor would be acting as a reader of the post-translational state of ligands and agonists, and relaying output through its ICD. By fusing the anti-biotinamide scFv to a SynNotch, a receptor with the ability to respond to biotinaminde, and to a slightly lesser degree, desthiobiotinamide was developed (FIG. 13B). The receptor is also activated by a Biotinidase-resistant form and a photocleavable form of conjugated biotin (FIG. 17A-17C). Similar to the original orientation, biocytin was an effective inhibitor of signaling via the binding of the anti-biotinamide scFv (FIG. 17D). Extending the use of the anti-biotinamide SynNotch as a reader of PTM state, a cell-surface ligand with a fused AP was developed, which when expressed in HEK293 cells with BirA-KDEL, was able to activate the anti-biotinamide SynNotch cells in coculture assays (FIG. 13C).

Figure 13D:
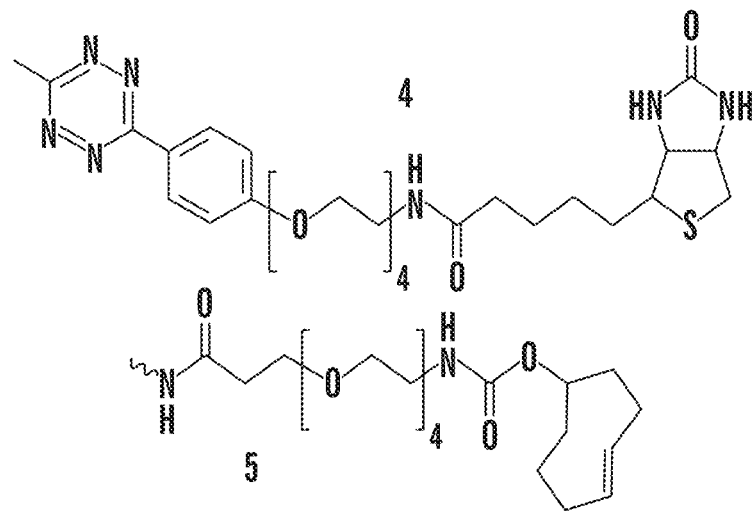
Figure 13E:
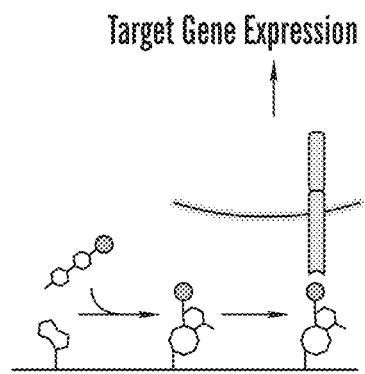
Figure 13F:
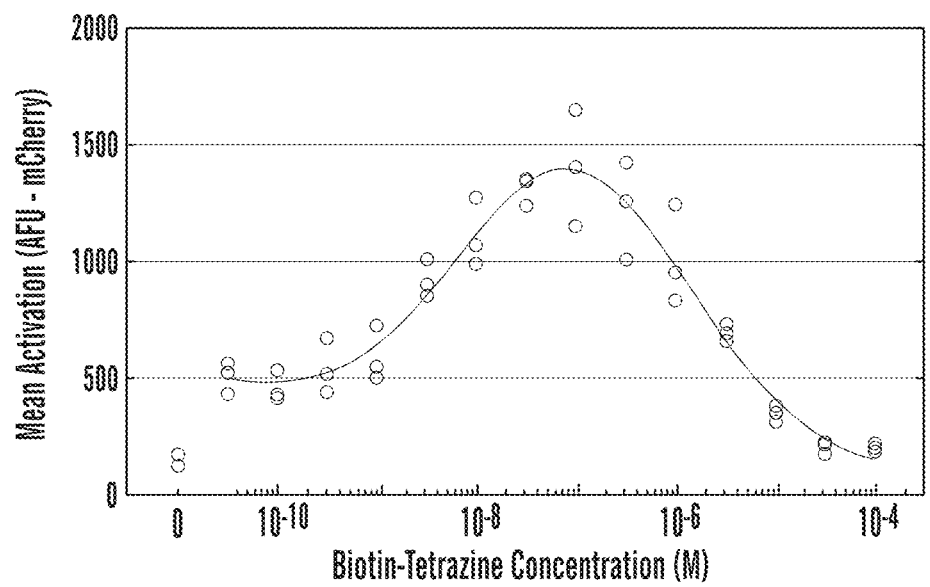

In an effort to develop synthetic agonists, a bioorthogonal chemical ligation was also exploited in order to convert a soluble biotin derivative into an immobilized (signaling competent) ligand in situ. Here, a tetrazine-functionalized biotinamide (4) was exploited as a "molecular switch," one that is capable of serving as a signaling inhibitor as a soluble compound, yet able to convert into a signaling-competent ligand upon bioorthogonal ligation to immobilized trans-cyclooctene (TCO) (5) groups (FIG. 13D-13E). This "switching" may represent a versatile strategy for ensuring highly-specific receptor activation, limiting signal transduction to prespecified areas in vivo, where TCO groups are immobilized, such as at sites where functionalized biomaterials may be introduced[31]. In this approach, biotin-tetrazine was added to wells in which anti-biotinamide SynNotch expressing cells were cultured on TCO coated wells. It was found that this receptor was able to activate reporter expression only when cultured with biotin-tetrazine and that receptor activation was able to be inhibited with high concentrations of the chemical (FIG. 13F).

Intracellular Signaling Via PTM-Dependent Domains

In a final demonstration of the use of biotin as a synthetic post-translational modification, it was aimed to extend the toolset for intracellular use. The functions of many intracellular proteins are regulated by their PTM state, including the Notch ICD. Its binding to transcriptional cofactors is modulated by phosphorylation state[32,33], thereby affecting its transcriptional capacity. Seeking to encode similar control into synthetic transcriptional systems, a strategy was developed to regulate gene expression by exploiting BirA activity to control the formation of intracellular PPIs.

Figure 14C:
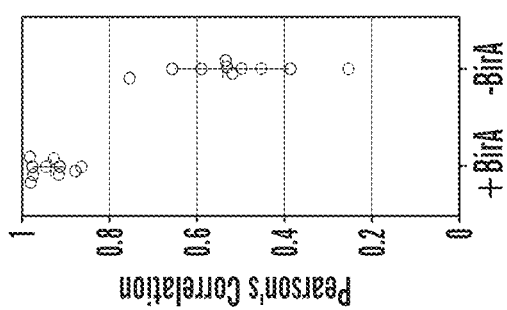
FIGS. 14A-14F demonstrate that a biotinamide-specific scFAB can act as a biotin-binding molecule in cells, and the interaction can be inhibited with biotin-cadaverine.
Figure 14B:
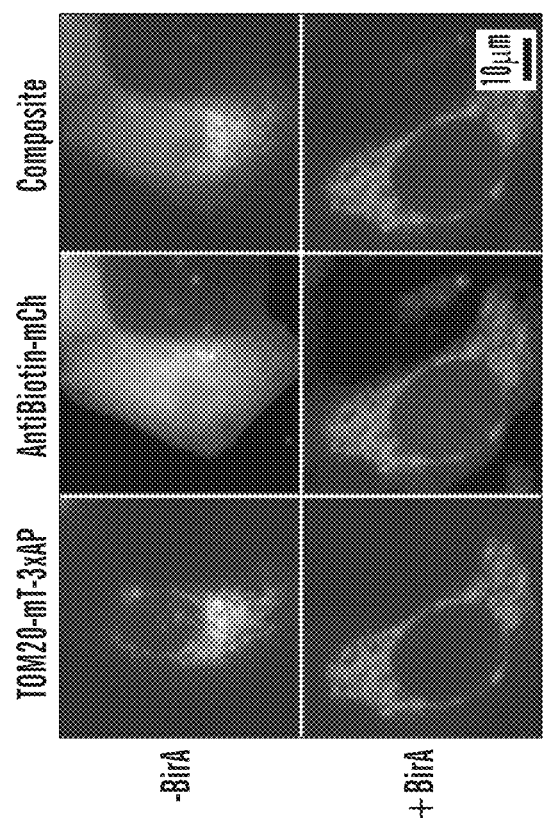
Figure 14A:
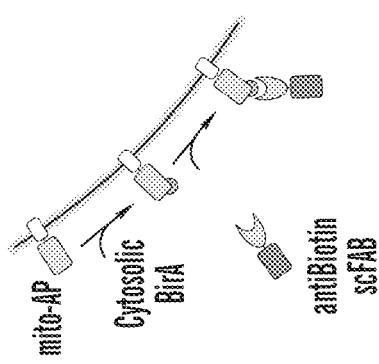

In this approach, it was hypothesized that conversion of the anti-biotinamide antibody to a single-chain Fab (scFab) format would permit its intracellular use, as has previously been demonstrated[34,35]. In order to generate a scFab, the heavy and light chains of the Anti-Biotinamide antibody were linked via a flexible linker sequence[34] and a C-terminal 3xFLAG epitope was added to permit immunodetection. To determine whether the scFab retained its ability to recognize biotinamide under cytosolic conditions, a fluorescence imaging analysis was carried out using an mCherry-tagged scFab (scFab-mCherry) in combination with a mitochondrially-targeted BirA substrate (TOM20-mTurq2-3xAP) (FIG. 14A). Reasoning that a functional scFab would localize to the mitochondrial outer membrane in cells containing biotinylated TOM20-mTurq2-3xAP, the colocalization between mTurq2 and mCherry fluorescent emissions in BirA expressing and non-expressing control cells was examined. Indeed, mitochondrial localization of scFab-mCherry was induced via BirA coexpression, whereas a diffuse cytoplasmic mCherry distribution was observed in control (non-BirA expressing) cells (FIG. 14B-14C). These results demonstrate that the Anti-Biotinamide antibody can be utilized as an intracellular biotinamide-binding protein when expressed as an scFab.

Next, aiming to mimic the natural regulation of the nuclear Notch ICD by PTM, it was sought to utilize BirA to gain PTM-dependent control over synthetic genetic systems. In this approach, biotinylation-dependent control was installed into the TRE3G promoter by generating a TetR domain containing a tandem AP fusion sequence (TetR-2xAP). This construct also contained a TRE3G promoter driving mTurquoise2 expression in order to quantify reporter output. In this design, it was anticipated that modification of TetR-2xAP could be used to recruit transcriptional activation machinery to the TRE3G promoter, via a biotinylation-induced interaction with the Anti-Biotinamide scFab fused to p65 and RTA domains (scFab-p65-RTA).

Figure 14F:
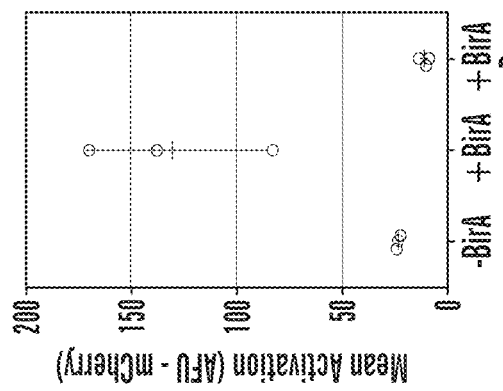

To test this hypothesis, TetR-2xAP and scFab-p65-RTA were co-expressed in TRE3G-mTurq2 reporter cells with and without BirA. Indeed, cells in which all three components were co-expressed led to the greatest mTurquoise2 expression (FIG. 14D). Interestingly, when only TetR-2xAP and BirA were co-expressed, there was also increased mTurquoise2 expression when compared to TetR-2xAP alone. It was hypothesized that the change in charge and hydrophobicity of installing biotin onto a lysine group may lead the AP to become a weak transcriptional activator.

Figure 14E:
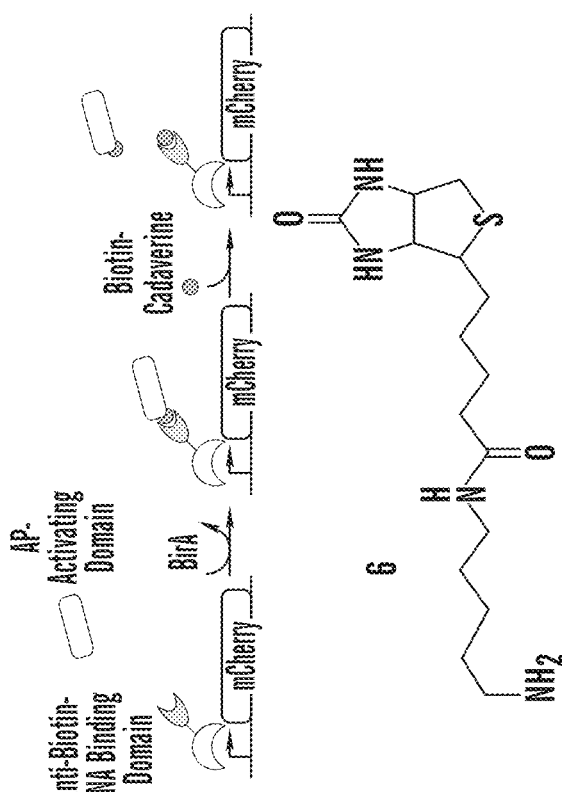
Figure 14D:
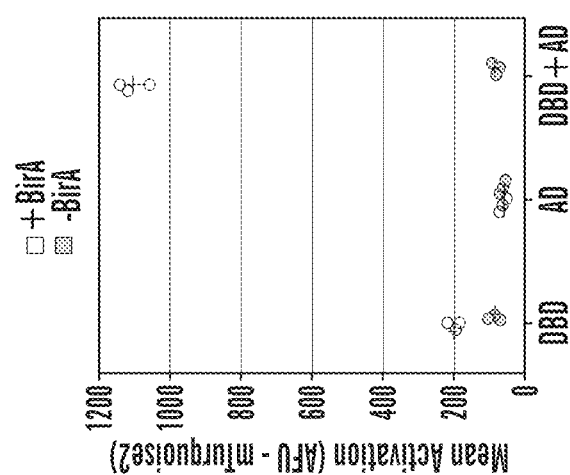

In an alternative design, a fusion between the antibiotinamide scFab and the Gal4 DNA binding domain (scFab-Gal4) was used in combination with an AP fused version of the transcriptional activator VP64 (AP-VP64) (FIG. 14E). In transfected UAS:H2B-mCherry reporter cells, these components were also able to facilitate biotinylation-dependent reporter expression (FIG. 14F). Together, these data demonstrate that BirA biotinylation can be utilized to regulate the formation of transcriptional complexes for gene expression control.

Figure 18:
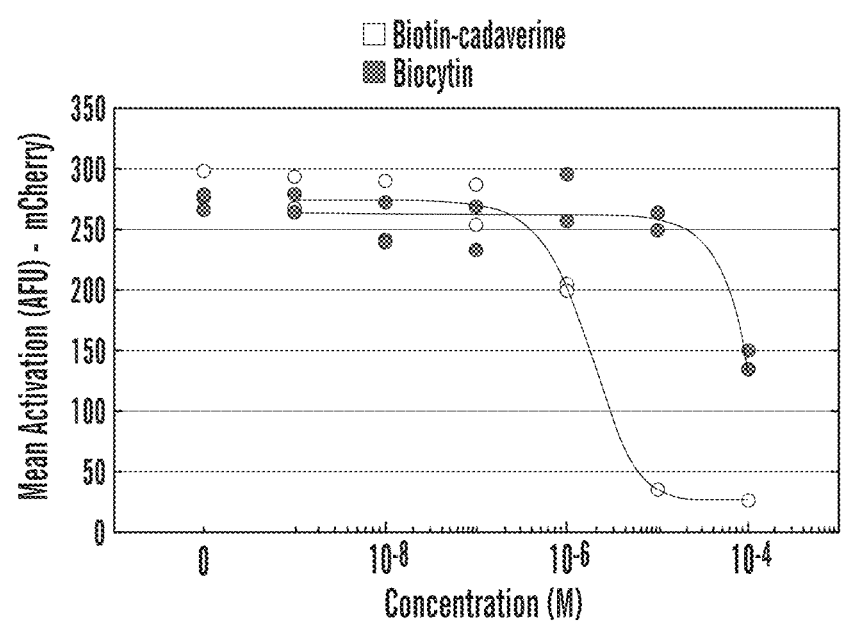
FIG. 18 demonstrates Biotin-cadaverine is an effective competitive inhibitor for intracellular biotin-dependent signaling. Reporter HEK293 cells with an integrated UAS:H2B-mCherry construct were transfected with a construct containing constitutive expression of AP-VP64 and AntiBiotinamide-scFAB-Gal4. The cells were cotransfected with a construct containing Citrine-HA-BirA. At the time of transfection, samples were incubated with different concentrations of Biocytin and Biotin-cadaverine. Samples were measured the next day with flow cytometry, gating for Citrine expression.

Lastly, it was asked whether intracellular protein complexes could be disrupted using exogenously applied biotinamide. To test this possibility, cells were treated with biocytin as well as biotin-cadaverine, a membrane-permeant biotinamide derivative (6). To measure the disruption of intracellular complexes, BirA was co-expressed alongside scFab-Gal4 and AP-VP64 in UAS:H2B-mCherry reporter cells, and the extent of mCherry expression was quantified from cells treated with varying concentrations of biocytin and biotin-cadaverine (FIG. 18A). As anticipated, cells treated with the membrane permeant biotin-cadaverine were more sensitive to the inhibitor.

Discussion

In summary, described herein is a chemogenetic toolkit for installing PTM-based control into synthetic biological systems. Drawing inspiration from natural regulatory mechanisms, an encodable "writer/reader" framework was constructed, leveraging *E. coli* BirA as an orthogonal "writer" module for modifying synthetic signaling proteins containing the AP substrate tag. To permit the programming of cellular activities in response to PTM events, synthetic "reader" elements were designed via a biotinamide specific antibody and fusion proteins containing the domain used in order to facilitate PTM-dependent functions.

In addition, demonstrated herein is the ability to modulate cell-cell communication by exerting genetic control over the expression of writer and reader elements. Through controlling not only the expression of the receptor, but also the modifying enzyme, it is possible to modulate the receptor's signaling capabilities. Chemical control over the assembly state and activity of the encoded modules was attained via treatment of cells with exogenous biotinamide-containing compounds. Finally, the use of these reader/writer domains was extended for use in intracellular contexts by converting the Anti-Biotinamide antibody to a scFAB, demonstrating that these proteins are functional for PTM-dependent intracellular signaling.

These tools can be used to probe the complexity of post-translational modifications in receptor biology, as well as aid in the creation of new receptors for immunotherapy. An advantageous feature of the anti-biotinamide scFv is its selectivity for biotinamide derivatives over that of free biotin. Biotin is present at low concentrations in serum, so this biocytinamide-specific binding molecule allows for preferential binding to the ligand of interest in vivo. The use of safe vitamin-based molecules as inhibitors allows additional control of therapeutic strategies.

Although this work demonstrates the use of BirA in installing orthogonal PTMs in mammalian cells, the enzyme can be adapted readily to further use cases. Chemogenetic and photogenetic changes to the localization or activity of BirA can lead to additional layers of control and more rapid changes in PTM state of specific populations of AP-tagged molecules. Further, the use of an additional orthogonal PTM, reader, and writer can provide increasing complexity in signaling states by effecting PTM-dependent changes in secondary enzyme activity.

A motivating rationale for the development of these tools is to permit the elaboration of synthetic signaling pathways in ways that more closely mimic the intricacies of natural systems. Indeed, it is anticipated that the sophistication of synthetic capabilities—especially regarding the development of complex multicellular systems—will emerge. Throughout natural systems, PTMs play a prominent and critical role, exhibiting the benefits of rapid tunability as a secondary control system.

Methods

Plasmid Construction

Standard cloning procedures were used in the generation of all DNA constructs. DNA fragments were amplified with Phusion High-Fidelity DNA polymerase (New England Biolabs), and Gibson assembly was accomplished using the NEBuilder HiFi DNA Assembly master mix (New England Biolabs). New England Biolabs restriction enzymes were used to digest DNA, and T4 DNA Ligase (New England Biolabs) was used for ligation. The pDisplay-BirA-ER construct is (Addgene #20856). The pLV-EBFP2-nuc construct is (Addgene #36085).

Mammalian Cell Culture

Mammalian cell lines were cultured in a humidified incubator maintained at 37° C. with 5% CO2. HEK293FT cells (Thermo Fisher) were cultured in DMEM with 10% FBS supplemented with nonessential amino acids (Life Technologies). Glutamax (Life Technologies), Penicillin-Streptomycin (50 units-tg/mL; Gibco), and G418 (500 tg/mL; Invitrogen). Stable cell lines with resistance markers were maintained in Zeocin (100 tg/mL; Invitrogen), Puromycin (500 ng/mL; Invitrogen), Hygromycin B (75 tg/mL; Invitrogen), or Blasticidin (10 tg/mL; Invitrogen).

DNA Transfection

DNA transfections were carried out with Lipofectamine 3000 Reagent (Thermo Fisher) according to the manufacturer's instructions. For coculture assays, luciferase reporter plasmids were reverse transfected into synthetic Notch receiver cells.

Stable Cell Line Generation

HEK293FT cells were grown in 6-well plates and cotransfected with lentivirus packaging and envelope plasmids (VSV-G and psPAX2) in addition to plasmids containing the gene of interest. Supernatant was collected 24 hr and 48 hr after, spun down to remove cell debris, and filtered with a 0.45 tm filter. The media containing lentivirus was then added to cell lines for 48 hr. The appropriate antibiotic was added for ten days, and single clones were isolated via limited dilution. For cell lines established with a pcDNA3.1 vector, cells were transfected with linearized DNA, and 48 hr post-transfection, antibiotic and limited dilution protocols were performed as above.

Western Blots

Cell lysates were prepared by direct lysis in RIPA Lysis and Extraction Buffer (Thermo), and denaturing polyacrylamide gel electrophoresis was accomplished with NuPAGE (Thermo Fisher). Proteins were transferred to membranes for probing with Streptavidin-HRP and anti-myc. Detection of the labeled antigens was done by chemiluminescence via the SuperSignal West Pico PLUS Chemiluminescent Substrate (Pierce).

Fluorescence Microscopy

Cells were imaged by epifluorescence microscopy after having been plated on 8-well Optically Clear Plastic Bottom slides (Ibidi) coated with Fibronectin. During imaging, cells were maintained in PBS or standard culture media. For immunofluorescent staining of fixed cells, cells were fixed for 10 min at room temperature with paraformaldehyde (4% v/v in PBS from 16% solutions purchased from Thermo Fisher) and rinsed with PBS. Cells were blocked with a BSA solution (5% in PBS) before being incubated with fluorophore conjugated streptavidin or antibody. Images were acquired with ZEN imaging software (Zeiss). Image files were processed with a custom MATLAB (Mathworks) script in order to adjust contrast uniformly across experiments.

Plated Ligand Assay

Nontreated 96-well plates were coated with Fibronectin (5 ng/mL) and plated ligand in 50 µL PBS for 1 hr. Initial experiments were done with a serial dilution of ligand to determine working concentrations. The wells were rinsed three times with 200 µL PBS, and 40 k synthetic Notch receiver cells were plated in each well. Receptor activation was measured 24 hr post-plating via fluorescence microscopy or flow cytometry.

Figure 19C:
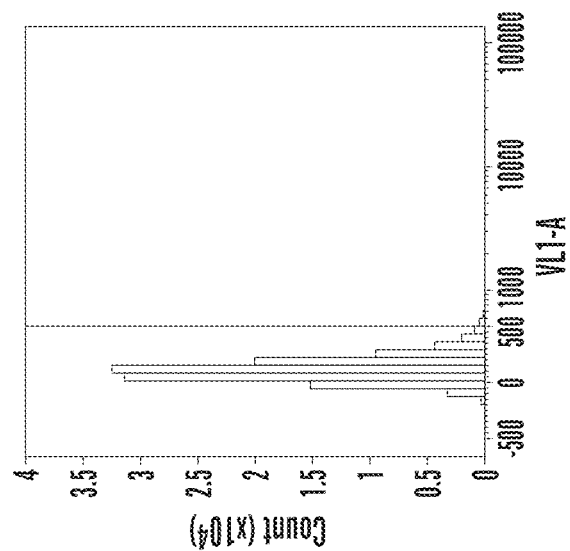
FIGS. 19A-19C demonstrate Gating Schemes for Flow Cytometry.
Figure 19B:
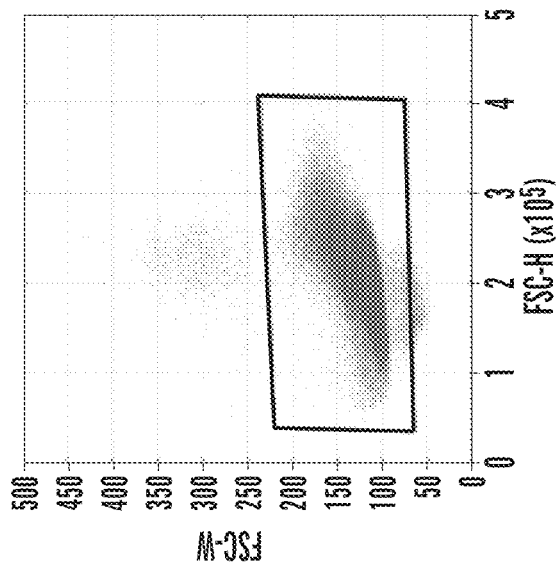
Figure 19A:
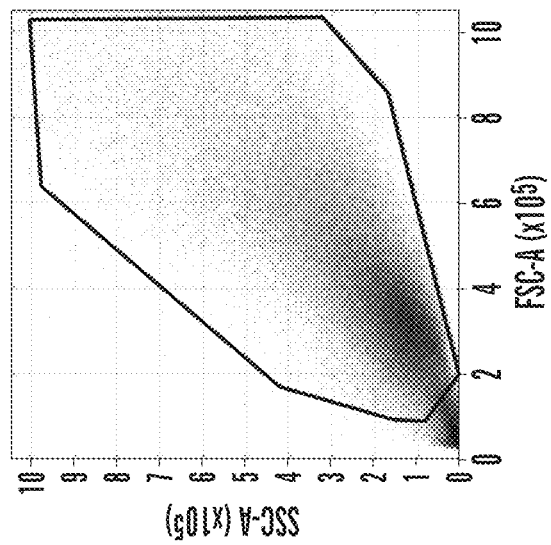

Flow Cytometry Cells analyzed with an Attune NxT flow cytometer and were gated for single cells by scatter detection (FIGS. 19A-19C). Output files were analyzed with a custom MATLAB (Mathworks) script. The percent activation was determined by calculating the percentage of cells with mCherry expression levels above a determined threshold using the non-transfected control as a guide.

Coculture Luciferase Assay

The luciferase assay used for coculture studies was adapted from Gordon et al[59]. Synthetic Notch receiver cells were reverse transfected in a 96-well plate (50 k cells per well) with 9.9 ng of UAS:Firefly-Luciferase plasmid and 0.1 ng Nanoluc plasmid per well. 24 hr post-transfection, 80 k sender cells were added to each well. 48 hr post-transfection, cells were lysed (Nano-Go Dual-Luciferase Reporter Assay System, Promega) and the luminescence was found following the manufacturer's instructions. Each well was normalized to the luminescence output of Nanoluc (transfection control).

Protein Conjugation

Bovine Serum Albumin was conjugated with biotin or desthiobiotin via an NHS ester/amine reaction. 75 µM BSA in bicarbonate buffer and 20% DMSO was mixed with 7.5 mM TAMRA biotin/desthiobiotin succinimidyl ester (Click Chemistry Tools 1048, 1110, respectively) in ultra-dry DMSO in a 9:1 mixture on ice. The reaction proceeded for 1 hour at room temperature and went through 3 rounds of dialysis in PBS. The solution was diluted and filter sterilized. The final concentration of the hapten conjugated to BSA was calculated by measuring the absorbance at 555 nm and using the extinction coefficient of TAMRA ($92000\ M^{-1}\ cm^{-1}$). The reaction of photocleavable biotin (Click Chemistry Tools 1225) to BSA occurred in a similar reaction, and the hapten concentration was determined with the HABA Assay.

REFERENCES

1. Sekine. R., Shibata, T. & Ebisuya, M. Synthetic mammalian pattern formation driven by differential diffusivity of Nodal and Lefty. *Nat Commun* 9, 5456 (2018).

2. Endo, M., Iwawaki, T., Yoshimura. H. & Ozawa, T. Photocleavable Cadherin Inhibits Cell-to-Cell Mechanotransduction by Light. *Acs Chem Biol* 14, 2206-2214 (2019).
3. Toettcher, J. E., Weiner, O. D. & Lim, W. A. Using Optogenetics to Interrogate the Dynamic Control of Signal Transmission by the Ras/Erk Module. *Cell* 155, 1422-1434 (2013).
4. Cho, J. H. et al. Engineering Axl specific CAR and SynNotch receptor for cancer therapy. *Sci Rep-uk* 8, 3846 (2018).
5. Gordon, W. R. et al. Mechanical Allostery: Evidence for a Force Requirement in the Proteolytic Activation of Notch. *Dev Cell* 33, 729-736 (2015).
6. Roybal, K. T. et al. Precision Tumor Recognition by T Cells With Combinatorial Antigen-Sensing Circuits. *Cell* 164, 770-779 (2016).
7. Morsut, L. et al. Engineering Customized Cell Sensing and Response Behaviors Using Synthetic Notch Receptors. *Cell* 164, 780-791 (2016).
8. Toda, S., Blauch, L. R., Tang, S. K. Y., Morsut, L. & Lim, W. A. Programming self-organizing multicellular structures with synthetic cell-cell signaling. *Science* 361, eaat0271 (2018).
9. Toda, S. et al. Engineering synthetic morphogen systems that can program multicellular patterning. *Science* 370, 327-331 (2020).
10. Bray, S. J. Notch signalling in context. *Nat Rev Mol Cell Bio* 17, 722-735 (2016).
11. Kakuda, S. & Haltiwanger, R. S. Deciphering the Fringe-Mediated Notch Code: Identification of Activating and Inhibiting Sites Allowing Discrimination between Ligands. *Dev Cell* 40, 193-201(2017).
12. Panin, V. M. et al. Notch Ligands Are Substrates for ProteinO-Fucosyltransferase-1 and Fringe. *J. Biol Chem* 277, 29945-29952 (2002).
13. Fleming, R. J., Gu. Y. & Hukriede, N. A. Serrate-mediated activation of Notch is specifically blocked by the product of the gene fringe in the dorsal compartment of the *Drosophila* wing imaginal disc. *Dev Camb Engl* 124, 2973-81 (1997).
14. LeBon, L., Lee, T. V., Sprinzak, D. Jafar-Nejad, H. & Elowitz, M. B. Fringe proteins modulate Notch-ligand cis and trans interactions to specify signaling states. *Elife* 3, e02950 (2014).
15. Yoshioka-Kobayashi, K. et al. Coupling delay controls synchronized oscillation in the segmentation clock. *Nature* 580, 119-123 (2020).
16. Tague, E. P., Dotson, H. L., Tunney, S. N., Sloas, D. C. & Ngo, J. T. Chemogenetic control of gene expression and cell signaling with antiviral drugs. *Nat Methods* 15, 519-522 (2018).
17. Gao, X. J., Chong, L. S., Kim, M. S. & Elowitz, M. B. Programmable protein circuits in living cells. *Science* 361, 1252-1258 (2018).
18. Zalatan, J. G., Coyle, S. M., Rajan, S., Sidhu, S. S. & Lim, W. A. Conformational Control of the Stc5 Scaffold Protein Insulates Against MAP Kinase Misactivation. *Science* 337, 1218-1222 (2012).
19. Scheller, L. et al. Phosphoregulated orthogonal signal transduction in mammalian cells. *Nat Commun* 11, 3085 (2020).
20. Beckett, D., Kovaleva, E. & Schatz, P. J. A minimal peptide substrate in biotin holoenzyme synthetase-catalyzed biotinylation. *Protein Sci* 8, 921-929 (1999).
21. Weber, W., Bacchus, W., Baba, M. D.-E. & Fussenegger. M. Vitamin H-regulated transgene expression in mammalian cells. *Nucleic Acids Res* 35, e116-e116 (2007).
22. Weber, W. et al. A synthetic time-delay circuit in mammalian cells and mice. *Proc National Acad Sci* 104, 2643-2648 (2007).
23. Chen, I., Howarth, M., Lin, W. & Ting, A. Y. Site-specific labeling of cell surface proteins with biophysical probes using biotin ligase. *Nat Methods* 2, 99-104 (2005).
24. Howarth, M., Takao, K., Hayashi, Y. & Ting, A. Y. Targeting quantum dots to surface proteins in living cells with biotin ligase. *P Natl Acad Sci Usa* 102, 7583-7588 (2005).
25. Branon, T. C. et al. Efficient proximity labeling in living cells and organisms with TurboID. *Nat Biotechnol* 36, 880-887 (2018).
26. Logeat, F. et al. The Notch receptor is cleaved constitutively by a furin-like convertase. *Proc National Acad Sci* 95, 8108-8112 (1998).
27. Kiernan, A. E., Cordes, R., Kopan, R., Gossler, A. & Gridley, T. The Notch ligands DLL1 and JAG2 act synergistically to regulate hair cell development in the mammalian inner ear. *Development* 132, 4353-4362 (2005).
28. Johnston, S. H. et al. A family of mammalian Fringe genes implicated in boundary determination and the Notch pathway. *Dev Camb Engl* 124, 2245-54 (1997).
29. Kageyama, R. & Ohtsuka, T. The Notch-Hes pathway in mammalian neural development *Cell Res* 9, 179-188 (1999).
30. Dengl, S. et al. Hapten-directed spontaneous disulfide shuffling: a universal technology for site-directed covalent coupling of payloads to antibodies. *Faseb J* 29, 1763-1779 (2015).
31. Matikonda, S. S. et al. Bioorthogonal prodrug activation driven by a strain-promoted 1,3-dipolar cycloaddition. *Chem Sci* 6, 1212-1218 (2014).
32. Fernandez-Martinez, J. et al. Attenuation of Notch signalling by the Down-syndrome-associated kinase DYRK1A. *J Cell Sci* 122, 1574-1583 (2009).
33. Ishitani, T. et al. Nemo-like kinase suppresses Notch signalling by interfering with formation of the Notch active transcriptional complex. *Nat Cell Biol* 12, 278-285 (2010).
34. Koerber, J. T., Homsby, M. J. & Wells, J. A. An Improved Single-Chain Fab Platform for Efficient Display and Recombinant Expression. *J Mol Biol* 427, 576-586 (2015).
35. Hill, Z. B., Martinko, A. J., Nguyen, D. P. & Wells, J. A. Human antibody-based chemically induced dimerizers for cell therapeutic applications. *Nat Chem Biol* 14, 112-117 (2018).

Example 4

The biotin modification site of polypeptides described herein need not be directly adjacent to the membrane-localizing domain. The position of the modification can be located at multiple positions within the sequence, including in between individual signaling domains within the polypeptide. In addition, multiple modification sites can be used in tandem, and such repeat sequences retain function, with modification and subsequently recognition occurring efficiently within cells.

Described herein is click Chemistry/Bioorthogonal Chemistry inducible signaling via the antiBiotinamide Syn- Notch (FIGS. 13E-13F). This permits targeting the receptor to biomaterials which have been labeled with the TCO group.

Further described herein are embodiments in which the the anti-biotinamide antibody to a single chain fragment antigen-binding (scFAB) for use in intracellular contexts. (FIG. 14). Such embodiments can be used in PTM-dependent translocation and signaling contexts.

Example 5

Figure 20:
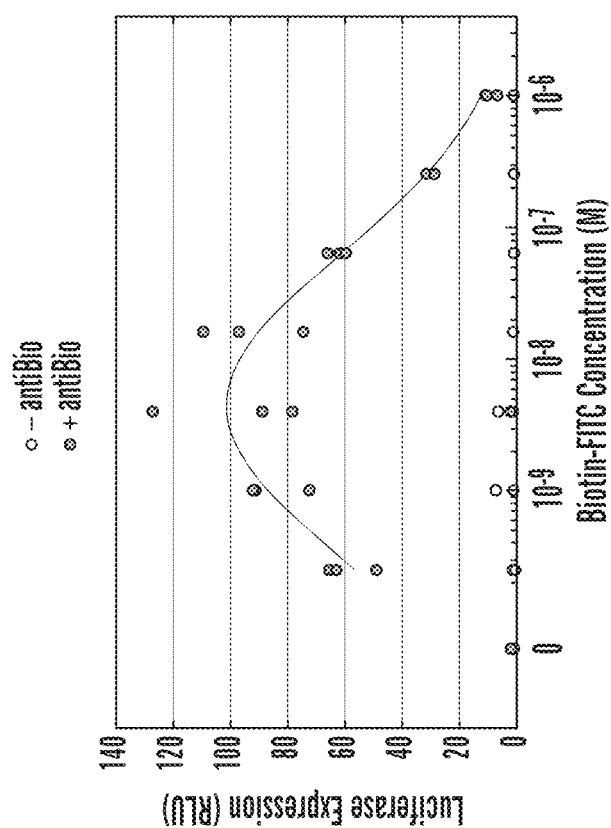
FIG. 20 depicts graphs in which the x-axis of the plot is the biotin-FTC concentration, the y-axis is the extent of signaling (via a Luciferase reporter). The legend gives two different sender-cells used in the coculture—one with the anti-biotin ligand, and one without.
Figure 20:
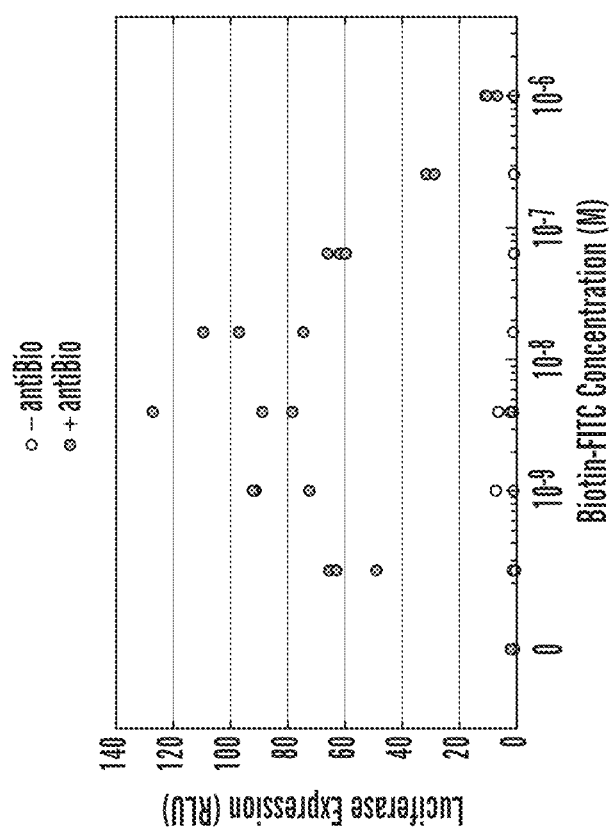

Described herein is the use of biotin-FITC as a small-molecule linker with the ability to induce trans-cellular signaling. In this coculture system, a first group of cells expressed an anti-FITC Synthetic Notch, which can bind one end of the biotin-FITC, and a second group of cells expressed an anti-biotin ligand (described in other Examples herein), which binds the other end. The signaling capacity is concentration dependent—low concentrations do not induce signaling, and high concentrations lead to lower signaling due to the ability of soluble ligand to act as a competitive inhibitor (FIG. 20).

MAb M33 Heavy Chain Fab Fragment Sequence
SEQ ID NO: 1
EVQLQQSGAELVKPGASVKLSCTSSGFNNKDTFFQWVKQRPEEGLEWI
GRIDPANGFTKYDPKFQGKATITVDTSSNTAYLQLNSLTSEDTALYYC
TRWDTYGAAWFAYWGQGTLVTVSAAKTTPPSVYPLAPGSAAQTNSMVT
LGCLVKGYFPEPVTVTWNSGSLSSGVHTFPAVLQSDLYTLSSSVTVPS
STWPSETVTCNVAHPASSTKVDKKIVPR MAb M33 Light Chain Fab Fragment Sequence
SEQ ID NO: 2
DIQMTQSPASLSASVGETVTITCRASGNIHNYLSWFQQKQGKSPQLLV
YSAKTLADGVPSRFSGSGSGTQYSLKINSLQPEDFGTYYCQHFWSSIY
TFGGGTKLEIKRADAAPTVSIFPPSSEQLTSGGASVVCFLNNFYPKDI
NVKWKIDGSERQNGVLNSWTDQDSKDSTYSMSSTLTLTKDEYERHNSY
TCEATHKTSTSPIVKSFNRNEC

SEQ ID NO: 3
GGSSRSSSGGGGSGGGG

---

What is claimed herein is:

1. A synthetic signaling system comprising:
a small molecule-controlled signaling polypeptide comprising
   i) a small molecule acceptor peptide and
   ii) at least a first signaling domain,
   wherein the i) a small molecule acceptor peptide and ii) at least a first signaling domain of the small molecule-controlled signaling polypeptide are not found as part of the same polypeptide in nature; and
a polypeptide comprising a domain that binds specifically to the small molecule; and
a surface-attached molecule comprising:
   a) a binding domain specific for a target, and
   b) a small molecule acceptor peptide.

2. The system of claim 1, wherein the at least a first signaling domain comprises an extracellular domain that interacts with an upstream signaling binding partner; and
wherein the small molecule-controlled signaling polypeptide further comprises a transmembrane domain.

3. The system of claim 2, wherein the polypeptide comprising a domain that binds specifically to a small molecule further comprises a signaling domain comprising an intracellular CAR stimulatory domain.

4. The system of claim 1, wherein the at least first signaling domain of the small molecule-controlled signaling polypeptide comprises a CAR stimulatory domain.

5. The system of claim 4, wherein the CAR stimulatory domain is a CD3ζ signaling domain.

6. The system of claim 4, wherein the polypeptide comprising a domain that binds specifically to a small molecule further comprises:
a signaling domain comprising an extracellular domain that binds specifically to a target; and
a transmembrane domain.

7. The system of claim 1, wherein the small molecule is biotin, a biotinylamide, fluorescein, digoxigenin, or fluorescein isothiocyanate (FITC).

8. The system of claim 1, wherein the domain that binds specifically to the small molecule is an antibody or antibody reagent.

9. The system of claim 1, wherein the at least a first signaling domain comprises a Notch receptor signaling domain.

10. The system of claim 9, wherein the small molecule-controlled signaling polypeptide comprises a Notch core, the Notch core comprising the Notch receptor signaling domain.

11. The system of claim 1, wherein the at least a first signaling domain comprises a transcriptional activator.

12. The system of claim 1, wherein the at least a first signaling domain is a nuclear-acting signaling domain.

13. The system of claim 12, wherein the nuclear-acting signaling domain comprises a DNA-binding domain.

14. The system of claim 1, further comprising a soluble molecule comprising a small molecule acceptor peptide or a small molecule.

15. A combination comprising:
I) a cell or set of cells comprising one or more nucleic acids encoding:
   A) one of:
      i) a small molecule-controlled signaling polypeptide comprising:
         1) A small molecule acceptor peptide and
         2) at least a first signaling domain;
         wherein the 1) a small molecule acceptor peptide and 2) at least a first signaling domain of the small molecule-controlled signaling polypeptide are not found as part of the same polypeptide in nature; and
      ii) a small molecule-controlled signaling polypeptide comprising at least a first signaling domain; and
   B) a polypeptide comprising a domain that binds specifically to the small molecule; and
II) a surface-attached molecule comprising:
   a) a binding domain specific for a target, and
   b) a small molecule acceptor peptide.

16. The combination of claim 15, wherein the domain that binds specifically to the small molecule; and/or the small molecule acceptor peptide are extracellular.

17. The combination of claim 15, wherein the domain that binds specifically to the small molecule; and/or the small molecule acceptor peptide are intracellular.

18. The combination of claim 15, wherein the small molecule is biotin or a biotinylamide and the cell or set of cells further comprises a nucleic acid encoding biotin ligase.

19. A combination comprising:
I) a cell or set of cells comprising a nucleic acid encoding a small molecule-controlled signaling polypeptide, the small molecule-controlled signaling polypeptide comprising i) a small molecule acceptor peptide and ii) at least a first signaling domain; and
II) a surface-attached molecule comprising:
   a) a binding domain specific for a target, and
   b) a small molecule acceptor peptide.

20. The combination of claim 19, wherein the small molecule is biotin or a biotinylamide and the cell further comprises a nucleic acid encoding biotin ligase.

21. A method of treating a subject in need of immunotherapy, the method comprising administering to the subject an immune cell comprising a synthetic signaling system comprising:
- a small molecule-controlled signaling polypeptide comprising
  - i) a small molecule acceptor peptide and
  - ii) at least a first signaling domain,
  - wherein the i) a small molecule acceptor peptide and ii) at least a first signaling domain of the small molecule-controlled signaling polypeptide are not found as part of the same polypeptide in nature; and
- a polypeptide comprising a domain that binds specifically to the small molecule.

22. The method of claim 21, wherein the at least a first signaling domain comprises an extracellular binding domain that interacts with an upstream signaling binding partner.

23. The method of claim 21, wherein the immune cell is a T cell.

\* \* \* \* \*